US009683215B2

(12) United States Patent
Melton et al.

(10) Patent No.: US 9,683,215 B2
(45) Date of Patent: Jun. 20, 2017

(54) METHODS OF REPROGRAMMING CELLS

(75) Inventors: Douglas A. Melton, Lexington, MA (US); Qiao Zhou, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 124 days.

(21) Appl. No.: 13/060,123

(22) PCT Filed: Aug. 24, 2009

(86) PCT No.: PCT/US2009/054789
§ 371 (c)(1),
(2), (4) Date: Apr. 19, 2011

(87) PCT Pub. No.: WO2010/022395
PCT Pub. Date: Feb. 25, 2010

(65) Prior Publication Data

US 2011/0280842 A1 Nov. 17, 2011

Related U.S. Application Data

(60) Provisional application No. 61/090,936, filed on Aug. 22, 2008.

(51) Int. Cl.
*C12N 15/85* (2006.01)
*C12N 5/071* (2010.01)

(52) U.S. Cl.
CPC ........ *C12N 5/0676* (2013.01); *C12N 2501/60* (2013.01); *C12N 2799/022* (2013.01)

(58) Field of Classification Search
CPC .............. C12N 5/0676; C12N 2501/16; C12N 2506/02; C12N 2501/115; C12N 2501/415; C12N 2501/385; C12N 5/0678; C12N 2501/41; C12N 2501/105; C12N 2501/70; C12N 2501/999; C12N 2501/117; C12N 2501/119; C12N 5/0606; C12N 2501/12
See application file for complete search history.

(56) References Cited

U.S. PATENT DOCUMENTS

2005/0090465 A1* 4/2005 Ferber .............................. 514/44
2006/0281174 A1* 12/2006 Xu ....................... C12N 5/0676 435/325
2007/0259421 A1* 11/2007 D'Amour ............ C12N 5/0676 435/366
2008/0267928 A1* 10/2008 Yang .......................... 424/93.21
2010/0137202 A1* 6/2010 Yang ............................... 514/12

FOREIGN PATENT DOCUMENTS

WO WO 2008013737 A2 * 1/2008

OTHER PUBLICATIONS

Kroon, Evert et al . Pancreatic Endoderm Derived from Human Embryonic Stem Cells Generates Glucose-Responsive Insulin-Secreting Cells in vivo. Nature Biotechnology, 2008. vol. 26 (4). pp. 443-452.*
Zhou, Qiao et al. In vivo Reprogramming of Adult Pancreatic Exocrine Cells to β-cells. Nature. Macmillian Publishers Limited. Oct. 2008. vol. 455. pp. 627-633.*
Kaneto, Hideaki et al. A Crucial Role of MafA as a Novel Therapeutic Target for Diabetes. The Journal of Biological Chemistry. 2005. vol. 280(15). pp. 15047-15052.*
ATCC® (Product Information Sheet for HB-8065TM). Downloaded from the ATCC Website on Oct. 21, 2012: <http://www.atcc.org/ATCCAdvancedCatalogSearch/ProductDetails/tabid/452/Default.aspx?ATCCNum=HB-8065&Template=cellBiology>.*
Zaret, Kenneth et al. Generation and Regeneration of Cells of the Liver and Pancreas. Organ Development. Science. 2008. vol. 322. pp. 1490-1494.*
Artner, Isabella et al. MafA is a Dedicated Activator of the Insulin Gene in vivo. Journal of Endocrinology. May 2008. vol. 198. pp. 271-279.*
Zhou, Qiao et al. In vivo Reprogramming of Adult Pancreatic Exocrine Cells to β-cells. Nature| vol. 455|Oct. 2, 2008. pp. 627-632.*
Bernado, A.S., et al., "Pancreatic transcription factors and their role in the birth life and survival of the pancreatic beta cell," Molecular and cellular endocrinology, Jul. 2008, vol. 294. p. 1-9.
Xu, X., et al., "Beta cells can be generated from endogenous progenitors in injured adult mouse pancreas," Cell, Jan. 2008, vol. 132, pp. 197-207.

* cited by examiner

*Primary Examiner* — Scott Long
*Assistant Examiner* — Nghi Nguyen
(74) *Attorney, Agent, or Firm* — Lisa M. Warren, Esq.; Morse, Barnes-Brown & Pendleton, P.C.

(57) ABSTRACT

The present invention provides methods of reprogramming cells, for example, directly reprogramming a somatic cell of a first cell type into a somatic cell of a second cell type, are described herein. In particular, the present invention generally relates to methods for reprogramming a cell of an endoderm origin to a cell having pancreatic β-cell characteristics. The present invention also relates to an isolated population comprising reprogrammed cells, compositions and their use in the treatment of diabetes mellitus. In particular, the present invention relates to reprogramming a cell of an endoderm origin to a cell having pancreatic β-cell characteristics by increasing the protein expression of at least one transcription factor selected from Pdx1, Ngn3 or MafA in the cell of endoderm origin to reprogram the cell of an endoderm cell to a cell which exhibits at least one or at least two characteristics of an endogenous pancreatic β-cell.

12 Claims, 8 Drawing Sheets

2B

*Cpa1CreER;R26R* → TM injection → pAd-M3 injection → Analysis

6A

6B

SEQUENCE LISTING

```
<160> NUMBER OF SEQ ID NOS: 102

<210> SEQ ID NO 1
<211> LENGTH: 284
<212> TYPE: PRT
<213> ORGANISM: Mus musculus

<400> SEQUENCE: 1

Met Asn Ser Glu Glu Gln Tyr Tyr Ala Ala Thr Gln Leu Tyr Lys Asp
1               5                   10                  15

Pro Cys Ala Phe Gln Arg Gly Pro Val Pro Glu Phe Ser Ala Asn Pro
            20                  25                  30

Pro Ala Cys Leu Tyr Met Gly Arg Gln Pro Pro Pro Pro Pro Pro Pro
        35                  40                  45

Gln Phe Thr Ser Ser Leu Gly Ser Leu Glu Gln Gly Ser Pro Pro Asp
    50                  55                  60

Ile Ser Pro Tyr Glu Val Pro Pro Leu Ala Ser Asp Asp Pro Ala Gly
65                  70                  75                  80

Ala His Leu His His His Leu Pro Ala Gln Leu Gly Leu Ala His Pro
                85                  90                  95

Pro Pro Gly Pro Phe Pro Asn Gly Thr Glu Pro Gly Gly Leu Glu Glu
            100                 105                 110

Pro Asn Arg Val Gln Leu Pro Phe Pro Trp Met Lys Ser Thr Lys Ala
        115                 120                 125
```

```
His Ala Trp Lys Gly Gln Trp Ala Gly Gly Ala Tyr Thr Ala Glu Pro
    130                 135                 140

Glu Glu Asn Lys Arg Thr Arg Thr Ala Tyr Thr Arg Ala Gln Leu Leu
145                 150                 155                 160

Glu Leu Glu Lys Glu Phe Leu Phe Asn Lys Tyr Ile Ser Arg Pro Arg
                165                 170                 175

Arg Val Glu Leu Ala Val Met Leu Asn Leu Thr Glu Arg His Ile Lys
            180                 185                 190

Ile Trp Phe Gln Asn Arg Arg Met Lys Trp Lys Lys Glu Glu Asp Lys
        195                 200                 205

Lys Arg Ser Ser Gly Thr Pro Ser Gly Gly Gly Gly Gly Glu Glu Pro
    210                 215                 220

Glu Gln Asp Cys Ala Val Thr Ser Gly Glu Glu Leu Leu Ala Val Pro
225                 230                 235                 240

Pro Leu Pro Pro Pro Gly Gly Ala Val Pro Pro Gly Val Pro Ala Ala
                245                 250                 255

Val Arg Glu Gly Leu Leu Pro Ser Gly Leu Ser Val Ser Pro Gln Pro
            260                 265                 270

Ser Ser Ile Ala Pro Leu Arg Pro Gln Glu Pro Arg
        275                 280


<210> SEQ ID NO 2
<211> LENGTH: 214
<212> TYPE: PRT
<213> ORGANISM: Mus musculus

<400> SEQUENCE: 2

Met Ala Pro His Pro Leu Asp Ala Leu Thr Ile Gln Val Ser Pro Glu
1               5                   10                  15

Thr Gln Gln Pro Phe Pro Gly Ala Ser Asp His Glu Val Leu Ser Ser
            20                  25                  30

Asn Ser Thr Pro Pro Ser Pro Thr Leu Ile Pro Arg Asp Cys Ser Glu
        35                  40                  45

Ala Glu Val Gly Asp Cys Arg Gly Thr Ser Arg Lys Leu Arg Ala Arg
    50                  55                  60

Arg Gly Gly Arg Asn Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Phe Tyr Gly Pro Glu Pro Pro Val Pro Cys Gly Glu Leu Gly Ser
145                 150                 155                 160

Pro Gly Gly Gly Ser Asn Gly Asp Trp Gly Ser Ile Tyr Ser Pro Val
                165                 170                 175

Ser Gln Ala Gly Asn Leu Ser Pro Thr Ala Ser Leu Glu Glu Phe Pro
            180                 185                 190

Gly Leu Gln Val Pro Ser Ser Pro Ser Tyr Leu Leu Pro Gly Ala Leu
        195                 200                 205

Val Phe Ser Asp Phe Leu
    210
```

<210> SEQ ID NO 3
<211> LENGTH: 359
<212> TYPE: PRT
<213> ORGANISM: Mus musculus

<400> SEQUENCE: 3

```
Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Ala Gly
65                  70                  75                  80

Gly Gly Gly Ser Ala Ala Gln Ala Gly Gly Ala Pro Gly Pro Pro Ser
                85                  90                  95

Gly Gly Pro Gly Thr Val Gly Gly Ala Ser Gly Lys Ala Val Leu Glu
            100                 105                 110

Asp Leu Tyr Trp Met Ser Gly Tyr Gln His His Leu Asn Pro Glu Ala
        115                 120                 125

Leu Asn Leu Thr Pro Glu Asp Ala Val Glu Ala Leu Ile Gly Ser Gly
    130                 135                 140

His His Gly Ala His His Gly Ala His His Pro Ala Ala Ala Ala Ala
145                 150                 155                 160

Tyr Glu Ala Phe Arg Gly Gln Ser Phe Ala Gly Gly Gly Gly Ala Asp
                165                 170                 175

Asp Met Gly Ala Gly His His His Gly Ala His His Thr Ala His His
            180                 185                 190

His His Ser Ala His His His His His His His His His His Gly Gly
        195                 200                 205

Ser Gly His His Gly Gly Gly Ala Gly His Gly Gly Gly Gly Ala Gly
    210                 215                 220

His His Val Arg Leu Glu Glu Arg Phe Ser Asp Asp Gln Leu Val Ser
225                 230                 235                 240

Met Ser Val Arg Glu Leu Asn Arg Gln Leu Arg Gly Phe Ser Lys Glu
                245                 250                 255

Glu Val Ile Arg Leu Lys Gln Lys Arg Arg Thr Leu Lys Asn Arg Gly
            260                 265                 270

Tyr Ala Gln Ser Cys Arg Phe Lys Arg Val Gln Gln Arg His Ile Leu
        275                 280                 285

Glu Ser Glu Lys Cys Gln Leu Gln Ser Gln Val Glu Gln Leu Lys Leu
    290                 295                 300

Glu Val Gly Arg Leu Ala Lys Glu Arg Asp Leu Tyr Lys Glu Lys Tyr
305                 310                 315                 320

Glu Lys Leu Ala Gly Arg Gly Gly Pro Gly Gly Ala Gly Gly Ala Gly
                325                 330                 335

Phe Pro Arg Glu Pro Ser Pro Ala Gln Ala Gly Pro Gly Ala Ala Lys
            340                 345                 350

Gly Ala Pro Asp Phe Phe Leu
        355
```

<210> SEQ ID NO 4
<211> LENGTH: 357
<212> TYPE: PRT
<213> ORGANISM: Mus musculus

<400> SEQUENCE: 4

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Glu Asp Glu
    50                  55                  60

Asp Leu Glu Glu Glu Glu Glu Glu Glu Glu Glu Glu Glu Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

Phe Asp Ser His Ser His His Glu Arg Val Met Ser Ala Gln Leu Asn
            340                 345                 350

Ala Ile Phe His Asp
        355
```

<210> SEQ ID NO 5
<211> LENGTH: 273

<212> TYPE: PRT
<213> ORGANISM: Mus musculus

<400> SEQUENCE: 5

```
Met Ser Leu Thr Asn Thr Lys Thr Gly Phe Ser Val Lys Asp Ile Leu
1               5                   10                  15

Asp Leu Pro Asp Thr Asn Asp Glu Asp Gly Ser Val Ala Glu Gly Pro
            20                  25                  30

Glu Glu Glu Ser Glu Gly Pro Glu Pro Ala Lys Arg Ala Gly Pro Leu
        35                  40                  45

Gly Gln Gly Ala Leu Asp Ala Val Gln Ser Leu Pro Leu Lys Ser Pro
    50                  55                  60

Phe Tyr Asp Ser Ser Asp Asn Pro Tyr Thr Arg Trp Leu Ala Ser Thr
65                  70                  75                  80

Glu Gly Leu Gln Tyr Ser Leu His Gly Leu Ala Ala Ser Ala Pro Pro
                85                  90                  95

Gln Asp Ser Ser Ser Lys Ser Pro Glu Pro Ser Ala Asp Glu Ser Pro
            100                 105                 110

Asp Asn Asp Lys Glu Thr Gln Gly Gly Gly Gly Asp Ala Gly Lys Lys
        115                 120                 125

Arg Lys Arg Arg Val Leu Phe Ser Lys Ala Gln Thr Tyr Glu Leu Glu
    130                 135                 140

Arg Arg Phe Arg Gln Gln Arg Tyr Leu Ser Ala Pro Glu Arg Glu His
145                 150                 155                 160

Leu Ala Ser Leu Ile Arg Leu Thr Pro Thr Gln Val Lys Ile Trp Phe
                165                 170                 175

Gln Asn His Arg Tyr Lys Met Lys Arg Ala Arg Ala Glu Lys Gly Met
            180                 185                 190

Glu Val Thr Pro Leu Pro Ser Pro Arg Arg Val Ala Val Pro Val Leu
        195                 200                 205

Val Arg Asp Gly Lys Pro Cys His Ala Leu Lys Ala Gln Asp Leu Ala
    210                 215                 220

Ala Ala Thr Phe Gln Ala Gly Ile Pro Phe Ser Ala Tyr Ser Ala Gln
225                 230                 235                 240

Ser Leu Gln His Met Gln Tyr Asn Ala Gln Tyr Ser Ser Ala Ser Thr
                245                 250                 255

Pro Gln Tyr Pro Thr Ala His Pro Leu Val Gln Ala Gln Gln Trp Thr
            260                 265                 270

Trp
```

<210> SEQ ID NO 6
<211> LENGTH: 365
<212> TYPE: PRT
<213> ORGANISM: Mus musculus

<400> SEQUENCE: 6

```
Met Leu Ala Val Gly Ala Met Glu Gly Pro Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Thr Gly Pro Pro
        35                  40                  45

Ser Ser Ser Ser Ser Ser Ser Ser Ser Ser Ser Pro Ser Pro Pro Leu
    50                  55                  60

Gly Ser His Asn Pro Gly Gly Leu Lys Pro Pro Ala Ala Gly Gly Leu
```

```
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Thr Ser Ala Ser Ala Ala Ala Ala Ala Ala Ala
    130                 135                 140

Ala Ala Ala Ala Ala Ala Ala Ser Ser Pro Ala Gly Leu Leu Ala Gly
145                 150                 155                 160

Leu Pro Arg Phe Ser Ser Leu Ser Pro Pro Pro Pro Pro Pro Gly Leu
                165                 170                 175

Tyr Phe Ser Pro Ser Ala Ala Ala Val Ala Ala Val Gly Arg Tyr Pro
            180                 185                 190

Lys Pro Leu Ala Glu Leu Pro Gly Arg Thr Pro Ile Phe Trp Pro Gly
        195                 200                 205

Val Met Gln Ser Pro Pro Trp Arg Asp Ala Arg Leu Ala Cys Thr Pro
    210                 215                 220

His Gln Gly Ser Ile Leu Leu Asp Lys Asp Gly Lys Arg Lys His Thr
225                 230                 235                 240

Arg Pro Thr Phe Ser Gly Gln Gln Ile Phe Ala Leu Glu Lys Thr Phe
                245                 250                 255

Glu Gln Thr Lys Tyr Leu Ala Gly Pro Glu Arg Ala Arg Leu Ala Tyr
            260                 265                 270

Ser Leu Gly Met Thr Glu Ser Gln Val Lys Val Trp Phe Gln Asn Arg
        275                 280                 285

Arg Thr Lys Trp Arg Lys Lys His Ala Ala Glu Met Ala Thr Ala Lys
    290                 295                 300

Lys Lys Gln Asp Ser Glu Thr Glu Arg Leu Lys Gly Thr Ser Glu Asn
305                 310                 315                 320

Glu Glu Asp Asp Asp Asp Tyr Asn Lys Pro Leu Asp Pro Asn Ser Asp
                325                 330                 335

Asp Glu Lys Ile Thr Gln Leu Leu Lys Lys His Lys Ser Ser Gly Gly
            340                 345                 350

Ser Leu Leu Leu His Ala Ser Glu Ala Glu Gly Ser Ser
        355                 360                 365


<210> SEQ ID NO 7
<211> LENGTH: 349
<212> TYPE: PRT
<213> ORGANISM: Mus musculus

<400> SEQUENCE: 7

Met Gln Gln Asp Gly Leu Ser Ser Val Asn Gln Leu Gly Gly Leu Phe
1               5                   10                  15

Val Asn Gly Arg Pro Leu Pro Leu Asp Thr Arg Gln Gln Ile Val Gln
            20                  25                  30

Leu Ala Ile Arg Gly Met Arg Pro Cys Asp Ile Ser Arg Ser Leu Lys
        35                  40                  45

Val Ser Asn Gly Cys Val Ser Lys Ile Leu Gly Arg Tyr Tyr Arg Thr
    50                  55                  60

Gly Val Leu Glu Pro Lys Cys Ile Gly Gly Ser Lys Pro Arg Leu Ala
65                  70                  75                  80
```

```
Thr Pro Ala Val Val Ala Arg Ile Ala Gln Leu Lys Asp Glu Tyr Pro
                85                  90                  95

Ala Leu Phe Ala Trp Glu Ile Gln His Gln Leu Cys Thr Glu Gly Leu
            100                 105                 110

Cys Thr Gln Asp Lys Ala Pro Ser Val Ser Ser Ile Asn Arg Val Leu
        115                 120                 125

Arg Ala Leu Gln Glu Asp Gln Ser Leu His Trp Thr Gln Leu Arg Ser
    130                 135                 140

Pro Ala Val Leu Ala Pro Val Leu Pro Ser Pro His Ser Asn Cys Gly
145                 150                 155                 160

Ala Pro Arg Gly Pro His Pro Gly Thr Ser His Arg Asn Arg Thr Ile
                165                 170                 175

Phe Ser Pro Gly Gln Ala Glu Ala Leu Glu Lys Glu Phe Gln Arg Gly
            180                 185                 190

Gln Tyr Pro Asp Ser Val Ala Arg Gly Lys Leu Ala Ala Ala Thr Ser
        195                 200                 205

Leu Pro Glu Asp Thr Val Arg Val Trp Phe Ser Asn Arg Arg Ala Lys
    210                 215                 220

Trp Arg Arg Gln Glu Lys Leu Lys Trp Glu Ala Gln Leu Pro Gly Ala
225                 230                 235                 240

Ser Gln Asp Leu Thr Val Pro Lys Asn Ser Pro Gly Ile Ile Ser Ala
                245                 250                 255

Gln Gln Ser Pro Gly Ser Val Pro Ser Ala Ala Leu Pro Val Leu Glu
            260                 265                 270

Pro Leu Ser Pro Ser Phe Cys Gln Leu Cys Cys Gly Thr Ala Pro Gly
        275                 280                 285

Arg Cys Ser Ser Asp Thr Ser Ser Gln Ala Tyr Leu Gln Pro Tyr Trp
    290                 295                 300

Asp Cys Gln Ser Leu Leu Pro Val Ala Ser Ser Ser Tyr Val Glu Phe
305                 310                 315                 320

Ala Trp Pro Cys Leu Thr Thr His Pro Val His His Leu Ile Gly Gly
                325                 330                 335

Pro Gly Gln Val Pro Ser Thr His Cys Ser Asn Trp Pro
            340                 345


<210> SEQ ID NO 8
<211> LENGTH: 436
<212> TYPE: PRT
<213> ORGANISM: Mus musculus

<400> SEQUENCE: 8

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Glu Asn Val Ser Asn
    50                  55                  60

Gly Cys Val Ser Lys Ile Leu Gly Arg Tyr Tyr Glu Thr Gly Ser Ile
65                  70                  75                  80

Arg Pro Arg Ala Ile Gly Gly Ser Lys Pro Arg Val Ala Thr Pro Glu
                85                  90                  95

Val Val Ser Lys Ile Ala Gln Tyr Lys Arg Glu Cys Pro Ser Ile Phe
            100                 105                 110
```

```
Ala Trp Glu Ile Arg Asp Arg Leu Leu Ser Glu Gly Val Cys Thr Asn
        115                 120                 125

Asp Asn Ile Pro Ser Val Ser Ser Ile Asn Arg Val Leu Arg Asn Leu
    130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
                165                 170                 175

Tyr Pro Gly Thr Ser Val Pro Gly Gln Pro Thr Gln Asp Gly Cys Gln
            180                 185                 190

Gln Gln Glu Gly Gly Gly Glu Asn Thr Asn Ser Ile Ser Ser Asn Gly
        195                 200                 205

Glu Asp Ser Asp Glu Ala Gln Met Arg Leu Gln Leu Lys Arg Lys Leu
    210                 215                 220

Gln Arg Asn Arg Thr Ser Phe Thr Gln Glu Gln Ile Glu Ala Leu Glu
225                 230                 235                 240

Lys Glu Phe Glu Arg Thr His Tyr Pro Asp Val Phe Ala Arg Glu Arg
                245                 250                 255

Leu Ala Ala Lys Ile Asp Leu Pro Glu Ala Arg Ile Gln Val Trp Phe
            260                 265                 270

Ser Asn Arg Arg Ala Lys Trp Arg Arg Glu Glu Lys Leu Arg Asn Gln
        275                 280                 285

Arg Arg Gln Ala Ser Asn Thr Pro Ser His Ile Pro Ile Ser Ser Ser
    290                 295                 300

Phe Ser Thr Ser Val Tyr Gln Pro Ile Pro Gln Pro Thr Thr Pro Val
305                 310                 315                 320

Ser Ser Phe Thr Ser Gly Ser Met Leu Gly Arg Thr Asp Thr Ala Leu
                325                 330                 335

Thr Asn Thr Tyr Ser Ala Leu Pro Pro Met Pro Ser Phe Thr Met Ala
            340                 345                 350

Asn Asn Leu Pro Met Gln Pro Pro Val Pro Ser Gln Thr Ser Ser Tyr
        355                 360                 365

Ser Cys Met Leu Pro Thr Ser Pro Ser Val Asn Gly Arg Ser Tyr Asp
    370                 375                 380

Thr Tyr Thr Pro Pro His Met Gln Thr His Met Asn Ser Gln Pro Met
385                 390                 395                 400

Gly Thr Ser Gly Thr Thr Ser Thr Gly Leu Ile Ser Pro Gly Val Ser
                405                 410                 415

Val Pro Val Gln Val Pro Gly Ser Glu Pro Asp Met Ser Gln Tyr Trp
            420                 425                 430

Pro Arg Leu Gln
        435


<210> SEQ ID NO 9
<211> LENGTH: 349
<212> TYPE: PRT
<213> ORGANISM: Mus musculus

<400> SEQUENCE: 9

Met Gly Asp Met Gly Asp Pro Pro Lys Lys Lys Arg Leu Ile Ser Leu
1               5                   10                  15

Cys Val Gly Cys Gly Asn Gln Ile His Asp Gln Tyr Ile Leu Arg Val
            20                  25                  30

Ser Pro Asp Leu Glu Trp His Ala Ala Cys Leu Lys Cys Ala Glu Cys
```

```
        35                  40                  45

Asn Gln Tyr Leu Asp Glu Ser Cys Thr Cys Phe Val Arg Asp Gly Lys
    50                  55                  60

Thr Tyr Cys Lys Arg Asp Tyr Ile Arg Leu Tyr Gly Ile Lys Cys Ala
65                  70                  75                  80

Lys Cys Ser Ile Gly Phe Ser Lys Asn Asp Phe Val Met Arg Ala Arg
                85                  90                  95

Ser Lys Val Tyr His Ile Glu Cys Phe Arg Cys Val Ala Cys Ser Arg
            100                 105                 110

Gln Leu Ile Pro Gly Asp Glu Phe Ala Leu Arg Glu Asp Gly Leu Phe
        115                 120                 125

Cys Arg Ala Asp His Asp Val Val Glu Arg Ala Ser Leu Gly Ala Gly
    130                 135                 140

Asp Pro Leu Ser Pro Leu His Pro Ala Arg Pro Leu Gln Met Ala Ala
145                 150                 155                 160

Glu Pro Ile Ser Ala Arg Gln Pro Ala Leu Arg Pro His Val His Lys
                165                 170                 175

Gln Pro Glu Lys Thr Thr Arg Val Arg Thr Val Leu Asn Glu Lys Gln
            180                 185                 190

Leu His Thr Leu Arg Thr Cys Tyr Ala Ala Asn Pro Arg Pro Asp Ala
        195                 200                 205

Leu Met Lys Glu Gln Leu Val Glu Met Thr Gly Leu Ser Pro Arg Val
    210                 215                 220

Ile Arg Val Trp Phe Gln Asn Lys Arg Cys Lys Asp Lys Lys Arg Ser
225                 230                 235                 240

Ile Met Met Lys Gln Leu Gln Gln Gln Gln Pro Asn Asp Lys Thr Asn
                245                 250                 255

Ile Gln Gly Met Thr Gly Thr Pro Met Val Ala Ala Ser Pro Glu Arg
            260                 265                 270

His Asp Gly Gly Leu Gln Ala Asn Pro Val Glu Val Gln Ser Tyr Gln
        275                 280                 285

Pro Pro Trp Lys Val Leu Ser Asp Phe Ala Leu Gln Ser Asp Ile Asp
    290                 295                 300

Gln Pro Ala Phe Gln Gln Leu Val Asn Phe Ser Glu Gly Gly Pro Gly
305                 310                 315                 320

Ser Asn Ser Thr Gly Ser Glu Val Ala Ser Met Ser Ser Gln Leu Pro
                325                 330                 335

Asp Thr Pro Asn Ser Met Val Ala Ser Pro Ile Glu Ala
            340                 345


<210> SEQ ID NO 10
<211> LENGTH: 324
<212> TYPE: PRT
<213> ORGANISM: Mus musculus

<400> SEQUENCE: 10

Met Asp Ala Val Leu Leu Glu His Phe Pro Gly Gly Leu Asp Thr Phe
1               5                   10                  15

Pro Ser Pro Tyr Phe Asp Glu Glu Asp Phe Phe Thr Asp Gln Ser Ser
            20                  25                  30

Arg Asp Pro Leu Glu Asp Ser Asp Glu Leu Leu Gly Asp Glu Gln Ala
        35                  40                  45

Glu Val Glu Phe Leu Ser His Gln Leu His Glu Tyr Cys Tyr Arg Asp
    50                  55                  60
```

```
Gly Ala Cys Leu Leu Leu Gln Pro Ala Pro Ser Ala Ala Pro His Ala
65                  70                  75                  80

Leu Ala Pro Pro Pro Leu Gly Asp Pro Gly Glu Pro Glu Asp Asn Val
                85                  90                  95

Ser Tyr Cys Cys Asp Ala Gly Ala Pro Leu Ala Ala Phe Pro Tyr Ser
            100                 105                 110

Pro Gly Ser Pro Pro Ser Cys Leu Ala Tyr Pro Cys Ala Ala Val Leu
        115                 120                 125

Ser Pro Gly Ala Arg Leu Gly Gly Leu Asn Gly Ala Ala Ala Ala Ala
    130                 135                 140

Ala Ala Arg Arg Arg Arg Arg Val Arg Ser Glu Ala Glu Leu Gln Gln
145                 150                 155                 160

Leu Arg Gln Ala Ala Asn Val Arg Glu Arg Arg Arg Met Gln Ser Ile
                165                 170                 175

Asn Asp Ala Phe Glu Gly Leu Arg Ser His Ile Pro Thr Leu Pro Tyr
            180                 185                 190

Glu Lys Arg Leu Ser Lys Val Asp Thr Leu Arg Leu Ala Ile Gly Tyr
        195                 200                 205

Ile Asn Phe Leu Ser Glu Leu Val Gln Ala Asp Leu Pro Leu Arg Gly
    210                 215                 220

Ser Gly Ala Gly Gly Cys Gly Gly Pro Gly Gly Ser Arg His Leu Gly
225                 230                 235                 240

Glu Asp Ser Pro Gly Asn Gln Ala Gln Lys Val Ile Ile Cys His Arg
                245                 250                 255

Gly Thr Arg Ser Pro Ser Pro Ser Asp Pro Asp Tyr Gly Leu Pro Pro
            260                 265                 270

Leu Ala Gly His Ser Leu Ser Trp Thr Asp Glu Lys Gln Leu Lys Glu
        275                 280                 285

Gln Asn Ile Ile Arg Thr Ala Lys Val Trp Thr Pro Glu Asp Pro Arg
    290                 295                 300

Lys Leu Asn Ser Lys Ser Phe Asp Asn Ile Glu Asn Glu Pro Pro Phe
305                 310                 315                 320

Glu Phe Val Ser


<210> SEQ ID NO 11
<211> LENGTH: 507
<212> TYPE: PRT
<213> ORGANISM: Mus musculus

<400> SEQUENCE: 11

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
        35                  40                  45

Gln Glu Asn Thr Phe Pro Lys Gly Glu Pro Asp Leu Lys Lys Glu Ser
    50                  55                  60

Glu Glu Asp Lys Phe Pro Val Cys Ile Arg Glu Ala Val Ser Gln Val
65                  70                  75                  80

Leu Lys Gly Tyr Asp Trp Thr Leu Val Pro Met Pro Val Arg Val Asn
                85                  90                  95

Gly Ser Ser Lys Asn Lys Pro His Val Lys Arg Pro Met Asn Ala Phe
            100                 105                 110
```

```
Met Val Trp Ala Gln Ala Ala Arg Arg Lys Leu Ala Asp Gln Tyr Pro
        115                 120                 125

His Leu His Asn Ala Glu Leu Ser Lys Thr Leu Gly Lys Leu Trp Arg
    130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Ser Gly Met Ser Glu Val His Ser Pro
    210                 215                 220

Gly Glu His Ser Gly Gln Ser Gln Gly Pro Pro Thr Pro Pro Thr Thr
225                 230                 235                 240

Pro Lys Thr Asp Val Gln Ala Gly Lys Val Asp Leu Lys Arg Glu Gly
                245                 250                 255

Arg Pro Leu Ala Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
    290                 295                 300

Gly Val Pro Ala Thr His Gly Gln Val Thr Tyr Thr Gly Ser Tyr Gly
305                 310                 315                 320

Ile Ser Ser Thr Ala Pro Thr Pro Ala Thr Ala Gly His Val Trp Met
                325                 330                 335

Ser Lys Gln Gln Ala Pro Pro Pro Pro Pro Gln Gln Pro Pro Gln Ala
            340                 345                 350

Pro Gln Ala Pro Gln Ala Pro Pro Gln Gln Gln Ala Pro Pro Gln Gln
        355                 360                 365

Pro Gln Ala Pro Gln Gln Gln Gln Ala His Thr Leu Thr Thr Leu Ser
    370                 375                 380

Ser Glu Pro Gly Gln Ser Gln Arg Thr His Ile Lys Thr Glu Gln Leu
385                 390                 395                 400

Ser Pro Ser His Tyr Ser Glu Gln Gln Gln His Ser Pro Gln Gln Ile
                405                 410                 415

Ser Tyr Ser Pro Phe Asn Leu Pro His Tyr Ser Pro Ser Tyr Pro Pro
            420                 425                 430

Ile Thr Arg Ser Gln Tyr Asp Tyr Ala Asp His Gln Asn Ser Gly Ser
        435                 440                 445

Tyr Tyr Ser His Ala Ala Gly Gln Gly Ser Gly Leu Tyr Ser Thr Phe
    450                 455                 460

Thr Tyr Met Asn Pro Ala Gln Arg Pro Met Tyr Thr Pro Ile Ala Asp
465                 470                 475                 480

Thr Ser Gly Val Pro Ser Ile Pro Gln Thr His Ser Pro Gln His Trp
                485                 490                 495

Glu Gln Pro Val Tyr Thr Gln Leu Thr Arg Pro
            500                 505
```

<210> SEQ ID NO 12
<211> LENGTH: 465
<212> TYPE: PRT

<213> ORGANISM: Mus musculus

<400> SEQUENCE: 12

```
Met Asn Ala Gln Leu Thr Met Glu Ala Ile Gly Glu Leu His Gly Val
1               5                   10                  15

Ser His Glu Pro Val Pro Ala Pro Ala Asp Leu Leu Gly Gly Ser Pro
            20                  25                  30

His Ala Arg Ser Ser Val Gly His Arg Gly Ser His Leu Pro Pro Ala
        35                  40                  45

His Pro Arg Ser Met Gly Met Ala Ser Leu Leu Asp Gly Gly Ser Gly
    50                  55                  60

Gly Ser Asp Tyr His His His His Arg Ala Pro Glu His Ser Leu Ala
65                  70                  75                  80

Gly Pro Leu His Pro Thr Met Thr Met Ala Cys Glu Thr Pro Pro Gly
                85                  90                  95

Met Ser Met Pro Thr Thr Tyr Thr Thr Leu Thr Pro Leu Gln Pro Leu
            100                 105                 110

Pro Pro Ile Ser Thr Val Ser Asp Lys Phe Pro His His His His His
        115                 120                 125

His His His His His His Pro His His His Gln Arg Leu Ala Gly Asn
    130                 135                 140

Val Ser Gly Ser Phe Thr Leu Met Arg Asp Glu Arg Gly Leu Ala Ser
145                 150                 155                 160

Met Asn Asn Leu Tyr Thr Pro Tyr His Lys Asp Val Ala Gly Met Gly
                165                 170                 175

Gln Ser Leu Ser Pro Leu Ser Gly Ser Gly Leu Gly Ser Ile His Asn
            180                 185                 190

Ser Gln Gln Gly Leu Pro His Tyr Ala His Pro Gly Ala Ala Met Pro
        195                 200                 205

Thr Asp Lys Met Leu Thr Pro Asn Gly Phe Glu Ala His His Pro Ala
    210                 215                 220

Met Leu Gly Arg His Gly Glu Gln His Leu Thr Pro Thr Ser Ala Gly
225                 230                 235                 240

Met Val Pro Ile Asn Gly Leu Pro Pro His His Pro His Ala His Leu
                245                 250                 255

Asn Ala Gln Gly His Gly Gln Leu Leu Gly Thr Ala Arg Glu Pro Asn
            260                 265                 270

Pro Ser Val Thr Gly Ala Gln Val Ser Asn Gly Ser Asn Ser Gly Gln
        275                 280                 285

Met Glu Glu Ile Asn Thr Lys Glu Val Ala Gln Arg Ile Thr Thr Glu
    290                 295                 300

Leu Lys Arg Tyr Ser Ile Pro Gln Ala Ile Phe Ala Gln Arg Val Leu
305                 310                 315                 320

Cys Arg Ser Gln Gly Thr Leu Ser Asp Leu Leu Arg Asn Pro Lys Pro
                325                 330                 335

Trp Ser Lys Leu Lys Ser Gly Arg Glu Thr Phe Arg Arg Met Trp Lys
            340                 345                 350

Trp Leu Gln Glu Pro Glu Phe Gln Arg Met Ser Ala Leu Arg Leu Ala
        355                 360                 365

Ala Cys Lys Arg Lys Glu Gln Glu His Gly Lys Asp Arg Gly Asn Thr
    370                 375                 380

Pro Lys Lys Pro Arg Leu Val Phe Thr Asp Val Gln Arg Arg Thr Leu
385                 390                 395                 400
```

```
His Ala Ile Phe Lys Glu Asn Lys Arg Pro Ser Lys Glu Leu Gln Ile
                405                 410                 415

Thr Ile Ser Gln Gln Leu Gly Leu Glu Leu Ser Thr Val Ser Asn Phe
            420                 425                 430

Phe Met Asn Ala Arg Arg Arg Ser Leu Asp Lys Trp Gln Asp Glu Gly
        435                 440                 445

Gly Ser Asn Ser Gly Ser Ser Ser Ser Ser Ser Ser Thr Cys Thr Lys
    450                 455                 460

Ala
465


<210> SEQ ID NO 13
<211> LENGTH: 558
<212> TYPE: PRT
<213> ORGANISM: Mus musculus

<400> SEQUENCE: 13

Met Val Ser Lys Leu Thr Ser Leu Gln Gln Glu Leu Leu Ser Ala Leu
1               5                   10                  15

Leu Ser Ser Gly Val Thr Lys Glu Val Leu Ile Gln Ala Leu Glu Glu
            20                  25                  30

Leu Leu Pro Ser Pro Asn Phe Gly Val Lys Leu Glu Thr Leu Pro Leu
        35                  40                  45

Ser Pro Gly Ser Gly Ala Asp Leu Asp Thr Lys Pro Val Phe His Thr
    50                  55                  60

Leu Thr Asn Gly His Ala Lys Gly Arg Leu Ser Gly Asp Glu Gly Ser
65                  70                  75                  80

Glu Asp Gly Asp Asp Tyr Asp Thr Pro Pro Ile Leu Lys Glu Leu Gln
                85                  90                  95

Ala Leu Asn Thr Glu Glu Ala Ala Glu Gln Arg Ala Glu Val Asp Arg
            100                 105                 110

Met Leu Ser Glu Asp Pro Trp Arg Ala Ala Lys Met Ile Lys Gly Tyr
        115                 120                 125

Met Gln Gln His Asn Ile Pro Gln Arg Glu Val Val Asp Val Thr Gly
    130                 135                 140

Leu Asn Gln Ser His Leu Ser Gln His Leu Asn Lys Gly Thr Pro Met
145                 150                 155                 160

Lys Thr Gln Lys Arg Ala Ala Leu Tyr Thr Trp Tyr Val Arg Lys Gln
                165                 170                 175

Arg Glu Ile Leu Arg Gln Phe Asn Gln Thr Val Gln Ser Ser Gly Asn
            180                 185                 190

Met Thr Asp Lys Ser Ser Gln Asp Gln Leu Leu Phe Leu Phe Pro Glu
        195                 200                 205

Phe Ser Gln Gln Asn Gln Gly Pro Gly Gln Ser Glu Asp Thr Cys Ser
    210                 215                 220

Glu Pro Thr Asn Lys Lys Met Arg Arg Asn Arg Phe Lys Trp Gly Pro
225                 230                 235                 240

Ala Ser Gln Gln Ile Leu Tyr Gln Ala Tyr Asp Arg Gln Lys Asn Pro
                245                 250                 255

Ser Lys Glu Glu Arg Glu Ala Leu Val Glu Glu Cys Asn Arg Ala Glu
            260                 265                 270

Cys Leu Gln Arg Gly Val Ser Pro Ser Lys Ala His Gly Leu Gly Ser
        275                 280                 285

Asn Leu Val Thr Glu Val Arg Val Tyr Asn Trp Phe Ala Asn Arg Arg
    290                 295                 300
```

```
Lys Glu Glu Ala Phe Arg Gln Lys Leu Ala Met Asp Ala Tyr Ser Ser
305                 310                 315                 320

Asn Gln Thr His Asn Leu Asn Pro Leu Leu Thr His Gly Ser Pro His
                325                 330                 335

His Gln Pro Ser Ser Ser Pro Pro Asn Lys Met Ser Gly Val Arg Tyr
            340                 345                 350

Asn Gln Pro Gly Asn Asn Glu Val Thr Ser Ser Ser Thr Ile Ser His
        355                 360                 365

His Gly Asn Ser Ala Met Val Thr Ser Gln Ser Val Leu Gln Gln Val
    370                 375                 380

Ser Pro Ala Ser Leu Asp Pro Gly His Ser Leu Leu Ser Pro Asp Ser
385                 390                 395                 400

Lys Met Gln Ile Thr Val Ser Gly Gly Gly Leu Pro Pro Val Ser Thr
                405                 410                 415

Leu Thr Asn Ile His Ser Leu Ser His His Asn Pro Gln Gln Ser Gln
            420                 425                 430

Asn Leu Ile Met Thr Pro Leu Ser Gly Val Met Ala Ile Ala Gln Ser
        435                 440                 445

Leu Asn Thr Ser Gln Ala Gln Gly Val Pro Val Ile Asn Ser Val Ala
    450                 455                 460

Ser Ser Leu Ala Ala Leu Gln Pro Val Gln Phe Ser Gln Gln Leu His
465                 470                 475                 480

Ser Pro His Gln Gln Pro Leu Met Gln Gln Ser Pro Gly Ser His Met
                485                 490                 495

Ala Gln Gln Pro Phe Met Ala Ala Val Thr Gln Leu Gln Asn Ser His
            500                 505                 510

Met Tyr Ala His Lys Gln Glu Pro Pro Gln Tyr Ser His Thr Ser Arg
        515                 520                 525

Phe Pro Ser Ala Met Val Val Thr Asp Thr Ser Ser Ile Asn Thr Leu
    530                 535                 540

Thr Ser Met Ser Ser Ser Lys Gln Cys Pro Leu Gln Ala Trp
545                 550                 555


<210> SEQ ID NO 14
<211> LENGTH: 459
<212> TYPE: PRT
<213> ORGANISM: Mus musculus

<400> SEQUENCE: 14

Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
            20                  25                  30

Ala Gly Leu Gly Met Asn Gly Met Asn Thr Tyr Met Ser Met Ser Ala
        35                  40                  45

Ala Ala Met Gly Gly Gly Ser Gly Asn Met Ser Ala Gly Ser Met Asn
    50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Ser Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
```

```
        115                 120                 125

Asn Met Asn Ser Met Ser Pro Met Tyr Gly Gln Ala Gly Leu Ser Arg
    130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
        195                 200                 205

His Ser Leu Ser Phe Asn Asp Cys Phe Leu Lys Val Pro Arg Ser Pro
    210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Ser Ser
            260                 265                 270

Gly Gly Lys Lys Thr Ala Pro Gly Ser Gln Ala Ser Gln Ala Gln Leu
        275                 280                 285

Gly Glu Ala Ala Gly Ser Ala Ser Glu Thr Pro Ala Gly Thr Glu Ser
    290                 295                 300

Pro His Ser Ser Ala Ser Pro Cys Gln Glu His Lys Arg Gly Gly Leu
305                 310                 315                 320

Ser Glu Leu Lys Gly Ala Pro Ala Ser Ala Leu Ser Pro Pro Glu Pro
                325                 330                 335

Ala Pro Ser Pro Gly Gln Gln Gln Gln Ala Ala Ala His Leu Leu Gly
            340                 345                 350

Pro Pro His His Pro Gly Leu Pro Pro Glu Ala His Leu Lys Pro Glu
        355                 360                 365

His His Tyr Ala Phe Asn His Pro Phe Ser Ile Asn Asn Leu Met Ser
    370                 375                 380

Ser Glu Gln Gln His His His Ser His His His His Gln Pro His Lys
385                 390                 395                 400

Met Asp Leu Lys Ala Tyr Glu Gln Val Met His Tyr Pro Gly Gly Tyr
                405                 410                 415

Gly Ser Pro Met Pro Gly Ser Leu Ala Met Gly Pro Val Thr Asn Lys
            420                 425                 430

Ala Gly Leu Asp Ala Ser Pro Leu Ala Ala Asp Thr Ser Tyr Tyr Gln
        435                 440                 445

Gly Val Tyr Ser Arg Pro Ile Met Asn Ser Ser
    450                 455


<210> SEQ ID NO 15
<211> LENGTH: 474
<212> TYPE: PRT
<213> ORGANISM: Mus musculus

<400> SEQUENCE: 15

Met Arg Leu Ser Lys Thr Leu Ala Gly Met Asp Met Ala Asp Tyr Ser
1               5                   10                  15

Ala Ala Leu Asp Pro Ala Tyr Thr Thr Leu Glu Phe Glu Asn Val Gln
            20                  25                  30
```

```
Val Leu Thr Met Gly Asn Asp Thr Ser Pro Ser Glu Gly Ala Asn Leu
        35                  40                  45

Asn Ser Ser Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Gln Gln Ile Thr Ser Pro Ile Ser Gly Ile Asn Gly Asp Ile
                165                 170                 175

Arg Ala Lys Lys Ile Ala Asn Ile Thr Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Leu Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Cys
        275                 280                 285

Leu Lys Ala Ile Ile Phe Phe Asp Pro Asp Ala Lys Gly Leu Ser Asp
    290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
        355                 360                 365

Leu Leu Gln Glu Met Leu Leu Gly Gly Ser Ala Ser Asp Ala Pro His
    370                 375                 380

Thr His His Pro Leu His Pro His Leu Met Gln Glu His Met Gly Thr
385                 390                 395                 400

Asn Val Ile Val Ala Asn Thr Met Pro Ser His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Ser Gly Ser Gly Ser Glu Ser Tyr Lys Leu
        435                 440                 445

Leu Pro Gly Ala Ile Thr Thr Ile Val Lys Pro Pro Ser Ala Ile Pro
```

```
    450                 455                 460

Gln Pro Thr Ile Thr Lys Gln Glu Ala Ile
465                 470


<210> SEQ ID NO 16
<211> LENGTH: 271
<212> TYPE: PRT
<213> ORGANISM: Mus musculus

<400> SEQUENCE: 16

Met Gln Phe Pro His Pro Gly Pro Ala Ala Ala Pro Ala Val Gly Val
1               5                   10                  15

Pro Leu Tyr Ala Pro Thr Pro Leu Leu Gln Pro Ala His Pro Thr Pro
            20                  25                  30

Phe Tyr Ile Asp Asp Ile Leu Gly Arg Gly Pro Ala Ala Pro Thr Pro
        35                  40                  45

Thr Pro Thr Leu Pro Ser Pro Asn Ser Ser Phe Thr Ser Leu Val Ser
    50                  55                  60

Ser Tyr Arg Thr Pro Val Tyr Glu Pro Thr Pro Val His Pro Ala Phe
65                  70                  75                  80

Ser His His Pro Ala Ala Ala Leu Ala Ala Ala Tyr Gly Pro Ser Gly
                85                  90                  95

Phe Gly Gly Pro Leu Tyr Pro Phe Pro Arg Thr Val Asn Asp Tyr Thr
            100                 105                 110

His Ala Leu Leu Arg His Asp Pro Leu Gly Lys Pro Leu Leu Trp Ser
        115                 120                 125

Pro Phe Leu Gln Arg Pro Leu His Lys Arg Lys Gly Gly Gln Val Arg
    130                 135                 140

Phe Ser Asn Asp Gln Thr Val Glu Leu Glu Lys Lys Phe Glu Thr Gln
145                 150                 155                 160

Lys Tyr Leu Ser Pro Pro Glu Arg Lys Arg Leu Ala Lys Met Leu Gln
                165                 170                 175

Leu Ser Glu Arg Gln Val Lys Thr Trp Phe Gln Asn Arg Arg Ala Lys
            180                 185                 190

Trp Arg Arg Leu Lys Gln Glu Asn Pro Gln Ser Asn Lys Lys Asp Ala
        195                 200                 205

Leu Asp Ser Leu Asp Thr Ser Cys Glu Gln Gly Gln Asp Leu Pro Ser
    210                 215                 220

Glu Gln Asn Lys Gly Ala Ser Leu Asp Arg Ser Gln Cys Ser Pro Ser
225                 230                 235                 240

Pro Ala Ser Gln Glu Asp Pro Asp Ser Glu Ile Ser Glu Asp Ser Asp
                245                 250                 255

Gln Glu Val Asp Ile Glu Gly Asp Lys Gly Tyr Phe Asn Ala Gly
            260                 265                 270


<210> SEQ ID NO 17
<211> LENGTH: 737
<212> TYPE: PRT
<213> ORGANISM: Mus musculus

<400> SEQUENCE: 17

Met Pro Asp His Asp Ser Thr Ala Leu Leu Ser Arg Gln Thr Lys Arg
1               5                   10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
```

```
        35                  40                  45

Gly Ser Glu Gln Asp Val Glu Tyr Ser Val Val Gln His Ala Asp Gly
    50                  55                  60

Glu Lys Ser Asn Val Leu Arg Lys Leu Leu Lys Arg Ala Asn Ser Tyr
65                  70                  75                  80

Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110

Ala Ser Gly Leu Ser Ser Thr Gly Ser Glu Val His Gln Glu Asp Ile
        115                 120                 125

Cys Ser Asn Ser Ser Arg Asp Ser Pro Pro Glu Cys Leu Ser Pro Phe
    130                 135                 140

Gly Arg Pro Thr Met Ser Gln Phe Asp Val Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
            180                 185                 190

Met Ala Pro Gln Ser Val Ser Pro Arg Glu Ser Tyr Arg Glu Asn Lys
        195                 200                 205

Arg Lys Gln Lys Leu Pro Gln Gln Gln Gln Gln Ser Phe Gln Gln Leu
    210                 215                 220

Val Ser Ala Arg Lys Glu Gln Lys Arg Glu Glu Arg Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Val Tyr Asp Ser Thr Asp Ser Glu Asn Asp Glu Asp Gly
            260                 265                 270

Asp Leu Ser Glu Asp Ser Met Arg Ser Glu Ile Leu Asp Ala Arg Ala
        275                 280                 285

Gln Asp Ser Val Gly Arg Ser Asp Asn Glu Met Cys Glu Leu Asp Pro
    290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Ser Asn Lys Glu Arg Asp His
                325                 330                 335

Gly Pro Asn Ser Leu Gln Pro Glu Gly Lys His Leu Ala Glu Thr Leu
            340                 345                 350

Lys Gln Glu Leu Asn Thr Ala Met Ser Gln Val Val Asp Thr Val Val
        355                 360                 365

Lys Val Phe Ser Ala Lys Pro Ser Arg Gln Val Pro Gln Val Phe Pro
    370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Ser Val Gln Met Pro Ser Ser
            420                 425                 430

Thr Asp Gln Thr Glu Ala Leu Pro Leu Val Val Arg Lys Asn Ser Ser
        435                 440                 445

Glu Gln Ser Ala Ser Gly Pro Ala Thr Gly Gly His His Gln Pro Leu
    450                 455                 460
```

```
His Gln Ser Pro Leu Ser Ala Thr Ala Gly Phe Thr Thr Pro Ser Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
            500                 505                 510

Glu Ser Leu Asp Leu Thr Arg Asp Thr Thr Ser Leu Arg Thr Lys Met
        515                 520                 525

Ser Ser His His Leu Ser His His Pro Cys Ser Pro Ala His Pro Pro
    530                 535                 540

Ser Thr Ala Glu Gly Leu Ser Leu Ser Leu Ile Lys Ser Glu Cys Gly
545                 550                 555                 560

Asp Leu Gln Asp Met Ser Asp Ile Ser Pro Tyr Ser Gly Ser Ala Met
                565                 570                 575

Gln Glu Gly Leu Ser Pro Asn His Leu Lys Lys Ala Lys Leu Met Phe
            580                 585                 590

Phe Tyr Thr Arg Tyr Pro Ser Ser Asn Met Leu Lys Thr Tyr Phe Ser
        595                 600                 605

Asp Val Lys Phe Asn Arg Cys Ile Thr Ser Gln Leu Ile Lys Trp Phe
    610                 615                 620

Ser Asn Phe Arg Glu Phe Tyr Tyr Ile Gln Met Glu Lys Tyr Ala Arg
625                 630                 635                 640

Gln Ala Ile Asn Asp Gly Val Thr Ser Thr Glu Glu Leu Ser Ile Thr
                645                 650                 655

Arg Asp Cys Glu Leu Tyr Arg Ala Leu Asn Met His Tyr Asn Lys Ala
            660                 665                 670

Asn Asp Phe Glu Val Pro Glu Arg Phe Leu Glu Val Ala Gln Ile Thr
        675                 680                 685

Leu Arg Glu Phe Phe Asn Ala Ile Ile Ala Gly Lys Asp Val Asp Pro
    690                 695                 700

Ser Trp Lys Lys Ala Ile Tyr Lys Val Ile Cys Lys Leu Asp Ser Glu
705                 710                 715                 720

Val Pro Glu Ile Phe Lys Ser Pro Asn Cys Leu Gln Glu Leu Leu His
                725                 730                 735

Glu


<210> SEQ ID NO 18
<211> LENGTH: 404
<212> TYPE: PRT
<213> ORGANISM: Mus musculus

<400> SEQUENCE: 18

Met Glu Lys Ser Lys Asn Phe Arg Ile Asp Ala Leu Leu Ala Val Asp
1               5                   10                  15

Pro Pro Arg Ala Ala Ser Thr Gln Ser Ala Pro Leu Ala Leu Val Thr
            20                  25                  30

Ser Leu Ala Thr Thr Val Ser Gly Pro Gly Arg Gly Gly Ser Gly Gly
        35                  40                  45

Gly Gly Thr Ser Ser Gly Ala Ser Arg Ser Cys Ser Pro Ala Ser Ser
    50                  55                  60

Glu Ala Thr Ala Ala Pro Gly Asp Arg Leu Arg Ala Glu Ser Pro Ser
65                  70                  75                  80

Pro Pro Arg Leu Leu Ala Ala His Cys Ala Leu Leu Pro Lys Pro Gly
                85                  90                  95
```

```
Phe Leu Gly Ala Gly Gly Gly Gly Gly Ala Ala Gly Gly Pro Gly Thr
            100                 105                 110

Pro His His His Ala His Pro Gly Ala Ala Ala Ala Ala Ala Ala Ala
        115                 120                 125

Ala Ala Ala Ala Ala Ala Gly Gly Leu Ala Leu Gly Leu His Pro Gly
    130                 135                 140

Gly Ala Gln Gly Gly Ala Gly Leu Pro Ala Gln Ala Ala Leu Tyr Gly
145                 150                 155                 160

His Pro Val Tyr Ser Tyr Ser Ala Ala Ala Ala Ala Ala Ala Leu Ala
                165                 170                 175

Gly Gln His Pro Ala Leu Ser Tyr Ser Tyr Pro Gln Val Gln Gly Ala
            180                 185                 190

His Pro Ala His Pro Ala Asp Pro Ile Lys Leu Gly Ala Ser Thr Phe
        195                 200                 205

Gln Leu Asp Gln Trp Leu Arg Ala Ser Thr Ala Gly Met Ile Leu Pro
    210                 215                 220

Lys Met Pro Asp Phe Ser Ser Gln Ala Gln Ser Asn Leu Leu Gly Lys
225                 230                 235                 240

Cys Arg Arg Pro Arg Thr Ala Phe Thr Ser Gln Gln Leu Leu Glu Leu
                245                 250                 255

Glu His Gln Phe Lys Leu Asn Lys Tyr Leu Ser Arg Pro Lys Arg Phe
            260                 265                 270

Glu Val Ala Thr Ser Leu Met Leu Thr Glu Thr Gln Val Lys Ile Trp
        275                 280                 285

Phe Gln Asn Arg Arg Met Lys Trp Lys Arg Ser Lys Lys Ala Lys Glu
    290                 295                 300

Gln Ala Ala Gln Glu Ala Glu Lys Gln Lys Gly Gly Gly Gly Gly Thr
305                 310                 315                 320

Gly Lys Gly Gly Ser Glu Glu Lys Thr Glu Glu Glu Leu Met Gly Pro
                325                 330                 335

Pro Val Ser Gly Asp Lys Ala Ser Gly Arg Arg Leu Arg Asp Leu Arg
            340                 345                 350

Asp Ser Asp Pro Asp Glu Asp Glu Asp Asp Glu Glu Glu Asp Asn Phe
        355                 360                 365

Pro Tyr Ser Asn Gly Ala Gly Ala His Ala Ala Ser Ser Asp Cys Ser
    370                 375                 380

Ser Glu Asp Asp Ser Pro Pro Pro Arg Leu Gly Gly Pro Gly His Gln
385                 390                 395                 400

Pro Leu Pro Gln


<210> SEQ ID NO 19
<211> LENGTH: 560
<212> TYPE: PRT
<213> ORGANISM: Mus musculus

<400> SEQUENCE: 19

Met Ser Ala Ser Leu Asp Thr Gly Asp Phe Gln Glu Phe Leu Lys His
1               5                   10                  15

Gly Leu Thr Ala Ile Ala Ser Ala Pro Gly Ser Glu Thr Arg His Ser
            20                  25                  30

Pro Lys Arg Glu Glu Gln Leu Arg Glu Lys Arg Ala Gly Leu Pro Asp
        35                  40                  45

Arg His Arg Arg Pro Ile Pro Ala Arg Ser Arg Leu Val Met Leu Pro
    50                  55                  60
```

```
Lys Val Glu Thr Glu Ala Pro Gly Leu Val Arg Ser His Gly Glu Gln
65                  70                  75                  80

Gly Gln Met Pro Glu Asn Met Gln Val Ser Gln Phe Lys Met Val Asn
                85                  90                  95

Tyr Ser Tyr Asp Glu Asp Leu Glu Glu Leu Cys Pro Val Cys Gly Asp
            100                 105                 110

Lys Val Ser Gly Tyr His Tyr Gly Leu Leu Thr Cys Glu Ser Cys Lys
        115                 120                 125

Gly Phe Phe Lys Arg Thr Val Gln Asn Gln Lys Arg Tyr Thr Cys Ile
    130                 135                 140

Glu Asn Gln Asn Cys Gln Ile Asp Lys Thr Gln Arg Lys Arg Cys Pro
145                 150                 155                 160

Tyr Cys Arg Phe Lys Lys Cys Ile Asp Val Gly Met Lys Leu Glu Ala
                165                 170                 175

Val Arg Ala Asp Arg Met Arg Gly Gly Arg Asn Lys Phe Gly Pro Met
            180                 185                 190

Tyr Lys Arg Asp Arg Ala Leu Lys Gln Gln Lys Lys Ala Leu Ile Arg
        195                 200                 205

Ala Asn Gly Leu Lys Leu Glu Ala Met Ser Gln Val Ile Gln Ala Met
    210                 215                 220

Pro Ser Asp Leu Thr Ser Ala Ile Gln Asn Ile His Ser Ala Ser Lys
225                 230                 235                 240

Gly Leu Pro Leu Ser His Val Ala Leu Pro Pro Thr Asp Tyr Asp Arg
                245                 250                 255

Ser Pro Phe Val Thr Ser Pro Ile Ser Met Thr Met Pro Pro His Ser
            260                 265                 270

Ser Leu His Gly Tyr Gln Pro Tyr Gly His Phe Pro Ser Arg Ala Ile
        275                 280                 285

Lys Ser Glu Tyr Pro Asp Pro Tyr Ser Ser Ser Pro Glu Ser Met Met
    290                 295                 300

Gly Tyr Ser Tyr Met Asp Gly Tyr Gln Thr Asn Ser Pro Ala Ser Ile
305                 310                 315                 320

Pro His Leu Ile Leu Glu Leu Leu Lys Cys Glu Pro Asp Glu Pro Gln
                325                 330                 335

Val Gln Ala Lys Ile Met Ala Tyr Leu Gln Gln Glu Gln Ser Asn Arg
            340                 345                 350

Asn Arg Gln Glu Lys Leu Ser Ala Phe Gly Leu Leu Cys Lys Met Ala
        355                 360                 365

Asp Gln Thr Leu Phe Ser Ile Val Glu Trp Ala Arg Ser Ser Ile Phe
    370                 375                 380

Phe Arg Glu Leu Lys Val Asp Asp Gln Met Lys Leu Leu Gln Asn Cys
385                 390                 395                 400

Trp Ser Glu Leu Leu Ile Leu Asp His Ile Tyr Arg Gln Val Ala His
                405                 410                 415

Gly Lys Glu Gly Thr Ile Phe Leu Val Thr Gly Glu His Val Asp Tyr
            420                 425                 430

Ser Thr Ile Ile Ser His Thr Glu Val Ala Phe Asn Asn Leu Leu Ser
        435                 440                 445

Leu Ala Gln Glu Leu Val Val Arg Leu Arg Ser Leu Gln Phe Asp Gln
    450                 455                 460

Arg Glu Phe Val Cys Leu Lys Phe Leu Val Leu Phe Ser Ser Asp Val
465                 470                 475                 480
```

```
Lys Asn Leu Glu Asn Leu Gln Leu Val Glu Gly Val Gln Glu Gln Val
                485                 490                 495

Asn Ala Ala Leu Leu Asp Tyr Thr Val Cys Asn Tyr Pro Gln Gln Thr
            500                 505                 510

Glu Lys Phe Gly Gln Leu Leu Leu Arg Leu Pro Glu Ile Arg Ala Ile
        515                 520                 525

Ser Lys Gln Ala Glu Asp Tyr Leu Tyr Tyr Lys His Val Asn Gly Asp
    530                 535                 540

Val Pro Tyr Asn Asn Leu Leu Ile Glu Met Leu His Ala Lys Arg Ala
545                 550                 555                 560


<210> SEQ ID NO 20
<211> LENGTH: 323
<212> TYPE: PRT
<213> ORGANISM: Mus musculus

<400> SEQUENCE: 20

Met Ala Ala Glu Leu Ser Met Gly Gln Glu Leu Pro Thr Ser Pro Leu
1               5                   10                  15

Ala Met Glu Tyr Val Asn Asp Phe Asp Leu Leu Lys Phe Asp Val Lys
            20                  25                  30

Lys Glu Pro Leu Gly Arg Ala Glu Arg Pro Gly Arg Pro Cys Thr Arg
        35                  40                  45

Leu Gln Pro Ala Gly Ser Val Ser Ser Thr Pro Leu Ser Thr Pro Cys
    50                  55                  60

Ser Ser Val Pro Ser Ser Pro Ser Phe Ser Pro Thr Glu Pro Lys Thr
65                  70                  75                  80

His Leu Glu Asp Leu Tyr Trp Met Ala Ser Asn Tyr Gln Gln Met Asn
                85                  90                  95

Pro Glu Ala Leu Asn Leu Thr Pro Glu Asp Ala Val Glu Ala Leu Ile
            100                 105                 110

Gly Ser His Pro Val Pro Gln Pro Leu Gln Ser Phe Asp Gly Phe Arg
        115                 120                 125

Ser Ala His His His His His His His His Pro His Pro His His Gly
    130                 135                 140

Tyr Pro Gly Ala Gly Val Thr His Asp Asp Leu Gly Gln His Ala His
145                 150                 155                 160

Pro His His His His His His Gln Ala Ser Pro Pro Pro Ser Ser Ala
                165                 170                 175

Ala Ser Pro Ala Gln Gln Leu Pro Thr Ser His Pro Gly Pro Gly Pro
            180                 185                 190

His Ala Thr Ala Ala Ala Thr Ala Ala Gly Gly Asn Gly Ser Val Glu
        195                 200                 205

Asp Arg Phe Ser Asp Asp Gln Leu Val Ser Met Ser Val Arg Glu Leu
    210                 215                 220

Asn Arg His Leu Arg Gly Phe Thr Lys Asp Glu Val Ile Arg Leu Lys
225                 230                 235                 240

Gln Lys Arg Arg Thr Leu Lys Asn Arg Gly Tyr Ala Gln Ser Cys Arg
                245                 250                 255

Tyr Lys Arg Val Gln Gln Lys His His Leu Glu Asn Glu Lys Thr Gln
            260                 265                 270

Leu Ile Gln Gln Val Glu Gln Leu Lys Gln Glu Val Ser Arg Leu Ala
        275                 280                 285

Arg Glu Arg Asp Ala Tyr Lys Val Lys Cys Glu Lys Leu Ala Asn Ser
    290                 295                 300
```

```
Gly Phe Arg Glu Ala Gly Ser Thr Ser Asp Ser Pro Ser Ser Pro Glu
305                 310                 315                 320

Phe Phe Leu


<210> SEQ ID NO 21
<211> LENGTH: 361
<212> TYPE: PRT
<213> ORGANISM: Mus musculus

<400> SEQUENCE: 21

Met Ala Thr Ala Ala Ser Asn Pro Tyr Ser Ile Leu Ser Ser Ser Ser
1               5                   10                  15

Leu Val His Ala Asp Ser Ala Gly Met Gln Gln Gly Ser Pro Phe Arg
            20                  25                  30

Asn Pro Gln Lys Leu Leu Gln Ser Asp Tyr Leu Gln Gly Val Pro Ser
        35                  40                  45

Asn Gly His Pro Leu Gly His His Trp Val Thr Ser Leu Ser Asp Gly
    50                  55                  60

Gly Pro Trp Ser Ser Thr Leu Ala Thr Ser Pro Leu Asp Gln Gln Asp
65                  70                  75                  80

Val Lys Pro Gly Arg Glu Asp Leu Gln Leu Gly Ala Ile Ile His His
                85                  90                  95

Arg Ser Pro His Val Ala His His Ser Pro His Thr Asn His Pro Asn
            100                 105                 110

Ala Trp Gly Ala Ser Pro Ala Pro Asn Ser Ser Ile Thr Ser Ser Gly
        115                 120                 125

Gln Pro Leu Asn Val Tyr Ser Gln Pro Gly Phe Thr Val Ser Gly Met
    130                 135                 140

Leu Glu His Gly Gly Leu Thr Pro Pro Pro Ala Ala Ala Ser Thr Gln
145                 150                 155                 160

Ser Leu His Pro Val Leu Arg Glu Pro Pro Asp His Gly Glu Leu Gly
                165                 170                 175

Ser His His Cys Gln Asp His Ser Asp Glu Glu Thr Pro Thr Ser Asp
            180                 185                 190

Glu Leu Glu Gln Phe Ala Lys Gln Phe Lys Gln Arg Arg Ile Lys Leu
        195                 200                 205

Gly Phe Thr Gln Ala Asp Val Gly Leu Ala Leu Gly Thr Leu Tyr Gly
    210                 215                 220

Asn Val Phe Ser Gln Thr Thr Ile Cys Arg Phe Glu Ala Leu Gln Leu
225                 230                 235                 240

Ser Phe Lys Asn Met Cys Lys Leu Lys Pro Leu Leu Asn Lys Trp Leu
                245                 250                 255

Glu Glu Ala Asp Ser Ser Thr Gly Ser Pro Thr Ser Ile Asp Lys Ile
            260                 265                 270

Ala Ala Gln Gly Arg Lys Arg Lys Lys Arg Thr Ser Ile Glu Val Ser
        275                 280                 285

Val Lys Gly Val Leu Glu Thr His Phe Leu Lys Cys Pro Lys Pro Ala
    290                 295                 300

Ala Gln Glu Ile Ser Ser Leu Ala Asp Ser Leu Gln Leu Glu Lys Glu
305                 310                 315                 320

Val Val Arg Val Trp Phe Cys Asn Arg Arg Gln Lys Glu Lys Arg Met
                325                 330                 335

Thr Pro Pro Gly Asp Gln Gln Pro His Glu Val Tyr Ser His Thr Val
            340                 345                 350
```

```
Lys Thr Asp Ala Ser Cys His Asp Leu
        355                 360


<210> SEQ ID NO 22
<211> LENGTH: 564
<212> TYPE: PRT
<213> ORGANISM: Mus musculus

<400> SEQUENCE: 22

Met Ser Asn Gln Tyr Gln Glu Glu Gly Cys Ser Glu Arg Pro Glu Cys
1               5                   10                  15

Lys Ser Lys Ser Pro Thr Leu Leu Ser Ser Tyr Cys Ile Asp Ser Ile
            20                  25                  30

Leu Gly Arg Arg Ser Pro Cys Lys Met Arg Leu Leu Gly Ala Ala Gln
        35                  40                  45

Ser Leu Pro Ala Pro Leu Ala Ser Arg Ala Asp Gln Glu Lys Ala Met
    50                  55                  60

Gln Gly Ser Pro Lys Ser Ser Ser Ala Pro Phe Glu Ala Glu Leu His
65                  70                  75                  80

Leu Pro Pro Lys Leu Arg Arg Leu Tyr Gly Pro Gly Gly Gly Arg Leu
                85                  90                  95

Leu Gln Gly Ala Ala Ala Ala Ala Ala Ala Ala Ala Ala Ala Ala Ala
            100                 105                 110

Ala Ala Thr Ala Thr Gly Thr Ala Gly Pro Arg Gly Glu Val Pro Pro
        115                 120                 125

Pro Pro Pro Pro Ala Ala Arg Pro Gly Glu Arg Gln Asp Ser Ala Gly
    130                 135                 140

Ala Val Ala Ala Ala Ala Ala Ala Ala Ala Trp Asp Thr Leu Lys Ile
145                 150                 155                 160

Ser Gln Ala Pro Gln Val Ser Ile Ser Arg Ser Lys Ser Tyr Arg Glu
                165                 170                 175

Asn Gly Ala Pro Phe Val Pro Pro Pro Pro Ala Leu Asp Glu Leu Ser
            180                 185                 190

Gly Pro Gly Gly Val Ala His Pro Glu Glu Arg Leu Ser Ala Ala Ser
        195                 200                 205

Gly Pro Gly Ser Ala Pro Ala Ala Gly Gly Gly Thr Gly Ala Glu Asp
    210                 215                 220

Asp Glu Glu Glu Leu Leu Glu Asp Glu Glu Asp Glu Glu Glu Glu Glu
225                 230                 235                 240

Glu Leu Leu Glu Asp Asp Asp Glu Glu Leu Leu Glu Asp Asp Ala Arg
                245                 250                 255

Ala Leu Leu Lys Glu Pro Arg Arg Cys Ser Val Ala Thr Thr Gly Thr
            260                 265                 270

Val Ala Ala Ala Ala Ala Ala Ala Ala Ala Ala Val Ala Thr Glu Gly
        275                 280                 285

Gly Glu Leu Ser Pro Lys Glu Glu Leu Leu Leu His Pro Glu Asp Ala
    290                 295                 300

Glu Gly Lys Asp Gly Glu Asp Ser Val Cys Leu Ser Ala Gly Ser Asp
305                 310                 315                 320

Ser Glu Glu Gly Leu Leu Lys Arg Lys Gln Arg Arg Tyr Arg Thr Thr
                325                 330                 335

Phe Thr Ser Tyr Gln Leu Glu Glu Leu Glu Arg Ala Phe Gln Lys Thr
            340                 345                 350

His Tyr Pro Asp Val Phe Thr Arg Glu Glu Leu Ala Met Arg Leu Asp
```

```
        355                 360                 365

Leu Thr Glu Ala Arg Val Gln Val Trp Phe Gln Asn Arg Arg Ala Lys
    370                 375                 380

Trp Arg Lys Arg Glu Lys Ala Gly Ala Gln Thr His Pro Pro Gly Leu
385                 390                 395                 400

Pro Phe Pro Gly Pro Leu Ser Ala Thr His Pro Leu Ser Pro Tyr Leu
                405                 410                 415

Asp Ala Ser Pro Phe Pro Pro His His Pro Ala Leu Asp Ser Ala Trp
            420                 425                 430

Thr Ala Ala Ala Ala Ala Ala Ala Ala Ala Phe Pro Ser Leu Pro Pro
        435                 440                 445

Pro Pro Gly Ser Ala Ser Leu Pro Pro Ser Gly Ala Pro Leu Gly Leu
    450                 455                 460

Ser Thr Phe Leu Gly Ala Ala Val Phe Arg His Pro Ala Phe Ile Ser
465                 470                 475                 480

Pro Ala Phe Gly Arg Leu Phe Ser Thr Met Ala Pro Leu Thr Ser Ala
                485                 490                 495

Ser Thr Ala Ala Ala Leu Leu Arg Gln Pro Thr Pro Ala Val Glu Gly
            500                 505                 510

Ala Val Ala Ser Gly Ala Leu Ala Asp Pro Ala Thr Ala Ala Ala Asp
        515                 520                 525

Arg Arg Ala Ser Ser Ile Ala Ala Leu Arg Leu Lys Ala Lys Glu His
    530                 535                 540

Ala Ala Gln Leu Thr Gln Leu Asn Ile Leu Pro Gly Thr Ser Thr Gly
545                 550                 555                 560

Lys Glu Val Cys


<210> SEQ ID NO 23
<211> LENGTH: 1127
<212> TYPE: PRT
<213> ORGANISM: Mus musculus

<400> SEQUENCE: 23

Met Ser Ser Glu Ser Asp Asp Lys Arg Ala Arg Thr Arg Ser Lys Thr
1               5                   10                  15

Leu Arg Gly Pro Pro Glu Thr Thr Gly Ala Asp Leu Ser Cys Pro Thr
            20                  25                  30

Pro Gly Cys Thr Gly Ser Gly His Val Arg Gly Lys Tyr Ser Arg His
        35                  40                  45

Arg Ser Leu Gln Ser Cys Pro Leu Ala Lys Lys Arg Lys Leu Glu Asp
    50                  55                  60

Ala Glu Thr Glu His Leu Val Ser Lys Arg Lys Ser His Pro Leu Arg
65                  70                  75                  80

Leu Ala Leu Asp Glu Gly Tyr Arg Met Asp Ser Asp Gly Ser Glu Asp
                85                  90                  95

Ala Glu Val Lys Asp Val Ser Val Ser Asp Glu Ser Glu Gly Pro Leu
            100                 105                 110

Glu Glu Ala Glu Ala Glu Met Ser Gly Gln Glu Glu Ile His His Pro
        115                 120                 125

Gln Thr Ala Glu Gly Lys Ser Leu Ile Lys Pro His Phe Asp Ser Asn
    130                 135                 140

Pro Thr Ser Ser Pro Ser Gly Phe Ser Lys Ser Ser Tyr Ser Ser Tyr
145                 150                 155                 160

Gln Gly Ile Ile Ala Thr Ser Leu Leu Asn Leu Gly Gln Ile Ala Glu
```

```
                165                 170                 175

Glu Ala Leu Val Lys Glu Asp Ser Val Ser Val Ala Lys Leu Ser Pro
            180                 185                 190

Thr Val Val His Gln Leu Gln Asp Glu Ala Ala Met Gly Val Asn Ser
        195                 200                 205

Asp Glu Gly Glu Lys Asp Leu Phe Ile Gln Pro Glu Asp Val Glu Glu
    210                 215                 220

Val Ile Glu Val Thr Ser Glu Arg Ser Gln Glu Pro Cys Pro Gln Ser
225                 230                 235                 240

Leu Lys Asp Met Val Ser Glu Glu Ser Ser Lys Gln Lys Gly Val Leu
                245                 250                 255

Gly His Glu Glu Glu Gly Glu Glu Glu Glu Glu Asp Glu Glu Glu Glu
            260                 265                 270

Asp Glu Glu Glu Glu Glu Glu Gly Glu Glu Gly Glu Glu Glu Glu Glu
        275                 280                 285

Glu Glu Glu Glu Glu Glu Glu Glu Glu Asp Glu Glu Glu Glu Glu Glu
    290                 295                 300

Glu Glu Glu Ala Ala Pro Asn Val Ile Phe Gly Glu Asp Thr Ser His
305                 310                 315                 320

Thr Ser Val Gln Lys Ala Ser Pro Glu Phe Arg Gly Pro Glu Leu Ser
                325                 330                 335

Ser Pro Lys Pro Glu Tyr Ser Val Ile Val Glu Val Arg Ser Asp Asp
            340                 345                 350

Asp Lys Asp Glu Asp Ser Arg Ser Gln Lys Ser Ala Val Thr Asp Glu
        355                 360                 365

Ser Glu Met Tyr Asp Met Met Thr Arg Gly Asn Leu Gly Leu Leu Glu
    370                 375                 380

Gln Ala Ile Ala Leu Lys Ala Glu Gln Val Arg Ala Val Cys Glu Ser
385                 390                 395                 400

Gly Cys Pro Pro Ala Glu Gln Gly His Leu Gly Pro Gly Glu Pro Gly
                405                 410                 415

Lys Met Ala Lys Pro Leu Asp Val Val Arg Lys Ser Cys Tyr Ser Lys
            420                 425                 430

Asp Pro Ser Arg Val Glu Lys Arg Glu Ile Lys Cys Pro Thr Pro Gly
        435                 440                 445

Cys Asp Gly Thr Gly His Val Thr Gly Leu Tyr Pro His His Arg Ser
    450                 455                 460

Leu Ser Gly Cys Pro His Lys Asp Arg Ile Pro Pro Glu Ile Leu Ala
465                 470                 475                 480

Met His Glu Asn Val Leu Lys Cys Pro Thr Pro Gly Cys Thr Gly Gln
                485                 490                 495

Gly His Val Asn Ser Asn Arg Asn Thr His Arg Ser Leu Ser Gly Cys
            500                 505                 510

Pro Ile Ala Ala Ala Glu Lys Leu Ala Lys Ser His Glu Lys Gln Gln
        515                 520                 525

Leu Gln Thr Gly Asp Pro Pro Lys Asn Asn Ser Asn Ser Asp Arg Ile
    530                 535                 540

Leu Arg Pro Met Cys Phe Val Lys Gln Leu Glu Val Pro Pro Tyr Gly
545                 550                 555                 560

Ser Tyr Arg Pro Asn Val Ala Pro Ala Thr Pro Arg Ala Asn Leu Ala
                565                 570                 575

Lys Glu Leu Glu Lys Phe Ser Lys Val Thr Phe Asp Tyr Ala Ser Phe
            580                 585                 590
```

```
Asp Ala Gln Val Phe Gly Lys Arg Met Leu Ala Pro Lys Ile Gln Thr
        595                 600                 605

Ser Glu Thr Ser Pro Lys Ala Phe Gln Cys Phe Asp Tyr Ser His Asp
    610                 615                 620

Ala Glu Ala Ala His Met Ala Ala Thr Ala Ile Leu Asn Leu Ser Thr
625                 630                 635                 640

Arg Cys Trp Glu Met Pro Glu Asn Leu Ser Thr Lys Pro Gln Asp Leu
                645                 650                 655

Pro Ser Lys Ala Val Asp Ile Glu Val Asp Glu Asn Gly Thr Leu Asp
            660                 665                 670

Leu Ser Met His Lys His Arg Lys Arg Glu Asn Thr Phe Pro Ser Ser
        675                 680                 685

Ser Ser Cys Ser Ser Ser Pro Gly Val Lys Ser Pro Asp Val Ser Gln
    690                 695                 700

Arg Gln Ser Ser Thr Ser Ala Pro Ser Ser Ser Met Thr Ser Pro Gln
705                 710                 715                 720

Ser Ser Gln Ala Ser Arg Gln Asp Glu Trp Asp Arg Pro Leu Asp Tyr
                725                 730                 735

Thr Lys Pro Ser Arg Leu Arg Glu Glu Glu Pro Glu Glu Ser Glu Pro
            740                 745                 750

Ala Ala His Ser Phe Ala Ser Ser Glu Ala Asp Asp Gln Glu Val Ser
        755                 760                 765

Glu Glu Asn Phe Glu Glu Arg Lys Tyr Pro Gly Glu Val Thr Leu Thr
    770                 775                 780

Asn Phe Lys Leu Lys Phe Leu Ser Lys Asp Ile Lys Lys Glu Leu Leu
785                 790                 795                 800

Thr Cys Pro Thr Pro Gly Cys Asp Gly Ser Gly His Ile Thr Gly Asn
                805                 810                 815

Tyr Ala Ser His Arg Ser Leu Ser Gly Cys Pro Leu Ala Asp Lys Ser
            820                 825                 830

Leu Arg Asn Leu Met Ala Ala His Ser Ala Asp Leu Lys Cys Pro Thr
        835                 840                 845

Pro Gly Cys Asp Gly Ser Gly His Ile Thr Gly Asn Tyr Ala Ser His
    850                 855                 860

Arg Ser Leu Ser Gly Cys Pro Arg Ala Lys Lys Ser Gly Leu Lys Val
865                 870                 875                 880

Ala Pro Thr Lys Asp Asp Lys Glu Asp Pro Glu Leu Met Lys Cys Pro
                885                 890                 895

Val Pro Gly Cys Val Gly Leu Gly His Ile Ser Gly Lys Tyr Ala Ser
            900                 905                 910

His Arg Ser Ala Ser Gly Cys Pro Leu Ala Ala Arg Arg Gln Lys Glu
        915                 920                 925

Gly Ala Leu Asn Gly Ser Ser Phe Ser Trp Lys Ser Leu Lys Asn Glu
    930                 935                 940

Gly Pro Thr Cys Pro Thr Pro Gly Cys Asp Gly Ser Gly His Ala Asn
945                 950                 955                 960

Gly Ser Phe Leu Thr His Arg Ser Leu Ser Gly Cys Pro Arg Ala Thr
                965                 970                 975

Phe Ala Gly Lys Lys Gly Lys Leu Ser Gly Asp Glu Ile Leu Ser Pro
            980                 985                 990

Lys Phe Lys Thr Ser Asp Val Leu  Glu Asn Asp Glu Glu  Ile Lys Gln
        995                 1000                 1005
```

```
Leu Asn  Gln Glu Ile Arg Asp  Leu Asn Glu Ser Asn  Ser Glu Met
    1010                 1015                 1020

Glu Ala  Ala Met Val Gln Leu  Gln Ser Gln Ile Ser  Ser Met Glu
    1025                 1030                 1035

Lys Asn  Leu Lys Asn Ile Glu  Glu Glu Asn Lys Leu  Ile Glu Glu
    1040                 1045                 1050

Gln Asn  Glu Ala Leu Phe Leu  Glu Leu Ser Gly Leu  Ser Gln Ala
    1055                 1060                 1065

Leu Ile  Gln Ser Leu Ala Asn  Ile Arg Leu Pro His  Met Glu Pro
    1070                 1075                 1080

Ile Cys  Glu Gln Asn Phe Asp  Ala Tyr Val Asn Thr  Leu Thr Asp
    1085                 1090                 1095

Met Tyr  Ser Asn Gln Asp Cys  Tyr Gln Asn Pro Glu  Asn Lys Gly
    1100                 1105                 1110

Leu Leu  Glu Thr Ile Lys Gln  Ala Val Arg Gly Ile  Gln Val
    1115                 1120                 1125


<210> SEQ ID NO 24
<211> LENGTH: 864
<212> TYPE: PRT
<213> ORGANISM: Mus musculus

<400> SEQUENCE: 24

Met Ala Arg Ala Leu Ala Asp Leu Ser Val Asn Leu Gln Val Pro Arg
1               5                   10                  15

Val Val Pro Ser Pro Asp Ser Asp Ser Asp Thr Asp Leu Glu Asp Pro
            20                  25                  30

Ser Pro Arg Arg Ser Ala Gly Gly Leu His Arg Ser Gln Val Ile His
        35                  40                  45

Ser Gly His Phe Met Val Ser Ser Pro His Ser Asp Ser Leu Thr Arg
    50                  55                  60

Arg Arg Asp Gln Glu Gly Pro Val Gly Leu Ala Asp Phe Gly Pro Arg
65                  70                  75                  80

Ser Ile Asp Pro Thr Leu Thr His Leu Phe Glu Cys Leu Ser Leu Ala
                85                  90                  95

Tyr Ser Gly Lys Leu Val Ser Pro Lys Trp Lys Asn Phe Lys Gly Leu
            100                 105                 110

Lys Leu Leu Cys Arg Asp Lys Ile Arg Leu Asn Asn Ala Ile Trp Arg
        115                 120                 125

Ala Trp Tyr Ile Gln Tyr Val Gln Arg Arg Lys Ser Pro Val Cys Gly
    130                 135                 140

Phe Val Thr Pro Leu Gln Gly Ser Glu Ala Asp Glu His Arg Lys Pro
145                 150                 155                 160

Glu Ala Val Ile Leu Glu Gly Asn Tyr Trp Lys Arg Arg Ile Glu Val
                165                 170                 175

Val Met Arg Glu Tyr His Lys Trp Arg Ile Tyr Tyr Lys Lys Arg Leu
            180                 185                 190

Arg Lys Ser Ser Arg Glu Gly Asp Phe Leu Ala Pro Lys Gln Val Glu
        195                 200                 205

Gly Gly Trp Pro Pro Pro Glu Arg Trp Cys Glu Gln Leu Phe Ser Ser
    210                 215                 220

Val Val Pro Val Leu Leu Gly Gly Ser Glu Glu Glu Pro Gly Gly Arg
225                 230                 235                 240

Gln Leu Leu Asp Leu Asp Cys Phe Leu Ser Asp Ile Ser Asp Thr Leu
                245                 250                 255
```

```
Phe Thr Met Thr Gln Pro Ser Pro Ser Ser Leu Gln Leu Pro Pro Glu
            260                 265                 270

Asp Ala Tyr Val Gly Asn Ala Asp Met Ile Gln Pro Asp Leu Thr Pro
        275                 280                 285

Leu Gln Pro Ser Leu Asp Asp Phe Met Glu Ile Ser Asp Phe Phe Thr
    290                 295                 300

Asn Tyr Arg Pro Pro Gln Thr Pro Thr Ser Ser Asn Tyr Ile Glu Ser
305                 310                 315                 320

Pro Ser Phe Gly Pro Met Ala Asp Ser Leu Phe Ser Ser Gly Ile Leu
                325                 330                 335

Ala Pro Glu Met Pro Ser Pro Ala Ser Ser Ser Ser Ser Ser Gly Met
            340                 345                 350

Thr Pro His Ser Gly Asn Thr Arg Leu Gln Ala Arg Asn Ser Cys Ser
        355                 360                 365

Gly Pro Leu Asp Pro Asn Pro Phe Leu Ser Ser Glu Phe Leu Leu Pro
    370                 375                 380

Glu Asp Pro Lys Thr Lys Ile Pro Pro Ala Pro Gly Pro Thr Pro Leu
385                 390                 395                 400

Leu Pro Phe Pro Thr Pro Val Lys Val His Gly Leu Glu Pro Cys Thr
                405                 410                 415

Pro Ser Pro Phe Pro Thr Met Ala Pro Pro Pro Ser Leu Leu Pro Glu
            420                 425                 430

Glu Ser Leu Leu Ser Ala Arg Phe Pro Phe Thr Ser Ala Pro Pro Ala
        435                 440                 445

Pro Gly Val Ser Thr Leu Pro Ala Pro Thr Thr Phe Val Pro Thr Pro
    450                 455                 460

Gln Pro Gly Pro Gly Pro Val Pro Phe Ser Val Asp His Leu Pro His
465                 470                 475                 480

Gly Tyr Leu Glu Pro Val Phe Gly Pro His Phe Thr Val Pro Gln Gly
                485                 490                 495

Met Gln Pro Arg Cys Lys Pro Ser Ser Pro Ser Pro Gly Gly Gln Lys
            500                 505                 510

Ala Ser Pro Pro Thr Leu Ala Ser Ala Thr Ala Ser Pro Thr Ala Thr
        515                 520                 525

Ala Thr Ala Arg Asp Asn Asn Pro Cys Leu Thr Gln Leu Leu Arg Ala
    530                 535                 540

Ala Lys Pro Glu Gln Ala Leu Glu Pro Pro Thr Met Pro Gly Thr Leu
545                 550                 555                 560

Leu Arg Pro Pro Glu Ser Pro Gln Asp Thr Val Ser Glu Ile Pro Arg
                565                 570                 575

Ala Arg Ala Phe Phe Pro Pro Ile Pro Ala Pro Thr Pro Pro Arg Pro
            580                 585                 590

Pro Pro Gly Pro Ala Thr Leu Ala Pro Pro Arg Ser Leu Val Val Pro
        595                 600                 605

Lys Ala Glu Arg Leu Ser Pro Pro Ala Ser Ser Gly Ser Glu Arg Arg
    610                 615                 620

Leu Ser Gly Asp Leu Asn Ser Ile Gln Pro Ser Gly Ala Leu Ser Val
625                 630                 635                 640

His Leu Ser Pro Pro Gln Thr Val Leu Ser Arg Gly Arg Val Asp Asn
                645                 650                 655

Asn Lys Met Glu Asn Arg Arg Ile Thr His Ile Ser Ala Glu Gln Lys
            660                 665                 670
```

Arg Arg Phe Asn Ile Lys Leu Gly Phe Asp Thr Leu His Gly Leu Val
675 680 685

Ser Thr Leu Ser Ala Gln Pro Ser Leu Lys Val Ser Lys Ala Thr Thr
690 695 700

Leu Gln Lys Thr Ala Glu Tyr Ile Leu Met Leu Gln Gln Glu Arg Ala
705 710 715 720

Ala Met Gln Glu Glu Ala Gln Gln Leu Arg Asp Glu Ile Glu Glu Leu
725 730 735

Asn Ala Ala Ile Asn Leu Cys Gln Gln Gln Leu Pro Ala Thr Gly Val
740 745 750

Pro Ile Thr His Gln Arg Phe Asp Gln Met Arg Asp Met Phe Asp Asp
755 760 765

Tyr Val Arg Thr Arg Thr Leu His Asn Trp Lys Phe Trp Val Phe Ser
770 775 780

Ile Leu Ile Arg Pro Leu Phe Glu Ser Phe Asn Gly Met Val Ser Thr
785 790 795 800

Ala Ser Leu His Ser Leu Arg Gln Thr Ser Leu Ala Trp Leu Glu Gln
805 810 815

Tyr Cys Ser Leu Pro Ala Leu Arg Pro Thr Val Leu Asn Ser Leu Arg
820 825 830

Gln Leu Ser Thr Ser Thr Ser Ile Leu Thr Asp Pro Ser Leu Val Pro
835 840 845

Glu Gln Ala Thr Arg Ala Val Thr Glu Gly Thr Leu Gly Arg Pro Leu
850 855 860

<210> SEQ ID NO 25
<211> LENGTH: 422
<212> TYPE: PRT
<213> ORGANISM: Mus musculus

<400> SEQUENCE: 25

Met Glu Ala Met Ala Ala Ser Thr Ser Leu Pro Asp Pro Gly Asp Phe
1 5 10 15

Asp Arg Asn Val Pro Arg Ile Cys Gly Val Cys Gly Asp Arg Ala Thr
20 25 30

Gly Phe His Phe Asn Ala Met Thr Cys Glu Gly Cys Lys Gly Phe Phe
35 40 45

Arg Arg Ser Met Lys Arg Lys Ala Leu Phe Thr Cys Pro Phe Asn Gly
50 55 60

Asp Cys Arg Ile Thr Lys Asp Asn Arg Arg His Cys Gln Ala Cys Arg
65 70 75 80

Leu Lys Arg Cys Val Asp Ile Gly Met Met Lys Glu Phe Ile Leu Thr
85 90 95

Asp Glu Glu Val Gln Arg Lys Arg Glu Met Ile Met Lys Arg Lys Glu
100 105 110

Glu Glu Ala Leu Lys Asp Ser Leu Arg Pro Lys Leu Ser Glu Glu Gln
115 120 125

Gln His Ile Ile Ala Ile Leu Leu Asp Ala His His Lys Thr Tyr Asp
130 135 140

Pro Thr Tyr Ala Asp Phe Arg Asp Phe Arg Pro Pro Ile Arg Ala Asp
145 150 155 160

Val Ser Thr Gly Ser Tyr Ser Pro Arg Pro Thr Leu Ser Phe Ser Gly
165 170 175

Asp Ser Ser Ser Asn Ser Asp Leu Tyr Thr Pro Ser Leu Asp Met Met
180 185 190

```
Glu Pro Ala Ser Phe Ser Thr Met Asp Leu Asn Glu Glu Gly Ser Asp
        195                 200                 205

Asp Pro Ser Val Thr Leu Asp Leu Ser Pro Leu Ser Met Leu Pro His
    210                 215                 220

Leu Ala Asp Leu Val Ser Tyr Ser Ile Gln Lys Val Ile Gly Phe Ala
225                 230                 235                 240

Lys Met Ile Pro Gly Phe Arg Asp Leu Thr Ser Asp Asp Gln Ile Val
                245                 250                 255

Leu Leu Lys Ser Ser Ala Ile Glu Val Ile Met Leu Arg Ser Asn Gln
            260                 265                 270

Ser Phe Thr Leu Asp Asp Met Ser Trp Asp Cys Gly Ser Gln Asp Tyr
        275                 280                 285

Lys Tyr Asp Ile Thr Asp Val Ser Arg Ala Gly His Thr Leu Glu Leu
    290                 295                 300

Ile Glu Pro Leu Ile Lys Phe Gln Val Gly Leu Lys Lys Leu Asn Leu
305                 310                 315                 320

His Glu Glu Glu His Val Leu Leu Met Ala Ile Cys Ile Val Ser Pro
                325                 330                 335

Asp Arg Pro Gly Val Gln Asp Ala Lys Leu Val Glu Ala Ile Gln Asp
            340                 345                 350

Arg Leu Ser Asn Thr Leu Gln Thr Tyr Ile Arg Cys Arg His Pro Pro
        355                 360                 365

Pro Gly Ser His Gln Leu Tyr Ala Lys Met Ile Gln Lys Leu Ala Asp
    370                 375                 380

Leu Arg Ser Leu Asn Glu Glu His Ser Lys Gln Tyr Arg Ser Leu Ser
385                 390                 395                 400

Phe Gln Pro Glu Asn Ser Met Lys Leu Thr Pro Leu Val Leu Glu Val
                405                 410                 415

Phe Gly Asn Glu Ile Ser
            420


<210> SEQ ID NO 26

<400> SEQUENCE: 26

000


<210> SEQ ID NO 27
<211> LENGTH: 652
<212> TYPE: PRT
<213> ORGANISM: Mus musculus

<400> SEQUENCE: 27

Met Ala Glu Ala Pro Gln Val Val Glu Thr Asp Pro Asp Phe Glu Pro
1               5                   10                  15

Leu Pro Arg Gln Arg Ser Cys Thr Trp Pro Leu Pro Arg Pro Glu Phe
            20                  25                  30

Asn Gln Ser Asn Ser Thr Thr Ser Ser Pro Ala Pro Ser Gly Gly Ala
        35                  40                  45

Ala Ala Asn Pro Asp Ala Ala Ala Ser Leu Ala Ser Ala Ser Ala Val
    50                  55                  60

Ser Thr Asp Phe Met Ser Asn Leu Ser Leu Leu Glu Glu Ser Glu Asp
65                  70                  75                  80

Phe Ala Arg Ala Pro Gly Cys Val Ala Val Ala Ala Ala Ala Ala Ala
                85                  90                  95
```

```
Ser Arg Gly Leu Cys Gly Asp Phe Gln Gly Pro Glu Ala Gly Cys Val
            100                 105                 110

His Pro Ala Pro Pro Gln Pro Pro Pro Thr Gly Pro Leu Ser Gln Pro
        115                 120                 125

Pro Pro Val Pro Pro Ser Ala Ala Ala Ala Ala Gly Pro Leu Ala Gly
    130                 135                 140

Gln Pro Arg Lys Thr Ser Ser Ser Arg Arg Asn Ala Trp Gly Asn Leu
145                 150                 155                 160

Ser Tyr Ala Asp Leu Ile Thr Lys Ala Ile Glu Ser Ser Ala Glu Lys
                165                 170                 175

Arg Leu Thr Leu Ser Gln Ile Tyr Glu Trp Met Val Lys Ser Val Pro
            180                 185                 190

Tyr Phe Lys Asp Lys Gly Asp Ser Asn Ser Ser Ala Gly Trp Lys Asn
        195                 200                 205

Ser Ile Arg His Asn Leu Ser Leu His Ser Lys Phe Ile Arg Val Gln
    210                 215                 220

Asn Glu Gly Thr Gly Lys Ser Ser Trp Trp Met Leu Asn Pro Glu Gly
225                 230                 235                 240

Gly Lys Ser Gly Lys Ser Pro Arg Arg Arg Ala Ala Ser Met Asp Asn
                245                 250                 255

Asn Ser Lys Phe Ala Lys Ser Arg Gly Arg Ala Ala Lys Lys Lys Ala
            260                 265                 270

Ser Leu Gln Ser Gly Gln Glu Gly Pro Gly Asp Ser Pro Gly Ser Gln
        275                 280                 285

Phe Ser Lys Trp Pro Ala Ser Pro Gly Ser His Ser Asn Asp Asp Phe
    290                 295                 300

Asp Asn Trp Ser Thr Phe Arg Pro Arg Thr Ser Ser Asn Ala Ser Thr
305                 310                 315                 320

Ile Ser Gly Arg Leu Ser Pro Ile Met Thr Glu Gln Asp Asp Leu Gly
                325                 330                 335

Asp Gly Asp Val His Ser Leu Val Tyr Pro Pro Ser Ala Ala Lys Met
            340                 345                 350

Ala Ser Thr Leu Pro Ser Leu Ser Glu Ile Ser Asn Pro Glu Asn Met
        355                 360                 365

Glu Asn Leu Leu Asp Asn Leu Asn Leu Leu Ser Ser Pro Thr Ser Leu
    370                 375                 380

Thr Val Ser Thr Gln Ser Ser Pro Gly Ser Met Met Gln Gln Thr Pro
385                 390                 395                 400

Cys Tyr Ser Phe Ala Pro Pro Asn Thr Ser Leu Asn Ser Pro Ser Pro
                405                 410                 415

Asn Tyr Ser Lys Tyr Thr Tyr Gly Gln Ser Ser Met Ser Pro Leu Pro
            420                 425                 430

Gln Met Pro Met Gln Thr Leu Gln Asp Ser Lys Ser Ser Tyr Gly Gly
        435                 440                 445

Leu Asn Gln Tyr Asn Cys Ala Pro Gly Leu Leu Lys Glu Leu Leu Thr
    450                 455                 460

Ser Asp Ser Pro Pro His Asn Asp Ile Met Ser Pro Val Asp Pro Gly
465                 470                 475                 480

Val Ala Gln Pro Asn Ser Arg Val Leu Gly Gln Asn Val Met Met Gly
                485                 490                 495

Pro Asn Ser Val Met Pro Ala Tyr Gly Ser Gln Ala Ser His Asn Lys
            500                 505                 510

Met Met Asn Pro Ser Ser His Thr His Pro Gly His Ala Gln Gln Thr
```

```
        515                 520                 525

Ala Ser Val Asn Gly Arg Thr Leu Pro His Val Val Asn Thr Met Pro
    530                 535                 540

His Thr Ser Ala Met Asn Arg Leu Thr Pro Val Lys Thr Pro Leu Gln
545                 550                 555                 560

Val Pro Leu Ser His Pro Met Gln Met Ser Ala Leu Gly Ser Tyr Ser
                565                 570                 575

Ser Val Ser Ser Cys Asn Gly Tyr Gly Arg Met Gly Val Leu His Gln
            580                 585                 590

Glu Lys Leu Pro Ser Asp Leu Asp Gly Met Phe Ile Glu Arg Leu Asp
        595                 600                 605

Cys Asp Met Glu Ser Ile Ile Arg Asn Asp Leu Met Asp Gly Asp Thr
    610                 615                 620

Leu Asp Phe Asn Phe Asp Asn Val Leu Pro Asn Gln Ser Phe Pro His
625                 630                 635                 640

Ser Val Lys Thr Thr Thr His Ser Trp Val Ser Gly
                645                 650


<210> SEQ ID NO 28
<211> LENGTH: 628
<212> TYPE: PRT
<213> ORGANISM: Mus musculus

<400> SEQUENCE: 28

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Met Val Gly Glu Gly Pro Leu Asp Lys Gly Glu
        35                  40                  45

Ser Cys Gly Gly Ser Arg Gly Asp Leu Thr Glu Leu Pro Asn Gly Leu
    50                  55                  60

Gly Glu Thr Arg Gly Ser Glu Asp Asp Thr Asp Asp Asp Gly Glu Asp
65                  70                  75                  80

Phe Ala Pro Pro Ile Leu Lys Glu Leu Glu Asn Leu Ser Pro Glu Glu
                85                  90                  95

Ala Ala His Gln Lys Ala Val Val Glu Ser Leu Leu Gln Glu Asp Pro
            100                 105                 110

Trp Arg Val Ala Lys Met Val Lys Ser Tyr Leu Gln Gln His Asn Ile
        115                 120                 125

Pro Gln Arg Glu Val Val Asp Thr Thr Gly Leu Asn Gln Ser His Leu
    130                 135                 140

Ser Gln His Leu Asn Lys Gly Thr Pro Met Lys Thr Gln Lys Arg Ala
145                 150                 155                 160

Ala Leu Tyr Thr Trp Tyr Val Arg Lys Gln Arg Glu Val Ala Gln Gln
                165                 170                 175

Phe Thr His Ala Gly Gln Gly Gly Leu Ile Glu Glu Pro Thr Gly Asp
            180                 185                 190

Glu Leu Pro Thr Lys Lys Gly Arg Arg Asn Arg Phe Lys Trp Gly Pro
        195                 200                 205

Ala Ser Gln Gln Ile Leu Phe Gln Ala Tyr Glu Arg Gln Lys Asn Pro
    210                 215                 220

Ser Lys Glu Glu Arg Glu Thr Leu Val Glu Glu Cys Asn Arg Ala Glu
225                 230                 235                 240
```

```
Cys Ile Gln Arg Gly Val Ser Pro Ser Gln Ala Gln Gly Leu Gly Ser
                245                 250                 255

Asn Leu Val Thr Glu Val Arg Val Tyr Asn Trp Phe Ala Asn Arg Arg
            260                 265                 270

Lys Glu Glu Ala Phe Arg His Lys Leu Ala Met Asp Thr Tyr Asn Gly
        275                 280                 285

Pro Pro Pro Gly Pro Gly Pro Gly Pro Ala Leu Pro Ala His Ser Ser
    290                 295                 300

Pro Gly Leu Pro Thr Thr Thr Leu Ser Pro Ser Lys Val His Gly Val
305                 310                 315                 320

Arg Tyr Gly Gln Ser Ala Thr Ser Glu Ala Ala Glu Val Pro Ser Ser
                325                 330                 335

Ser Gly Gly Pro Leu Val Thr Val Ser Ala Ala Leu His Gln Val Ser
            340                 345                 350

Pro Thr Gly Leu Glu Pro Ser Ser Leu Leu Ser Thr Glu Ala Lys Leu
        355                 360                 365

Val Ser Ala Thr Gly Gly Pro Leu Pro Pro Val Ser Thr Leu Thr Ala
    370                 375                 380

Leu His Ser Leu Glu Gln Thr Ser Pro Gly Leu Asn Gln Gln Pro Gln
385                 390                 395                 400

Asn Leu Ile Met Ala Ser Leu Pro Gly Val Met Thr Ile Gly Pro Gly
                405                 410                 415

Glu Pro Ala Ser Leu Gly Pro Thr Phe Thr Asn Thr Gly Ala Ser Thr
            420                 425                 430

Leu Val Ile Gly Leu Ala Ser Thr Gln Ala Gln Ser Val Pro Val Ile
        435                 440                 445

Asn Ser Met Gly Ser Ser Leu Thr Thr Leu Gln Pro Val Gln Phe Ser
    450                 455                 460

Gln Pro Leu His Pro Ser Tyr Gln Gln Pro Leu Met Pro Pro Val Gln
465                 470                 475                 480

Ser His Val Ala Gln Ser Pro Phe Met Ala Thr Met Ala Gln Leu Gln
                485                 490                 495

Ser Pro His Ala Leu Tyr Ser His Lys Pro Glu Val Ala Gln Tyr Thr
            500                 505                 510

His Thr Ser Leu Leu Pro Gln Thr Met Leu Ile Thr Asp Thr Asn Leu
        515                 520                 525

Ser Thr Leu Ala Ser Leu Thr Pro Thr Lys Gln Val Phe Thr Ser Asp
    530                 535                 540

Thr Glu Ala Ser Ser Glu Pro Gly Leu His Glu Pro Pro Ser Pro Ala
545                 550                 555                 560

Thr Thr Ile His Ile Pro Ser Gln Asp Pro Ser Asn Ile Gln His Leu
                565                 570                 575

Gln Pro Ala His Arg Leu Ser Thr Ser Pro Thr Val Ser Ser Ser Ser
            580                 585                 590

Leu Val Leu Tyr Gln Ser Ser Asp Ser Asn Gly His Ser His Leu Leu
        595                 600                 605

Pro Ser Asn His Ser Val Ile Glu Thr Phe Ile Ser Thr Gln Met Ala
    610                 615                 620

Ser Ser Ser Gln
625
```

<210> SEQ ID NO 29
<211> LENGTH: 468
<212> TYPE: PRT

<213> ORGANISM: Mus musculus

<400> SEQUENCE: 29

```
Met Leu Gly Thr Val Lys Met Glu Gly His Glu Ser Asn Asp Trp Asn
1               5                   10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Thr Gly Leu Gly Ala Gly Leu Ser Pro Gly
65                  70                  75                  80

Ala Val Ala Gly Met Pro Gly Ala Ser Ala Gly Ala Met Asn Ser Met
                85                  90                  95

Thr Ala Ala Gly Val Thr Ala Met Gly Thr Ala Leu Ser Pro Gly Gly
            100                 105                 110

Met Gly Ser Met Gly Ala Gln Pro Ala Thr Ser Met Asn Gly Leu Gly
        115                 120                 125

Pro Tyr Ala Ala Ala Met Asn Pro Cys Met Ser Pro Met Ala Tyr Ala
    130                 135                 140

Pro Ser Asn Leu Gly Arg Ser Arg Ala Gly Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
225                 230                 235                 240

Gly Ser Tyr Trp Thr Leu His Pro Asp Ser Gly Asn Met Phe Glu Asn
                245                 250                 255

Gly Cys Tyr Leu Arg Arg Gln Lys Arg Phe Lys Cys Glu Lys Gln Pro
            260                 265                 270

Gly Ala Gly Gly Gly Ser Gly Gly Gly Gly Ser Lys Gly Gly Pro Glu
        275                 280                 285

Ser Arg Lys Asp Pro Ser Gly Pro Gly Asn Pro Ser Ala Glu Ser Pro
    290                 295                 300

Leu His Arg Gly Val His Gly Lys Ala Ser Gln Leu Glu Gly Ala Pro
305                 310                 315                 320

Ala Pro Gly Pro Ala Ala Ser Pro Gln Thr Leu Asp His Ser Gly Ala
                325                 330                 335

Thr Ala Thr Gly Gly Ala Ser Glu Leu Lys Ser Pro Ala Ser Ser Ser
            340                 345                 350

Ala Pro Pro Ile Ser Ser Gly Pro Gly Ala Leu Ala Ser Val Pro Pro
        355                 360                 365

Ser His Pro Ala His Gly Leu Ala Pro His Glu Ser Gln Leu His Leu
    370                 375                 380

Lys Gly Asp Pro His Tyr Ser Phe Asn His Pro Phe Ser Ile Asn Asn
385                 390                 395                 400
```

```
Leu Met Ser Ser Ser Glu Gln Gln His Lys Leu Asp Phe Lys Ala Tyr
                405                 410                 415

Glu Gln Ala Leu Gln Tyr Ser Pro Tyr Gly Ala Thr Leu Pro Ala Ser
            420                 425                 430

Leu Pro Leu Gly Ser Ala Ser Val Ala Thr Arg Ser Pro Ile Glu Pro
        435                 440                 445

Ser Ala Leu Glu Pro Ala Tyr Tyr Gln Gly Val Tyr Ser Arg Pro Val
    450                 455                 460

Leu Asn Thr Ser
465


<210> SEQ ID NO 30
<211> LENGTH: 474
<212> TYPE: PRT
<213> ORGANISM: Mus musculus

<400> SEQUENCE: 30

Met Arg Leu Ser Lys Thr Leu Ala Gly Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Ala Asn Leu
        35                  40                  45

Asn Ser Ser Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Gln Gln Ile Thr Ser Pro Ile Ser Gly Ile Asn Gly Asp Ile
                165                 170                 175

Arg Ala Lys Lys Ile Ala Asn Ile Thr Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Leu Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Cys
        275                 280                 285

Leu Lys Ala Ile Ile Phe Phe Asp Pro Asp Ala Lys Gly Leu Ser Asp
    290                 295                 300
```

```
Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
        355                 360                 365

Leu Leu Gln Glu Met Leu Leu Gly Gly Ser Ala Ser Asp Ala Pro His
    370                 375                 380

Thr His His Pro Leu His Pro His Leu Met Gln Glu His Met Gly Thr
385                 390                 395                 400

Asn Val Ile Val Ala Asn Thr Met Pro Ser His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Ser Gly Ser Gly Ser Glu Ser Tyr Lys Leu
        435                 440                 445

Leu Pro Gly Ala Ile Thr Thr Ile Val Lys Pro Pro Ser Ala Ile Pro
    450                 455                 460

Gln Pro Thr Ile Thr Lys Gln Glu Ala Ile
465                 470


<210> SEQ ID NO 31
<211> LENGTH: 283
<212> TYPE: PRT
<213> ORGANISM: Homo sapiens

<400> SEQUENCE: 31

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125

Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
```

```
        195                 200                 205

Arg Gly Gly Gly Thr Ala Val Gly Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280


<210> SEQ ID NO 32
<211> LENGTH: 214
<212> TYPE: PRT
<213> ORGANISM: Homo sapiens

<400> SEQUENCE: 32

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Glu Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
    50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
                85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
        115                 120                 125

His Asn Tyr Ile Trp Ala Leu Thr Gln Thr Leu Arg Ile Ala Asp His
    130                 135                 140

Ser Leu Tyr Ala Leu Glu Pro Pro Ala Pro His Cys Gly Glu Leu Gly
145                 150                 155                 160

Ser Pro Gly Gly Ser Pro Gly Asp Trp Gly Ser Leu Tyr Ser Pro Val
                165                 170                 175

Ser Gln Ala Gly Ser Leu Ser Pro Ala Ala Ser Leu Glu Glu Arg Pro
            180                 185                 190

Gly Leu Leu Gly Ala Thr Phe Ser Ala Cys Leu Ser Pro Gly Ser Leu
        195                 200                 205

Ala Phe Ser Asp Phe Leu
    210


<210> SEQ ID NO 33
<211> LENGTH: 353
<212> TYPE: PRT
<213> ORGANISM: Homo sapiens

<400> SEQUENCE: 33

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
```

```
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly Gly
65                  70                  75                  80

Ala Gly Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Gly Ala Gly His His Val Arg Leu Glu
    210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
    290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
            340                 345                 350

Leu
```

<210> SEQ ID NO 34
<211> LENGTH: 2573
<212> TYPE: DNA
<213> ORGANISM: Homo sapiens

<400> SEQUENCE: 34

```
gggtggcgcc gggagtggga acgccacaca gtgccaaatc cccggctcca gctcccgact      60

cccggctccc ggctcccggc tcccggtgcc caatcccggg ccgcagccat gaacggcgag     120

gagcagtact acgcggccac gcagctttac aaggacccat gcgcgttcca gcgaggcccg     180

gcgccggagt tcagcgccag ccccccctgcg tgcctgtaca tgggccgcca gcccccgccg     240
```

```
ccgccgccgc acccgttccc tggcgccctg ggcgcgctgg agcagggcag ccccccggac    300
atctccccgt acgaggtgcc ccccctcgcc gacgaccccg cggtggcgca ccttcaccac    360
cacctcccgg ctcagctcgc gctcccccac ccgcccgccg ggcccttccc ggagggagcc    420
gagccgggcg tcctggagga gcccaaccgc gtccagctgc ctttcccatg gatgaagtct    480
accaaagctc acgcgtggaa aggccagtgg gcaggcggcg cctacgctgc ggagccggag    540
gagaacaagc ggacgcgcac ggcctacacg cgcgcacagc tgctagagct ggagaaggag    600
ttcctattca acaagtacat ctcacggccg cgccgggtgg agctggctgt catgttgaac    660
ttgaccgaga gacacatcaa gatctggttc caaaaccgcc gcatgaagtg gaaaaaggag    720
gaggacaaga agcgcggcgg cgggacagct gtcgggggtg gcggggtcgc ggagcctgag    780
caggactgcg ccgtgacctc cggcgaggag cttctggcgc tgccgccgcc gccgcccccc    840
ggaggtgctg tgccgcccgc tgcccccgtt gccgcccgag agggccgcct gccgcctggc    900
cttagcgcgt cgccacagcc ctccagcgtc gcgcctcggc ggccgcagga accacgatga    960
gaggcaggag ctgctcctgg ctgaggggct tcaaccactc gccgaggagg agcagagggc   1020
ctaggaggac cccgggcgtg gaccacccgc cctggcagtt gaatggggcg gcaattgcgg   1080
ggcccacctt agaccgaagg ggaaaacccg ctctctcagg cgcatgtgcc agttggggcc   1140
ccgcgggtag atgccggcag gccttccgga agaaaaagag ccattggttt ttgtagtatt   1200
ggggccctct tttagtgata ctggattggc gttgtttgtg gctgttgcgc acatccctgc   1260
cctcctacag cactccacct tgggacctgt ttagagaagc cggctcttca aagacaatgg   1320
aaactgtacc atacacattg gaaggctccc taacacacac agcggggaag ctgggccgag   1380
taccttaatc tgccataaag ccattcttac tcgggcgacc cctttaagtt tagaaataat   1440
tgaaaggaaa tgtttgagtt ttcaaagatc ccgtgaaatt gatgccagtg gaatacagtg   1500
agtcctcctc ttcctcctcc tcctcttccc cctccccttc ctcctcctcc tcttcttttc   1560
cctcctcttc ctcttcctcc tgctctcctt tcctcccccct cctcttttcc ctcctcttcc   1620
tcttcctcct gctctccttt cctccccctc ctctttctcc tcctcctcct cttcttcccc   1680
ctcctctccc tcctcctctt cttccccctc ctctccctcc tcctcttctt ctccctcctc   1740
ttcctcttcc tcctcttcca cgtgctctcc tttcctcccc ctcctcttgc tccccttctt   1800
ccccgtcctc ttcctcctcc tcctcttctt ctccctcctc ttcctcctcc tctttcttcc   1860
tgacctcttt ctttctcctc ctcctccttc tacctcccct tctcatccct cctcttcctc   1920
ttctctagct gcacacttca ctactgcaca tcttataact tgcacccctt tcttctgagg   1980
aagagaacat cttgcaaggc agggcgagca gcggcagggc tggcttagga gcagtgcaag   2040
agtccctgtg ctccagttcc acactgctgg cagggaaggc aagggggggac gggcctggat   2100
ctgggggtga gggagaaaga tggacccctg ggtgaccact aaaccaaaga tattcggaac   2160
tttctattta ggatgtggac gtaattcctg ttccgaggta gaggctgtgc tgaagacaag   2220
cacagtggcc tggtgcgcct tggaaaccaa caactattca cgagccagta tgaccttcac   2280
atctttagaa attatgaaaa cgtatgtgat tggagggttt ggaaaaccag ttatcttatt   2340
taacatttta aaaattacct aacagttatt tacaaacagg tctgtgcatc ccaggtctgt   2400
cttcttttca aggtctgggc cttgtgctcg ggttatgttt gtgggaaatg cttaataaat   2460
actgataata tgggaagaga tgaaaactga ttctcctcac tttgtttcaa acctttctgg   2520
cagtgggatg attcgaattc acttttaaaa ttaaattagc gtgttttgtt ttg          2573
```

<210> SEQ ID NO 35
<211> LENGTH: 1167
<212> TYPE: DNA
<213> ORGANISM: Homo sapiens

<400> SEQUENCE: 35

```
cctcggaccc cattctctct tcttttctcc tttggggctg gggcaactcc caggcggggg     60
cgcctgcagc tcagctgaac ttggcgacca gaagcccgct gagctcccca cggccctcgc    120
tgctcatcgc tctctattct tttgcgccgg tagaaaggat gacgcctcaa ccctcgggtg    180
cgcccactgt ccaagtgacc cgtgagacgg agcggtcctt ccccagagcc tcggaagacg    240
aagtgacctg ccccacgtcc gccccgccca gccccactcg cacacggggg aactgcgcag    300
aggcggaaga gggaggctgc cgaggggccc cgaggaagct ccgggcacgg cgcgggggac    360
gcagccggcc taagagcgag ttggcactga gcaagcagcg acggagtcgg cgaaagaagg    420
ccaacgaccg cgagcgcaat cgaatgcaca acctcaactc ggcactggac gccctgcgcg    480
gtgtcctgcc caccttccca gacgacgcga agctcaccaa gatcgagacg ctgcgcttcg    540
cccacaacta catctgggcg ctgactcaaa cgctgcgcat agcggaccac agcttgtacg    600
cgctggagcc gccggcgccg cactgcgggg agctgggcag cccaggcggt tcccccgggg    660
actgggggtc cctctactcc ccagtctccc aggctggcag cctgagtccc gccgcgtcgc    720
tggaggagcg acccgggctg ctgggggcca ccttttccgc ctgcttgagc ccaggcagtc    780
tggctttctc agattttctg tgaaaggacc tgtctgtcgc tgggctgtgg gtgctaaggg    840
taagggagag ggagggagcc gggagccgta gagggtggcc gacggcggcg gccctcaaaa    900
gcacttgttc cttctgcttc tccctggctg accccctggcc ggcccaggcc tccacggggg    960
cggcaggctg ggttcattcc ccggccctcc gagccgcgcc aacgcacgca acccttgctg   1020
ctgcccgcgc gaagtgggca ttgcaaagtg cgctcatttt aggcctcctc tctgccacca   1080
ccccataatc tcattcaaag aatactagaa tggtagcact acccggccgg agccgcccac   1140
cgtcttgggt cgccctaccc tcactca                                       1167
```

<210> SEQ ID NO 36
<211> LENGTH: 1062
<212> TYPE: DNA
<213> ORGANISM: Homo sapiens

<400> SEQUENCE: 36

```
atggccgcgg agctggcgat gggcgccgag ctgcccagca gcccgctggc catcgagtac     60
gtcaacgact tcgacctgat gaagttcgag gtgaagaagg agcctcccga ggccgagcgc    120
ttctgccacc gcctgccgcc aggctcgctg tcctcgacgc cgctcagcac gccctgctcc    180
tccgtgccct cctcgcccag cttctgcgcg cccagcccgg gcaccggcgg cggcggcggc    240
gcggggggcg gcggcggctc gtctcaggcc gggggcgccc ccgggccgcc gagcgggggc    300
cccggcgccg tcgggggcac ctcggggaag ccggcgctgg aggatctgta ctggatgagc    360
ggctaccagc atcacctcaa ccccgaggcg ctcaacctga cgcccgagga cgcggtggag    420
gcgctcatcg gcagcggcca ccacggcgcg caccacggcg cgcaccaccc ggcggccgcc    480
gcagcctacg aggctttccg cggcccgggc ttcgcgggcg gcggcggagc ggacgacatg    540
ggcgccggcc accaccacgg cgcgcaccac gccgcccacc atcaccacgc cgcccaccac    600
caccaccacc accaccacca ccatggcggc gcgggacacg gcggtggcgc gggccaccac    660
gtgcgcctgg aggagcgctt ctccgacgac cagctggtgt ccatgtcggt gcgcgagctg    720
```

```
aaccggcagc tccgcggctt cagcaaggag gaggtcatcc ggctcaagca gaagcggcgc    780

acgctcaaga accgcggcta cgcgcagtcc tgccgcttca agcgggtgca gcagcggcac    840

attctggaga gcgagaagtg ccaactccag agccaggtgg agcagctgaa gctggaggtg    900

gggcgcctgg ccaaagagcg ggacctgtac aaggagaaat acgagaagct ggcgggccgg    960

ggcggccccg ggagcgcggg cggggccggt ttcccgcggg agccttcgcc gccgcaggcc   1020

ggtcccggcg gggccaaggg cacggccgac ttcttcctgt ag                      1062
```

<210> SEQ ID NO 37
<211> LENGTH: 1287
<212> TYPE: DNA
<213> ORGANISM: Mus musculus

<400> SEQUENCE: 37

```
gtcaaagcga tctggggtgg cgtagagagt ccgcgagcca cccagcgcct aaggcctggc     60

ttgtagctcc gacccggggc tgctggcccc caagtgccgg ctgccaccat gaacagtgag    120

gagcagtact acgcggccac acagctctac aaggacccgt gcgcattcca gaggggcccg    180

gtgccagagt tcagcgctaa ccccccctgcg tgcctgtaca tgggccgcca gcccccacct    240

ccgccgccac cccagtttac aagctcgctg ggatcactgg agcagggaag tcctccggac    300

atctccccat acgaagtgcc cccgctcgcc tccgacgacc cggctggcgc tcacctccac    360

caccaccttc cagctcagct cgggctcgcc catccacctc ccggaccttt cccgaatgga    420

accgagcctg gggggcctgga agagcccaac cgcgtccagc tccctttccc gtggatgaaa    480

tccaccaaag ctcacgcgtg gaaaggccag tgggcaggag gtgcttacac agcggaaccc    540

gaggaaaaca agaggacccg tactgcctac acccgggcgc agctgctgga gctggagaag    600

gaattcttat ttaacaaata catctcccgg ccccgccggg tggagctggc agtgatgttg    660

aacttgaccg agagacacat caaaatctgg ttccaaaacc gtcgcatgaa gtggaaaaaa    720

gaggaagata agaaacgtag tagcgggacc ccgagtgggg gcggtggggg cgaagagccg    780

gagcaagatt gtgcggtgac ctcgggcgag gagctgctgg cagtgccacc gctgccacct    840

cccggaggtg ccgtgccccc aggcgtccca gctgcagtcc gggagggcct actgccttcg    900

ggccttagcg tgtcgccaca gccctccagc atcgcgccac tgcgaccgca ggaaccccgg    960

tgaggacagc agtctgaggg tgagcgggtc tgggacccag agtgtggacg tgggagcggg   1020

cagctggata agggaactta acctaggcgt cgcacaagaa gaaaattctt gagggcacga   1080

gagccagttg ggtatagccg gagagatgct ggcagacttc tggaaaaaca gccctgagct   1140

tctgaaaact ttgaggctgc ttctgatgcc aagcgaatgg ccagatctgc ctctaggact   1200

ctttcctggg accaatttag acaacctggg ctccaaactg aggacaataa aaagggtaca   1260

aacttgagcg ttccaatacg gaccagc                                       1287
```

<210> SEQ ID NO 38
<211> LENGTH: 1540
<212> TYPE: DNA
<213> ORGANISM: Mus musculus

<400> SEQUENCE: 38

```
atgcagctca gaaatccctc tgggtctcat cactgcagca gtggtcgagt acctcctcgg     60

agcttttcta cgacttccag acgcaattta ctccaggcga gggcgcctgc agtttagcag    120

aacttcagag ggagcagaga ggctcagcta tccactgctg cttgacactg accctatcca    180
```

```
ctgctgcttg tcactgactg acctgctgct ctctattctt ttgagtcggg agaactagga    240

tggcgcctca tcccttggat gcgctcacca tccaagtgtc cccagagaca caacaacctt    300

ttcccggagc ctcggaccac gaagtgctca gttccaattc caccccacct agccccactc    360

tcatacctag ggactgctcc gaagcagaag tgggtgactg ccgagggacc tcgaggaagc    420

tccgcgcccg acgcggaggg cgcaacaggc ccaagagcga gttggcactc agcaaacagc    480

gaagaagccg gcgcaagaag gccaatgatc gggagcgcaa tcgcatgcac aacctcaact    540

cggcgctgga tgcgctgcgc ggtgtcctgc ccaccttccc ggatgacgcc aaacttacaa    600

agatcgagac cctgcgcttc gcccacaact acatctgggc actgactcag acgctgcgca    660

tagcggacca cagcttctat ggcccggagc cccctgtgcc ctgtggagag ctggggagcc    720

ccggaggtgg ctccaacggg gactggggct ctatctactc cccagtctcc caagcgggta    780

acctgagccc cacggcctca ttggaggaat tccctggcct gcaggtgccc agctccccat    840

cctatctgct cccgggagca ctggtgttct cagacttctt gtgaagagac ctgtctggct    900

ctgggtggtg ggtgctagtg gaaagggagg ggaccagagc cgtctggagt gggaggtagt    960

ggaggctctc aagcatctcg cctcttctgg ctttcactac ttggatccct agccctctca   1020

cagggcttaa ctaggcttct catcggtacc cttgctgctg cgcacagcag acattggggg   1080

ctgctcttct cttaactctc ctcggtgcag ccacatcaaa ctctcgctcc aagcatttga   1140

gaatggtagc actacctagt tggagactcc catacttcct ggtgagtctg ccctcattca   1200

aatctgccgg cctccgacca tccatcactt tttccagggt gacctaatcc agtgttgcgt   1260

cttacctcac tggctcctcc atccagctct tggcccatag atgatgttcg tcgtctttac   1320

tgcccgctac atgcagggtt tctgagcttc tccattctgc cttagtccac gaaggtgatc   1380

tgccttcttc tgcacttttc aagtcgttac ccttccccca agggagacca ggctgtgaac   1440

cggaaagccc tagcctatgg ctagagcatc tctccaactt gtctcccgtg tctaaagtgt   1500

gagttgcagg gacggttcct gaagcactgt ttgtctccct                          1540
```

<210> SEQ ID NO 39
<211> LENGTH: 1080
<212> TYPE: DNA
<213> ORGANISM: Mus musculus

<400> SEQUENCE: 39

```
atggccgcgg agctggcgat gggcgcagag ctgcccagca gcccactggc catcgagtac     60

gtcaacgact tcgacctgat gaagttcgag gtgaagaagg agccgcccga ggccgagcgc    120

ttctgccacc gcctgccgcc cggctcgctg tcctcgacgc ccctcagcac gccctgctcc    180

tcggtgccct cttcgcccag cttctgcgca cccagcccgg gcacaggcgg cggcgcgggc    240

ggcgggggca gcgcggctca ggccgggggc gccccggggc cgccgagtgg aggccccggc    300

actgtcgggg gcgcctcagg aaaagcggtg ctggaggatc tgtactggat gagcgggtac    360

cagcaccacc tgaaccccga ggcgctcaac ctgacgccgg aggacgcggt ggaggcgctc    420

atcggcagcg gccaccacgg cgcgcaccac ggcgcgcatc acccggcggc tgctgcggcc    480

tatgaggcct tccggggtca gagcttcgcg ggcggcggcg gcgcggacga catgggtgcc    540

ggccaccacc acggcgcaca ccacactgcc caccatcatc actctgccca ccatcaccat    600

caccaccatc accaccacgg aggctctggc caccacggcg gaggcgcggg tcacggcgga    660

ggcggcgcag gccaccacgt gcgcttggag gagcgcttct ccgacgacca gctggtatcc    720

atgtccgtgc gggagctgaa ccggcagctc cgcggcttca gcaaggagga ggtcatccga    780
```

```
ctgaaacaga agcggcgcac gctcaagaac cgcggctacg cgcagtcgtg ccgcttcaag    840

cgggtgcagc agcggcacat tctggagagc gagaagtgcc agctccagag ccaggtggag    900

cagctgaagc tggaggtggg gcgtctggcc aaggagcggg acctgtacaa ggagaaatac    960

gagaagttgg cgggccgggg cggccccggg ggcgcgggcg gggccggctt ccctcgggag   1020

ccctcgccag cgcaggctgg ccccggggcg gccaaaggcg cacccgactt ctttctgtga   1080


<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

cagacgctgc gcatagcgga ccac                                            24


<210> SEQ ID NO 41
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

gcggcttcgg ccagtaacgt tag                                             23


<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

ggagcaagat tgtgcggtga cctc                                            24


<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

acattctgga gagcgagaag tgcc                                            24


<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

accacagtcc atgccatcac                                                 20


<210> SEQ ID NO 45
<211> LENGTH: 20
```

<212> TYPE: DNA
<213> ORGANISM: Artificial Sequence
<220> FEATURE:
<223> OTHER INFORMATION: Description of Artificial Sequence: Synthetic primer

<400> SEQUENCE: 45

```
tccaccaccc tgttgctgta                                              20
```

<210> SEQ ID NO 46
<211> LENGTH: 524
<212> TYPE: PRT
<213> ORGANISM: Homo sapiens

<400> SEQUENCE: 46

```
Met Thr Glu Asp Lys Val Thr Gly Thr Leu Val Phe Thr Val Ile Thr
1               5                   10                  15

Ala Val Leu Gly Ser Phe Gln Phe Gly Tyr Asp Ile Gly Val Ile Asn
            20                  25                  30

Ala Pro Gln Gln Val Ile Ile Ser His Tyr Arg His Val Leu Gly Val
        35                  40                  45

Pro Leu Asp Asp Arg Lys Ala Ile Asn Asn Tyr Val Ile Asn Ser Thr
    50                  55                  60

Asp Glu Leu Pro Thr Ile Ser Tyr Ser Met Asn Pro Lys Pro Thr Pro
65                  70                  75                  80

Trp Ala Glu Glu Glu Thr Val Ala Ala Ala Gln Leu Ile Thr Met Leu
                85                  90                  95

Trp Ser Leu Ser Val Ser Ser Phe Ala Val Gly Gly Met Thr Ala Ser
            100                 105                 110

Phe Phe Gly Gly Trp Leu Gly Asp Thr Leu Gly Arg Ile Lys Ala Met
        115                 120                 125

Leu Val Ala Asn Ile Leu Ser Leu Val Gly Ala Leu Leu Met Gly Phe
    130                 135                 140

Ser Lys Leu Gly Pro Ser His Ile Leu Ile Ile Ala Gly Arg Ser Ile
145                 150                 155                 160

Ser Gly Leu Tyr Cys Gly Leu Ile Ser Gly Leu Val Pro Met Tyr Ile
                165                 170                 175

Gly Glu Ile Ala Pro Thr Ala Leu Arg Gly Ala Leu Gly Thr Phe His
            180                 185                 190

Gln Leu Ala Ile Val Thr Gly Ile Leu Ile Ser Gln Ile Ile Gly Leu
        195                 200                 205

Glu Phe Ile Leu Gly Asn Tyr Asp Leu Trp His Ile Leu Leu Gly Leu
    210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Glu Val Lys Ala
                245                 250                 255

Lys Gln Ser Leu Lys Arg Leu Arg Gly Tyr Asp Asp Val Thr Lys Asp
            260                 265                 270

Ile Asn Glu Met Arg Lys Glu Arg Glu Glu Ala Ser Ser Glu Gln Lys
        275                 280                 285

Val Ser Ile Ile Gln Leu Phe Thr Asn Ser Ser Tyr Arg Gln Pro Ile
    290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
```

```
                325                 330                 335

Lys Pro Val Tyr Ala Thr Ile Gly Val Gly Ala Val Asn Met Val Phe
            340                 345                 350

Thr Ala Val Ser Val Phe Leu Val Glu Lys Ala Gly Arg Arg Ser Leu
        355                 360                 365

Phe Leu Ile Gly Met Ser Gly Met Phe Val Cys Ala Ile Phe Met Ser
    370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
            420                 425                 430

Pro Ala Ala Leu Ala Ile Ala Ala Phe Ser Asn Trp Thr Cys Asn Phe
        435                 440                 445

Ile Val Ala Leu Cys Phe Gln Tyr Ile Ala Asp Phe Cys Gly Pro Tyr
    450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
            500                 505                 510

Val Glu Met Lys Phe Leu Gly Ala Thr Glu Thr Val
        515                 520


<210> SEQ ID NO 47
<211> LENGTH: 523
<212> TYPE: PRT
<213> ORGANISM: Mus musculus

<400> SEQUENCE: 47

Met Ser Glu Asp Lys Ile Thr Gly Thr Leu Ala Phe Thr Val Phe Thr
1               5                   10                  15

Ala Val Leu Ser Ser Phe Gln Phe Gly Tyr Asp Ile Gly Val Ile Asn
            20                  25                  30

Ala Pro Gln Glu Val Ile Ile Ser His Tyr Arg His Val Leu Gly Val
        35                  40                  45

Pro Leu Asp Asp Arg Lys Ala Ala Ile Asn Tyr Asp Val Asn Gly Thr
    50                  55                  60

Asp Thr Pro Leu Thr Val Thr Pro Ala Tyr Thr Thr Pro Ala Pro Trp
65                  70                  75                  80

Asp Glu Glu Glu Thr Glu Gly Ser Ala His Ile Val Thr Met Leu Trp
                85                  90                  95

Ser Leu Ser Val Ser Ser Phe Ala Val Gly Gly Met Val Ala Ser Phe
            100                 105                 110

Phe Gly Gly Trp Leu Gly Asp Lys Leu Gly Arg Ile Lys Ala Met Leu
        115                 120                 125

Ala Ala Asn Ser Leu Ser Leu Thr Gly Ala Leu Leu Met Gly Cys Ser
    130                 135                 140

Lys Phe Gly Pro Ala His Ala Leu Ile Ile Ala Gly Arg Ser Val Ser
145                 150                 155                 160

Gly Leu Tyr Cys Gly Leu Ile Ser Gly Leu Val Pro Met Tyr Ile Gly
                165                 170                 175
```

```
Glu Ile Ala Pro Thr Thr Leu Arg Gly Ala Leu Gly Thr Leu His Gln
            180                 185                 190

Leu Ala Leu Val Thr Gly Ile Leu Ile Ser Gln Ile Ala Gly Leu Ser
        195                 200                 205

Phe Ile Leu Gly Asn Gln Asp His Trp His Ile Leu Leu Gly Leu Ser
    210                 215                 220

Ala Val Pro Ala Leu Leu Gln Cys Leu Leu Leu Leu Phe Cys Pro Glu
225                 230                 235                 240

Ser Pro Arg Tyr Leu Tyr Ile Lys Leu Glu Glu Glu Val Arg Ala Lys
                245                 250                 255

Lys Ser Leu Lys Arg Leu Arg Gly Thr Glu Asp Val Thr Lys Asp Ile
            260                 265                 270

Asn Glu Met Lys Lys Glu Lys Glu Glu Ala Ser Thr Glu Gln Lys Val
        275                 280                 285

Ser Val Ile Gln Leu Phe Thr Asp Ala Asn Tyr Arg Gln Pro Ile Leu
    290                 295                 300

Val Ala Leu Met Leu His Met Ala Gln Gln Phe Ser Gly Ile Asn Gly
305                 310                 315                 320

Ile Phe Tyr Tyr Ser Thr Ser Ile Phe Gln Thr Ala Gly Ile Ser Gln
                325                 330                 335

Pro Val Tyr Ala Thr Ile Gly Val Gly Ala Ile Asn Met Ile Phe Thr
            340                 345                 350

Ala Val Ser Val Leu Leu Val Glu Lys Ala Gly Arg Arg Thr Leu Phe
        355                 360                 365

Leu Thr Gly Met Ile Gly Met Phe Phe Cys Thr Ile Phe Met Ser Val
    370                 375                 380

Gly Leu Val Leu Leu Asp Lys Phe Ala Trp Met Ser Tyr Val Ser Met
385                 390                 395                 400

Thr Ala Ile Phe Leu Phe Val Ser Phe Phe Glu Ile Gly Pro Gly Pro
                405                 410                 415

Ile Pro Trp Phe Met Val Ala Glu Phe Phe Ser Gln Gly Pro Arg Pro
            420                 425                 430

Thr Ala Leu Ala Leu Ala Ala Phe Ser Asn Trp Val Cys Asn Phe Val
        435                 440                 445

Ile Ala Leu Cys Phe Gln Tyr Ile Ala Asp Phe Leu Gly Pro Tyr Val
    450                 455                 460

Phe Phe Leu Phe Ala Gly Val Val Leu Val Phe Thr Leu Phe Thr Phe
465                 470                 475                 480

Phe Lys Val Pro Glu Thr Lys Gly Lys Ser Phe Glu Glu Ile Ala Ala
                485                 490                 495

Glu Phe Arg Lys Lys Ser Gly Ser Ala Pro Pro Arg Lys Ala Ala Val
            500                 505                 510

Gln Met Glu Phe Leu Ala Ser Ser Glu Ser Val
        515                 520
```

<210> SEQ ID NO 48
<211> LENGTH: 3439
<212> TYPE: DNA
<213> ORGANISM: Homo sapiens

<400> SEQUENCE: 48

```
tctggtttgt aacttatgcc taagggacct gctcccattt tctttcctag tggaacaaag      60

gtattgaagc cacaggttgc tgaggcaaag cacttattga ttagattccc atcaatattc     120

agctgccgct gagaagatta gacttggact ctcaggtctg ggtagcccaa ctcctccctc     180
```

```
tccttgctcc tcctcctgca atgcataact aggcctaggc agagctgcga ataaacaggc    240
aggagctagt caggtgcatg tgccacactc acacaagacc tggaattgac aggactccca    300
actagtacaa tgacagaaga taaggtcact gggaccctgg ttttcactgt catcactgct    360
gtgctgggtt ccttccagtt tggatatgac attggtgtga tcaatgcacc tcaacaggta    420
ataatatctc actatagaca tgttttgggt gttccactgg atgaccgaaa agctatcaac    480
aactatgtta tcaacagtac agatgaactg cccacaatct catactcaat gaacccaaaa    540
ccaacccctt gggctgagga agagactgtg gcagctgctc aactaatcac catgctctgg    600
tccctgtctg tatccagctt tgcagttggt ggaatgactg catcattctt tggtgggtgg    660
cttggggaca cacttggaag aatcaaagcc atgttagtag caaacattct gtcattagtt    720
ggagctctct tgatggggtt ttcaaaattg ggaccatctc atatacttat aattgctgga    780
agaagcatat caggactata ttgtgggcta atttcaggcc tggttcctat gtatatcggt    840
gaaattgctc caaccgctct caggggagca cttggcactt ttcatcagct ggccatcgtc    900
acgggcattc ttattagtca gattattggt cttgaattta tcttgggcaa ttatgatctg    960
tggcacatcc tgcttggcct gtctggtgtg cgagccatcc ttcagtctct gctactcttt   1020
ttctgtccag aaagccccag ataccttac atcaagttag atgaggaagt caaagcaaaa   1080
caaagcttga aaagactcag aggatatgat gatgtcacca aagatattaa tgaaatgaga   1140
aaagaaagag aagaagcatc gagtgagcag aaagtctcta taattcagct cttcaccaat   1200
tccagctacc gacagcctat tctagtggca ctgatgctgc atgtggctca gcaattttcc   1260
ggaatcaatg gcatttttta ctactcaacc agcatttttc agacggctgg tatcagcaaa   1320
cctgtttatg caaccattgg agttggcgct gtaaacatgg ttttcactgc tgtctctgta   1380
ttccttgtgg agaaggcagg gcgacgttct ctctttctaa ttggaatgag tgggatgttt   1440
gtttgtgcca tcttcatgtc agtgggactt gtgctgctga ataagttctc ttggatgagt   1500
tatgtgagca tgatagccat cttcctcttt gtcagcttct ttgaaattgg gccaggcccg   1560
atcccctggt tcatggtggc tgagtttttc agtcaaggac cacgtcctgc tgctttagca   1620
atagctgcat tcagcaattg gacctgcaat ttcattgtag ctctgtgttt ccagtacatt   1680
gcggacttct gtggacctta tgtgtttttc ctctttgctg gagtgctcct ggcctttacc   1740
ctgttcacat tttttaaagt tccagaaacc aaaggaaagt cttttgagga aattgctgca   1800
gaattccaaa agaagagtgg ctcagcccac aggccaaaag ctgctgtaga aatgaaattc   1860
ctaggagcta cagagactgt gtaaaaaaaa aaccctgctt tttgacatga acagaaacaa   1920
taagggaacc gtctgttttt aaatgatgat tccttgagca ttttatatcc acatctttaa   1980
gtattgtttt atttttatgt gctctcatca gaaatgtcat caaatattac caaaaaagta   2040
tttttttaag ttagagaata tatttttgat ggtaagactg taattaagta aaccaaaaag   2100
gctagtttat tttgttacac taaagggcag gtggttctaa tatttttagc tctgttcttt   2160
ataacaaggt tcttctaaaa ttgaagagat ttcaacatat catttttta acacataact    2220
agaaacctga ggatgcaaca aatatttata tatttgaata tcattaaatt ggaattttct   2280
tacccatata tcttatgtta aaggagatat ggctagtggc aataagttcc atgttaaaat   2340
agacaactct tccatttatt gcactcagct tttttcttga gtactagaat ttgtattttg   2400
cttaaaattt tacttttgtt ctgtattttc atgtggaatg gattatagag tatactaaaa   2460
aatgtctata gagaaaaact ttcatttttg gtaggcttat caaaatcttt cagcactcag   2520
```

```
aaaagaaaac cattttagtt cctttattta atggccaaat ggtttttgca agatttaaca   2580
ctaaaaaggt ttcacctgat catatagcgt gggttatcag ttaacattaa catctattat   2640
aaaaccatgt tgattccctt ctggtacaat cctttgagtt atagtttgct ttgcttttta   2700
attgaggaca gcctggtttt cacatacact caaacaatca tgagtcagac atttggtata   2760
ttacctcaaa ttcctaataa gtttgatcaa atctaatgta agaaaatttg aagtaaagga   2820
ttgatcactt tgttaaaaat attttctgaa ttattatgtc tcaaaataag ttgaaaaggt   2880
agggtttgag gattcctgag tgtgggcttc tgaaacttca taaatgttca gcttcagact   2940
tttatcaaaa tccctattta attttcctgg aaagactgat tgttttatgg tgtgttccta   3000
acataaaata atcgtctcct ttgacatttc cttctttgtc ttagctgtat acagattcta   3060
gccaaactat tctatggcca ttactaacac gcattgtaca ctatctatct gcctttacct   3120
acataggcaa attggaaata cacagatgat taaacagact ttagcttaca gtcaatttta   3180
caattatgga aatatagttc tgatgggtcc caaaagctta gcagggtgct aacgtatctc   3240
taggctgttt tctccaccaa ctggagcact gatcaatcct tcttatgttt gctttaatgt   3300
gtattgaaga aaagcacttt ttaaaaagta ctctttaaga gtgaaataat taaaaaccac   3360
tgaacatttg ctttgttttc taaagttgtt cacatatatg taatttagca gtccaaagaa   3420
caagaaattg tttcttttc                                                3439
```

<210> SEQ ID NO 49
<211> LENGTH: 2571
<212> TYPE: DNA
<213> ORGANISM: Mus musculus

<400> SEQUENCE: 49

```
gctcctcctc ctcctacaat gtataaccag gtagagtgag cactctggct ggtcagctat     60
tcatccacat tcagtacagg acctggatta agaggacaat tccacacaca cacaatgtca    120
gaagacaaga tcaccggaac cttggctttc actgtcttca ctgctgtact gagttccttc    180
cagttcggct atgacatcgg tgtgatcaat gcacctcaag aggtaataat atcccattat    240
cgacatgttt tgggtgttcc actggatgac cggaaagctg ccattaacta tgacgtcaat    300
ggcacagaca ccccacttac agtcacacca gcatacacaa caccagctcc ctgggatgaa    360
gaggagactg aaggatctgc tcacatagtc actatgctct ggtctctgtc tgtgtccagc    420
tttgcagtgg gcggaatggt cgcctcattc tttggtgggt ggctcgggga caaacttgga    480
aggatcaaag caatgttggc tgcaaacagc ctctcattga ctggagccct cttgatggga    540
tgttccaaat ttggaccggc acacgccctc atcattgctg gacgaagtgt atcaggactg    600
tattgtgggc taatttcagg actggttcca atgtacattg gagagatcgc tccaaccaca    660
ctcaggggtg ccctgggtac tcttcaccaa ctggcccttg tcacaggcat tcttattagt    720
cagattgctg gcctcagctt tattctgggc aatcaggatc attggcacat cctacttggc    780
ctatctgctg tgccagctct tctgcagtgt ctgctactgc tcttctgtcc agaaagcccc    840
agataccttt atataaagtt ggaagaggaa gtcagggcaa agaaaagctt gaagagacta    900
agaggaactg aggatgtcac caaagatatt aatgagatga agaaagaaaa ggaagaggca    960
tcgactgagc agaaggtctc cgtgatccag ctcttcacgg atgccaatta ccgacagccc   1020
atcctcgtgg cgctgatgct gcacatggcc cagcagttct caggaatcaa tgggatattt   1080
tactattcaa ccagcatttt tcagacagct ggcatcagcc agcctgtgta tgcaaccatt   1140
ggtgttgggg ccatcaacat gatcttcacg gctgtctctg tgctgcttgt ggagaaggca   1200
```

```
gggcggcgga ccctgttcct aaccgggatg attggcatgt ttttctgcac catcttcatg   1260

tcggtgggac ttgtgctgct ggataaattc gcctggatga gttacgtgag catgactgcc   1320

atcttcctct ttgtcagttt ctttgagatt gggccaggtc caatcccttg gttcatggtt   1380

gctgaatttt tcagccaagg accccgtcct acggctctgg cactggctgc cttcagcaac   1440

tgggtctgca attttgtcat cgccctctgc ttccagtaca ttgcggactt ccttgggcct   1500

tacgtgttct tcctcttcgc tggggtggtc ctggtcttca ccctgtttac attctttaaa   1560

gttccagaaa ccaaaggaaa gtcttttgag gaaatcgctg cagaattccg gaagaagagt   1620

ggttcggccc caccacgcaa agctgctgta caaatggaat tcctggcgtc ttcagagagt   1680

gtgtgaggat gacctgccta aaaccgagga accgaccagg aggaaccacg cgctccctct   1740

taaaccgatt ccttcctcgg tgtgcgacta cacccaggag tatcgtttat tcatttggaa   1800

gaatttttac agactccgat tagaaatatc aacatatatt attaccaaag aaagtatttt   1860

tttaacttaa agaatctatt tttgatggta acactcttca gtaaaccaga ggctattttg   1920

ctactctaca gggaagtgtg taataacctt cctagccctg ttctactgaa attgaagagc   1980

tttcaacata tcgctgcttt ttaaagcacg tgactaagaa atctgcagct acaactgcta   2040

tctagatatt taattacacc ggaatgttct tagccccaga tcagaagcta aaggacatac   2100

ggctggtgtc agcaaggctc acattcaaac tgactttctg ttacctttcc tcggcttctc   2160

tcacttggat tagacttcgg gttttgcgta cagccatttt ctgcattttt atatagaatt   2220

cctgagtatg ttaaactgta tttgtaatga gaaactcttt ttttatagct accaaaagct   2280

tcctacagtg agagaaaaca ttttagtttc tttgatgtat tttgcaaggt taaatgcttg   2340

agttgttctt agctgtagag ctcagattat cagttagtta tattagcatc caaagcatgt   2400

tagtttctca ccacttcagt ctttgtgttg tacttatact tgtttttttt aattgcccat   2460

ggcacacact taaaccatta ggagtcagcc attttgcata ttgcctaaaa atctaataaa   2520

ctgggtcaat cacagggaaa tctggaataa agagtttttc tatttgttaa a            2571
```

<210> SEQ ID NO 50
<211> LENGTH: 465
<212> TYPE: PRT
<213> ORGANISM: Homo sapiens

<400> SEQUENCE: 50

```
Met Leu Asp Asp Arg Ala Arg Met Glu Ala Ala Lys Lys Glu Lys Val
1               5                   10                  15

Glu Gln Ile Leu Ala Glu Phe Gln Leu Gln Glu Glu Asp Leu Lys Lys
            20                  25                  30

Val Met Arg Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Glu
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125
```

```
Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Val Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp His Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Leu Val Asp Glu Ser Ser Ala Asn Pro Gly Gln Gln Leu
        275                 280                 285

Tyr Glu Lys Leu Ile Gly Gly Lys Tyr Met Gly Glu Leu Val Arg Leu
    290                 295                 300

Val Leu Leu Arg Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Thr Gly Asp Arg Lys Gln Ile Tyr Asn Ile Leu
            340                 345                 350

Ser Thr Leu Gly Leu Arg Pro Ser Thr Thr Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Ser Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Gly
    450                 455                 460

Gln
465


<210> SEQ ID NO 51
<211> LENGTH: 465
<212> TYPE: PRT
<213> ORGANISM: Mus musculus

<400> SEQUENCE: 51

Met Leu Asp Asp Arg Ala Arg Met Glu Ala Thr Lys Lys Glu Lys Val
1               5                   10                  15

Glu Gln Ile Leu Ala Glu Phe Gln Leu Gln Glu Glu Asp Leu Lys Lys
            20                  25                  30
```

```
Val Met Ser Arg Met Gln Lys Glu Met Asp Arg Gly Leu Lys Leu Glu
        35                  40                  45

Thr His Gln Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Ala
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
        115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Ile Asp
145                 150                 155                 160

Lys Gly Ile Leu Leu Asn Trp Thr Lys Gly Phe Lys Ala Ser Gly Ala
                165                 170                 175

Glu Gly Asn Asn Ile Val Gly Leu Leu Arg Asp Ala Ile Lys Arg Arg
            180                 185                 190

Gly Asp Phe Glu Met Asp Val Val Ala Met Val Asn Asp Thr Val Ala
        195                 200                 205

Thr Met Ile Ser Cys Tyr Tyr Glu Asp Arg Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asn Ser Gly Glu Leu Asp Glu Phe Leu Leu Glu
            260                 265                 270

Tyr Asp Arg Met Val Asp Glu Ser Ser Val Asn Pro Gly Gln Gln Leu
        275                 280                 285

Tyr Glu Lys Ile Ile Gly Gly Lys Tyr Met Gly Glu Leu Val Arg Leu
    290                 295                 300

Val Leu Leu Lys Leu Val Glu Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Ser Gly Asp Arg Arg Gln Ile Leu Asn Ile Leu
            340                 345                 350

Ser Thr Leu Gly Leu Arg Pro Ser Val Ala Asp Cys Asp Ile Val Arg
        355                 360                 365

Arg Ala Cys Glu Ser Val Ser Thr Arg Ala Ala His Met Cys Ser Ala
    370                 375                 380

Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Asn Cys Glu Ile Thr Phe Ile Glu Ser Glu Glu Gly Ser Gly Arg Gly
        435                 440                 445
```

```
Ala Ala Leu Val Ser Ala Val Ala Cys Lys Lys Ala Cys Met Leu Gly
    450                 455                 460

Gln
465


<210> SEQ ID NO 52
<211> LENGTH: 2741
<212> TYPE: DNA
<213> ORGANISM: Homo sapiens

<400> SEQUENCE: 52

gagcaggaaa tgccgagcgg cgcctgagcc ccagggaagc aggctaggat gtgagagaca     60

cagtcacctg cagcctaatt actcaaaagc tgtccccagg tcacagaagg gagaggacat    120

ttcccactga atctgtctga aggacactaa gccccacagc tcaacacaac caggagagaa    180

agcgctgagg acgccaccca agcgcccagc aatggccctg cctggagaac atccaggctc    240

agtgaggaag ggtccagaag ggaatgcttg ccgactcgtt ggagaacaat gaaaaggagg    300

aaactgtgac tgaacctcaa accccaaacc agcccgagga gaaccacatt ctcccaggga    360

cccagggcgg gccgtgaccc ctgcggcgga gaagccttgg atatttccac ttcagaagcc    420

tactggggaa ggctgagggg tcccagctcc ccacgctggc tgctgtgcag atgctggacg    480

acagagccag gatggaggcc gccaagaagg agaaggtaga gcagatcctg gcagagttcc    540

agctgcagga ggaggacctg aagaaggtga tgagacggat gcagaaggag atggaccgcg    600

gcctgaggct ggagacccat gaagaggcca gtgtgaagat gctgcccacc tacgtgcgct    660

ccaccccaga aggctcagaa gtcggggact tcctctccct ggacctgggt ggcactaact    720

tcagggtgat gctggtgaag gtgggagaag gtgaggaggg gcagtggagc gtgaagacca    780

aacaccagat gtactccatc cccgaggacg ccatgaccgg cactgctgag atgctcttcg    840

actacatctc tgagtgcatc tccgacttcc tggacaagca tcagatgaaa cacaagaagc    900

tgcccctggg cttcaccttc tcctttcctg tgaggcacga agacatcgat aagggcatcc    960

ttctcaactg gaccaagggc ttcaaggcct caggagcaga agggaacaat gtcgtggggc   1020

ttctgcgaga cgctatcaaa cggagagggg actttgaaat ggatgtggtg gcaatggtga   1080

atgacacggt ggccacgatg atctcctgct actacgaaga ccatcagtgc gaggtcggca   1140

tgatcgtggg cacgggctgc aatgcctgct acatggagga gatgcagaat gtggagctgg   1200

tggaggggga cgagggccgc atgtgcgtca ataccgagtg gggcgccttc ggggactccg   1260

gcgagctgga cgagttcctg ctggagtatg accgcctggt ggacgagagc tctgcaaacc   1320

ccggtcagca gctgtatgag aagctcatag gtggcaagta catgggcgag ctggtgcggc   1380

ttgtgctgct caggctcgtg gacgaaaacc tgctcttcca cggggaggcc tccgagcagc   1440

tgcgcacacg cggagccttc gagacgcgct tcgtgtcgca ggtggagagc gacacgggcg   1500

accgcaagca gatctacaac atcctgagca cgctggggct gcgaccctcg accaccgact   1560

gcgacatcgt gcgccgcgcc tgcgagagcg tgtctacgcg cgctgcgcac atgtgctcgg   1620

cggggctggc gggcgtcatc aaccgcatgc gcgagagccg cagcgaggac gtaatgcgca   1680

tcactgtggg cgtggatggc tccgtgtaca agctgcaccc cagcttcaag gagcggttcc   1740

atgccagcgt gcgcaggctg acgcccagct gcgagatcac cttcatcgag tcggaggagg   1800

gcagtggccg gggcgcggcc ctggtctcgg cggtggcctg taagaaggcc tgtatgctgg   1860

gccagtgaga gcagtggccg caagcgcagg gaggatgcca cagccccaca gcacccaggc   1920

tccatgggga agtgctcccc acacgtgctc gcagcctggc ggggcaggag gcctggcctt   1980
```

```
gtcaggaccc aggccgcctg ccataccgct ggggaacaga gcgggcctct tccctcagtt   2040
tttcggtggg acagccccag ggccctaacg ggggtgcggc aggagcagga acagagactc   2100
tggaagcccc ccacctttct cgctggaatc aatttcccag aagggagttg ctcactcagg   2160
actttgatgc atttccacac tgtcagagct gttggcctcg cctgggccca ggctctggga   2220
aggggtgccc tctggatcct gctgtggcct cacttccctg ggaactcatc ctgtgtgggg   2280
aggcagctcc aacagcttga ccagacctag acctgggcca aaagggcagc caggggctgc   2340
tcatcaccca gtcctggcca ttttcttgcc tgaggctcaa gaggcccagg gagcaatggg   2400
agggggctcc atggaggagg tgtcccaagc tttgaatacc cccagagacc ttttctctcc   2460
cataccatca ctgagtggct tgtgattctg ggatggaccc tcgcagcagg tgcaagagac   2520
agagccccca agcctctgcc ccaaggggcc cacaaagggg agaagggcca gccctacatc   2580
ttcagctccc atagcgctgg ctcaggaaga aaccccaagc agcattcagc acaccccaag   2640
ggacaacccc atcatatgac atgccaccct ctccatgccc aacctaagat tgtgtgggtt   2700
ttttaattaa aaatgttaaa agttttaaac atgaaaaaaa a                        2741
```

<210> SEQ ID NO 53
<211> LENGTH: 2245
<212> TYPE: DNA
<213> ORGANISM: Mus musculus

<400> SEQUENCE: 53

```
atgctggatg acagagccag gatggaggcc accaagaagg aaaaggtaga gcagatcctg     60
gcagagttcc agctgcagga ggaagacctg aagaaggtga tgagccggat gcagaaggag    120
atggaccgtg gcctgaagct ggagacccat caggaggcca gtgtaaagat gttgcccacc    180
tacgtgcgtt ccaccccaga aggctcagaa gttggagact ttctctcctt agacctggga    240
ggaaccaact tcagggtgat gctggtgaaa gtgggggagg gggaggcagg acagtggagc    300
gtgaagacga aacaccagat gtattccatc cccgaggacg ccatgacggg cactgcggag    360
atgctctttg actacatctc tgagtgcatc tctgacttcc tggacaagca tcagatgaaa    420
cacaagaaac tacccctggg cttcaccttc tccttccctg taaggcacga agacatagac    480
aagggcatcc tgctcaactg gaccaagggc ttcaaggcct ccggagcaga agggaacaac    540
atcgtgggac ttctccgaga tgctatcaag aggagagggg actttgagat ggatgtggtg    600
gcaatggtga atgacacggt ggccacaatg atctcctgct actatgaaga ccgccaatgt    660
gaggtcggca tgattgtggg caccggctgc aacgcctgct acatggagga gatgcagaat    720
gtggagctgg tggaaggcga tgaggggcgc atgtgtgtca acacagagtg gggcgccttc    780
gggaactccg gtgagctgga cgagttcctc ctggagtacg accggatggt ggatgagagc    840
tcagtgaacc ccggtcagca gctgtacgaa aagatcattg gcggaaagta catgggcgag    900
ctggtacgac ttgtgctgct caagctggta gaggagaatc ttctgttcca cggagaggcc    960
tcagagcagc tgcgcacacg tggtgctttt gagacccgtt ttgtgtcgca ggtggagagc   1020
gactctgggg accgaaggca gatccttaac atcctgagca ctctgggcct tcgaccctct   1080
gtcgccgact gcgacattgt gcgccgtgcc tgtgaaagcg tgtccactcg cgccgcccac   1140
atgtgctcag caggactagc gggggtcata aatcgcatgc gcgaaagccg cagtgaggac   1200
gtgatgcgca tcacggtggg cgtggatggc tccgtgtaca agctgcaccc gagcttcaag   1260
gagcggtttc acgccagtgt gcgcaggctg acacccaact gcgaaatcac cttcattgaa   1320
```

```
tcagaggagg gcagcggcag gggagccgca ctggtctctg cggtggcctg caagaaggct   1380

tgcatgctgg gccagtgaaa tccaggcaag gacagggacc tgggttccac ggggactcca   1440

caccccacaa atgctcccag tccactaggg caggagacct attctgctgc tacccctgga   1500

aaatggggag aggcccctgc aagccaagtc agccagtgag acagccctag ggctctcagc   1560

ctggggcaag gggcaagagg atcagcggca ccaaaagcct ttcttgctag aatcaactac   1620

agagaaaggt gaagcacact caggtcttgc tctttcagct tctggcctcc cacagctgtg   1680

ggtctggcct cccaagggag tgcctcctgg acttgcaatg gcctggcttc cctgggaaca   1740

catctccatg gggaggtagc ttcagcagct tggccagacc agacctgggc ccccagaaga   1800

gtaagggctg cccagacctg gctgttttct tgcctgtggc tgaagaggct gcaaaaccat   1860

gggagaccga ctatctagct acatggaggg gactttccag gccacaaaca ttccagagac   1920

agtctccttc atatacctcc acccctgagt ggcttacagt tctgggatga accctcctag   1980

gagatgccag aggatagagg cccagagtcc ttgctctagg ggacctgaag gggagcgcct   2040

cactctgcac tgttagcagg atggcagctt caacactcac atcagtgatc cgggaagaga   2100

agcaagccac ccacagcatc tctccaggaa accacccagg tccctctgtc cctcatccct   2160

gtcaggtttc ccagatgcca tgccgccctc tccacaccag cttggaacca tgggggagtt   2220

tttaattaaa tatttaaaac tactt                                          2245
```

<210> SEQ ID NO 54
<211> LENGTH: 753
<212> TYPE: PRT
<213> ORGANISM: Homo sapiens

<400> SEQUENCE: 54

```
Met Glu Arg Arg Ala Trp Ser Leu Gln Cys Thr Ala Phe Val Leu Phe
1               5                   10                  15

Cys Ala Trp Cys Ala Leu Asn Ser Ala Lys Ala Lys Arg Gln Phe Val
            20                  25                  30

Asn Glu Trp Ala Ala Glu Ile Pro Gly Gly Pro Glu Ala Ala Ser Ala
        35                  40                  45

Ile Ala Glu Glu Leu Gly Tyr Asp Leu Leu Gly Gln Ile Gly Ser Leu
    50                  55                  60

Glu Asn His Tyr Leu Phe Lys His Lys Asn His Pro Arg Arg Ser Arg
65                  70                  75                  80

Arg Ser Ala Phe His Ile Thr Lys Arg Leu Ser Asp Asp Asp Arg Val
                85                  90                  95

Ile Trp Ala Glu Gln Gln Tyr Glu Lys Glu Arg Ser Lys Arg Ser Ala
            100                 105                 110

Leu Arg Asp Ser Ala Leu Asn Leu Phe Asn Asp Pro Met Trp Asn Gln
        115                 120                 125

Gln Trp Tyr Leu Gln Asp Thr Arg Met Thr Ala Ala Leu Pro Lys Leu
    130                 135                 140

Asp Leu His Val Ile Pro Val Trp Gln Lys Gly Ile Thr Gly Lys Gly
145                 150                 155                 160

Val Val Ile Thr Val Leu Asp Asp Gly Leu Glu Trp Asn His Thr Asp
                165                 170                 175

Ile Tyr Ala Asn Tyr Asp Pro Glu Ala Ser Tyr Asp Phe Asn Asp Asn
            180                 185                 190

Asp His Asp Pro Phe Pro Arg Tyr Asp Pro Thr Asn Glu Asn Lys His
        195                 200                 205
```

```
Gly Thr Arg Cys Ala Gly Glu Ile Ala Met Gln Ala Asn Asn His Lys
    210                 215                 220

Cys Gly Val Gly Val Ala Tyr Asn Ser Lys Val Gly Gly Ile Arg Met
225                 230                 235                 240

Leu Asp Gly Ile Val Thr Asp Ala Ile Glu Ala Ser Ser Ile Gly Phe
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Asn Asn Pro Gly Trp Lys Lys Asn Gly Ala Gly
            420                 425                 430

Leu Met Val Asn Ser Arg Phe Gly Phe Gly Leu Leu Asn Ala Lys Ala
        435                 440                 445

Leu Val Asp Leu Ala Asp Pro Arg Thr Trp Arg Ser Val Pro Glu Lys
    450                 455                 460

Lys Glu Cys Val Val Lys Asp Asn Asp Phe Glu Pro Arg Ala Leu Lys
465                 470                 475                 480

Ala Asn Gly Glu Val Ile Ile Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Ala Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Ile Gly Thr Trp Thr Leu Arg Ile Thr Asp Met Ser Gly
                565                 570                 575

Arg Ile Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
    610                 615                 620

Asp Pro Gly Glu Glu Gln Pro Thr Gln Glu Asn Pro Lys Glu Asn Thr
```

625 630 635 640

Leu Val Ser Lys Ser Pro Ser Ser Ser Ser Val Gly Gly Arg Arg Asp
645 650 655

Glu Leu Glu Glu Gly Ala Pro Ser Gln Ala Met Leu Arg Leu Leu Gln
660 665 670

Ser Ala Phe Ser Lys Asn Ser Pro Pro Lys Gln Ser Pro Lys Lys Ser
675 680 685

Pro Ser Ala Lys Leu Asn Ile Pro Tyr Glu Asn Phe Tyr Glu Ala Leu
690 695 700

Glu Lys Leu Asn Lys Pro Ser Gln Leu Lys Asp Ser Glu Asp Ser Leu
705 710 715 720

Tyr Asn Asp Tyr Val Asp Val Phe Tyr Asn Thr Lys Pro Tyr Lys His
725 730 735

Arg Asp Asp Arg Leu Leu Gln Ala Leu Val Asp Ile Leu Asn Glu Glu
740 745 750

Asn

<210> SEQ ID NO 55
<211> LENGTH: 753
<212> TYPE: PRT
<213> ORGANISM: Mus musculus

<400> SEQUENCE: 55

Met Glu Gln Arg Gly Trp Thr Leu Gln Cys Thr Ala Phe Ala Phe Phe
1 5 10 15

Cys Val Trp Cys Ala Leu Asn Ser Val Lys Ala Lys Arg Gln Phe Val
20 25 30

Asn Glu Trp Ala Ala Glu Ile Pro Gly Gly Gln Glu Ala Ala Ser Ala
35 40 45

Ile Ala Glu Glu Leu Gly Tyr Asp Leu Leu Gly Gln Ile Gly Ser Leu
50 55 60

Glu Asn His Tyr Leu Phe Lys His Lys Ser His Pro Arg Arg Ser Arg
65 70 75 80

Arg Ser Ala Leu His Ile Thr Lys Arg Leu Ser Asp Asp Asp Arg Val
85 90 95

Thr Trp Ala Glu Gln Gln Tyr Glu Lys Glu Arg Ser Lys Arg Ser Val
100 105 110

Gln Lys Asp Ser Ala Leu Asp Leu Phe Asn Asp Pro Met Trp Asn Gln
115 120 125

Gln Trp Tyr Leu Gln Asp Thr Arg Met Thr Ala Ala Leu Pro Lys Leu
130 135 140

Asp Leu His Val Ile Pro Val Trp Glu Lys Gly Ile Thr Gly Lys Gly
145 150 155 160

Val Val Ile Thr Val Leu Asp Asp Gly Leu Glu Trp Asn His Thr Asp
165 170 175

Ile Tyr Ala Asn Tyr Asp Pro Glu Ala Ser Tyr Asp Phe Asn Asp Asn
180 185 190

Asp His Asp Pro Phe Pro Arg Tyr Asp Leu Thr Asn Glu Asn Lys His
195 200 205

Gly Thr Arg Cys Ala Gly Glu Ile Ala Met Gln Ala Asn Asn His Lys
210 215 220

Cys Gly Val Gly Val Ala Tyr Asn Ser Lys Val Gly Gly Ile Arg Met
225 230 235 240

Leu Asp Gly Ile Val Thr Asp Ala Ile Glu Ala Ser Ser Ile Gly Phe

```
                245                 250                 255

Asn Pro Gly His Val Asp Ile Tyr Ser Ala Ser Trp Gly Pro Asn Asp
            260                 265                 270

Asp Gly Lys Thr Val Glu Gly Pro Gly Arg Leu Ala Gln Lys Ala Phe
        275                 280                 285

Glu Tyr Gly Val Lys Gln Gly Arg Gln Gly Lys Gly Ser Ile Phe Val
    290                 295                 300

Trp Ala Ser Gly Asn Gly Gly Arg Gln Gly Asp Asn Cys Asp Cys Asp
305                 310                 315                 320

Gly Tyr Thr Asp Ser Ile Tyr Thr Ile Ser Ile Ser Ser Ala Ser Gln
                325                 330                 335

Gln Gly Leu Ser Pro Trp Tyr Ala Glu Lys Cys Ser Ser Thr Leu Ala
            340                 345                 350

Thr Ser Tyr Ser Ser Gly Asp Tyr Thr Asp Gln Arg Ile Thr Ser Ala
        355                 360                 365

Asp Leu His Asn Asp Cys Thr Glu Thr His Thr Gly Thr Ser Ala Ser
    370                 375                 380

Ala Pro Leu Ala Ala Gly Ile Phe Ala Leu Ala Leu Glu Ala Asn Pro
385                 390                 395                 400

Asn Leu Thr Trp Arg Asp Met Gln His Leu Val Val Trp Thr Ser Glu
                405                 410                 415

Tyr Asp Pro Leu Ala Ser Asn Pro Gly Trp Lys Lys Asn Gly Ala Gly
            420                 425                 430

Leu Met Val Asn Ser Arg Phe Gly Phe Gly Leu Leu Asn Ala Lys Ala
        435                 440                 445

Leu Val Asp Leu Ala Asp Pro Arg Thr Trp Arg Asn Val Pro Glu Lys
    450                 455                 460

Lys Glu Cys Val Val Lys Asp Asn Asn Phe Glu Pro Arg Ala Leu Lys
465                 470                 475                 480

Ala Asn Gly Glu Val Ile Val Glu Ile Pro Thr Arg Ala Cys Glu Gly
                485                 490                 495

Gln Glu Asn Ala Ile Lys Ser Leu Glu His Val Gln Phe Glu Ala Thr
            500                 505                 510

Ile Glu Tyr Ser Arg Arg Gly Asp Leu His Val Thr Leu Thr Ser Ala
        515                 520                 525

Val Gly Thr Ser Thr Val Leu Leu Ala Glu Arg Glu Arg Asp Thr Ser
    530                 535                 540

Pro Asn Gly Phe Lys Asn Trp Asp Phe Met Ser Val His Thr Trp Gly
545                 550                 555                 560

Glu Asn Pro Val Gly Thr Trp Thr Leu Lys Ile Thr Asp Met Ser Gly
                565                 570                 575

Arg Met Gln Asn Glu Gly Arg Ile Val Asn Trp Lys Leu Ile Leu His
            580                 585                 590

Gly Thr Ser Ser Gln Pro Glu His Met Lys Gln Pro Arg Val Tyr Thr
        595                 600                 605

Ser Tyr Asn Thr Val Gln Asn Asp Arg Arg Gly Val Glu Lys Met Val
    610                 615                 620

Asn Val Val Glu Lys Arg Pro Thr Gln Lys Ser Leu Asn Gly Asn Leu
625                 630                 635                 640

Leu Val Pro Lys Asn Ser Ser Ser Ser Asn Val Glu Gly Arg Arg Asp
                645                 650                 655

Glu Gln Val Gln Gly Thr Pro Ser Lys Ala Met Leu Arg Leu Leu Gln
            660                 665                 670
```

```
Ser Ala Phe Ser Lys Asn Ala Leu Ser Lys Gln Ser Pro Lys Lys Ser
        675                 680                 685

Pro Ser Ala Lys Leu Ser Ile Pro Tyr Glu Ser Phe Tyr Glu Ala Leu
    690                 695                 700

Glu Lys Leu Asn Lys Pro Ser Lys Leu Glu Gly Ser Glu Asp Ser Leu
705                 710                 715                 720

Tyr Ser Asp Tyr Val Asp Val Phe Tyr Asn Thr Lys Pro Tyr Lys His
                725                 730                 735

Arg Asp Asp Arg Leu Leu Gln Ala Leu Met Asp Ile Leu Asn Glu Glu
            740                 745                 750

Asn


<210> SEQ ID NO 56
<211> LENGTH: 5054
<212> TYPE: DNA
<213> ORGANISM: Homo sapiens

<400> SEQUENCE: 56

actcagcctg gagaccgaag cgcttcactg agcgctcgcc gccgcccagc ctctcctctc      60

gcgcctccta gctcttcgca gagcaaccag gagccaggag tggtctagag cccgagggtg     120

ggaaggggga gtctgtctgg cttttctcct atcttgcttc tttttcctct tcccttccca     180

ctcttgttca agcgagtgtg tgagctatgg agcgaagagc ctggagtctg cagtgcactg     240

ctttcgtcct cttttgcgct tggtgtgcac tgaacagtgc aaaagcgaaa aggcaatttg     300

tcaatgaatg ggcagcggag atccccgggg gcccggaagc agcctcggcc atcgccgagg     360

agctgggcta tgaccttttg ggtcagattg gttcacttga aaatcactac ttattcaaac     420

ataaaaacca ccccagaagg tctcgaagga gtgcctttca tatcactaag agattatctg     480

atgatgatcg tgtgatatgg gctgaacaac agtatgaaaa agaaagaagt aaacgttcag     540

ctctaaggga ctcagcacta aatctcttca atgatcccat gtggaatcag caatggtact     600

tgcaagatac caggatgacg gcagccctgc ccaagctgga ccttcatgtg atacctgttt     660

ggcaaaaagg cattacgggc aaaggagttg ttatcaccgt actggatgat ggtttggagt     720

ggaatcacac ggacatttat gccaactatg atccagaggc tagctatgat tttaatgata     780

atgaccatga tccatttccc cgatatgatc ccacaaacga gaacaaacac gggaccagat     840

gtgcaggaga aattgccatg caagcaaata atcacaaatg cggggttgga gttgcataca     900

attccaaagt tggaggcata agaatgctgg atggcattgt gacggatgct attgaggcca     960

gttcaattgg attcaatcct ggacacgtgg atatttacag tgcaagctgg ggccctaatg    1020

atgatgggaa aactgtggag gggcctggcc ggctagccca gaaggctttt gaatatggtg    1080

tcaaacaggg gagacagggg aaggggtcca tcttcgtctg ggcttcggga aacgggggc     1140

gtcagggaga taattgtgac tgtgatggct acacagacag catctacacc atctccatca    1200

gcagtgcctc ccagcaaggc ctatcccccct ggtacgctga gaagtgctcc tccacactgg   1260

ccacctctta cagcagcgga gattacaccg accagagaat cacgagcgct gacctgcaca    1320

atgactgcac ggagacgcac acaggcacct cggcctctgc acctctggct gctggcatct    1380

tcgctctggc cctggaagca aacccaaatc tcacctggcg agatatgcag cacctggttg    1440

tctggacctc tgagtatgac ccgctggcca ataaccctgg atggaaaaag aatggagcag    1500

gcttgatggt gaatagtcga tttggatttg gcttgctaaa tgccaaagct ctggtggatt    1560

tagctgaccc caggacctgg aggagcgtgc ctgagaagaa agagtgtgtt gtaaaggaca    1620
```

```
atgactttga gcccagagcc ctgaaagcta atggagaagt tatcattgaa attccaacaa   1680
gagcttgtga aggacaagaa aatgctatca agtccctgga gcatgtacaa tttgaagcaa   1740
caattgaata ttcccgaaga ggagaccttc atgtcacact tacttctgct gctggaacta   1800
gcactgtgct cttggctgaa agagaacggg atacatctcc taatggcttt aagaactggg   1860
acttcatgtc tgttcacaca tggggagaga accctatagg tacttggact ttgagaatta   1920
cagacatgtc tggaagaatt caaaatgaag gaagaattgt gaactggaag ctgattttgc   1980
acgggacctc ttctcagcca gagcatatga agcagcctcg tgtgtacacg tcctacaaca   2040
ctgttcagaa tgacagaaga ggggtggaga agatggtgga tccaggggag gagcagccca   2100
cacaagagaa ccctaaggag aacaccctgg tgtccaaaag ccccagcagc agcagcgtag   2160
ggggccggag ggatgagttg gaggagggag ccccttccca ggccatgctg cgactcctgc   2220
aaagtgcttt cagtaaaaac tcaccgccaa agcaatcacc aaagaagtcc ccaagtgcaa   2280
agctcaacat cccttatgaa aacttctacg aagccctgga aaagctgaac aaaccttccc   2340
agcttaaaga ctctgaagac agtctgtata atgactatgt tgatgttttt tataacacta   2400
aaccttacaa gcacagagac gaccggctgc ttcaagctct ggtggacatt ctgaatgagg   2460
aaaattaaaa taagtgtgtg gtcccaagtt ggaaatattc atgcttcttc cttaccctgc   2520
gattttgcct gtgtctgaag tggttgtttt gtcatgaatt cttatgctta taatatcctt   2580
tgtggcacct tttctttttc tccctaaact gtacatgtga aggggatgag ctcaagcagg   2640
aagttcaact tccagaattg atcataggta tttcaaaaca catctttcct gtctgcacaa   2700
gtgaagtgtt ttgttctttc tggagtcaca gttgacaaaa agctcttaca ctacattaga   2760
acactgcatt agagcccatt tcaattctca aaagaaaagg caaaacctgg gatatcaatt   2820
aatttgaaaa cataatctgc aaagaatgag aaggagtcag aaactgtttc tgtagcttgt   2880
tccctgtctt gtccatgtgg ttcttcaaat tttgatgcca agaaagtatt tggtaggcct   2940
aatgaaggag ttcactgtaa gactcattcc ctagatcttt ctattccaaa gtgccactca   3000
ttcctgtagt caaaatctgg tcatgttggt caaaagctgg attatttaga tctagaaaca   3060
gatcttgaaa tctgaatgct ctggtttgag caattttcga acattctttg cctggtgcac   3120
tgtgtctgtg gtgccagagg cgtccgtgga tccagaggtg gttatgactc gtgctgcatg   3180
cctggtcttt cctctgtttc tccttctgaa agttttctat acctgtctcc tttctcagcc   3240
acaaaataaa tgttgggaga aatgatatat accactttcc cagaaaaaaa aaaacttaca   3300
cttgggactt ggcaaattcc tagtcacaat ttttttcagc agtaacagga aaccacttat   3360
cacatggaga cctaatgtaa taatagaaaa atactcataa tagggagaaa ccaagagaag   3420
ttttgttttt gttttttttcc aactgtgttc attagaacag cgtgttctaa gtatttgaaa   3480
ctgaatgttt attccttgat actaaaagtt cttctccaat cctatcactg atagtgtcca   3540
aattctcacc aaattgctcc taagcttcaa atcagaagca gaaactggca ggccatggac   3600
cttaattgtc cctcaggtag attttgtttg gtatgcagaa tgtttttaaa atatgagtgg   3660
ttattgaaaa tatgatgttt cacataaaac ctcattctcg gacccatctt tgctcatggc   3720
aacagttagc tggagctgag tagcagctgc ctgattagat gactctcagt ccccatggca   3780
ccctgctcca tgttacctag agcaggcact tgattccttg ctgggcagta tccaataggc   3840
atttgatttt gcccactcct acactaagcg aatgtgtaca aagtgtaaat gcattaggaa   3900
aaacaaacta cccgcatctt ctgttaggca ggatctgtac aataataatt atgagtttgc   3960
```

```
ttatgtaatc tcacctcacc tggatgatca ctaatactaa ttcatttatt actaaccttc   4020
tggcttcctt ctctcaatat gcttacaaag tctccagtca cctacaatgc tggctttctc   4080
ccactgagtt tgctgtttgc aatttttcca tgaagtttga acttcataag gtaattcatg   4140
gcattgaact ggttcatgaa aagaacacta gagtctgtca tttgctttgg cttgaagtat   4200
ggttggtaac acaaattttc acctgctctt ctaccatttg aatttgtgta gagggtgttt   4260
gcagagcaat gcccgtaatg cttagagaat gttctcctaa aagacttgcg gaatcactct   4320
gtccttggaa gtttcatata ttgtttgata tgaagtgtta gatagaattt ccaatattgg   4380
agcatatcaa aaagtattaa aactaaaaag gaccagagaa ttcttagatt ggcccggaaa   4440
ggccaataaa gagttagaat gaaaactcat tacttttcca ttcccaatct agtgctagat   4500
gtataaatct ttcttttgat tcttcctaac aaaatatttt ctgggttaaa accccagcca   4560
actcattggg ttgtagccaa aggttcactc tcaagaagct ttaatattta aataaaatca   4620
tattgaatgt ttccaacctg gagtataata ttcagatata aaacagtttt gtcagtcttt   4680
cttagtgcct gtgtggattt ttgtgaaaat gtcaaagaga aaacttatat actatttccc   4740
ttgaaatttt aaactatatt ttctttacag gtatttataa tataccaatg cttttatcaa   4800
acagaatttt aaagagcata ataaattata ttaaagaacc aaaagttttc ctgagaataa   4860
gaaagtttca cccaataaaa tatttttgaa aggcatgttc ctctgtcaat gaaaaaaagt   4920
acatgtatgt gttgtgatat taaaagtgac atttgtctaa tagcctaata caacatgtag   4980
ctgagtttaa catgtgtggt cttggtattc ttaagggaac ttccacatta tacatttgat   5040
gtattgacca gaat                                                     5054
```

<210> SEQ ID NO 57
<211> LENGTH: 2516
<212> TYPE: DNA
<213> ORGANISM: Mus musculus

<400> SEQUENCE: 57

```
tctagctggt gtgtctctga tcttgcttct tttctcccag cccttcctac ttgtgtgaga     60
acaaggtttt gagccatgga gcaaagaggt tggactctgc agtgtactgc tttcgccttc    120
ttttgcgttt ggtgtgcact aaacagtgta aaagcaaaga ggcagtttgt taatgaatgg    180
gcggcggaga tccccggagg gcaagaagct gcctctgcca tcgccgaaga actggggtat    240
gaccttttgg gtcagattgg atcacttgaa aatcactatt tattcaaaca caaaagccat    300
cctcggaggt cccgaagaag cgctcttcat atcactaaga ggttatctga tgatgatcgt    360
gtgacgtggg ctgaacaaca gtatgaaaaa gagagaagta aacgttcagt tcaaaaagac    420
tcagcattgg atctcttcaa tgatccaatg tggaatcagc agtggtactt gcaagatacc    480
agaatgactg cagctctgcc caagctggac cttcatgtaa tacctgtttg ggaaaagggt    540
attactggca aaggagttgt tattactgta ctggatgatg gcttggagtg gaatcacaca    600
gacatttatg ccaattatga tccagaggct agctatgatt ttaacgataa tgatcatgat    660
ccatttcccc gatatgatct cacaaatgaa aacaaacatg gaacaagatg tgcaggtgaa    720
attgccatgc aagcaaataa tcacaagtgt ggggttggag ttgcatataa ttccaaagtt    780
ggaggcataa gaatgctgga tggcattgta actgatgcca ttgaggctag ttcaattgga    840
ttcaaccctg gccatgtgga tatttacagt gcaagctggg gccctaatga tgatggaaaa    900
actgtggagg ggcctggcag actagcccag aaggcatttg aatatggtgt caaacagggg    960
agacaaggga aaggctccat ctttgtctgg gcttcaggga atgggggtcg tcagggagat   1020
```

```
aactgtgact gtgatggcta cacagacagc atttacacca tctctatcag cagtgcctcc   1080
cagcaaggcc tgtcaccttg gtatgcagag aagtgttctt ccacattggc tacctcctac   1140
agcagtggtg attacacaga ccagcgaata acaagcgctg acctgcacaa tgactgcaca   1200
gagacccaca caggcacctc ggcttcagca cccctggctg ctggtatctt tgctctggcc   1260
ttggaggcaa acccaaatct tacctggaga gatatgcagc atctggttgt ctggacctct   1320
gagtacgacc cattggccag taacccaggt tggaaaaaga atggggcagg cttgatggtg   1380
aacagccgat ttggatttgg cttgctaaat gccaaagctc tggtggattt ggctgatcct   1440
aggacctgga gaaatgtgcc tgagaagaaa gaatgtgttg taaaagacaa taactttgag   1500
cctagagccc tgaaagctaa tggagaagta attgttgaaa tcccaacaag agcttgtgaa   1560
ggacaagaaa atgctatcaa gtctctggaa catgtgcaat ttgaagcaac aattgaatat   1620
tctcgtagag gagaccttca tgtcacactc acttctgctg ttggaaccag cactgtactg   1680
ttggctgaaa gggaaagaga tacatccccc aatggcttta agaattggga cttcatgtct   1740
gttcatacat ggggagagaa tcctgtaggc acctggacat tgaaaattac agacatgtct   1800
ggaagaatgc aaaatgaagg aaggattgtg aactggaagt tgattttgca tgggacatct   1860
tctcaaccag agcacatgaa gcagcctcgt gtgtacacat cctacaatac agtccagaat   1920
gacaggagag gagtggaaaa gatggtgaat gttgtggaga agcggcccac acaaaagagc   1980
ctgaatggca atctcctggt acccaaaaac tccagcagca gcaatgtgga gggtagaagg   2040
gatgagcagg tacaaggaac tccttcaaag gccatgctgc gactcctaca aagtgctttt   2100
agcaagaatg cactttcaaa acaatcacca aagaagtctc caagtgcaaa gctcagcatc   2160
ccttatgaaa gtttctatga agccttggaa aagctcaaca agccctccaa gcttgaaggc   2220
tctgaagaca gtctgtacag tgactatgtt gatgtattct ataacacaaa accttataag   2280
catagagatg acaggctgct gcaagctctc atggacatcc taaatgagga gaattaaaat   2340
aagtgtgttg cctgagttgg gaatcttcat gcaccctcct tttccttaaa tgttcctggg   2400
tctggagttg ttgtgtccct ggtttttatg cttataatgt ccttcattgt aattttactt   2460
tttctttcaa actgtacttt ggagtgagtt tcaaaatgaa agccaacttc atcatt       2516
```

<210> SEQ ID NO 58
<211> LENGTH: 356
<212> TYPE: PRT
<213> ORGANISM: Homo sapiens

<400> SEQUENCE: 58

```
Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110
```

```
Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355


<210> SEQ ID NO 59
<211> LENGTH: 357
<212> TYPE: PRT
<213> ORGANISM: Mus musculus

<400> SEQUENCE: 59

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Glu Leu Glu Ala Met Asn Ala
        35                  40                  45

Glu Glu Asp Ser Leu Arg Asn Gly Gly Glu Glu Glu Glu Glu Asp Glu
    50                  55                  60

Asp Leu Glu Glu Glu Glu Glu Glu Glu Glu Glu Glu Glu Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
```

```
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Pro Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Pro Gln Ser His Gly Ser Ile Phe Ser Ser
305                 310                 315                 320

Gly Ala Ala Ala Pro Arg Cys Glu Ile Pro Ile Asp Asn Ile Met Ser
                325                 330                 335

Phe Asp Ser His Ser His His Glu Arg Val Met Ser Ala Gln Leu Asn
            340                 345                 350

Ala Ile Phe His Asp
        355


<210> SEQ ID NO 60
<211> LENGTH: 2641
<212> TYPE: DNA
<213> ORGANISM: Homo sapiens

<400> SEQUENCE: 60

gagaacgggg agcgcacagc ctggacgcgt gcgcaggcgt caggcgcata gacctgctag      60

cccctcagct agcggccccg cccgcgctta gcatcactaa ctgggctata taacctgagc     120

gcccgcgcgg ccacgacacg aggaattcgc ccacgcagga ggcgcggcgt ccggaggccc     180

cagggttatg agactatcac tgctcaggac ctactaacaa caaaggaaat cgaaacatga     240

ccaaatcgta cagcgagagt gggctgatgg gcgagcctca gccccaaggt cctccaagct     300

ggacagacga gtgtctcagt tctcaggacg aggagcacga ggcagacaag aaggaggacg     360

acctcgaagc catgaacgca gaggaggact cactgaggaa cgggggagag gaggaggacg     420

aagatgagga cctggaagag gaggaagaag aggaagagga ggatgacgat caaaagccca     480

agagacgcgg ccccaaaaag aagaagatga ctaaggctcg cctggagcgt tttaaattga     540

gacgcatgaa ggctaacgcc cgggagcgga accgcatgca cggactgaac gcggcgctag     600

acaacctgcg caaggtggtg ccttgctatt ctaagacgca gaagctgtcc aaaatcgaga     660

ctctgcgctt ggccaagaac tacatctggg ctctgtcgga gatcctgcgc tcaggcaaaa     720
```

```
gcccagacct ggtctccttc gttcagacgc tttgcaaggg cttatcccaa cccaccacca    780

acctggttgc gggctgcctg caactcaatc ctcggacttt tctgcctgag cagaaccagg    840

acatgccccc ccacctgccg acggccagcg cttccttccc tgtacacccc tactcctacc    900

agtcgcctgg gctgcccagt ccgccttacg gtaccatgga cagctcccat gtcttccacg    960

ttaagcctcc gccgcacgcc tacagcgcag cgctggagcc cttctttgaa agccctctga   1020

ctgattgcac cagcccttcc tttgatggac ccctcagccc gccgctcagc atcaatggca   1080

acttctcttt caaacacgaa ccgtccgccg agtttgagaa aaattatgcc tttaccatgc   1140

actatcctgc agcgacactg gcaggggccc aaagccacgg atcaatcttc tcaggcaccg   1200

ctgcccctcg ctgcgagatc cccatagaca atattatgtc cttcgatagc cattcacatc   1260

atgagcgagt catgagtgcc cagctcaatg ccatatttca tgattagagg cacgccagtt   1320

tcaccatttc cgggaaacga acccactgtg cttacagtga ctgtcgtgtt tacaaaaggc   1380

agccctttgg gtactactgc tgcaaagtgc aaatactcca agcttcaagt gatatatgta   1440

tttattgtca ttactgcctt tggaagaaac aggggatcaa agttcctgtt caccttatgt   1500

attattttct atagctcttc tatttaaaaa ataaaaaaat acagtaaagt ttaaaaaata   1560

caccacgaat ttggtgtggc tgtattcaga tcgtattaat tatctgatcg ggataacaaa   1620

atcacaagca ataattagga tctatgcaat ttttaaacta gtaatgggcc aattaaaata   1680

tatataaata tatattttc aaccagcatt ttactacttg ttacctttcc catgctgaat   1740

tattttgttg tgattttgta cagaattttt aatgactttt tataatgtgg atttcctatt   1800

ttaaaaccat gcagcttcat caatttttat acatatcaga aaagtagaat tatatctaat   1860

ttatacaaaa taatttaact aatttaaacc agcagaaaag tgcttagaaa gttattgtgt   1920

tgccttagca cttctttcct ctccaattgt aaaaaaaaaa aaaaaaaaaa aaaaaaaaaa   1980

aaaattgcac aatttgagca attcatttca ctttaaagtc tttccgtctc cctaaaataa   2040

aaaccagaat cataattttc aagagaagaa aaaattaaga gatacattcc ctatcaaaac   2100

atatcaattc aacacattac ttgcacaagc ttgtatatac atattataaa taaatgccaa   2160

catacccttc tttaaatcaa aagctgcttg actatcacat acaatttgca ctgttacttt   2220

ttagtctttt actcctttgc attccatgat tttacagaga atctgaagct attgatgttt   2280

ccagaaaata taaatgcatg attttataca tagtcacaaa aatggtggtt tgtcatatat   2340

tcatgtaata aatctgagcc taaatctaat caggttgtta atgttgggat ttatatctat   2400

agtagtcaat tagtacagta gcttaaataa attcaaacca tttaattcat aattagaaca   2460

atagctattg catgtaaaat gcagtccaga ataagtgctg tttgagatgt gatgctggta   2520

ccactggaat cgatctgtac tgtaattttg tttgtaatcc tgtatattat ggtgtaatgc   2580

acaatttaga aaacattcat ccagttgcaa taaaatagta ttgaaagtga aaaaaaaaaa   2640

a                                                                   2641


<210> SEQ ID NO 61
<211> LENGTH: 2494
<212> TYPE: DNA
<213> ORGANISM: Mus musculus

<400> SEQUENCE: 61

acgaggaatt cgcccacgca gaaggcaagg tgtcccgagg ctccagggtt atgagatcgt     60

cactattcag aacctttaa caacaggaag tggaaacatg accaaatcat acagcgagag    120

cgggctgatg ggcgagcctc agccccaagg tcccccaagc tggacagatg agtgtctcag    180
```

```
ttctcaggac gaggaacacg aggcagacaa gaaagaggac gagcttgaag ccatgaatgc    240
agaggaggac tctctgagaa acgggggaga ggaggaggag gaagatgagg atctagagga    300
agaggaggaa gaagaagagg aggaggagga tcaaaagccc aagagacggg gtcccaaaaa    360
gaaaaagatg accaaggcgc gcctagaacg ttttaaatta aggcgcatga aggccaacgc    420
ccgcgagcgg aaccgcatgc acgggctgaa cgcggcgctg gacaacctgc gcaaggtggt    480
accttgctac tccaagaccc agaaactgtc taaaatagag acactgcgct tggccaagaa    540
ctacatctgg gctctgtcag agatcctgcg ctcaggcaaa agccctgatc tggtctcctt    600
cgtacagacg ctctgcaaag gtttgtccca gcccactacc aatttggtcg ccggctgcct    660
gcagctcaac cctcggactt tcttgcctga gcagaacccg gacatgcccc cgcatctgcc    720
aaccgccagc gcttccttcc cggtgcatcc ctactcctac cagtcccctg gactgcccag    780
cccgccctac ggcaccatgg acagctccca cgtcttccac gtcaagccgc cgccacacgc    840
ctacagcgca gctctggagc ccttctttga aagcccccta actgactgca ccagcccttc    900
ctttgacgga cccctcagcc cgccgctcag catcaatggc aacttctctt tcaaacacga    960
accatccgcc gagtttgaaa aaaattatgc ctttaccatg cactaccctg cagcgacgct   1020
ggcagggccc caaagccacg gatcaatctt ctcttccggt gccgctgccc ctcgctgcga   1080
gatccccata gacaacatta tgtctttcga tagccattcg catcatgagc gagtcatgag   1140
tgcccagctt aatgccatct ttcacgatta gaggcacgtc agtttcacta ttcccgggaa   1200
acgaatccac tgtgcgtaca gtgactgtcc tgtttacaga aggcagccct tttgctaaga   1260
ttgctgcaaa gtgcaaatac tcaaagcttc aagtgatata tgtatttatt gtcgttactg   1320
cctttggaag aaacagggga tcaaagttcc tgttcacctt atgtattgtt ttctatagct   1380
cttctatttt aaaaataata atacagtaaa gtaaaaaaga aaatgtgtac cacgaatttc   1440
gtgtagctgt attcagatcg tattaattat ctgatcggga taaaaaaaat cacaagcaat   1500
aattaggatc tatgcaattt ttaaactagt aatgggccaa ttaaaatata tataaatata   1560
tatttttcaa ccagcatttt actacctgtg acctttccca tgctgaatta ttttgttgtg   1620
attttgtaca gaatttttaa tgacttttta taacgtggat ttcctatttt aaaaccatgc   1680
agcttcatca atttttatac atatcagaaa agtagaatta tatctaattt atacaaaata   1740
atttaactaa tttaaaccag cagaaaagtg cttagaaagt tattgcgttg ccttagcact   1800
tctttcttct ctaattgtaa aaaagaaaag aaaagaaaaa aaaccaacaa attgcacaat   1860
ttgagcaatt catctcactt taaagttttt cctgctcgct ccctaaaata gaaaccagac   1920
ccataacact caagaggatg aaaaccgaaa tgcattcctt atcaaaacac atcaattcat   1980
tacttgcaca agcttgtaaa tacatattat aaataaatgc caacacacac tcctttaaat   2040
caaaagctgc ttgactatca catacaattt gcactctttc tttttagtct tttacttctt   2100
tgaattccat gattttacgg agtgtttgaa gatattgatg tttccagaaa atataaatgc   2160
atgattttat acatagtcaa acaaatggtg gtttgtcatc tattcatgta ataaatttga   2220
gcctaaattt attcaggttg ttaatgttgg gtttttatac ctgtgtagtc agttagtaca   2280
gtagtttaaa taaaattcaa accatcgaat tcataattag aacaatagct gttgcatgta   2340
aaatgcagtc cagaataagt gctgtttgag atgtgatgct ggtactactg gaattgacat   2400
gtactgtaat cttgtttgta atcctgtgta ttatggtgta atgcacaatt tagaaaactc   2460
ccatgcagtt gcaataaaaa tagtatggaa aatc                                2494
```

<210> SEQ ID NO 62
<211> LENGTH: 273
<212> TYPE: PRT
<213> ORGANISM: Homo sapiens

<400> SEQUENCE: 62

```
Met Ser Leu Thr Asn Thr Lys Thr Gly Phe Ser Val Lys Asp Ile Leu
1               5                   10                  15

Asp Leu Pro Asp Thr Asn Asp Glu Glu Gly Ser Val Ala Glu Gly Pro
            20                  25                  30

Glu Glu Glu Asn Glu Gly Pro Glu Pro Ala Lys Arg Ala Gly Pro Leu
        35                  40                  45

Gly Gln Gly Ala Leu Asp Ala Val Gln Ser Leu Pro Leu Lys Asn Pro
    50                  55                  60

Phe Tyr Asp Ser Ser Asp Asn Pro Tyr Thr Arg Trp Leu Ala Ser Thr
65                  70                  75                  80

Glu Gly Leu Gln Tyr Ser Leu His Gly Leu Ala Ala Gly Ala Pro Pro
                85                  90                  95

Gln Asp Ser Ser Ser Lys Ser Pro Glu Pro Ser Ala Asp Glu Ser Pro
            100                 105                 110

Asp Asn Asp Lys Glu Thr Pro Gly Gly Gly Gly Asp Ala Gly Lys Lys
        115                 120                 125

Arg Lys Arg Arg Val Leu Phe Ser Lys Ala Gln Thr Tyr Glu Leu Glu
    130                 135                 140

Arg Arg Phe Arg Gln Gln Arg Tyr Leu Ser Ala Pro Glu Arg Glu His
145                 150                 155                 160

Leu Ala Ser Leu Ile Arg Leu Thr Pro Thr Gln Val Lys Ile Trp Phe
                165                 170                 175

Gln Asn His Arg Tyr Lys Met Lys Arg Ala Arg Ala Glu Lys Gly Met
            180                 185                 190

Glu Val Thr Pro Leu Pro Ser Pro Arg Arg Val Ala Val Pro Val Leu
        195                 200                 205

Val Arg Asp Gly Lys Pro Cys His Ala Leu Lys Ala Gln Asp Leu Ala
    210                 215                 220

Ala Ala Thr Phe Gln Ala Gly Ile Pro Phe Ser Ala Tyr Ser Ala Gln
225                 230                 235                 240

Ser Leu Gln His Met Gln Tyr Asn Ala Gln Tyr Ser Ser Ala Ser Thr
                245                 250                 255

Pro Gln Tyr Pro Thr Ala His Pro Leu Val Gln Ala Gln Gln Trp Thr
            260                 265                 270

Trp
```

<210> SEQ ID NO 63
<211> LENGTH: 248
<212> TYPE: PRT
<213> ORGANISM: Mus musculus

<400> SEQUENCE: 63

```
Met Ser Leu Thr Asn Thr Lys Thr Gly Phe Ser Val Lys Asp Ile Leu
1               5                   10                  15

Asp Leu Pro Asp Thr Asn Asp Glu Asp Gly Ser Val Ala Glu Gly Pro
            20                  25                  30

Glu Glu Glu Ser Glu Gly Pro Glu Pro Ala Lys Arg Ala Gly Pro Leu
        35                  40                  45

Gly Gln Gly Ala Leu Asp Ala Val Gln Ser Leu Pro Leu Lys Ser Pro
```

```
    50                  55                  60

Phe Tyr Asp Ser Ser Asp Asn Pro Tyr Thr Arg Trp Leu Ala Ser Thr
65                  70                  75                  80

Glu Gly Leu Gln Tyr Ser Leu His Gly Leu Ala Ala Ser Ala Pro Pro
                85                  90                  95

Gln Asp Ser Ser Ser Lys Ser Pro Glu Pro Ser Ala Asp Glu Ser Pro
            100                 105                 110

Asp Asn Asp Lys Glu Thr Gln Gly Gly Gly Gly Asp Ala Gly Lys Lys
        115                 120                 125

Arg Lys Arg Arg Val Leu Phe Ser Lys Ala Gln Thr Tyr Glu Leu Glu
    130                 135                 140

Arg Arg Phe Arg Gln Gln Arg Tyr Leu Ser Ala Pro Glu Arg Glu His
145                 150                 155                 160

Leu Ala Ser Leu Ile Arg Leu Thr Pro Thr Gln Val Lys Ile Trp Phe
                165                 170                 175

Gln Asn His Arg Tyr Lys Met Lys Arg Ala Arg Ala Glu Lys Ala Phe
            180                 185                 190

Gln Asn Arg Arg Met Asp Ala Arg Ile Glu Ala Ala Val Pro Ile Val
        195                 200                 205

Ser Ala Arg Trp Ser Asp Trp Ile Arg Lys Gln Phe Gln Val Gly Arg
    210                 215                 220

Leu Thr Gln Ala Trp Glu His Asn Leu Val Ile Cys Gly Phe Glu Gly
225                 230                 235                 240

Cys Leu Gly Lys Val His Leu Gln
                245


<210> SEQ ID NO 64
<211> LENGTH: 2092
<212> TYPE: DNA
<213> ORGANISM: Homo sapiens

<400> SEQUENCE: 64

gcggccgccg gagcccgagc tgacgccgcc ttggcacccc tcctggagtt agaaactaag     60

gccggggccc gcggcgctcg gcgcgcaggc cgcccggctt cctgcgtcca tttccgcgtg    120

ctttcaaaga agacagagag aggcactggg ttgggcttca ttttttttcct ccccatcccc    180

agtttctttc tctttttaaa aataataatt atcccaataa ttaaagccaa ttcccccctc    240

ccctccccca gtccctcccc ccaactcccc cctcccccgc ccgccggggc aggggagcgc    300

cacgaattga ccaagtgaag ctacaacttt gcgacataaa ttttggggtc tcgaaccatg    360

tcgctgacca acacaaagac ggggttttcg gtcaaggaca tcttagacct gccggacacc    420

aacgatgagg agggctctgt ggccgaaggt ccggaggaag agaacgaggg gcccgagcca    480

gccaagaggg ccgggccgct ggggcagggc gccctggacg cggtgcagag cctgcccctg    540

aagaacccct tctacgacag cagcgacaac ccgtacacgc gctggctggc cagcaccgag    600

ggccttcagt actccctgca cggtctggct gccggggcgc cccctcagga ctcaagctcc    660

aagtccccgg agccctcggc cgacgagtca ccggacaatg acaaggagac cccgggcggc    720

ggggggggacg ccggcaagaa gcgaaagcgg cgagtgcttt tctccaaggc gcagacctac    780

gagctggagc ggcgctttcg gcagcagcgg tacctgtcgg cgcccgagcg cgaacacctg    840

gccagcctca tccgcctcac gcccacgcag gtcaagatct ggttccagaa ccaccgctac    900

aagatgaagc gcgcccgggc cgagaaaggt atggaggtga cgcccctgcc ctcgccgcgc    960

cgggtggccg tgcccgtctt ggtcagggac ggcaaaccat gtcacgcgct caaagcccag   1020
```

```
gacctggcag ccgccacctt ccaggcgggc attccctttt ctgcctacag cgcgcagtcg   1080

ctgcagcaca tgcagtacaa cgcccagtac agctcggcca gcacccccca gtacccgaca   1140

gcacaccccc tggtccaggc ccagcagtgg acttggtgag cgccgcccca acgagactcg   1200

cggccccagg cccaggcccc accccggcgg cggtggcggc gaggaggcct cggtccttat   1260

ggtggttatt attattatta taattattat tatggagtcg agttgactct cggctccact   1320

agggaggcgc cgggaggttg cctgcgtctc cttggagtgg cagattccac ccacccagct   1380

ctgcccatgc ctctccttct gaaccttggg agagggctga actctacgcc gtgtttacag   1440

aatgtttgcg cagcttcgct tctttgcctc tccccggggg gaccaaaccg tcccagcgtt   1500

aatgtcgtca cttgaaaacg agaaaaagac cgacccccca cccctgcttt cgtgcatttt   1560

gtaaaatatg tttgtgtgag tagcgatatt gtcagccgtc ttctaaagca agtggagaac   1620

actttaaaaa tacagagaat ttcttccttt ttttaaaaaa aaataagaaa atgctaaata   1680

tttatggcca tgtaaacgtt ctgacaactg gtggcagatt tcgcttttcg ttgtaaatat   1740

cggtggtgat tgttgccaaa atgaccttca ggaccggcct gtttcccgtc tgggtccaac   1800

tcctttcttt gtggcttgtt tgggtttgtt ttttgttttg tttttgtttt tgcgttttcc   1860

cctgctttct tcctttctct ttttatttta ttgtgcaaac atttctcaaa tatggaaaag   1920

aaaaccctgt aggcagggag ccctctgccc tgtcctccgg gccttcagcc ccgaacttgg   1980

agctcagcta ttcggcgcgg ttccccaaca gcgccgggcg cagaaagctt tcgatttttt   2040

aaataagaat tttaataaaa atcctgtgtt taaaaaagaa aaaaagaaaa aa           2092
```

<210> SEQ ID NO 65
<211> LENGTH: 1354
<212> TYPE: DNA
<213> ORGANISM: Mus musculus

<400> SEQUENCE: 65

```
tttttcctc gccaccagcc gccaccgcgc gcggagcggc cgccggagcc ggagctgacg     60

gcaccttggc acctctcctg gagttacaaa ctgaggccgc gcggcgctgg gcgcgcaggc    120

ccccagtcac agcctacatt tctgcgtgct ttccgagaag agagaggcac cgggtgggct    180

ttattttttt tccccttccc cttttccccc cacagtgtcc tctcatttta aataataatt    240

atcccaataa ttaaaaccca tcccccatcc ctcccccccat tcctttcctt aaaccccccct    300

cccccgcccg ctggggctgg ggagagccac gaattgacca agtgaggcta caactttgtg    360

gcataaattg cggggtccgg aaccatgtcg ctgaccaaca caaagacggg gttttcagtc    420

aaggacatct tggaccttcc ggacaccaac gatgaagacg gctcggtggc cgaagggcca    480

gaggaggaga gcgaagggcc ggagcccgcc aagagggccg ggccgctggg gcagggcgcc    540

ctggacgctg tgcagagcct gcccccttaag agccctttct acgacagcag cgacaacccc    600

tacactcgct ggctggccag caccgagggc ctccaatact ccctgcacgg gctggcggcc    660

agcgctcccc cccaagactc gagctccaaa tccccagagc cctcggctga cgagtcaccg    720

gacaatgaca aggagaccca gggcggcggg ggggacgcag gcaagaagcg gaagcgccga    780

gtgctcttct ccaaagcgca gacctacgag ctggagcggc gcttccggca gcagcggtac    840

ctgtcggcgc ccgagcgcga gcacctggcc agcctcatcc gtctcacgcc gacacaggtc    900

aagatctggt tccagaacca tcgctacaag atgaaacgtg cccgggcgga gaaagcattt    960

caaaaccgac ggatggatgc caggatcgaa gctgcggtgc ccatagtgtc cgcaaggtgg   1020
```

-continued

```
agcgattgga taagaaaaca atttcaggtc gggcgactga ctcaggcctg ggagcacaat   1080

ctggtcatct gtggatttga gggatgtctg ggtaaagtcc atttacagta ggaccacaat   1140

gccaaagaaa gaattacaat tctttggctt ggtgcttgtc ccttggagtg tgatgaaaag   1200

gttgatggca ttcaaccttt ttctttcgtc tgccttgtgg atgtcaactg tctctgttac   1260

tgtcaccacc acaattgaag catatatttc cacctcttca aaatgtttcc tgtgccagga   1320

aaatgtaatt tattctaata aaaaataacc tgac                               1354


<210> SEQ ID NO 66
<211> LENGTH: 367
<212> TYPE: PRT
<213> ORGANISM: Homo sapiens

<400> SEQUENCE: 66

Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ser Ala Ser Ala Ala Ala Ala Ala Ala Ala
    130                 135                 140

Ala Ala Ala Ala Ala Ala Ser Ser Pro Ala Gly Leu Leu Ala Gly Leu
145                 150                 155                 160

Pro Arg Phe Ser Ser Leu Ser Pro Pro Pro Pro Pro Pro Gly Leu Tyr
                165                 170                 175

Phe Ser Pro Ser Ala Ala Ala Val Ala Ala Val Gly Arg Tyr Pro Lys
            180                 185                 190

Pro Leu Ala Glu Leu Pro Gly Arg Thr Pro Ile Phe Trp Pro Gly Val
        195                 200                 205

Met Gln Ser Pro Pro Trp Arg Asp Ala Arg Leu Ala Cys Thr Pro His
    210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285

Thr Lys Trp Arg Lys Lys His Ala Ala Glu Met Ala Thr Ala Lys Lys
    290                 295                 300

Lys Gln Asp Ser Glu Thr Glu Arg Leu Lys Gly Ala Ser Glu Asn Glu
305                 310                 315                 320
```

```
Glu Glu Asp Asp Asp Tyr Asn Lys Pro Leu Asp Pro Asn Ser Asp Asp
                325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
        355                 360                 365


<210> SEQ ID NO 67
<211> LENGTH: 365
<212> TYPE: PRT
<213> ORGANISM: Mus musculus

<400> SEQUENCE: 67

Met Leu Ala Val Gly Ala Met Glu Gly Pro Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Thr Gly Pro Pro
        35                  40                  45

Ser Ser Ser Ser Ser Ser Ser Ser Ser Ser Ser Pro Ser Pro Pro Leu
    50                  55                  60

Gly Ser His Asn Pro Gly Gly Leu Lys Pro Pro Ala Ala Gly Gly Leu
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Thr Ser Ala Ser Ala Ala Ala Ala Ala Ala Ala
    130                 135                 140

Ala Ala Ala Ala Ala Ala Ala Ser Ser Pro Ala Gly Leu Leu Ala Gly
145                 150                 155                 160

Leu Pro Arg Phe Ser Ser Leu Ser Pro Pro Pro Pro Pro Pro Gly Leu
                165                 170                 175

Tyr Phe Ser Pro Ser Ala Ala Ala Val Ala Ala Val Gly Arg Tyr Pro
            180                 185                 190

Lys Pro Leu Ala Glu Leu Pro Gly Arg Thr Pro Ile Phe Trp Pro Gly
        195                 200                 205

Val Met Gln Ser Pro Pro Trp Arg Asp Ala Arg Leu Ala Cys Thr Pro
    210                 215                 220

His Gln Gly Ser Ile Leu Leu Asp Lys Asp Gly Lys Arg Lys His Thr
225                 230                 235                 240

Arg Pro Thr Phe Ser Gly Gln Gln Ile Phe Ala Leu Glu Lys Thr Phe
                245                 250                 255

Glu Gln Thr Lys Tyr Leu Ala Gly Pro Glu Arg Ala Arg Leu Ala Tyr
            260                 265                 270

Ser Leu Gly Met Thr Glu Ser Gln Val Lys Val Trp Phe Gln Asn Arg
        275                 280                 285

Arg Thr Lys Trp Arg Lys Lys His Ala Ala Glu Met Ala Thr Ala Lys
    290                 295                 300

Lys Lys Gln Asp Ser Glu Thr Glu Arg Leu Lys Gly Thr Ser Glu Asn
305                 310                 315                 320

Glu Glu Asp Asp Asp Asp Tyr Asn Lys Pro Leu Asp Pro Asn Ser Asp
```

```
                325                 330                 335

Asp Glu Lys Ile Thr Gln Leu Leu Lys Lys His Lys Ser Ser Gly Gly
            340                 345                 350

Ser Leu Leu Leu His Ala Ser Glu Ala Glu Gly Ser Ser
        355                 360                 365
```

<210> SEQ ID NO 68
<211> LENGTH: 1116
<212> TYPE: DNA
<213> ORGANISM: Homo sapiens

<400> SEQUENCE: 68

```
cgtgggatgt tagcggtggg ggcaatggag ggcacccggc agagcgcatt cctgctcagc      60

agccctcccc tggccgccct gcacagcatg gccgagatga agaccccgct gtaccctgcc     120

gcgtatcccc cgctgcctgc cggccccccc tcctcctcgt cctcgtcgtc gtcctcctcg     180

tcgccctccc cgcctctggg cacccacaac ccaggcggcc tgaagccccc ggccacgggg     240

gggctctcat ccctcggcag ccccccgcag cagctctcgg ccgccacccc acacggcatc     300

aacgatatcc tgagccggcc ctccatgccc gtggcctcgg gggccgccct gccctccgcc     360

tcgccctccg gttcctcctc ctcctcttcc tcgtccgcct ctgcctcctc cgcctctgcc     420

gccgccgcgg ctgctgccgc ggccgcagcc gccgcctcat ccccggcggg gctgctggcc     480

ggactgccac gctttagcag cctgagcccg ccgccgccgc cgcccgggct ctacttcagc     540

cccagcgccg cggccgtggc cgccgtgggc cggtacccca agccgctggc tgagctgcct     600

ggccggacgc ccatcttctg gcccggagtg atgcagagcc cgccctggag ggacgcacgc     660

ctggcctgta cccctcatca aggatccatt ttgttggaca aagacgggaa gagaaaacac     720

acgagaccca ctttttccgg acagcagatc ttcgccctgg agaagacttt cgaacaaaca     780

aaatacttgg cggggcccga gagggctcgt ttggcctatt cgttggggat gacagagagt     840

caggtcaagg tctggttcca gaaccgccgg accaagtgga ggaagaagca cgctgccgag     900

atggccacgg ccaagaagaa gcaggactcg gagacagagc gcctcaaggg ggcctcggag     960

aacgaggaag aggacgacga ctacaataag cctctggatc ccaactcgga cgacgagaaa    1020

atcacgcagc tgttgaagaa gcacaagtcc agcagcggcg gcggcggcgg cctcctactg    1080

cacgcgtccg agccggagag ctcatcctga acgccg                              1116
```

<210> SEQ ID NO 69
<211> LENGTH: 1808
<212> TYPE: DNA
<213> ORGANISM: Mus musculus

<400> SEQUENCE: 69

```
ccgccgggag agcggagcgt ccgagcgaga tcagaggcgc gcaccgggcg gaacgccgcc      60

cgctttgaag ctcccccagg cgagcgagcc ggcccccgcc ctcctacatc aaagcgaacg     120

ctccgcgcct cccaaccttg ttgcaaactc tctgggtcgg ctgcggggta cgtcttgctg     180

atttcccgcg ggggtggaga agatgagaag cagagcgctc tgagccggga acgagggacc     240

agcgcctggg atcgaatccg ggactcccga agccgaggaa gcgctgagcc cgcccgcgcc     300

cccgcagccc tcgcccctgc cgcctcccgc ggggcgtttg gacatttttg ctgcgcagct     360

cccggagccc gcggccgatc cacacttcgc ttgcgcgcgc ccccggcacc tcgggttctc     420

ccgagccccg gcggggccac cgacctgcgt ggctgcgggt tcgggtctgg ctgtgggatg     480

ttagctgtgg gggcgatgga gggccctcgg cagagcgcgt tcctgctcag cagcccgccc     540
```

```
ctggccgccc tgcacagtat ggccgagatg aagaccccgc tctaccccgc cgcttatccc     600

ccgctgccca ccgggccccc ctcctcctcg tcctcgtcct cctcgtcctc gtcgccctcc     660

ccacctttgg gctcacataa cccgggcggc ttgaagcccc cggccgcggg gggcctctcg     720

tccctgggca gtcccccgca gcagctttcg gcggccaccc cacacggcat caacgacatc     780

ctgagccggc cctctatgcc ggtggcctcg gggccgccc tgccctccgc ctcgccctcc      840

gggtcttcct cctcctcctc ctcgtccgcc tccgccacct cggcctctgc ggcggccgcc     900

gccgccgctg ctgctgccgc cgctgccgcc tcgtcgcccg ctgggctgct ggccggcctg     960

ccccgcttca gcagcctgag ccctccgcca ccgccgcccg ggctctactt tagccccagc    1020

gccgcggctg tggccgccgt gggccggtac cccaagcccc tggccgagct gcccggtcgg    1080

acgcccatct tctggcccgg agtgatgcag agtccgccgt ggagggacgc gcgccttgcc    1140

tgtacccccc atcaaggatc cattttgttg gacaaagatg ggaagagaaa acacaccaga    1200

cccacgttct ctggacagca aatcttcgcc ctggagaaga ctttcgaaca aacgaagtac    1260

ttggcaggac cagagagagc acgcttggcc tattctctgg ggatgacgga gagtcaggtc    1320

aaggtctggt tccagaaccg caggaccaag tggagaaaga agcacgcagc cgagatggcc    1380

acggccaaga agaagcagga ctcggagacc gagaggctca aggggacttc ggagaatgag    1440

gaggatgacg acgattacaa caaacctctg gacccgaact ctgacgacga gaaaatcact    1500

cagctgctga aaaagcacaa atcgagcggt ggcagcctcc tgctgcacgc gtcggaggcc    1560

gagggctcgt cctgagcgcg accagcaccg cggggatcgc gaccgcgtcc cacagccggt    1620

tcccccggcc cccagtatcc tggctgctcg ccgggccttt actattttct aagatgtaca    1680

tatctatttt tttaacctag aaattgtggc ggggagggtg cgggtcggta gcacggtgcg    1740

ctgatgagga gaaaaggagc ccgccaagtg cactgctcaa aaaaacaaaa aacaaaaaaa    1800

aaaaaaaa                                                              1808
```

<210> SEQ ID NO 70
<211> LENGTH: 110
<212> TYPE: PRT
<213> ORGANISM: Homo sapiens

<400> SEQUENCE: 70

```
Met Ala Leu Trp Met Arg Leu Leu Pro Leu Leu Ala Leu Leu Ala Leu
1               5                   10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
    50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 71
<211> LENGTH: 108
<212> TYPE: PRT
<213> ORGANISM: Mus musculus

<400> SEQUENCE: 71

Met Ala Leu Leu Val His Phe Leu Pro Leu Leu Ala Leu Leu Ala Leu
1 5 10 15

Trp Glu Pro Lys Pro Thr Gln Ala Phe Val Lys Gln His Leu Cys Gly
20 25 30

Pro His Leu Val Glu Ala Leu Tyr Leu Val Cys Gly Glu Arg Gly Phe
35 40 45

Phe Tyr Thr Pro Lys Ser Arg Arg Glu Val Glu Asp Pro Gln Val Glu
50 55 60

Gln Leu Glu Leu Gly Gly Ser Pro Gly Asp Leu Gln Thr Leu Ala Leu
65 70 75 80

Glu Val Ala Arg Gln Lys Arg Gly Ile Val Asp Gln Cys Cys Thr Ser
85 90 95

Ile Cys Ser Leu Tyr Gln Leu Glu Asn Tyr Cys Asn
100 105

<210> SEQ ID NO 72
<211> LENGTH: 469
<212> TYPE: DNA
<213> ORGANISM: Homo sapiens

<400> SEQUENCE: 72
agccctccag gacaggctgc atcagaagag gccatcaagc agatcactgt ccttctgcca 60
tggccctgtg gatgcgcctc ctgcccctgc tggcgctgct ggccctctgg ggacctgacc 120
cagccgcagc ctttgtgaac caacacctgt gcggctcaca cctggtggaa gctctctacc 180
tagtgtgcgg ggaacgaggc ttcttctaca cacccaagac ccgccgggag gcagaggacc 240
tgcaggtggg gcaggtggag ctgggcgggg gccctggtgc aggcagcctg cagcccttgg 300
ccctggaggg gtccctgcag aagcgtggca ttgtggaaca atgctgtacc agcatctgct 360
ccctctacca gctggagaac tactgcaact agacgcagcc cgcaggcagc cccacacccg 420
ccgcctcctg caccgagaga gatggaataa agcccttgaa ccagcaaaa 469

<210> SEQ ID NO 73
<211> LENGTH: 1036
<212> TYPE: DNA
<213> ORGANISM: Mus musculus

<400> SEQUENCE: 73
cttcagcccc tctggccatc tgcctaccca ccccacctgg agaccttaat gggccaaaca 60
gcaaagtcca gggggcagag aggaggtact ttggactata aagctggtgg gcatccagta 120
acccccagcc cttagtgacc agctataatc agagaccatc agcaagcagg tcattgtttc 180
aacatggccc tgttggtgca cttcctaccc ctgctggccc tgcttgccct ctgggagccc 240
aaacccaccc aggcttttgt caaacagcat ctttgtggtc cccacctggt agaggctctc 300
tacctggtgt gtggggagcg tggcttcttc tacacaccca agtcccgccg tgaagtggag 360
gacccacaag tggaacaact ggagctggga ggaagccccg gggaccttca gaccttggcg 420
ttggaggtgg cccggcagaa gcgtggcatt gtggatcagt gctgcaccag catctgctcc 480
ctctaccagc tggagaacta ctgcaactaa ggcccacctc gacccgcccc acccctctgc 540
aatgaataaa acttttgaat aagcaccaaa aaaaagagtt ctataatgaa tgaaaaagga 600
ttgtgtatat agacatcttt ttctctggca tttattgtca tgttagcata ctattaaacc 660
attgttaggt tggatgatta tataatcatg tatgaagctt gtgataaaac accaggaata 720

```
attcaagtat ctggaattct gcttcctgcc caagaaggta ggcaaccgtg taaatgccac    780

tgaagctact agtctaaaag tgagttatct ctgtctttgt cttacccccct gatgctgtga    840

taaaaccctg acaagagcaa ctgactcctg agaggaaggt ttattctagc tcacaattcc    900

aggttacaaa cagtccatcc gtagcagggg agtcacagca acaggaacct cagggaactg    960

ctcctattat ccccacaatc aagaatagtg accaataaat aagtggatct tttctcaaaa   1020

aaaaaaaaaa aaaaaa                                                   1036


<210> SEQ ID NO 74
<211> LENGTH: 511
<212> TYPE: PRT
<213> ORGANISM: Homo sapiens

<400> SEQUENCE: 74

Met Lys Phe Phe Leu Leu Leu Phe Thr Ile Gly Phe Cys Trp Ala Gln
1               5                   10                  15

Tyr Ser Pro Asn Thr Gln Gln Gly Arg Thr Ser Ile Val His Leu Phe
            20                  25                  30

Glu Trp Arg Trp Val Asp Ile Ala Leu Glu Cys Glu Arg Tyr Leu Ala
        35                  40                  45

Pro Lys Gly Phe Gly Gly Val Gln Val Ser Pro Pro Asn Glu Asn Val
    50                  55                  60

Ala Ile Tyr Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
                85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
        115                 120                 125

Thr Cys Gly Ser Tyr Phe Asn Pro Gly Ser Arg Asp Phe Pro Ala Val
    130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
                165                 170                 175

Leu Thr Gly Leu Leu Asp Leu Ala Leu Glu Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Leu Asp Ala Ser Lys His Met Trp Pro Gly Asp Ile Lys Ala
    210                 215                 220

Ile Leu Asp Lys Leu His Asn Leu Asn Ser Asn Trp Phe Pro Ala Gly
225                 230                 235                 240

Ser Lys Pro Phe Ile Tyr Gln Glu Val Ile Asp Leu Gly Gly Glu Pro
                245                 250                 255

Ile Lys Ser Ser Asp Tyr Phe Gly Asn Gly Arg Val Thr Glu Phe Lys
            260                 265                 270

Tyr Gly Ala Lys Leu Gly Thr Val Ile Arg Lys Trp Asn Gly Glu Lys
        275                 280                 285

Met Ser Tyr Leu Lys Asn Trp Gly Glu Gly Trp Gly Phe Val Pro Ser
    290                 295                 300

Asp Arg Ala Leu Val Phe Val Asp Asn His Asp Asn Gln Arg Gly His
```

```
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
            340                 345                 350

Val Met Ser Ser Tyr Arg Trp Pro Arg Gln Phe Gln Asn Gly Asn Asp
        355                 360                 365

Val Asn Asp Trp Val Gly Pro Pro Asn Asn Asn Gly Val Ile Lys Glu
    370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
            420                 425                 430

Ala Phe Gly Arg Gly Asn Arg Gly Phe Ile Val Phe Asn Asn Asp Asp
        435                 440                 445

Trp Ser Phe Ser Leu Thr Leu Gln Thr Gly Leu Pro Ala Gly Thr Tyr
    450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
            500                 505                 510


<210> SEQ ID NO 75
<211> LENGTH: 508
<212> TYPE: PRT
<213> ORGANISM: Mus musculus

<400> SEQUENCE: 75

Met Lys Phe Val Leu Leu Leu Ser Leu Ile Gly Phe Cys Trp Ala Gln
1               5                   10                  15

Tyr Asp Pro His Thr Ser Asp Gly Arg Thr Ala Ile Val His Leu Phe
            20                  25                  30

Glu Trp Arg Trp Val Asp Ile Ala Lys Glu Cys Glu Arg Tyr Leu Ala
        35                  40                  45

Pro Lys Gly Phe Gly Gly Val Gln Val Ser Pro Pro Asn Glu Asn Val
    50                  55                  60

Val Val His Asn Pro Ser Arg Pro Trp Trp Glu Arg Tyr Gln Pro Ile
65                  70                  75                  80

Ser Tyr Lys Ile Cys Thr Arg Ser Gly Asn Glu Asp Glu Phe Arg Asp
                85                  90                  95

Met Val Thr Arg Cys Asn Asn Val Gly Val Arg Ile Tyr Val Asp Ala
            100                 105                 110

Val Ile Asn His Met Cys Gly Ala Gly Asn Pro Ala Gly Thr Ser Ser
        115                 120                 125

Thr Cys Gly Ser Tyr Leu Asn Pro Asn Asn Arg Glu Phe Pro Ala Val
    130                 135                 140

Pro Tyr Ser Ala Trp Asp Phe Asn Asp Asn Lys Cys Asn Gly Glu Ile
145                 150                 155                 160

Asp Asn Tyr Asn Asp Ala Tyr Gln Val Arg Asn Cys Arg Leu Thr Gly
                165                 170                 175
```

```
Leu Leu Asp Leu Ala Leu Glu Lys Asp Tyr Val Arg Thr Lys Val Ala
            180                 185                 190

Asp Tyr Met Asn His Leu Ile Asp Ile Gly Val Ala Gly Phe Arg Leu
        195                 200                 205

Asp Ala Ala Lys His Met Trp Pro Gly Asp Ile Lys Ala Val Leu Asp
    210                 215                 220

Lys Leu His Asn Leu Asn Thr Lys Trp Phe Ser Gln Gly Ser Arg Pro
225                 230                 235                 240

Phe Ile Phe Gln Glu Val Ile Asp Leu Gly Gly Glu Ala Ile Lys Gly
                245                 250                 255

Ser Glu Tyr Phe Gly Asn Gly Arg Val Thr Glu Phe Lys Tyr Gly Ala
            260                 265                 270

Lys Leu Gly Thr Val Ile Arg Lys Trp Asn Gly Glu Lys Met Ser Tyr
        275                 280                 285

Leu Lys Asn Trp Gly Glu Gly Trp Gly Leu Val Pro Ser Asp Arg Ala
    290                 295                 300

Leu Val Phe Val Asp Asn His Asp Asn Gln Arg Gly His Gly Ala Gly
305                 310                 315                 320

Gly Ser Ser Ile Leu Thr Phe Trp Asp Ala Arg Met Tyr Lys Met Ala
                325                 330                 335

Val Gly Phe Met Leu Ala His Pro Tyr Gly Phe Thr Arg Val Met Ser
            340                 345                 350

Ser Tyr Arg Trp Asn Arg Asn Phe Gln Asn Gly Lys Asp Gln Asn Asp
        355                 360                 365

Trp Ile Gly Pro Pro Asn Asn Asn Gly Val Thr Lys Glu Val Thr Ile
    370                 375                 380

Asn Ala Asp Thr Thr Cys Gly Asn Asp Trp Val Cys Glu His Arg Trp
385                 390                 395                 400

Arg Gln Ile Arg Asn Met Val Ala Phe Arg Asn Val Val Asn Gly Gln
                405                 410                 415

Pro Phe Ser Asn Trp Trp Asp Asn Asn Ser Asn Gln Val Ala Phe Ser
            420                 425                 430

Arg Gly Asn Arg Gly Phe Ile Val Phe Asn Asn Asp Asp Trp Ala Leu
        435                 440                 445

Ser Ala Thr Leu Gln Thr Gly Leu Pro Ala Gly Thr Tyr Cys Asp Val
    450                 455                 460

Ile Ser Gly Asp Lys Val Asp Gly Asn Cys Thr Gly Leu Arg Val Asn
465                 470                 475                 480

Val Gly Ser Asp Gly Lys Ala His Phe Ser Ile Ser Asn Ser Ala Glu
                485                 490                 495

Asp Pro Phe Ile Ala Ile His Ala Asp Ser Lys Leu
            500                 505
```

<210> SEQ ID NO 76
<211> LENGTH: 1660
<212> TYPE: DNA
<213> ORGANISM: Homo sapiens

<400> SEQUENCE: 76

```
aaaatgtgct tcttacagga atataaatag tttctggaaa ggacactgac aacttcaaag      60

caaaatgaag ttctttctgt tgcttttcac cattgggttc tgctgggctc agtattcccc     120

aaatacacaa caaggacgga catctattgt tcatctgttt gaatggcgat gggttgatat     180

tgctcttgaa tgtgagcgat atttagctcc gaagggattt ggaggggttc aggtctctcc     240
```

```
accaaatgaa aatgttgcaa tttacaaccc tttcagacct tggtgggaaa gataccaacc    300
agttagctat aaattatgca caagatctgg aaatgaagat gaatttagaa acatggtgac    360
tagatgtaac aatgttgggg ttcgtattta tgtggatgct gtaattaatc atatgtgtgg    420
taacgctgtg agtgcaggaa caagcagtac ctgtggaagt tacttcaacc ctggaagtag    480
ggactttcca gcagtcccat attctggatg ggatttcaat gatggtaaat gtaaaactgg    540
aagtggagat atcgagaact acaatgatgc tactcaggtc agagattgtc gtctgactgg    600
tcttcttgat cttgcactgg agaaggatta cgtgcgttct aagattgccg aatatatgaa    660
ccatctcatt gacattggtg ttgcagggtt cagacttgat gcttccaagc acatgtggcc    720
tggagacata aaggcaattt tggacaaact gcataatcta aacagtaact ggttccctgc    780
aggaagtaaa cctttcattt accaggaggt aattgatctg ggtggtgagc caattaaaag    840
cagtgactac tttggtaatg gccgggtgac agaattcaag tatggtgcaa aactcggcac    900
agttattcgc aagtggaatg gagagaagat gtcttactta aagaactggg gagaaggttg    960
gggtttcgta ccttctgaca gagcgcttgt ctttgtggat aaccatgaca atcaacgagg   1020
acatggggct ggaggagcct ctattcttac cttctgggat gctaggctgt acaaaaatggc   1080
agttggattt atgcttgctc atccttacgg atttacacga gtaatgtcaa gctaccgttg   1140
gccaagacag tttcaaaatg gaaacgatgt taatgattgg gttgggccac caaataataa   1200
tggagtaatt aaagaagtta ctattaatcc agacactact tgtggcaatg actgggtctg   1260
tgaacatcga tggcgccaaa taaggaacat ggttattttc cgcaatgtag tggatggcca   1320
gccttttaca aattggtatg ataatgggag caaccaagtg gcttttggga gaggaaacag   1380
aggattcatt gttttcaaca atgatgactg gtcatttttct ttaactttgc aaactggtct   1440
tcctgctggc acatactgtg atgtcatttc tggagataaa attaatggca attgcacagg   1500
cattaaaatt tacgtttctg atgatggcaa agctcatttt tctattagta actctgctga   1560
agatccattt attgcaattc atgctgaatc taaattgtaa aatttaaaat taaatgcatg   1620
tcctcaaaac aaaaaaaaaa aaaaaaaaaa aaaaaaaaaa                           1660
```

<210> SEQ ID NO 77
<211> LENGTH: 1590
<212> TYPE: DNA
<213> ORGANISM: Mus musculus

<400> SEQUENCE: 77

```
cccacgcgtc cgatgaagtt cgttctgctg ctttccctca ttgggttctg ctgggctcaa     60
tatgacccac atacttcaga tgggaggact gctattgtcc acctgttcga gtggcgctgg    120
gttgatattg ccaaggaatg tgagcgatac ttagctccta agggatttgg aggggtgcag    180
gtctctccac ccaatgaaaa cgttgtagtt cataacccat caagaccttg gtgggaaaga    240
taccaaccaa tcagctataa aatctgcaca aggtctggaa atgaagatga attcagagac    300
atggtgacaa ggtgcaacaa tgttggtgtc cgtatttatg tggatgctgt cattaaccac    360
atgtgtggcg caggcaatcc tgcaggaaca agcagtacct gtggaagtta cctcaatcca    420
aataacaggg aattcccagc agttccatac tctgcttggg actttaacga taataaatgt    480
aatggagaaa ttgataacta caatgatgct tatcaggtca gaaattgtcg tctgactggc    540
cttctggatc ttgcacttga gaaagattat gttcgtacca aggtggctga ctatatgaac    600
catctcattg acattggagt agcagggttc agacttgatg ctgctaagca catgtggcct    660
ggagacataa aggcagtttt ggacaaactg cataatctca atacaaaatg gttctcccaa    720
```

```
ggaagcagac ctttcatttt ccaagaggtc attgatctgg gtggtgaggc aattaaaggt    780

agtgagtact ttggaaatgg ccgtgtgaca gaattcaagt atggtgcaaa acttggcaca    840

gttatccgca agtggaatgg cgagaagatg tcctatttaa agaactgggg agaaggttgg    900

ggtttggtgc cttctgacag agcccttgtg tttgtggaca accatgataa tcagcgagga    960

catggtgctg gaggatcatc catcctgaca ttctgggatg ctagaatgta taaaatggct   1020

gtcggattta tgttggctca tccttatgga ttcacaagag taatgtcaag ttaccgttgg   1080

aatagaaatt tccagaatgg aaaagatcag aatgactgga ttggaccacc caataacaat   1140

ggagtaacaa aagaagtgac cattaatgca gacactactt gtggcaatga ctgggtctgt   1200

gaacacagat ggcgtcaaat caggaacatg gttgccttca ggaatgtggt caatggtcag   1260

ccttttttcaa actggtggga taataacagc aaccaagtag cttttagcag aggaaacaga   1320

ggattcattg tctttaacaa tgatgactgg gctttgtcag ccactttaca gactggtctt   1380

cctgctggca catactgtga tgtcatctct ggagataagg tcgatggcaa ttgcactgga   1440

cttagagtga atgttggcag tgatggcaaa gctcactttt ccattagtaa ctctgctgag   1500

gacccattta ttgcaatcca tgctgactca aaattgtaag aatctatatt aaagagattt   1560

ggattaagca aaaaaaaaaa aaaaaaaaaa                                    1590
```

<210> SEQ ID NO 78
<211> LENGTH: 180
<212> TYPE: PRT
<213> ORGANISM: Homo sapiens

<400> SEQUENCE: 78

```
Met Lys Ser Ile Tyr Phe Val Ala Gly Leu Phe Val Met Leu Val Gln
1               5                   10                  15

Gly Ser Trp Gln Arg Ser Leu Gln Asp Thr Glu Glu Lys Ser Arg Ser
            20                  25                  30

Phe Ser Ala Ser Gln Ala Asp Pro Leu Ser Asp Pro Asp Gln Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Val Glu Glu Leu Gly Arg
    130                 135                 140

Arg His Ala Asp Gly Ser Phe Ser Asp Glu Met Asn Thr Ile Leu Asp
145                 150                 155                 160

Asn Leu Ala Ala Arg Asp Phe Ile Asn Trp Leu Ile Gln Thr Lys Ile
                165                 170                 175

Thr Asp Arg Lys
            180
```

<210> SEQ ID NO 79
<211> LENGTH: 180
<212> TYPE: PRT

<213> ORGANISM: Mus musculus

<400> SEQUENCE: 79

```
Met Lys Thr Ile Tyr Phe Val Ala Gly Leu Leu Ile Met Leu Val Gln
1               5                   10                  15

Gly Ser Trp Gln His Ala Leu Gln Asp Thr Glu Glu Asn Pro Arg Ser
            20                  25                  30

Phe Pro Ala Ser Gln Thr Glu Ala His Glu Asp Pro Asp Glu Met Asn
        35                  40                  45

Glu Asp Lys Arg His Ser Gln Gly Thr Phe Thr Ser Asp Tyr Ser Lys
    50                  55                  60

Tyr Leu Asp Ser Arg Arg Ala Gln Asp Phe Val Gln Trp Leu Met Asn
65                  70                  75                  80

Thr Lys Arg Asn Arg Asn Asn Ile Ala Lys Arg His Asp Glu Phe Glu
                85                  90                  95

Arg His Ala Glu Gly Thr Phe Thr Ser Asp Val Ser Ser Tyr Leu Glu
            100                 105                 110

Gly Gln Ala Ala Lys Glu Phe Ile Ala Trp Leu Val Lys Gly Arg Gly
        115                 120                 125

Arg Arg Asp Phe Pro Glu Glu Val Ala Ile Ala Glu Glu Leu Gly Arg
    130                 135                 140

Arg His Ala Asp Gly Ser Phe Ser Asp Glu Met Ser Thr Ile Leu Asp
145                 150                 155                 160

Asn Leu Ala Thr Arg Asp Phe Ile Asn Trp Leu Ile Gln Thr Lys Ile
                165                 170                 175

Thr Asp Lys Lys
            180
```

<210> SEQ ID NO 80
<211> LENGTH: 1128
<212> TYPE: DNA
<213> ORGANISM: Homo sapiens

<400> SEQUENCE: 80

```
acagagctta ggacacagag cacatcaaaa gttcccaaag agggcttgct ctctcttcac      60

ctgctctgtt ctacagcaca ctaccagaag acagcagaaa tgaaaagcat ttactttgtg     120

gctggattat ttgtaatgct ggtacaaggc agctggcaac gttcccttca agacacagag     180

gagaaatcca gatcattctc agcttcccag gcagacccac tcagtgatcc tgatcagatg     240

aacgaggaca agcgccattc acagggcaca ttcaccagtg actacagcaa gtatctggac     300

tccaggcgtg cccaagattt tgtgcagtgg ttgatgaata ccaagaggaa caggaataac     360

attgccaaac gtcacgatga atttgagaga catgctgaag ggacctttac cagtgatgta     420

agttcttatt tggaaggcca agctgccaag gaattcattg cttggctggt gaaaggccga     480

ggaaggcgag atttcccaga agaggtcgcc attgttgaag aacttggccg cagacatgct     540

gatggttctt tctctgatga gatgaacacc attcttgata atcttgccgc cagggacttt     600

ataaactggt tgattcagac caaaatcact gacaggaaat aactatatca ctattcaaga     660

tcatcttcac aacatcacct gctagccacg tgggatgttt gaaatgttaa gtcctgtaaa     720

tttaagaggt gtattctgag gccacattgc tttgcatgcc aataaataaa ttttctttta     780

gtgttgtgta gccaaaaatt acaaatggaa taaagtttta tcaaaatatt gctaaaatat     840

cagctttaaa atatgaaagt gctagattct gttattttct tcttattttg gatgaagtac     900

cccaacctgt ttacatttag cgataaaatt atttttctat gatataattt gtaaatgtaa     960
```

```
attattccga tctgacatat ctgcattata ataataggag aatagaagaa ctggtagcca   1020

cagtggtgaa attggaaaga gaactttctt cctgaaacct ttgtcttaaa aatactcagc   1080

tttcaatgta tcaaagatac aattaaataa aattttcaag cttcttta                1128


<210> SEQ ID NO 81
<211> LENGTH: 1091
<212> TYPE: DNA
<213> ORGANISM: Mus musculus

<400> SEQUENCE: 81

agaagggcag agcttgggcc caggacacac tcaaagttcc caaggggact ccctctgtct     60

acacctgttc gcagctcagg ctcacaaggc agaaaaaaaa atgaagacca tttactttgt    120

ggctggattg cttataatgc tggtgcaagg cagctggcag cacgcccttc aagacacaga    180

ggagaacccc agatcattcc cagcttccca gacagaagcg catgaggacc ctgatgagat    240

gaatgaagac aaacgccact cacagggcac attcaccagc gactacagca aatacctgga    300

ctcccgccgt gcccaagatt ttgtgcagtg gttgatgaac accaagagga accggaacaa    360

cattgccaaa cgtcatgatg aatttgagag gcatgctgaa gggaccttta ccagtgatgt    420

gagttcttac ttggagggcc aggcagcaaa ggaattcatt gcttggctgg tgaaaggccg    480

aggaaggcga gacttcccag aagaagtcgc cattgccgag gaactcggcc gcaggcacgc    540

tgatggctcc ttctctgacg agatgagcac cattctggat aatcttgcca ccagggactt    600

catcaactgg ctgattcaaa ccaagatcac tgacaagaaa taggtatttc accattcaca    660

accatcttca caacatctcg tgccagtcac ttgggatgta caatttcaaa gctatatcct    720

gaagctatat tgctttgcat gcagatgaat acatttccct ctagcattgt gtaacccaac    780

gattgtatat gaattaaagt atttccagga tgttgataaa aataacaact ttacagtatg    840

aaaattctgg attctcatat ttttttctcc tcattttaaa gtcccccccc ccccgagatt    900

atttttctgt gatataaatt gtaaattatc gcagtcacaa cacctggatt atactaacag    960

aagacatgac cacctggtaa ccgtagtggt aaacctggaa agagaacttc ttccttgaat   1020

cctttaccat aaatgcactc agcttttgat gtatcaagaa tagatttaaa taaatatttc   1080

attctttgtt a                                                        1091


<210> SEQ ID NO 82
<211> LENGTH: 116
<212> TYPE: PRT
<213> ORGANISM: Homo sapiens

<400> SEQUENCE: 82

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95
```

```
Ala Pro Arg Glu Arg Lys Ala Gly Cys Lys Asn Phe Phe Trp Lys Thr
            100                 105                 110

Phe Thr Ser Cys
        115


<210> SEQ ID NO 83
<211> LENGTH: 116
<212> TYPE: PRT
<213> ORGANISM: Mus musculus

<400> SEQUENCE: 83

Met Leu Ser Cys Arg Leu Gln Cys Ala Leu Ala Ala Leu Cys Ile Val
1               5                   10                  15

Leu Ala Leu Gly Gly Val Thr Gly Ala Pro Ser Asp Pro Arg Leu Arg
            20                  25                  30

Gln Phe Leu Gln Lys Ser Leu Ala Ala Ala Thr Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Pro Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115


<210> SEQ ID NO 84
<211> LENGTH: 665
<212> TYPE: DNA
<213> ORGANISM: Homo sapiens

<400> SEQUENCE: 84

gggagacggt tgagagcaca caagccgctt taggagcgag gttcggagcc atcgctgctg      60

cctgctgatc cgcgcctaga gtttgaccag ccactctcca gctcggcttt cgcggcgccg     120

agatgctgtc ctgccgcctc cagtgcgcgc tggctgcgct gtccatcgtc ctggccctgg     180

gctgtgtcac cggcgctccc tcggacccca gactccgtca gtttctgcag aagtccctgg     240

ctgctgccgc ggggaagcag gaactggcca agtacttctt ggcagagctg ctgtctgaac     300

ccaaccagac ggagaatgat gccctggaac ctgaagatct gtcccaggct gctgagcagg     360

atgaaatgag gcttgagctg cagagatctg ctaactcaaa cccggctatg gcaccccgag     420

aacgcaaagc tggctgcaag aatttcttct ggaagacttt cacatcctgt tagctttctt     480

aactagtatt gtccatatca gacctctgat ccctcgcccc cacaccccat ctctcttccc     540

taatcctcca agtcttcagc gagacccttg cattagaaac tgaaaactgt aaatacaaaa     600

taaaattatg gtgaaattat gaaaaatgtg aaaaaaaaaa aaaaaaaaaa aaaaaaaaaa     660

aaaaa                                                                 665


<210> SEQ ID NO 85
<211> LENGTH: 599
<212> TYPE: DNA
<213> ORGANISM: Mus musculus

<400> SEQUENCE: 85

agcggctgaa ggagacgcta ccgaagccgt cgctgctgcc tgaggacctg cgactagact      60
```

```
gacccaccgc gctccagctt ggctgcctga ggcaaggaag atgctgtcct gccgtctcca    120

gtgcgccctg gctgcgctct gcatcgtcct ggctttgggc ggtgtcaccg gcgcgccctc    180

ggaccccaga ctccgtcagt ttctgcagaa gtctctggcg gctgccaccg ggaaacagga    240

actggccaag tacttcttgg cagagctgct gtccgagccc aaccagacag agaatgatgc    300

cctggagccc gaggatttgc cccaggcagc tgagcaggac gagatgaggc tggagctgca    360

gaggtctgcc aactcgaacc cagcaatggc accccgggaa cgcaaagctg gctgcaagaa    420

cttcttctgg aagacattca catcctgtta gctttaatat tgttgtccta gccagacctc    480

tgatccctct cccccaaacc ccatatctct tccttaactc ctggcccccg atgctcaact    540

tgaccctgca ttagaaattg aagactgtaa atacaaaata aaattatggt gagattatg     599
```

<210> SEQ ID NO 86
<211> LENGTH: 328
<212> TYPE: PRT
<213> ORGANISM: Homo sapiens

<400> SEQUENCE: 86

```
Met Asp Ala Val Leu Leu Glu His Phe Pro Gly Gly Leu Asp Ala Phe
1               5                   10                  15

Pro Ser Ser Tyr Phe Asp Glu Asp Asp Phe Phe Thr Asp Gln Ser Ser
            20                  25                  30

Arg Asp Pro Leu Glu Asp Gly Asp Glu Leu Leu Ala Asp Glu Gln Ala
        35                  40                  45

Glu Val Glu Phe Leu Ser His Gln Leu His Glu Tyr Cys Tyr Arg Asp
    50                  55                  60

Gly Ala Cys Leu Leu Leu Gln Pro Ala Pro Pro Ala Ala Pro Leu Ala
65                  70                  75                  80

Leu Ala Pro Pro Ser Ser Gly Gly Leu Gly Glu Pro Asp Asp Gly Gly
                85                  90                  95

Gly Gly Gly Tyr Cys Cys Glu Thr Gly Ala Pro Pro Gly Gly Phe Pro
            100                 105                 110

Tyr Ser Pro Gly Ser Pro Pro Ser Cys Leu Ala Tyr Pro Cys Ala Gly
        115                 120                 125

Ala Ala Val Leu Ser Pro Gly Ala Arg Leu Arg Gly Leu Ser Gly Ala
    130                 135                 140

Ala Ala Ala Ala Ala Arg Arg Arg Arg Arg Val Arg Ser Glu Ala Glu
145                 150                 155                 160

Leu Gln Gln Leu Arg Gln Ala Ala Asn Val Arg Glu Arg Arg Arg Met
                165                 170                 175

Gln Ser Ile Asn Asp Ala Phe Glu Gly Leu Arg Ser His Ile Pro Thr
            180                 185                 190

Leu Pro Tyr Glu Lys Arg Leu Ser Lys Val Asp Thr Leu Arg Leu Ala
        195                 200                 205

Ile Gly Tyr Ile Asn Phe Leu Ser Glu Leu Val Gln Ala Asp Leu Pro
    210                 215                 220

Leu Arg Gly Gly Gly Ala Gly Gly Cys Gly Gly Pro Gly Gly Gly Gly
225                 230                 235                 240

Arg Leu Gly Gly Asp Ser Pro Gly Ser Gln Ala Gln Lys Val Ile Ile
                245                 250                 255

Cys His Arg Gly Thr Arg Ser Pro Ser Pro Ser Asp Pro Asp Tyr Gly
            260                 265                 270

Leu Pro Pro Leu Ala Gly His Ser Leu Ser Trp Thr Asp Glu Lys Gln
```

```
        275                 280                 285

Leu Lys Glu Gln Asn Ile Ile Arg Thr Ala Lys Val Trp Thr Pro Glu
    290                 295                 300

Asp Pro Arg Lys Leu Asn Ser Lys Ser Ser Phe Asn Asn Ile Glu Asn
305                 310                 315                 320

Glu Pro Pro Phe Glu Phe Val Ser
                325


<210> SEQ ID NO 87
<211> LENGTH: 324
<212> TYPE: PRT
<213> ORGANISM: Mus musculus

<400> SEQUENCE: 87

Met Asp Ala Val Leu Leu Glu His Phe Pro Gly Gly Leu Asp Thr Phe
1               5                   10                  15

Pro Ser Pro Tyr Phe Asp Glu Glu Asp Phe Phe Thr Asp Gln Ser Ser
            20                  25                  30

Arg Asp Pro Leu Glu Asp Ser Asp Glu Leu Leu Gly Asp Glu Gln Ala
        35                  40                  45

Glu Val Glu Phe Leu Ser His Gln Leu His Glu Tyr Cys Tyr Arg Asp
    50                  55                  60

Gly Ala Cys Leu Leu Leu Gln Pro Ala Pro Ser Ala Ala Pro His Ala
65                  70                  75                  80

Leu Ala Pro Pro Pro Leu Gly Asp Pro Gly Glu Pro Glu Asp Asn Val
                85                  90                  95

Ser Tyr Cys Cys Asp Ala Gly Ala Pro Leu Ala Ala Phe Pro Tyr Ser
            100                 105                 110

Pro Gly Ser Pro Pro Ser Cys Leu Ala Tyr Pro Cys Ala Ala Val Leu
        115                 120                 125

Ser Pro Gly Ala Arg Leu Gly Gly Leu Asn Gly Ala Ala Ala Ala Ala
    130                 135                 140

Ala Ala Arg Arg Arg Arg Arg Val Arg Ser Glu Ala Glu Leu Gln Gln
145                 150                 155                 160

Leu Arg Gln Ala Ala Asn Val Arg Glu Arg Arg Arg Met Gln Ser Ile
                165                 170                 175

Asn Asp Ala Phe Glu Gly Leu Arg Ser His Ile Pro Thr Leu Pro Tyr
            180                 185                 190

Glu Lys Arg Leu Ser Lys Val Asp Thr Leu Arg Leu Ala Ile Gly Tyr
        195                 200                 205

Ile Asn Phe Leu Ser Glu Leu Val Gln Ala Asp Leu Pro Leu Arg Gly
    210                 215                 220

Ser Gly Ala Gly Gly Cys Gly Gly Pro Gly Gly Ser Arg His Leu Gly
225                 230                 235                 240

Glu Asp Ser Pro Gly Asn Gln Ala Gln Lys Val Ile Ile Cys His Arg
                245                 250                 255

Gly Thr Arg Ser Pro Ser Pro Ser Asp Pro Asp Tyr Gly Leu Pro Pro
            260                 265                 270

Leu Ala Gly His Ser Leu Ser Trp Thr Asp Glu Lys Gln Leu Lys Glu
        275                 280                 285

Gln Asn Ile Ile Arg Thr Ala Lys Val Trp Thr Pro Glu Asp Pro Arg
    290                 295                 300

Lys Leu Asn Ser Lys Ser Phe Asp Asn Ile Glu Asn Glu Pro Pro Phe
305                 310                 315                 320
```

Glu Phe Val Ser

<210> SEQ ID NO 88
<211> LENGTH: 1339
<212> TYPE: DNA
<213> ORGANISM: Homo sapiens

<400> SEQUENCE: 88
atggacgcgg tgttgctgga gcacttcccc gggggcctag acgcctttcc ttcttcgtac 60
ttcgacgagg acgacttctt caccgaccag tcttcacggg accccctgga ggacggcgat 120
gagctgctgg cggacgagca ggccgaggtg gagttcctta gccaccagct ccacgagtac 180
tgctaccgcg acggggcgtg cctgctgctg cagcccgcgc ccccggccgc cccgctagcg 240
ctcgccccgc cgtcctcggg gggcctcggt gagccagacg acggcggcgg cggcggctac 300
tgctgcgaga cgggggcgcc cccaggcggc ttcccctact cgcccggctc gccgccctcg 360
tgcctggcct acccgtgcgc cggggcggca gtactgtctc ccggggcgcg gctgcgcggc 420
ctgagcggag cggcggctgc ggcggcgcgg cgccggcggc gggtgcgctc cgaggcggag 480
ctgcagcagc tgcggcaggc ggccaacgtg cgcgagcggc ggcgcatgca gtccatcaac 540
gacgccttcg aggggctgcg ctcgcacatc cccacgctgc cctacgagaa gcgcctctcc 600
aaggtggaca cgctgcgcct ggccatcggc tacatcaact tcctcagcga gctcgtgcag 660
gccgacctgc ccttgcgcgg cggtggcgcg ggcggctgcg gggggccggg cggcggcggg 720
cgcctgggcg gggacagccc gggcagccag gcccagaagg tcatcatctg ccatcggggc 780
acccggtccc cctcccccag cgaccctgat tatggcctcc ctcccctagc aggacactct 840
ctctcatgga ctgatgaaaa acaactcaag gaacaaaata ttatccgaac agccaaagtc 900
tggaccccag aggaccccag aaaactcaac agcaaatctt ccttcaacaa catagaaaac 960
gaaccaccat ttgagtttgt gtcctgagaa gtcccagact cggctgaaga tctgattatg 1020
tctctgtgca tattgtacat gtaaatatct ataatgtaaa tgtaatttaa gaatcaaatt 1080
tttcgaatgg caatcaactg tttattattt atctatttat tatcctgttg agttgatgaa 1140
atagatgatt tctttttaaa tatataattt atataactta tcctgatttt ctgaaaatat 1200
gcaatagcct atgattttcc tgaactctgt gttgttggga gaactctggc cagaaaacgt 1260
cctgcttatt tattgccaga tatggtttat ttctaagcgt tgtcaataaa tgctatttac 1320
accttttcct gaaaaaaaa 1339

<210> SEQ ID NO 89
<211> LENGTH: 1508
<212> TYPE: DNA
<213> ORGANISM: Mus musculus

<400> SEQUENCE: 89
tctccagtgc cagccagagc cagcggccgc gcgcactcca gggaggccct cgtgcgggga 60
cccgcggcca cctttgcctt ccccaacccc aaccccacga gggaggggct gagggaccta 120
cccgaattgc cacggatcac tcacaaagcg tcaccccgag cagcccattc gtccttccgg 180
gcctcggcgg ccgagggcat ggacgccgta ctcctggagc acttccccgg gggcctggac 240
accttcccat ccccttactt tgatgaggaa gatttcttca ccgaccagtc ctctcgggac 300
ccgctggagg acagcgacga gctgctgggg gacgagcaag cagaagtaga gttcctcagc 360
caccagctac acgaatactg ctaccgcgac ggggcgtgcc tgctgctgca acccgcgccc 420
tcggccgccc cgcacgcgct cgccccgccg cctttggggg atcctggcga gcccgaggac 480

```
aacgtcagct attgctgcga tgcaggggct cctctcgctg ccttccccta ctcgcctggc    540

tcaccgccct cgtgcctcgc ctacccgtgt gccgcggtgc tgtcccccgg tgcgcggctc    600

ggtggtttga acggggctgc ggcagcggcg gcagcaaggc ggcggcgacg cgtgcgctcc    660

gaggcggagc tgcagcagct gcgacaagcc gctaatgtgc gagagcggcg ccgcatgcag    720

tccatcaacg acgccttcga ggggctgcgt tcgcacatcc ccacgctacc ctacgaaaag    780

cgcctctcca aagtagacac gctgcgcttg gccataggct acattaactt cctcagcgag    840

ctggtgcaag ccgacctgcc gctgcgcggg agtggcgcag gtggttgcgg gggcccaggt    900

ggcagccggc acctcggaga ggacagtccc ggtaaccagg cccagaaggt tatcatctgc    960

catcgaggca cccgttcacc ctcccccagt gacccggatt atggtctccc tcctcttgca   1020

gggcactctc tttcctggac tgatgaaaaa cagctcaaag aacaaaatat catccgtaca   1080

gctaaagtgt ggaccccaga ggaccccaga aaactcaaca gtaaatcttt cgacaacata   1140

gagaacgaac caccctttga gtttgtgtcc tgagacagct cacatcgggt tggccgcgtc   1200

tttgtgcata ttgtacgtgt aaataaatac ctataatgta aatgtaattt aaagaccaca   1260

tttttctaat ggcaatcaac tgtttgttat ttatctattt attattctgt cgagttaatg   1320

aaatagattg tcttttaaaa tatataattt atataattta tcgtgatgtt ctataatatg   1380

atttcctgaa gcacctttga cagaagaact ggaagaactc tgtccaggaa actccgtgct   1440

tatttaatat cagaattggt ttatttctga gtgttgttaa taaatgttat tcacatgtgt   1500

ttctataa                                                             1508
```

<210> SEQ ID NO 90
<211> LENGTH: 400
<212> TYPE: PRT
<213> ORGANISM: Homo sapiens

<400> SEQUENCE: 90

```
Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Ser Gly Ala Tyr Gly Gly Gly
    50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
    130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
```

```
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
    210                 215                 220

Leu Arg Gly Gln Val Gly Gly Gln Val Ser Val Glu Val Asp Ser Ala
225                 230                 235                 240

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
        355                 360                 365

Ile Lys Ser Arg Leu Glu Gln Glu Ile Ala Thr Tyr Arg Ser Leu Leu
    370                 375                 380

Glu Gly Gln Glu Asp His Tyr Asn Asn Leu Ser Ala Ser Lys Val Leu
385                 390                 395                 400


<210> SEQ ID NO 91
<211> LENGTH: 403
<212> TYPE: PRT
<213> ORGANISM: Mus musculus

<400> SEQUENCE: 91

Met Thr Ser Tyr Ser Tyr Arg Gln Thr Ser Ala Met Ser Ser Phe Gly
1               5                   10                  15

Gly Thr Gly Gly Gly Ser Val Arg Ile Gly Ser Gly Gly Val Phe Arg
            20                  25                  30

Ala Pro Ser Ile His Gly Gly Ser Gly Gly Arg Gly Val Ser Val Ser
        35                  40                  45

Ser Thr Arg Phe Val Thr Ser Ser Ser Gly Ser Tyr Gly Gly Val Arg
    50                  55                  60

Gly Gly Ser Phe Ser Gly Thr Leu Ala Val Ser Asp Gly Leu Leu Ser
65                  70                  75                  80

Gly Asn Glu Lys Ile Thr Met Gln Asn Leu Asn Asp Arg Leu Ala Ser
                85                  90                  95

Tyr Leu Asp Lys Val Arg Ala Leu Glu Gln Ala Asn Gly Glu Leu Glu
            100                 105                 110

Val Lys Ile Arg Asp Trp Tyr Gln Lys Gln Gly Pro Gly Pro Ser Arg
        115                 120                 125

Asp Tyr Asn His Tyr Phe Lys Thr Ile Glu Asp Leu Arg Asp Lys Ile
    130                 135                 140

Leu Gly Ala Thr Ile Asp Asn Ser Lys Ile Val Leu Gln Ile Asp Asn
145                 150                 155                 160
```

```
Ala Arg Leu Ala Ala Asp Asp Phe Arg Thr Lys Phe Glu Thr Glu His
                165                 170                 175

Ala Leu Arg Leu Ser Val Glu Ala Asp Ile Asn Gly Leu Arg Arg Val
            180                 185                 190

Leu Asp Glu Leu Thr Leu Ala Arg Thr Asp Leu Glu Met Gln Ile Glu
        195                 200                 205

Ser Leu Lys Glu Glu Leu Ala Tyr Leu Lys Lys Asn His Glu Glu Glu
    210                 215                 220

Ile Thr Ala Leu Arg Ser Gln Val Gly Gly Gln Val Ser Val Glu Val
225                 230                 235                 240

Asp Ser Thr Pro Gly Val Asp Leu Ala Lys Ile Leu Ser Glu Met Arg
                245                 250                 255

Ser Gln Tyr Glu Ile Met Ala Glu Lys Asn Arg Lys Asp Ala Glu Ala
            260                 265                 270

Thr Tyr Leu Ala Arg Ile Glu Glu Leu Asn Thr Gln Val Ala Val His
        275                 280                 285

Ser Glu Gln Ile Gln Ile Ser Lys Thr Glu Val Thr Asp Leu Arg Arg
    290                 295                 300

Thr Leu Gln Gly Leu Glu Ile Glu Leu Gln Ser Gln Leu Ser Met Lys
305                 310                 315                 320

Ala Ala Leu Glu Gly Thr Leu Ala Glu Thr Glu Ala Arg Tyr Gly Val
                325                 330                 335

Gln Leu Ser Gln Ile Gln Ser Val Ile Ser Gly Phe Glu Ala Gln Leu
            340                 345                 350

Ser Asp Val Arg Ala Asp Ile Glu Arg Gln Asn Gln Glu Tyr Lys Gln
        355                 360                 365

Leu Met Asp Ile Lys Ser Arg Leu Glu Gln Glu Ile Ala Thr Tyr Arg
    370                 375                 380

Ser Leu Leu Glu Gly Gln Glu Ala His Tyr Asn Asn Leu Pro Thr Pro
385                 390                 395                 400

Lys Ala Ile


<210> SEQ ID NO 92
<211> LENGTH: 1490
<212> TYPE: DNA
<213> ORGANISM: Homo sapiens

<400> SEQUENCE: 92

agatatccgc ccctgacacc attcctccct tccccccctcc accggccgcg ggcataaaag      60

gcgccaggtg agggcctcgc cgctcctccc gcgaatcgca gcttctgaga ccagggttgc     120

tccgtccgtg ctccgcctcg ccatgacttc ctacagctat cgccagtcgt cggccacgtc     180

gtccttcgga ggcctgggcg gcggctccgt gcgttttggg ccgggggtcg cctttcgcgc     240

gcccagcatt cacgggggct ccggcggccg cggcgtatcc gtgtcctccg cccgctttgt     300

gtcctcgtcc tcctcggggg cctacggcgg cggctacggc ggcgtcctga ccgcgtccga     360

cgggctgctg gcgggcaacg agaagctaac catgcagaac ctcaacgacc gcctggcctc     420

ctacctggac aaggtgcgcg ccctggaggc ggccaacggc gagctagagg tgaagatccg     480

cgactggtac cagaagcagg ggcctgggcc ctcccgcgac tacagccact actacacgac     540

catccaggac ctgcgggaca agattcttgg tgccaccatt gagaactcca ggattgtcct     600

gcagatcgac aatgcccgtc tggctgcaga tgacttccga accaagtttg agacggaaca     660

ggctctgcgc atgagcgtgg aggccgacat caacggcctg cgcagggtgc tggatgagct     720
```

```
gaccctggcc aggaccgacc tggagatgca gatcgaaggc ctgaaggaag agctggccta    780
cctgaagaag aaccatgagg aggaaatcag tacgctgagg ggccaagtgg gaggccaggt    840
cagtgtggag gtggattccg ctccgggcac cgatctcgcc aagatcctga gtgacatgcg    900
aagccaatat gaggtcatgg ccgagcagaa ccggaaggat gctgaagcct ggttcaccag    960
ccggactgaa gaattgaacc gggaggtcgc tggccacacg gagcagctcc agatgagcag   1020
gtccgaggtt actgacctgc ggcgcaccct tcagggtctt gagattgagc tgcagtcaca   1080
gctgagcatg aaagctgcct tggaagacac actggcagaa acggaggcgc gctttggagc   1140
ccagctggcg catatccagg cgctgatcag cggtattgaa gcccagctgg gcgatgtgcg   1200
agctgatagt gagcggcaga atcaggagta ccagcggctc atggacatca agtcgcggct   1260
ggagcaggag attgccacct accgcagcct gctcgaggga caggaagatc actacaacaa   1320
tttgtctgcc tccaaggtcc tctgaggcag caggctctgg ggcttctgct gtcctttgga   1380
gggtgtcttc tgggtagagg gatgggaagg aagggaccct tacccccggc tcttctcctg   1440
acctgccaat aaaaatttat ggtccaaggg aaaaaaaaaa aaaaaaaaaa              1490
```

<210> SEQ ID NO 93
<211> LENGTH: 1509
<212> TYPE: DNA
<213> ORGANISM: Mus musculus

<400> SEQUENCE: 93

```
gcggccagca gttctcagac ctgcgtccct ttttccttcg ctctggtctc cctcctcatc     60
atgacttcct atagctatcg ccagacctca gctatgtctt cctttggggg tacgggcggg    120
ggttcagtac gcattgggtc agggggtgtt ttccgcgcac ccagcatcca cgggggctca    180
ggtggccgcg gcgtgtccgt gtcctccacc cgcttcgtga cctcgtcctc cgggagctat    240
ggcggagtcc gcggtggaag ttttagtggg accctggctg tgtctgatgg gctgctgtct    300
ggcaatgaga agatcaccat gcaaaacctc aatgatcgtc tcgcctccta cttggacaag    360
gtgcgcgccc tagagcaggc caatggcgag ctggaggtga agatccgcga ctggtaccag    420
aagcagggac ccggaccctc ccgagattac aaccactact ttaagaccat cgaggacttg    480
cgcgacaaga ttcttggtgc caccattgac aactccaaga ttgtcctaca gattgacaat    540
gctcgcctgg ctgcagatga cttcagaacc aagtttgaga cagaacacgc cttgcgtctg    600
agcgtggagg ccgacatcaa cggcctgcgc cgggtgctgg atgagctgac tctggccagg    660
actgacctgg agatgcagat tgagagcctg aaggaggagc tggcctacct gaagaagaac    720
catgaggagg aaattactgc cctgaggagc caggtgggtg gccaggtcag tgtggaggtg    780
gattccactc ccggtgtcga cctagccaag atcctgagtg agatgagaag tcagtatgag    840
atcatggccg agaagaaccg gaaggatgct gaagccacct accttgctcg gattgaggag    900
ctgaacaccc aggtcgccgt ccactctgag cagatccaga taagcaagac cgaagtcacg    960
gaccttcgac ggaccctcca gggccttgag attgagctgc agtcccagct cagcatgaaa   1020
gctgccctgg aaggcacgct ggcagagacg gaggcccgtt atggagtcca gctgtcacag   1080
atccagagcg tgatcagcgg ttttgaagcc cagctgagcg acgtgcgtgc cgacatagag   1140
cgccagaacc aggagtataa gcagctcatg gacatcaagt ccaggctgga gcaggagatc   1200
gccacctacc gcagcctgct ggagggccag gaagcccact acaacaatct gcccaccccc   1260
aaggccatct gagctaccag cgagactccc ctgggaaggg gcctgactgg ggtgataaaa   1320
gtttactcta acccctccct cgacttgtca ataaaactat cctccaaggg aaaaaaaaaa   1380
```

aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaaaaaa 1500
aaaaaaaaa 1509

<210> SEQ ID NO 94
<211> LENGTH: 1621
<212> TYPE: PRT
<213> ORGANISM: Homo sapiens

<400> SEQUENCE: 94

```
Met Glu Gly Cys Met Gly Glu Glu Ser Phe Gln Met Trp Glu Leu Asn
1               5                   10                  15

Arg Arg Leu Glu Ala Tyr Leu Ala Arg Val Lys Ala Leu Glu Glu Gln
            20                  25                  30

Asn Glu Leu Leu Ser Ala Glu Leu Gly Gly Leu Arg Ala Gln Ser Ala
        35                  40                  45

Asp Thr Ser Trp Arg Ala His Ala Asp Asp Glu Leu Ala Ala Leu Arg
    50                  55                  60

Ala Leu Val Asp Gln Arg Trp Arg Glu Lys His Ala Ala Glu Val Ala
65                  70                  75                  80

Arg Asp Asn Leu Ala Glu Glu Leu Glu Gly Val Ala Gly Arg Cys Gln
                85                  90                  95

Gln Leu Arg Leu Ala Arg Glu Arg Thr Thr Glu Glu Val Ala Arg Asn
            100                 105                 110

Arg Arg Ala Val Glu Ala Glu Lys Cys Ala Arg Ala Trp Leu Ser Ser
        115                 120                 125

Gln Val Ala Glu Leu Glu Arg Glu Leu Glu Ala Leu Arg Val Ala His
    130                 135                 140

Glu Glu Glu Arg Val Gly Leu Asn Ala Gln Ala Ala Cys Ala Pro Arg
145                 150                 155                 160

Cys Pro Ala Pro Pro Arg Gly Pro Pro Ala Pro Ala Pro Glu Val Glu
                165                 170                 175

Glu Leu Ala Arg Arg Leu Gly Glu Ala Trp Arg Gly Ala Val Arg Gly
            180                 185                 190

Tyr Gln Glu Arg Val Ala His Met Glu Thr Ser Leu Gly Gln Ala Arg
        195                 200                 205

Glu Arg Leu Gly Arg Ala Val Gln Gly Ala Arg Glu Gly Arg Leu Glu
    210                 215                 220

Leu Gln Gln Leu Gln Ala Glu Arg Gly Gly Leu Leu Glu Arg Arg Ala
225                 230                 235                 240

Ala Leu Glu Gln Arg Leu Glu Gly Arg Trp Gln Glu Arg Leu Arg Ala
                245                 250                 255

Thr Glu Lys Phe Gln Leu Ala Val Glu Ala Leu Glu Gln Glu Lys Gln
            260                 265                 270

Gly Leu Gln Ser Gln Ile Ala Gln Val Leu Glu Gly Arg Gln Gln Leu
        275                 280                 285

Ala His Leu Lys Met Ser Leu Ser Leu Glu Val Ala Thr Tyr Arg Thr
    290                 295                 300

Leu Leu Glu Ala Glu Asn Ser Arg Leu Gln Thr Pro Gly Gly Gly Ser
305                 310                 315                 320

Lys Thr Ser Leu Ser Phe Gln Asp Pro Lys Leu Glu Leu Gln Phe Pro
                325                 330                 335

Arg Thr Pro Glu Gly Arg Arg Leu Gly Ser Leu Leu Pro Val Leu Ser
```

```
            340                 345                 350

Pro Thr Ser Leu Pro Ser Pro Leu Pro Ala Thr Leu Glu Thr Pro Val
        355                 360                 365

Pro Ala Phe Leu Lys Asn Gln Glu Phe Leu Gln Ala Arg Thr Pro Thr
    370                 375                 380

Leu Ala Ser Thr Pro Ile Pro Pro Thr Pro Gln Ala Pro Ser Pro Ala
385                 390                 395                 400

Val Asp Ala Glu Ile Arg Ala Gln Asp Ala Pro Leu Ser Leu Leu Gln
                405                 410                 415

Thr Gln Gly Gly Arg Lys Gln Ala Pro Glu Pro Leu Arg Ala Glu Ala
            420                 425                 430

Arg Val Ala Ile Pro Ala Ser Val Leu Pro Gly Pro Glu Glu Pro Gly
        435                 440                 445

Gly Gln Arg Gln Glu Ala Ser Thr Gly Gln Ser Pro Glu Asp His Ala
    450                 455                 460

Ser Leu Ala Pro Pro Leu Ser Pro Asp His Ser Ser Leu Glu Ala Lys
465                 470                 475                 480

Asp Gly Glu Ser Gly Gly Ser Arg Val Phe Ser Ile Cys Arg Gly Glu
                485                 490                 495

Gly Glu Gly Gln Ile Trp Gly Leu Val Glu Lys Glu Thr Ala Ile Glu
            500                 505                 510

Gly Lys Val Val Ser Ser Leu Gln Gln Glu Ile Trp Glu Glu Glu Asp
        515                 520                 525

Leu Asn Arg Lys Glu Ile Gln Asp Ser Gln Val Pro Leu Glu Lys Glu
    530                 535                 540

Thr Leu Lys Ser Leu Gly Glu Glu Ile Gln Glu Ser Leu Lys Thr Leu
545                 550                 555                 560

Glu Asn Gln Ser His Glu Thr Leu Glu Arg Glu Asn Gln Glu Cys Pro
                565                 570                 575

Arg Ser Leu Glu Glu Asp Leu Glu Thr Leu Lys Ser Leu Glu Lys Glu
            580                 585                 590

Asn Lys Glu Leu Leu Lys Asp Val Glu Val Val Arg Pro Leu Glu Lys
        595                 600                 605

Glu Ala Val Gly Gln Leu Lys Pro Thr Gly Lys Glu Asp Thr Gln Thr
    610                 615                 620

Leu Gln Ser Leu Gln Lys Glu Asn Gln Glu Leu Met Lys Ser Leu Glu
625                 630                 635                 640

Gly Asn Leu Glu Thr Phe Leu Phe Pro Gly Thr Glu Asn Gln Glu Leu
                645                 650                 655

Val Ser Ser Leu Gln Glu Asn Leu Glu Ser Leu Thr Ala Leu Glu Lys
            660                 665                 670

Glu Asn Gln Glu Pro Leu Arg Ser Pro Glu Val Gly Asp Glu Glu Ala
        675                 680                 685

Leu Arg Pro Leu Thr Lys Glu Asn Gln Glu Pro Leu Arg Ser Leu Glu
    690                 695                 700

Asp Glu Asn Lys Glu Ala Phe Arg Ser Leu Glu Lys Glu Asn Gln Glu
705                 710                 715                 720

Pro Leu Lys Thr Leu Glu Glu Glu Asp Gln Ser Ile Val Arg Pro Leu
                725                 730                 735

Glu Thr Glu Asn His Lys Ser Leu Arg Ser Leu Glu Glu Gln Asp Gln
            740                 745                 750

Glu Thr Leu Arg Thr Leu Glu Lys Glu Thr Gln Gln Arg Arg Arg Ser
        755                 760                 765
```

```
Leu Gly Glu Gln Asp Gln Met Thr Leu Arg Pro Pro Glu Lys Val Asp
    770                 775                 780

Leu Glu Pro Leu Lys Ser Leu Asp Gln Glu Ile Ala Arg Pro Leu Glu
785                 790                 795                 800

Asn Glu Asn Gln Glu Phe Leu Lys Ser Leu Lys Glu Glu Ser Val Glu
                805                 810                 815

Ala Val Lys Ser Leu Glu Thr Glu Ile Leu Glu Ser Leu Lys Ser Ala
            820                 825                 830

Gly Gln Glu Asn Leu Glu Thr Leu Lys Ser Pro Glu Thr Gln Ala Pro
        835                 840                 845

Leu Trp Thr Pro Glu Glu Ile Asn Gln Gly Ala Met Asn Pro Leu Glu
    850                 855                 860

Lys Glu Ile Gln Glu Pro Leu Glu Ser Val Glu Val Asn Gln Glu Thr
865                 870                 875                 880

Phe Arg Leu Leu Glu Glu Glu Asn Gln Glu Ser Leu Arg Ser Leu Gly
                885                 890                 895

Ala Trp Asn Leu Glu Asn Leu Arg Ser Pro Glu Glu Val Asp Lys Glu
            900                 905                 910

Ser Gln Arg Asn Leu Glu Glu Glu Glu Asn Leu Gly Lys Gly Glu Tyr
        915                 920                 925

Gln Glu Ser Leu Arg Ser Leu Glu Glu Glu Gly Gln Glu Leu Pro Gln
    930                 935                 940

Ser Ala Asp Val Gln Arg Trp Glu Asp Thr Val Glu Lys Asp Gln Glu
945                 950                 955                 960

Leu Ala Gln Glu Ser Pro Pro Gly Met Ala Gly Val Glu Asn Glu Asp
                965                 970                 975

Glu Ala Glu Leu Asn Leu Arg Glu Gln Asp Gly Phe Thr Gly Lys Glu
            980                 985                 990

Glu Val Val Glu Gln Gly Glu Leu  Asn Ala Thr Glu Glu  Val Trp Ile
        995                 1000                1005

Pro Gly  Glu Gly His Pro Glu  Ser Pro Glu Pro Lys  Glu Gln Arg
    1010                1015                1020

Gly Leu  Val Glu Gly Ala Ser  Val Lys Gly Gly Ala  Glu Gly Leu
    1025                1030                1035

Gln Asp  Pro Glu Gly Gln Ser  Gln Gln Val Gly Ala  Pro Gly Leu
    1040                1045                1050

Gln Ala  Pro Gln Gly Leu Pro  Glu Ala Ile Glu Pro  Leu Val Glu
    1055                1060                1065

Asp Asp  Val Ala Pro Gly Gly  Asp Gln Ala Ser Pro  Glu Val Met
    1070                1075                1080

Leu Gly  Ser Glu Pro Ala Met  Gly Glu Ser Ala Ala  Gly Ala Glu
    1085                1090                1095

Pro Gly  Pro Gly Gln Gly Val  Gly Gly Leu Gly Asp  Pro Gly His
    1100                1105                1110

Leu Thr  Arg Glu Glu Val Met  Glu Pro Pro Leu Glu  Glu Glu Ser
    1115                1120                1125

Leu Glu  Ala Lys Arg Val Gln  Gly Leu Glu Gly Pro  Arg Lys Asp
    1130                1135                1140

Leu Glu  Glu Ala Gly Gly Leu  Gly Thr Glu Phe Ser  Glu Leu Pro
    1145                1150                1155

Gly Lys  Ser Arg Asp Pro Trp  Glu Pro Pro Arg Glu  Gly Arg Glu
    1160                1165                1170
```

-continued

```
Glu Ser  Glu Ala Glu Ala Pro  Arg Gly Ala Glu Glu  Ala Phe Pro
    1175                 1180                 1185

Ala Glu  Thr Leu Gly His Thr  Gly Ser Asp Ala Pro  Ser Pro Trp
    1190                 1195                 1200

Pro Leu  Gly Ser Glu Glu Ala  Glu Glu Asp Val Pro  Pro Val Leu
    1205                 1210                 1215

Val Ser  Pro Ser Pro Thr Tyr  Thr Pro Ile Leu Glu  Asp Ala Pro
    1220                 1225                 1230

Gly Pro  Gln Pro Gln Ala Glu  Gly Ser Gln Glu Ala  Ser Trp Gly
    1235                 1240                 1245

Val Gln  Gly Arg Ala Glu Ala  Leu Gly Lys Val Glu  Ser Glu Gln
    1250                 1255                 1260

Glu Glu  Leu Gly Ser Gly Glu  Ile Pro Glu Gly Pro  Gln Glu Glu
    1265                 1270                 1275

Gly Glu  Glu Ser Arg Glu Glu  Ser Glu Glu Asp Glu  Leu Gly Glu
    1280                 1285                 1290

Thr Leu  Pro Asp Ser Thr Pro  Leu Gly Phe Tyr Leu  Arg Ser Pro
    1295                 1300                 1305

Thr Ser  Pro Arg Trp Asp Pro  Thr Gly Glu Gln Arg  Pro Pro Pro
    1310                 1315                 1320

Gln Gly  Glu Thr Gly Lys Glu  Gly Trp Asp Pro Ala  Val Leu Ala
    1325                 1330                 1335

Ser Glu  Gly Leu Glu Ala Pro  Pro Ser Glu Lys Glu  Glu Gly Glu
    1340                 1345                 1350

Glu Gly  Glu Glu Glu Cys Gly  Arg Asp Ser Asp Leu  Ser Glu Glu
    1355                 1360                 1365

Phe Glu  Asp Leu Gly Thr Glu  Ala Pro Phe Leu Pro  Gly Val Pro
    1370                 1375                 1380

Gly Glu  Val Ala Glu Pro Leu  Gly Gln Val Pro Gln  Leu Leu Leu
    1385                 1390                 1395

Asp Pro  Ala Ala Trp Asp Arg  Asp Gly Glu Ser Asp  Gly Phe Ala
    1400                 1405                 1410

Asp Glu  Glu Glu Ser Gly Glu  Glu Gly Glu Glu Asp  Gln Glu Glu
    1415                 1420                 1425

Gly Arg  Glu Pro Gly Ala Gly  Arg Trp Gly Pro Gly  Ser Ser Val
    1430                 1435                 1440

Gly Ser  Leu Gln Ala Leu Ser  Ser Ser Gln Arg Gly  Glu Phe Leu
    1445                 1450                 1455

Glu Ser  Asp Ser Val Ser Val  Ser Val Pro Trp Asp  Asp Ser Leu
    1460                 1465                 1470

Arg Gly  Ala Val Ala Gly Ala  Pro Lys Thr Ala Leu  Glu Thr Glu
    1475                 1480                 1485

Ser Gln  Asp Ser Ala Glu Pro  Ser Gly Ser Glu Glu  Glu Ser Asp
    1490                 1495                 1500

Pro Val  Ser Leu Glu Arg Glu  Asp Lys Val Pro Gly  Pro Leu Glu
    1505                 1510                 1515

Ile Pro  Ser Gly Met Glu Asp  Ala Gly Pro Gly Ala  Asp Ile Ile
    1520                 1525                 1530

Gly Val  Asn Gly Gln Gly Pro  Asn Leu Glu Gly Lys  Ser Gln His
    1535                 1540                 1545

Val Asn  Gly Gly Val Met Asn  Gly Leu Glu Gln Ser  Glu Glu Val
    1550                 1555                 1560

Gly Gln  Gly Met Pro Leu Val  Ser Glu Gly Asp Arg  Gly Ser Pro
```

```
    1565                1570                1575

Phe Gln  Glu Glu Glu Gly Ser  Ala Leu Lys Thr Ser  Trp Ala Gly
    1580                1585                1590

Ala Pro  Val His Leu Gly Gln  Gly Gln Phe Leu Lys  Phe Thr Gln
    1595                1600                1605

Arg Glu  Gly Asp Arg Glu Ser  Trp Ser Ser Gly Glu  Asp
    1610                1615                1620


<210> SEQ ID NO 95
<211> LENGTH: 1864
<212> TYPE: PRT
<213> ORGANISM: Mus musculus

<400> SEQUENCE: 95

Met Glu Gly Cys Val Gly Glu Glu Ser Phe Gln Met Trp Glu Leu Asn
1               5                   10                  15

Arg Arg Leu Glu Ala Tyr Leu Thr Arg Val Lys Thr Leu Glu Glu Gln
            20                  25                  30

Asn Gln Leu Leu Ser Ala Glu Leu Gly Gly Leu Arg Ala Gln Ser Gly
        35                  40                  45

Asp Ala Ser Trp Arg Ala Arg Ala Asp Asp Glu Leu Ala Ala Leu Arg
    50                  55                  60

Val Leu Val Asp Gln Arg Trp Arg Glu Lys His Glu Ala Glu Val Gln
65                  70                  75                  80

Arg Asp Asn Leu Ala Glu Glu Leu Glu Ser Val Ala Gly Arg Cys Gln
                85                  90                  95

Gln Val Arg Leu Ala Arg Glu Arg Thr Ile Glu Glu Ala Ala Cys Ser
            100                 105                 110

Arg Arg Ala Leu Glu Ala Glu Lys Asn Ala Arg Gly Trp Leu Ser Thr
        115                 120                 125

Gln Ala Ala Glu Leu Glu Arg Glu Leu Glu Ala Leu Arg Ala Ser His
    130                 135                 140

Glu Glu Glu Arg Ala His Leu Asn Ala Gln Ala Ala Cys Thr Pro Arg
145                 150                 155                 160

Arg Pro Pro Ala Pro Ala His Ala Ser Pro Ile Arg Ala Pro Glu Val
                165                 170                 175

Glu Glu Leu Ala Arg Arg Leu Gly Glu Val Trp Arg Gly Ala Val Arg
            180                 185                 190

Asp Tyr Gln Glu Arg Val Ala His Met Glu Ser Ser Leu Gly Gln Ala
        195                 200                 205

Arg Glu Arg Leu Gly Gln Ala Val Arg Gly Ala Arg Glu Ser Arg Leu
    210                 215                 220

Glu Val Gln Gln Leu Gln Ala Asp Arg Asp Ser Leu Gln Glu Arg Arg
225                 230                 235                 240

Glu Ala Leu Glu Gln Arg Leu Glu Gly Arg Trp Gln Asp Arg Leu Gln
                245                 250                 255

Ala Thr Glu Lys Phe Gln Leu Ala Val Glu Ala Leu Glu Gln Glu Lys
            260                 265                 270

Gln Gly Leu Gln Ser Gln Ile Ala Gln Ile Leu Glu Gly Gly Gln Gln
        275                 280                 285

Leu Ala His Leu Lys Met Ser Leu Ser Leu Glu Val Ala Thr Tyr Arg
    290                 295                 300

Thr Leu Leu Glu Ala Glu Asn Ser Arg Leu Gln Thr Pro Gly Arg Ser
305                 310                 315                 320
```

```
Ser Gln Ala Ser Leu Gly Phe Pro Asp Pro Lys Leu Lys Leu His Phe
                325                 330                 335

Leu Gly Ile Pro Glu Asp Gln His Leu Gly Ser Val Leu Pro Val Leu
            340                 345                 350

Ser Pro Thr Ser Phe Ser Ser Pro Leu Pro Asn Thr Leu Glu Thr Pro
        355                 360                 365

Val Thr Ala Phe Leu Lys Thr Gln Glu Phe Leu Lys Ala Arg Thr Pro
    370                 375                 380

Thr Leu Ala Ser Thr Pro Ile Pro Pro Met Ser Glu Ala Pro Tyr Pro
385                 390                 395                 400

Lys Asn Ala Glu Val Arg Ala Gln Asp Val Pro His Ser Leu Leu Gln
                405                 410                 415

Gly Gly Arg Gln Gln Ala Pro Glu Pro Leu Trp Ala Glu Ala Thr Val
            420                 425                 430

Pro Ser Ser Thr Gly Val Leu Pro Glu Leu Glu Glu Pro Gly Gly Glu
        435                 440                 445

Gln Pro Asp His Phe Pro Asp Asp Pro Thr Ser Leu Ala Pro Pro Leu
    450                 455                 460

Asn Pro His His Ser Ile Leu Glu Ala Lys Asp Arg Glu Ser Ser Glu
465                 470                 475                 480

Ser Arg Val Ser Ser Ile Phe Gln Glu Glu Gly Gln Ile Trp Glu
                485                 490                 495

Leu Val Lys Lys Glu Ala Ala Thr Glu Val Lys Val Glu Asn Ser Leu
            500                 505                 510

Ala Gln Glu Ile Gln Glu Ser Gly Leu Asp Thr Glu Glu Ile Gln Asp
        515                 520                 525

Ser Gln Gly Pro Leu Gln Met Glu Thr Leu Glu Ala Leu Gly Asp Glu
    530                 535                 540

Pro Leu Met Ser Leu Lys Thr Gln Asn His Glu Thr Pro Gly Lys Glu
545                 550                 555                 560

Asn Cys Asn Ser Ser Ile Glu Glu Asn Ser Gly Thr Val Lys Ser Pro
                565                 570                 575

Glu Lys Glu Lys Gln Thr Pro Leu Lys Ser Leu Glu Glu Lys Asn Val
            580                 585                 590

Glu Ala Glu Lys Thr Leu Glu Asn Gly Val Leu Glu Leu Ser Lys Pro
        595                 600                 605

Leu Gly Glu Glu Glu Pro Arg Met Glu Asp Gln Glu Leu Met Ser Pro
    610                 615                 620

Glu His Thr Leu Glu Thr Val Ser Phe Leu Gly Lys Glu Asn Gln Glu
625                 630                 635                 640

Val Val Arg Ser Ser Glu Glu Gln Asn Leu Glu Ser Leu Ile Thr Phe
                645                 650                 655

Lys Glu Glu Ser Gln Tyr Pro Leu Gly Gly Pro Glu Ala Glu Asp Gln
            660                 665                 670

Met Leu Glu Arg Leu Val Glu Lys Glu Asp Gln Arg Phe Pro Arg Ser
        675                 680                 685

Pro Glu Glu Asp Gln Gln Ala Phe Arg Pro Leu Glu Lys Glu Asn Gln
    690                 695                 700

Glu Pro Leu Arg Phe Glu Glu Ala Glu Asp Gln Val Leu Glu Arg Leu
705                 710                 715                 720

Ile Glu Lys Glu Arg Gln Glu Ser Leu Lys Ser Pro Glu Glu Glu Asp
                725                 730                 735

Gln Gln Ala Phe Arg Leu Leu Glu Lys Glu Asn Gln Glu Pro Leu Arg
```

```
            740                 745                 750

Phe Glu Asp Ala Glu Asp Gln Val Leu Glu Arg Leu Ile Glu Lys Glu
        755                 760                 765

Arg Gln Glu Ser Leu Lys Ser Pro Glu Glu Glu Asp Gln Gln Ala Phe
    770                 775                 780

Arg Leu Leu Glu Lys Glu Asn Gln Glu Pro Leu Arg Phe Glu Glu Ala
785                 790                 795                 800

Glu Asp Gln Val Leu Glu Arg Leu Val Glu Lys Glu Ser Gln Glu Ser
                805                 810                 815

Leu Lys Ser Pro Glu Glu Glu Asp Gln Arg Thr Gly Lys Pro Leu Glu
            820                 825                 830

Lys Glu Asn Gln Glu Ser Leu Arg Ser Leu Asp Glu Asn Gln Glu Thr
        835                 840                 845

Ile Val Leu Leu Glu Ser Lys Asn Gln Arg Pro Leu Arg Ser Leu Glu
    850                 855                 860

Val Glu Glu Glu Glu Gln Arg Ile Val Lys Pro Leu Glu Lys Val Ser
865                 870                 875                 880

Gln Val Ser Leu Glu Ser Leu Glu Lys Glu Asn Val Gln Ser Pro Arg
                885                 890                 895

Tyr Leu Glu Glu Asp Asp His Met Ile Lys Ser Leu Leu Glu Asp Lys
            900                 905                 910

Thr His Glu Ile Leu Gly Ser Leu Glu Asp Arg Asn Gly Glu Asn Phe
        915                 920                 925

Ile Pro Pro Glu Asn Glu Thr Gln Gly Ser Leu Arg Pro Pro Glu Glu
    930                 935                 940

Glu Asp Gln Arg Ile Val Asn His Leu Glu Lys Glu Ser Gln Glu Phe
945                 950                 955                 960

Leu Arg Ser Pro Glu Ala Glu Glu Glu Glu Glu Gln Val Met Val Arg
                965                 970                 975

Ser Leu Glu Gly Glu Asn His Asp Pro Leu Ser Ser Val Val Lys Glu
            980                 985                 990

Glu Gln Met Ala Glu Ser Lys Leu  Glu Asn Glu Ser Gln  Asp Ser Arg
        995                 1000                1005

Lys Ser  Leu Glu Asp Glu Ser  Gln Glu Thr Phe Gly  Ser Leu Glu
    1010                1015                1020

Lys Glu  Asn Leu Glu Ser Leu  Arg Ser Leu Ala Gly  Gln Asp Gln
    1025                1030                1035

Glu Glu  Gln Lys Leu Glu Gln  Glu Thr Gln Gln Pro  Leu Arg Ala
    1040                1045                1050

Val Glu  Asp Glu Gln Met Thr  Val Asn Pro Pro Glu  Lys Val Asp
    1055                1060                1065

Pro Glu  Leu Pro Lys Pro Leu  Arg Asn Asp Gln Glu  Val Val Arg
    1070                1075                1080

Ser Leu  Asp Lys Glu Asn Gln  Glu Ser Leu Val Ser  Leu Asn Glu
    1085                1090                1095

Gly Gly  Met Glu Thr Val Lys  Ser Ser Glu Thr Glu  Asn Ile Glu
    1100                1105                1110

Ser Leu  Glu Thr Val Gly Glu  Cys Leu Gly Arg Arg  Lys Ser Val
    1115                1120                1125

Asp Thr  Gln Glu Pro Leu Trp  Ser Thr Glu Val Thr  Ser Glu Thr
    1130                1135                1140

Ile Glu  Pro Leu Glu Asp Glu  Thr Gln Glu Pro Leu  Gly Cys Val
    1145                1150                1155
```

```
Asp Glu  Asn Gln Glu Val Leu  Thr Pro Leu Glu Arg  Glu Ser Gln
    1160                 1165                 1170

Glu Leu  Arg Ser Leu Gly Lys  Trp Asn Pro Glu Thr  Val Glu Ser
    1175                 1180                 1185

Pro Gly  Gly Val Glu Asp Ser  Gln Gln Cys Leu Glu  Val Glu Glu
    1190                 1195                 1200

Gly Pro  Glu Arg Glu Gln His  Gln Glu Ser Leu Arg  Ser Leu Gly
    1205                 1210                 1215

Glu Val  Glu Trp Glu Leu Pro  Gly Ser Gly Ser Gln  Gln Arg Trp
    1220                 1225                 1230

Glu Asp  Val Val Glu Asp Gly  Glu Gly Gln Glu Ala  Ser Leu Gly
    1235                 1240                 1245

Ala Thr  Gly Val Glu Thr Glu  Asp Lys Ala Glu Leu  His Leu Arg
    1250                 1255                 1260

Gly Gln  Gly Gly Glu Glu Lys  Ala Val Glu Glu Gly  Glu Leu Leu
    1265                 1270                 1275

Gln Asp  Ala Val Gly Glu Ala  Trp Ser Leu Gly Ser  Ser Glu Pro
    1280                 1285                 1290

Lys Glu  Gln Arg Val Pro Ala  Glu Pro Leu Asp Asp  Leu Glu Gly
    1295                 1300                 1305

Gln Pro  Glu Gln Thr Gly Thr  Leu Glu Val Pro Val  Ala Gln Gly
    1310                 1315                 1320

Met Pro  Glu Ala Thr Glu Gln  Asp Glu Asp Arg Ala  Gln Ala Gly
    1325                 1330                 1335

Glu Gln  Asp Ser Val Glu Val  Thr Leu Gly Leu Glu  Ala Ala Arg
    1340                 1345                 1350

Ala Gly  Leu Glu Leu Glu Gln  Glu Val Val Gly Leu  Glu Asp Pro
    1355                 1360                 1365

Arg His  Phe Ala Arg Glu Glu  Ala Ile His Pro Ser  Leu Gly Glu
    1370                 1375                 1380

Glu Ser  Val Lys Ala Lys Ile  Asp Gln Gly Leu Glu  Glu Pro Gly
    1385                 1390                 1395

Lys Glu  Pro Lys Glu Ala Gly  Ala Leu Asp Ser Gly  Ile Pro Glu
    1400                 1405                 1410

Leu Pro  Lys Thr Ser Ser Glu  Thr Leu Glu Cys Lys  Gly Trp Glu
    1415                 1420                 1425

Glu Ser  Gly Glu Gly Trp Gly  Glu Glu Glu Ala Ser  Leu Glu Thr
    1430                 1435                 1440

Ser Asp  His Glu Gly Ser His  Ala Pro Gln Pro Arg  Pro Pro Lys
    1445                 1450                 1455

Thr Glu  Glu Asp Glu Gly Leu  Gln Ala Ala Leu Thr  Val Pro Gly
    1460                 1465                 1470

Pro Lys  Leu Leu Glu Pro Cys  Ser Pro Ile Pro Ile  Leu Thr Asp
    1475                 1480                 1485

Ala His  Glu Leu Gln Pro Gln  Ala Glu Gly Ile Gln  Glu Ala Gly
    1490                 1495                 1500

Trp Gln  Pro Glu Ala Gly Thr  Glu Ala Leu Gly Arg  Val Glu Asp
    1505                 1510                 1515

Glu Pro  Glu Phe Gly Arg Gly  Glu Ile Pro Glu Gly  Leu Gln Asp
    1520                 1525                 1530

Trp Glu  Glu Gly Arg Glu Asp  Ser Glu Ala Asp Glu  Leu Gly Glu
    1535                 1540                 1545
```

```
Thr Leu  Pro Asp Ser Thr Pro  Leu Gly Leu Tyr Leu  Lys Ser Pro
    1550                 1555                 1560

Ala Ser  Pro Lys Trp Glu Gln  Ala Gly Glu Gln Arg  Leu Phe Pro
    1565                 1570                 1575

Gln Gly  Glu Ala Arg Lys Glu  Gly Trp Ser Pro Ala  Ala Leu Ala
    1580                 1585                 1590

Ala Gln  Gly Leu Ser Asp Pro  Pro Glu Glu Glu Gln  Gln Gly His
    1595                 1600                 1605

Asp Ser  Asp Leu Ser Ser Glu  Glu Phe Glu Asp Leu  Gly Thr Glu
    1610                 1615                 1620

Ala Ser  Leu Leu Pro Gly Val  Pro Lys Glu Val Ser  Asp His Leu
    1625                 1630                 1635

Gly Gln  Glu Pro Pro Val Leu  Gln Pro Ala Cys Trp  Asp Gln Gly
    1640                 1645                 1650

Gly Glu  Ser Asp Gly Phe Ala  Asp Glu Glu Glu Ser  Gly Glu Glu
    1655                 1660                 1665

Gly Glu  Glu Glu Asp Ala Asp  Glu Glu Glu Gly Ala  Glu Ser Gly
    1670                 1675                 1680

Thr Gln  Trp Trp Gly Pro Gly  Pro Ser Gly Gly Gly  Val Lys Val
    1685                 1690                 1695

Gln Asp  Val Thr Gln Arg Gly  Asp Leu Glu His Glu  Ser Val Gly
    1700                 1705                 1710

Asp Ser  Gly Leu Trp Asp Asp  Gly Leu Ser Gly Ala  Ala Ala Asn
    1715                 1720                 1725

Val Leu  Val Thr Ala Leu Glu  Thr Val Ser Gln Asp  Ser Ala Glu
    1730                 1735                 1740

Pro Ser  Gly Ser Glu Gly Ser  Glu Ser Ala Ser Leu  Glu Gly Glu
    1745                 1750                 1755

Glu Gly  Gln Ala Ile Asp His  Leu Asp Ala Pro Gln  Glu Val Thr
    1760                 1765                 1770

Ser Val  Val Pro Gly Ala Gly  Asp Thr Phe Asp Ile  Ser Gly Gln
    1775                 1780                 1785

Gly Pro  Asn Leu Glu Ser Glu  Gln Val Asn Gly Arg  Met Glu Asn
    1790                 1795                 1800

Gly Leu  Glu Gln Ala Glu Gly  Gln Val Val Leu His  Gly Asp Glu
    1805                 1810                 1815

Asp Gln  Gly Ile Pro Leu Gln  Glu Gln Gly Thr Leu  Lys Ala Pro
    1820                 1825                 1830

Leu Val  Gly Ser Pro Val His  Leu Gly Pro Ser Gln  Pro Leu Lys
    1835                 1840                 1845

Phe Thr  Leu Ser Gly Val Asp  Gly Asp Ser Trp Ser  Ser Gly Glu
    1850                 1855                 1860

Asp


<210> SEQ ID NO 96
<211> LENGTH: 5591
<212> TYPE: DNA
<213> ORGANISM: Homo sapiens

<400> SEQUENCE: 96

gctactccca ccccgccccg ccccgtcatt gtccccgtcg gtctcttttc tcttccgtcc     60

taaaagctct gcgagccgct cccttctccc ggtgccccgc gtctgtccat cctcagtggg    120

tcagacgagc aggatggagg gctgcatggg ggaggagtcg tttcagatgt gggagctcaa    180
```

-continued

```
tcggcgcctg gaggcctacc tggcccgggt caaggcgctg gaggagcaga atgagctgct    240
cagcgcggag ctcgggggc tccgggcaca atccgcggac acctcctggc gggcgcatgc     300
cgacgacgag ctggcggccc tgcgggccct cgttgaccaa cgctggcggg agaagcacgc    360
ggccgaggtg gcgcgcgaca acctggctga agagctggag ggcgtggcag gccgatgcca    420
gcagctgcgg ctggcccggg agcggacgac ggaggaggta gcccgcaacc ggcgcgccgt    480
cgaggcagag aaatgcgccc gggcctggct gagtagccag gtggcagagc tggagcgcga    540
gctagaggct ctacgcgtgg cgcacgagga ggagcgcgtc ggcctgaacg cgcaggctgc    600
ctgtgccccc cgctgccccg cgccgccccg cgggcctccc gcgccggccc cggaggtaga    660
ggagctggca aggcgactgg gcgaggcgtg gcgcggggca gtgcgcggct accaggagcg    720
cgtggcacac atggagacgt cgctgggcca ggcccgcgag cggctgggcc gggcggtgca    780
gggtgcccgc gagggccgcc tggagctgca gcagctccag gctgagcgcg gaggcctcct    840
ggagcgcagg gcagcgttgg aacagaggtt ggagggccgc tggcaggagc ggctgcgggc    900
tactgaaaag ttccagctgg ctgtggaggc cctggagcag gagaaacagg gcctacagag    960
ccagatcgct caggtcctgg aaggtcggca gcagctggcg cacctcaaga tgtccctcag   1020
cctggaggtg gccacgtaca ggaccctcct ggaggctgag aactcccggc tgcaaacacc   1080
tggcggtggc tccaagactt ccctcagctt tcaggacccc aagctggagc tgcaattccc   1140
taggacccca gagggccggc gtcttggatc tttgctccca gtcctgagcc caacttccct   1200
cccctcaccc ttgcctgcta cccttgagac acctgtgcca gcctttctta agaaccaaga   1260
attcctccag gcccgtaccc ctaccttggc cagcaccccc atccccccca cacctcaggc   1320
accctctcct gctgtagatg cagagatcag agcccaggat gctcctctct ctctgctcca   1380
gacacagggt gggaggaaac aggctccaga gcccctgcgg gctgaagcca gggtggccat   1440
tcctgccagc gtcctgcctg gaccagagga gcctgggggc cagcggcaag aggccagtac   1500
aggccagtcc ccagaggacc atgcctcctt ggcaccaccc ctcagccctg accactccag   1560
tttagaggct aaggatggag aatccggtgg gtctagagtg ttcagcatat gccgagggga   1620
aggtgaaggg caaatctggg ggttggtaga gaaagaaaca gccatagagg gcaaagtggt   1680
aagcagcttg cagcaggaaa tatgggaaga agaggatcta aacaggaagg aaatccagga   1740
ctcccaggtt cctttggaaa aagaaaccct gaagtctctg ggagaggaga ttcaagagtc   1800
actgaagact ctggaaaacc agagccatga gacactagaa agggagaatc aagaatgtcc   1860
gaggtcttta gaagaagact tagaaacact aaaaagtcta gaaaaggaaa ataaagagct   1920
attaaaggat gtggaggtag tgagacctct agaaaaagag gctgtaggcc aacttaagcc   1980
tacaggaaaa gaggacacac agacattgca atccctgcaa aaggagaatc aagaactaat   2040
gaaatctctt gaaggtaatc tagagacatt tttatttcca ggaacggaaa atcaagaatt   2100
agtaagttct ctgcaagaga acttagagtc attgacagct ctggaaaagg agaatcaaga   2160
gccactgaga tctccagaag taggggatga ggaggcactg agacctctga caaaggagaa   2220
tcaggaaccc ctgaggtctc ttgaagatga gaacaaagag gcctttagat ctctagaaaa   2280
agagaaccag gagccactga agactctaga agaagaggac cagagtattg tgagacctct   2340
agaaacagag aatcacaaat cactgaggtc tttagaagaa caggaccaag agacattgag   2400
aactcttgaa aaagagactc aacagcgacg gaggtctcta ggggaacagg atcagatgac   2460
attaagaccc ccagaaaaag tggatctaga accactgaag tctcttgacc aggagatagc   2520
tagacctctt gaaaatgaga atcaagagtt cttaaagtca ctcaaagaag agagcgtaga   2580
```

-continued

```
ggcagtaaaa tctttagaaa cagagatcct agaatcactg aagtctgcgg gacaagagaa   2640
cctggaaaca ctgaaatctc cagaaactca agcaccactg tggactccag aagaaataaa   2700
tcagggggca atgaatcctc tagaaaagga aattcaagaa ccactggagt ctgtggaagt   2760
gaaccaagag acattcagac tcctggaaga ggagaatcag gaatcattga gatctctggg   2820
agcatggaac ctggagaatt tgagatctcc agaggaggta gacaaggaaa gtcaaaggaa   2880
tctggaagag gaagagaacc tgggaaaggg agagtaccaa gagtcactga ggtctctgga   2940
ggaggaggga caggagctgc cgcagtctgc agatgtgcag aggtgggaag atacggtgga   3000
gaaggaccaa gaactggctc aggaaagccc tcctgggatg gctggagtgg aaaatgagga   3060
tgaggcagag ctgaatctga gggagcagga tggcttcact gggaaggagg aggtggtaga   3120
gcagggagag ctgaatgcca cagaggaggt ctggatccca ggcgaggggc acccagagag   3180
ccctgagccc aaagagcaga gaggcctggt tgagggagcc agtgtgaagg gaggggctga   3240
gggcctccag gaccctgaag ggcaatcaca acaggtgggg gccccaggcc tccaggctcc   3300
ccaggggctg ccagaggcga tagagcccct ggtggaagat gatgtggccc caggggtga    3360
ccaagcctcc ccagaggtca tgttggggtc agagcctgcc atgggtgagt ctgctgcggg   3420
agctgagcca ggcccggggc agggggtggg agggctgggg gacccaggcc atctgaccag   3480
ggaagaggtg atggaaccac ccctggaaga ggagagtttg gaggcaaaga gggttcaggg   3540
cttggaaggg cctagaaagg acctagagga ggcaggtggt ctggggacag agttctccga   3600
gctgcctggg aagagcagag acccttggga gcctcccagg gagggtaggg aggagtcaga   3660
ggctgaggcc cccaggggag cagaggaggc gttccctgct gagaccctgg gccacactgg   3720
aagtgatgcc ccttcacctt ggcctctggg gtcagaggaa gctgaggagg atgtaccacc   3780
agtgctggtc tcccccagcc caacgtacac cccgatcctg gaagatgccc ctgggcctca   3840
gcctcaggct gaagggagtc aggaggctag ctgggggggtg caggggaggg ctgaagccct   3900
ggggaaagta gagagcgagc aggaggagtt gggttctggg gagatccccg agggccccca   3960
ggaggaaggg gaggagagca gagaagagag cgaggaggat gagctcgggg agacccttcc   4020
agactccact cccctgggct tctacctcag gtcccccacc tcccccaggt gggaccccac   4080
tggagagcag aggccacccc ctcaagggga gactggaaag gagggctggg atcctgctgt   4140
cctggcttcc gagggccttg aggccccacc ctcagaaaag gaggaggggg aggagggaga   4200
agaggagtgt ggccgtgact ctgacctgtc agaagaattt gaggacctgg ggactgaggc   4260
accttttctt cctggggtcc ctggggaggt ggcagaacct ctgggccagg tgccccagct   4320
gctactggat cctgcagcct gggatcgaga tggggagtcc gatgggtttg cagatgagga   4380
agaaagtggg gaggagggag aggaggatca ggaggagggg agggagccag ggctgggcg    4440
gtgggggcca gggtcttctg ttggcagcct ccaggccctg agtagctccc agagagggga   4500
attcctggag tctgattctg tgagtgtcag tgtcccctgg gatgacagct tgaggggtgc   4560
agtggctggt gcccccaaga ctgccctgga aacggagtcc caggacagtg ctgagccttc   4620
tggctcagag gaagagtctg accctgtttc cttggagagg gaggacaaag tccctggccc   4680
tctagagatc cccagtggga tggaggatgc aggcccaggg gcagacatca ttggtgttaa   4740
tggccagggt cccaacttgg aggggaagtc acagcatgtg aatgggggag tgatgaacgg   4800
gctggagcag tctgaggaag tggggcaagg aatgccgcta gtctctgagg gagaccgagg   4860
gagccccttt caggaggagg aggggagtgc tctgaagacc tcttgggcag ggctcctgt    4920
```

```
tcacctgggc cagggtcagt tcctgaagtt cactcagagg gaaggagata gagagtcctg   4980
gtcctcaggg gaggactagg aaaagaccat ctgcccggca ctggggactt aggggtgcgg   5040
ggaggggaag gacgcctcca agcccgctcc ctgctcagga gcagcactct taacttacga   5100
tctcttgaca tatggtttct ggctgagagg cctggcccgc taaggtgaaa aggggtgtgg   5160
caaaggagcc tactccaaga atggaggctg taggaatata acctcccacc ctgcaaaggg   5220
aatctcttgc ctgctccatc tcataggcta agtcagctga atcccgatag tactaggtcc   5280
ccttccctcc gcatcccgtc agctggaaaa ggcctgtggc ccagaggctt ctccaaaggg   5340
agggtgacat gctggctttt gtgcccaagc tcaccagccc tgcgccacct cactgcagta   5400
gtgcaccatc tcactgcagt agcacgccct cctgggccgt ctggcctgtg gctaatggag   5460
gtgacggcac tcccatgtgc tgactccccc catccctgcc acgctgtggc cctgcctggc   5520
tagtccctgc ctgaataaag taatgcctcc gcttcaaaaa aaaaaaaaaa aaaaaaaaaa   5580
aaaaaaaaaa a                                                        5591
```

<210> SEQ ID NO 97
<211> LENGTH: 6143
<212> TYPE: DNA
<213> ORGANISM: Mus musculus

<400> SEQUENCE: 97

```
cgctgggtca ctgtcgccgc tactcccttt ctccccctta aaagctccaa gggccactcc     60
cttctctagt gctccacgtc cgcttgccct cggggggcca gaccagcgac atggagggtt    120
gcgtcgggga agaatctttt cagatgtggg agctcaatcg acgcctggag gcctacctga    180
cccgggtcaa gacgctggag gagcagaacc agctgctcag tgccgagctt ggggggactcc   240
gggcgcagtc cggggacgcc tcctggcgag cccgagccga cgacgagctg gcagccctgc    300
gggtcctcgt cgatcagcgc tggcgggaga agcacgaggc tgaggtgcag cgcgacaacc    360
ttgccgaaga gctggagagc gtggcgggcc ggtgccagca ggtgcggctc gcccgggagc    420
ggaccatcga ggaggcggcc tgcagccggc gcgcgctcga ggcggagaag aatgcgcggg    480
gctggctgag cacccaggct gccgagctgg agcgcgagtt agaggctctg cgagcgtcgc    540
acgaggagga gcgcgcgcac ctgaacgccc aggccgcctg tacgccgcgc cgaccccccg    600
cgccggccca cgcatccccc atccgggccc ctgaagtcga ggagctggcc aggcgcctag    660
gcgaagtgtg gcgcggggcg gtgcgtgact accaggagcg cgtggctcac atggagagct    720
cgctgggcca ggcccgcgag cgtctgggcc aagccgtgcg gggcgctcgg gagagtcgct    780
tagaggtgca gcagctgcag gctgatcgcg acagcctcca ggagcgcaga gaggcgctgg    840
aacagagatt ggaaggccgc tggcaggacc ggctgcaggc cactgaaaag ttccagctgg    900
ctgtggaagc cctggagcag gagaagcagg gtctacagag tcagatcgct cagatcctgg    960
aaggtgggca gcaactggca cacctcaaga tgtcccttag tctggaagtg gctacataca   1020
ggactctgct ggaggctgag aactctcgct tgcagacacc tggaagaagt tcccaggctt   1080
ctcttggctt tcctgacccc aagctgaagc tgcatttcct tgggatacca gaggaccagc   1140
acctgggatc tgtgctccct gtcctcagcc caacatcctt ctcttccccc ttgcctaata   1200
cccttgagac tcctgtgaca gcctttctga agacacagga attccttaag gccagaaccc   1260
ccaccttggc cagcactccc atcccaccta tgtctgaggc tccctatcct aaaaatgcag   1320
aggtcagagc ccaggatgtc ccccattccc tgctccaggg tgggaggcaa caggctccag   1380
agcctctttg ggctgaggcc acagtgccca gttctactgg tgtcctccca gagctggagg   1440
```

```
agcctggggg cgagcagccg gaccacttcc ctgatgatcc aacctcctta gccccacccc   1500
tcaaccctca ccactctatt ttagaggcta aagatagaga atccagtgag tctagagttt   1560
ctagcatatt ccaggaagaa gaagggcaaa tctgggaact tgtaaagaaa gaagcagcca   1620
cagaggtaaa agtagaaaac agcttagcac aggaaataca agaaagtggt ctggacacag   1680
aagaaatcca ggattcccag ggacctttgc agatggaaac cctggaggct ctaggagatg   1740
agccactgat gtctctgaaa acccagaacc atgagacccc aggaaaggag aattgcaatt   1800
catctataga agagaactcg ggacagtaa aaagcccaga aaaagaaaaa caaacaccac   1860
tgaagtcttt agaagaaaag aatgtagagg cagagaaaac tctagaaaat ggggttcttg   1920
aactatctaa acctttagga gaagaagaac caagaatgga ggatcaagaa ttaatgtctc   1980
ctgaacacac actagagaca gtttcatttc taggaaagga aaatcaggaa gtagtgaggt   2040
cttcagaaga acagaactta gaatcattga taacttttaa agaggagagc caatacccac   2100
tgggaggtcc agaagccgag gaccagatgc ttgaaagact ggtagagaaa gaggatcaga   2160
ggttcccaag gtctccagaa gaagaccagc aggcgtttag acctctggag aaagagaatc   2220
aggagccact aagatttgaa gaagcagagg accaggtgct tgagagactg atagaaaagg   2280
aaaggcagga gtccctgaag tctccagaag aagaggacca gcaggcattt agacttctgg   2340
agaaagagaa tcaagaacca ctaaggtttg aagacgcaga ggaccaggtg cttgagagac   2400
tgatagaaaa ggaaagacag gagtccctga agtctccaga agaagaggac cagcaggcat   2460
ttagacttct ggagaaagag aatcaagaac cactaaggtt tgaagaagca gaggaccagg   2520
tgcttgagag actggtagaa aaggaaagtc aggagtccct gaagtctcca gaagaggagg   2580
accagaggac tgggaagcct ctagaaaaag aaaatcagga atctctgagg tctcttgatg   2640
aaaaccagga gacaattgta ctgctagaaa gcaagaacca gaggccactg agatctctag   2700
aagtagaaga ggaggagcag agaattgtga aacctctaga aaaagtgagc caggtctccc   2760
tcgaatctct cgaaaaagag aatgtgcagt caccaaggta tctggaagaa gatgaccaca   2820
tgattaagag cctgctagaa gacaagactc atgagatcct gggatctctt gaagatagaa   2880
atggggagaa ctttatacca cctgaaaatg agacccaggg ttcattgagg cctccagaag   2940
aagaggacca gaggattgtg aaccatctag aaaaagaaag ccaggagttc ctgaggtctc   3000
cagaagcaga ggaagaagaa gagcaggtga tggtgagatc tctagaagga gagaaccacg   3060
acccactgag ctctgtggtg aaagaggagc agatggctga gagcaagcta gagaacgaga   3120
gtcaggactc caggaagtct cttgaagatg agagccagga gacctttggg tctctggaaa   3180
aagagaatct agagtccctg aggtctctag caggacagga ccaagaggaa cagaaactcg   3240
aacaagagac ccagcagcca ctgagggctg tagaagatga gcagatgaca gtgaaccctc   3300
cagaaaaggt ggatccagag ttaccaaagc ctcttagaaa tgaccaggaa gtagtcagat   3360
ctcttgacaa ggagaatcaa gagtcactag tgtcactgaa tgaaggaggt atggagacag   3420
tgaagtcttc agaaacagag aacatagaat cactggagac tgtgggagag tgcctgggaa   3480
gaaggaagtc tgtagatact caagagccat tgtggtctac ggaagtgact agtgagacaa   3540
tagaacctct agaagatgag acccaagaac cactggggtg tgtggatgag aaccaagagg   3600
tgctgacacc ccttgaaagg gagagtcaag aactgagatc tctgggcaag tggaacccag   3660
agactgtgga atcaccagga ggggtggagg acagtcagca gtgcctggaa gtggaagagg   3720
gcccggagag ggagcagcac caagagtctc tgaggtctct gggagaggtg gaatgggagc   3780
tgcctggatc tggaagtcaa cagaggtggg aggatgtggt ggaggatgga gaaggtcagg   3840
```

-continued

```
aagcatccct gggggctaca ggagtggaaa ctgaggataa ggcagagttg catctgaggg   3900
gccaaggtgg ggaggagaaa gctgtagagg agggagagct gctgcaggat gctgtggggg   3960
aggcctggag tctggggagc tcggagccca aggagcagag ggtccctgct gagcccctcg   4020
atgacctgga gggacaacca gagcagacgg gaaccctaga ggtcccagtt gctcagggaa   4080
tgccagaggc aacagagcaa gatgaggaca gagcccaagc aggtgaacaa gactccgtag   4140
aggtgaccct tgggttagag gctgccagag ctggactgga actcgagcag gaagtggtag   4200
ggctagagga cccaaggcat ttcgccaggg aggaggccat tcacccatcc ctgggggagg   4260
aaagtgtgaa ggcaaagata gatcagggct tggaagagcc tggaaaggaa ccaaaagagg   4320
caggtgctct ggactcaggc atccctgaat tacccaagac tagcagtgag actctggaat   4380
gcaagggctg ggaagagtct ggggagggct ggggagaaga ggaggcctcg ctggagacct   4440
cagaccatga gggcagccat gcccctcagc ccaggccccc taagacagag gaagatgagg   4500
gtctacaggc agcgctaaca gtccctggtc ccaagctcct ggaaccctgt tcacccatcc   4560
cgatcttgac agatgcccat gagctgcagc cccaagctga ggggatccag gaggctgggt   4620
ggcagccgga agctgggact gaagcactgg gaagagtaga agatgagcca gagtttggtc   4680
gtggggagat tcctgagggc ctccaggatt gggaggaggg cagagaagac agtgaggcag   4740
atgagttagg ggaaactctc cctgactcta ctcccttggg cctctacctg aagtctcctg   4800
cctccccaaa gtgggagcaa gctggagaac agaggctttt ccctcaaggg gaggccagga   4860
aggaaggctg gagtcctgct gccctggctg cccagggtct cagtgaccca ccagaggaag   4920
agcagcaagg ccatgactct gacctctcat ctgaggaatt tgaggaccta gggactgagg   4980
cctctcttct tccaggggtt cccaaagagg tgtccgatca tctgggccaa gagcccccg    5040
tactgcagcc tgcatgctgg gatcagggtg gggagtctga tgggtttgct gatgaggaag   5100
agagtgggga agagggagag gaagaagatg ctgatgaaga agaaggagca gagtcaggga   5160
ctcagtggtg gggggccaggg ccctctggtg gaggtgtcaa ggtccaggat gtcacccaga   5220
gaggggacct ggaacatgaa tctgtgggtg acagtggcct ctgggatgat ggcttgagtg   5280
gggctgcagc taatgttctt gtaactgccc tagagacggt gtctcaggac agtgctgagc   5340
cttccgggtc agaggggtct gagtctgctt ccttggaggg ggaggaaggt caagcgattg   5400
accatttaga tgccccccaa gaggtgacta gcgtggtccc aggggcagga gacacctttg   5460
atatcagtgg ccagggcccc aacctggagt cagagcaagt gaatgggagg atggagaatg   5520
gactagagca ggctgagggt caggtggttc tgcatgggga cgaggatcaa ggcatccctt   5580
tacaggaaca gggtaccctc aaggcccctt tagtagggtc tcctgtgcat ctaggcccaa   5640
gccagccgct gaagttcact ctgagtgggg tagatggaga ctcctggtcc tcaggggaag   5700
attagaaact gcccctctgg cactgaggac ttagtggggg gtggggggaa tgtccctccc   5760
tgctctgggc cagcactctt agctttgata acttgacctg tggtatctct cgtggagagg   5820
tgtggctggc tgagacaggt gagatcctgc ctggatcacc ctgaaggctc aggtcagctg   5880
agcctatagt tcaacgcccc ctttcttctg tggctcacct gctggaagag gcttgggccc   5940
agagctttcc cacgagactg ctctggccag agcttgctag ccctgcctgt ctacagtagc   6000
accacctgca cagggtctgg tgcatgccca gaggagcagc aatgatgagt gactctcatc   6060
atctcagcct gctgagatct tgtttctctc ttcctccctt gaataaagct gtatccctac   6120
ctacaaaaaa aaaaaaaaaa aaa                                            6143
```

<210> SEQ ID NO 98
<211> LENGTH: 466
<212> TYPE: PRT
<213> ORGANISM: Homo sapiens

<400> SEQUENCE: 98

```
Met Ser Thr Arg Ser Val Ser Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ala Ser Ser Pro Gly Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380
```

```
Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465


<210> SEQ ID NO 99
<211> LENGTH: 466
<212> TYPE: PRT
<213> ORGANISM: Mus musculus

<400> SEQUENCE: 99

Met Ser Thr Arg Ser Val Ser Ser Ser Ser Tyr Arg Arg Met Phe Gly
1               5                   10                  15

Gly Ser Gly Thr Ser Ser Arg Pro Ser Ser Asn Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ser Ser Ser Pro Gly Gly Ala Tyr Val Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Ser Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Asp Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285
```

```
Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Leu Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Thr Phe Ser Ser Leu Asn Leu Arg Glu Thr Asn Leu Glu Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465


<210> SEQ ID NO 100
<211> LENGTH: 2151
<212> TYPE: DNA
<213> ORGANISM: Homo sapiens

<400> SEQUENCE: 100

gcctctccaa aggctgcaga agtttcttgc taacaaaaag tccgcacatt cgagcaaaga     60

caggctttag cgagttatta aaaacttagg ggcgctcttg tcccccacag ggcccgaccg    120

cacacagcaa ggcgatggcc cagctgtaag ttggtagcac tgagaactag cagcgcgcgc    180

ggagcccgct gagacttgaa tcaatctggt ctaacggttt cccctaaacc gctaggagcc    240

ctcaatcggc gggacagcag ggcgcgtcct ctgccactct cgctccgagg tccccgcgcc    300

agagacgcag ccgcgctccc accacccaca cccaccgcgc cctcgttcgc ctcttctccg    360

ggagccagtc cgcgccaccg ccgccgccca ggccatcgcc accctccgca gccatgtcca    420

ccaggtccgt gtcctcgtcc tcctaccgca ggatgttcgg cggcccgggc accgcgagcc    480

ggccgagctc cagccggagc tacgtgacta cgtccacccg cacctacagc ctgggcagcg    540

cgctgcgccc cagcaccagc cgcagcctct acgcctcgtc cccgggcggc gtgtatgcca    600

cgcgctcctc tgccgtgcgc ctgcggagca gcgtgcccgg ggtgcggctc ctgcaggact    660

cggtggactt ctcgctggcc gacgccatca acaccgagtt caagaacacc cgcaccaacg    720

agaaggtgga gctgcaggag ctgaatgacc gcttcgccaa ctacatcgac aaggtgcgct    780

tcctggagca gcagaataag atcctgctgg ccgagctcga gcagctcaag ggccaaggca    840

agtcgcgcct gggggacctc tacgaggagg agatgcggga gctgcgccgg caggtggacc    900

agctaaccaa cgacaaagcc cgcgtcgagg tggagcgcga caacctggcc gaggacatca    960

tgcgcctccg ggagaaattg caggaggaga tgcttcagag agaggaagcc gaaaacaccc   1020

tgcaatcttt cagacaggat gttgacaatg cgtctctggc acgtcttgac cttgaacgca   1080
```

```
aagtggaatc tttgcaagaa gagattgcct ttttgaagaa actccacgaa gaggaaatcc   1140
aggagctgca ggctcagatt caggaacagc atgtccaaat cgatgtggat gtttccaagc   1200
ctgacctcac ggctgccctg cgtgacgtac gtcagcaata tgaaagtgtg gctgccaaga   1260
acctgcagga ggcagaagaa tggtacaaat ccaagtttgc tgacctctct gaggctgcca   1320
accggaacaa tgacgccctg cgccaggcaa agcaggagtc cactgagtac cggagacagg   1380
tgcagtccct cacctgtgaa gtggatgccc ttaaaggaac caatgagtcc ctggaacgcc   1440
agatgcgtga aatggaagag aactttgccg ttgaagctgc taactaccaa gacactattg   1500
gccgcctgca ggatgagatt cagaatatga aggaggaaat ggctcgtcac cttcgtgaat   1560
accaagacct gctcaatgtt aagatggccc ttgacattga gattgccacc tacaggaagc   1620
tgctggaagg cgaggagagc aggatttctc tgcctcttcc aaacttttcc tccctgaacc   1680
tgagggaaac taatctggat tcactccctc tggttgatac ccactcaaaa aggacacttc   1740
tgattaagac ggttgaaact agagatggac aggttatcaa cgaaacttct cagcatcacg   1800
atgaccttga ataaaaattg cacacactca gtgcagcaat atattaccag caagaataaa   1860
aaagaaatcc atatcttaaa gaaacagctt tcaagtgcct ttctgcagtt tttcaggagc   1920
gcaagataga tttggaatag gaataagctc tagttcttaa caaccgacac tcctacaaga   1980
tttagaaaaa agtttacaac ataatctagt ttacagaaaa atcttgtgct agaatacttt   2040
ttaaaaggta ttttgaatac cattaaaact gctttttttt ttccagcaag tatccaacca   2100
acttggttct gcttcaataa atctttggaa aaactcaaaa aaaaaaaaaa a            2151
```

<210> SEQ ID NO 101
<211> LENGTH: 1834
<212> TYPE: DNA
<213> ORGANISM: Mus musculus

<400> SEQUENCE: 101

```
ctctgccact cttgctccgg gaccccagag accccagcgc tcctacgatt cacagccacc     60
gcgccctcat tcccttgttg cagtttttcc agccgcagca agccagccca ccttcgaagc    120
catgtctacc aggtctgtgt cctcgtcctc ctaccgcagg atgttcggtg gctccggcac    180
atcgagccgg cccagctcca accggagcta tgtgaccacg tccacacgca cctacagtct    240
gggcagcgca ctgcgcccca gcactagccg cagcctctat tcctcatccc ccggtggcgc    300
ctatgtgacc cggtcctcgg cagtgcgcct gcggagcagc gtgccgggcg tgcggctgct    360
tcaagactcg gtggacttct cgctggccga cgccatcaac actgagttca agaacacccg    420
caccaacgag aaggtagaac tgcaggagct gaatgaccgc tttgccaact acatcgacaa    480
ggtgcgcttc ctcgagcagc agaacaaaat cctgctggct gagctcgagc agctcaaggg    540
ccagggcaag tcgcgcctgg gcgacctgta cgaggaggag atgcgggagc tgcgccggca    600
ggtggatcag ctcaccaacg acaaggcccg tgtcgaggtg gagcgggaca acctggccga    660
ggacatcatg cggctgcgag agaaattgca ggaggagatg ctccagagag aggaagccga    720
aagcaccctg cagtcattca gacaggatgt tgacaatgct tctctggcac gtcttgacct    780
tgaacggaaa gtggaatcct tgcaggaaga aattgccttt ttgaagaaac tgcacgatga    840
agagatccag gagctgcagg cccagattca ggaacagcat gtccagatcg atgtggacgt    900
ttccaagcct gacctcactg ctgccctgcg tgatgtgcgc cagcagtatg aaagcgtggc    960
tgccaagaac ctccaggagg ccgaggaatg gtacaagtcc aagtttgctg acctctctga   1020
ggctgccaac cggaacaacg atgccctgcg ccaggccaag caggagtcaa acgagtaccg   1080
```

-continued

```
gagacaggtg cagtcactca cctgtgaagt ggatgccctt aaaggcacta acgagtccct   1140

ggagcgccag atgcgtgaga tggaagagaa ttttgccctt gaagctgcta actaccagga   1200

cactattggc cgcctgcagg atgagatcca aaacatgaag gaagagatgg ctcgtcacct   1260

tcgtgaatac caagatctgc tcaatgttaa gatggccctg gacattgaga tcgccaccta   1320

caggaagctg ctggaaggcg aggagagcag gatttctctg cctctgccaa ccttttcttc   1380

cctgaacctg agagaaacta acctggagtc acttcctctg gttgacaccc actcaaaaag   1440

aacactcctg attaagacgg ttgagaccag agatggacag gtgatcaatg agacttctca   1500

gcatcacgat gaccttgaat aaaaattgca cacacttggt gcaacagtgc agtaccagca   1560

agaaggaaaa aaaaatcgta tcttaggaaa acagctttca agtgccttta ctgcagtttt   1620

tcaggagcgc aagatagatt tggaatagaa agaagctcag cacttaacaa ctgacacccc   1680

aaaagacgta gaaaaggttt acaaaataat ctagtttacg aagaaatctt gtgctagaat   1740

actttttaaa gtatttttga ataccattaa aactgctttt ttccagtaaa tatctgacca   1800

acttgttact gcttcaataa atcttcaaaa atac                               1834


<210> SEQ ID NO 102
<211> LENGTH: 31
<212> TYPE: PRT
<213> ORGANISM: Homo sapiens

<400> SEQUENCE: 102

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30
```

METHODS OF REPROGRAMMING CELLS

CROSS REFERENCE TO RELATED APPLICATIONS

This application is a 35 U.S.C. §371 National Phase Entry Application of International Application No. PCT/US2009/054789 filed Aug. 24, 2009, which designates the United States, and which claims benefit of priority under 35 U.S.C. §119(e) of the U.S. Provisional Application No. 61/090,936 filed Aug. 22, 2008, the contents of which are incorporated herein by reference in their entirety.

GOVERNMENT SUPPORT

This invention was made with the Government Support under DK077445 awarded by the National Institutes of Health. The Government has certain rights to this invention.

SEQUENCE LISTING

The instant application contains a Sequence Listing which has been submitted via EFS-Web and is hereby incorporated by reference in its entirety. Said ASCII copy, created on Dec. 18, 2009, is named 00280606.txt, and is 334,313 bytes in size.

FIELD OF INVENTION

The invention relates to methods for reprogramming a cell of an endoderm origin to a cell having pancreatic β-cell characteristics. The present invention also relates to an isolated population comprising reprogrammed cells, compositions and their use in the treatment of diabetes mellitus.

BACKGROUND OF THE INVENTION

One goal of regenerative medicine is to be able to convert adult cells into other cell types for tissue repair and regeneration. Cells of adult organisms arise from sequential differentiation steps that are generally thought to be irreversible[1]. Biologists often describe this process of development as proceeding from an undifferentiated (embryonic) cell to a terminally differentiated cell that forms part of an adult tissue or organ. There are rare examples, however, in which cells of one type can be converted to another type in a process called cellular reprogramming or lineage reprogramming (Hochedlinger et al., Nature, 2006, 441, 1061-1067; Orkin S et al., Cell, 2008; 132; 631-644). Various forms of cellular reprogramming are referred to in the literature as transdifferentiation, dedifferentiation, or transdetermination[2]. For example, cellular reprogramming has been reported in amphibian limb regeneration and fly imaginal disc identity switches[3,4], and it may be central to certain types of pathological metaplasia[2]. There is long standing interest and fascination in reprogramming studies, in part because of the promise of harnessing this phenomenon for regenerative medicine whereby abundant adult cells that can be easily harvested would be converted to other medically important cell types to repair diseased or damaged tissues.

Somatic cell nuclear transfer (SCNT), developed in the 1960s, demonstrated that nuclei from differentiated adult cells could be reprogrammed to a totipotent state following injection into enucleated eggs[5,6]. More recently, it was shown that a small number of transcription factors can reprogram cultured adult skin cells to pluripotent stem cells[7-12]. These studies point to the possibility of regenerating mammalian tissues by first reverting skin or other adult cells to pluripotent stem cells and then redifferentiating these into various cell types.

SUMMARY OF THE INVENTION

The present invention relates to methods for direct reprogramming (i.e. cellular reprogramming) of cells, such as a cell of endoderm origin to a cell having characteristics of a pancreatic β-cell (i.e. a pancreatic β-like cell). In particular, the present invention relates to a method for reprogramming a cell of endoderm origin, such as, a pancreatic cell (e.g. an exocrine pancreatic cell, a pancreatic duct cell, or an acinar pancreatic cell), or a liver cell by increasing the protein expression of at least two transcription factors selected from any of Ngn3, Pdx1 and MafA in the cell of endoderm origin. In some embodiments, the method comprises increasing the expression of at least three transcription factors selected from Ngn3, Pdx1 and MafA. In some embodiments, the method comprises increasing the protein expression of a functional fragment of at least two transcription factors selected from Ngn3, Pdx1 and MafA in a cell of endoderm origin. In some embodiments, the method further comprises increasing the protein expression of additional transcription factors in addition to at least two selected from Ngn3, Pdx1 and MafA.

Accordingly, the present invention relates to methods, compositions and kits for producing a pancreatic β-like cell from a cell of endoderm origin. Other embodiments of the present invention relate to an isolated population of pancreatic β-like cells produced by increasing the protein expression of at least two transcription factors selected from any combination of Ngn3, Pdx1 and MafA in the cell of endoderm origin.

In some embodiments, the pancreatic β-like cell produced by the methods as disclosed herein secretes at least 15%, or at least 25% or at least 30% of the insulin that endogenous β-cells secrete, or alternatively, in some embodiments, a pancreatic β-like cell exhibits at least two characteristics of an endogenous pancreatic β-cell, for example, but not limited to, secretion of insulin in response to glucose, and expression of β-cell markers, such as for example, c-peptide, Pdx-1, Glut-2. In some embodiments, the β-like cell express insulin. In some embodiments, the β-like cells express VEGF. In some embodiments, the β-like cell expresses other cell markers, such as GCK, PCI/3, and transcription factors NeuroD, Nkx2.2 and Nkx6.2. In some embodiments, the β-like cell express GCK, PCI/3, NeuroD, Nkx2.2 and Nkx6 at a statistically significant increased level as compared to the cell of endoderm origin from which the β-like cell arises. In some embodiments, the β-like cell expresses insulin at a statistically significant increased level as compared to the cell of endoderm origin from which the β-like cell arises. In some embodiments, the β-like cell expresses VEGF at a statistically significant increased level as compared to the cell of endoderm origin from which the β-like cell arises.

In some embodiments, the β-like cell does not express markers Amylase, Ptf1a, Ck19 (Krt19), somatastatin/pancreatic polypeptide (SomPP), glucagon, mesenchymal markers, Nestin, Vimentin or Tuji. In some embodiments, the β-like cell expresses Amylase, Ptf1a, Ck19 (Krt19), somatastatin/pancreatic polypeptide (SomPP), glucagon, mesenchymal markers, Nestin, Vimentin or Tuji at at a statistically significant decreased level as compared to the cell of endoderm origin from which the β-like cell arise.

In some embodiments, an isolated population of pancreatic β-like cells produced by the methods and compositions as disclosed herein, is a population mammalian pancreatic β-like cell, for example, a population of human pancreatic β-like cell.

In some embodiments, an isolated population of pancreatic β-like cells and compositions is produced by the methods comprising contacting a cell or a population of cells of endoderm origin with an agent, such as a nucleic acid agent, peptide, polypeptide aptamer, antibody, antibody fragment, ribosomes, small molecule and the like, which increases the protein expression of at least two transcription factors selected from any combination of Ngn3, Pdx1 and MafA in the cell of endoderm origin. In some embodiments, the method to produce an isolated population of pancreatic β-like cells comprises introducing a nucleic acid sequence encoding at least two of the transcription factors Ngn3, Pdx1 and MafA, or functional fragments thereof into the cell of endoderm origin. In some embodiments, the nucleic acid sequence encoding at least two of the transcription factors Ngn3, Pdx1 and MafA, or functional fragments thereof is expressed transiently for a transient increase the protein expression of the polypeptides Ngn3, Pdx1 and MafA in the cell of endoderm origin.

Herein, the inventors have demonstrated using a strategy of re-expressing key developmental regulators in vivo, specific combinations are identified of three transcription factors (Ngn3, Pdx1 and MafA) that reprogram differentiated pancreatic exocrine cells in adult animals into cells that closely resemble β-cells. The pancreatic β-like cells are substantially indistinguishable from endogenous islet β-cells in size, shape, and ultrastructure. The pancreatic β-like cells express genes essential for β-cell function and can ameliorate hyperglycemia by remodeling local vasculature and secreting insulin. Accordingly, the present invention relates to a method of cellular reprogramming with defined factors, such as at least two of the transcription factors Ngn3, Pdx1 and MafA in an adult organ. The present invention also relates to a general paradigm for directing adult cell reprogramming without reversion to a pluripotent stem cell state.

One aspect of the present invention provides a method for reprogramming a cell of endoderm origin, the method comprising increasing the protein expression of at least two transcription factors selected from Pdx1, Ngn3, or MafA in the cell of enodermal origin, wherein the cell of enodermal origin is reprogrammed to exhibit at least two characteristics of a pancreatic β-cell. In some embodiments, the protein expression of Pdx1, Ngn3, and MafA are increased in the cell of enodermal origin. In some embodiments, the cell of endoderm origin is a pancreatic cell, such as, for example, a exocrine cell, a pancreatic duct cell, and an acinar pancreatic cell. In some embodiments, the cell of endoderm origin is a liver cell. In some embodiments, the cell of endoderm origin is a gall bladder cell.

In some embodiments, a characteristic of a pancreatic β-cell phenotype is secreting insulin in response to glucose. In all aspects of the present invention, a characteristic of a pancreatic β-cell phenotype is expression of at least one marker selected from the group consisting of: Ngn3−, Pdx1+ and MafA+.

In some embodiments, in increase in the protein expression of a transcription factor selected from Pdx1, Ngn3, or MafA is achieved by contacting the cell of endoderm origin with an agent which increases the expression of the transcription factor, where an agent can be selected from the group consisting of: a nucleotide sequence, a protein, an aptamer and small molecule, ribosome, RNAi agent and peptide-nucleic acid (PNA) and anologues or variants thereof. In some embodiments, protein expression is increased by introducing at least one nucleic acid sequence encoding a transcription factor protein selected from Pdx1, Ngn3, or MafA, or encoding a functional fragment thereof, in the cell of endoderm origin.

In some embodiments, protein expression of Pdx1 is increased by introducing a nucleic acid sequence encoding a Pdx1 polypeptide comprising SEQ ID NO: 2 or 32 or a functional fragment of SEQ ID NO: 2 or 32 into the cell of endoderm origin.

In some embodiments, the protein expression of Ngn3 is increased by introducing a nucleic acid sequence encoding a Ngn3 polypeptide comprising SEQ ID NO: 2 or 32 or a functional fragment of SEQ ID NO: 2 or 32 into the cell of endoderm origin.

In some embodiments, the protein expression of MafA is increased by introducing a nucleic acid sequence encoding a MafA polypeptide comprising SEQ ID NO: 3 or 33 or a functional fragment of SEQ ID NO: 3 or 33 into the cell of endoderm origin.

In some embodiments, a nucleic acid sequence is in a vector, such as a viral vector or a non-viral vector. In some embodiments, the vector is a viral vector comprising a genome that does not integrate into the host cell genome.

In some embodiments, cell of endoderm origin is in vitro. In some embodiments, cell of endoderm origin is ex vivo.

The method of any of paragraphs 1 to 19, wherein the cell of endoderm origin is in vivo or present in a subject. In some embodiments, the subject is a human subject. In some embodiments, the subject has, or is at risk of developing, diabetes, such as Type I diabetes, Type II diabetes or pre-diabetes. In some embodiments, the subject has or is at risk of developing a metabolic disorder. In some embodiments, a cell of endoderm origin is a mammalian cell, such as a human cell.

In some embodiments, the methods as disclosed herein for reprogramming a cell of endoderm origin further comprises contacting the cell of endoderm origin with at least one agent which increases the protein expression of at least one of the transcription factors selected from the group consisting of: NeuroD, Nkx2.2, Nkx6.1, Pax4, Pax6 or Isl1. In some embodiments, the pancreatic β-cell expresses a marker selected from the group consisting of: NeuroD, Nkx2.2, Nkx6.1, Pax4, Pax6 or Isl1.

In some embodiments, the cell of endoderm origin is reprogrammed to a pancreatic β-cell which is a pancreatic β-like cell. In some embodiments, the pancreatic β-like cell has an increased expression of a marker selected from the group consisting of: c-peptide, glucose transporter 2 (Glut2), glucokinase (GCK), prohormone convertase ⅓ (PC1/3), β-cell transcription factors NeuroD, Nkx2.2 and Nkx6.1 by a statistically significant amount relative to the cell of endoderm origin from which the pancreatic β-like cell was derived. In some embodiments, the pancreatic β-like cell has a decreased expression of a marker selected from the group consisting of: Amylase (Amy), glucagon, somatostatin/pancreatic polypeptide (SomPP), Ck19, Nestin, Vimentin and Tuji by a statistically significant amount relative to the cell of endoderm origin from which the pancreatic β-like cell was derived.

Another aspect of the present invention relates to an isolated population of pancreatic β-like cells obtained from a population of non-insulin producing cells of endoderm origin by a process comprising increasing the protein expression of at least two transcription factors selected from Ngn3, Pdx1 or MafA, or a functional fragment thereof, in the non-insulin producing cells of endoderm origin. In some embodiments, expression is transient expression.

In some embodiments, the isolated population of pancreatic β-like cells comprise pancreatic β-like cells which secrete insulin in response to an increase in glucose. In some embodiments, the isolated population of pancreatic β-like cells comprise pancreatic β-like cells which have a distinct morphology and localization as compared to endogenous pancreatic β-cells, for example, where the pancreatic β-like cells have at least one characteristic selected from the group consisting of: cobblestone cell morphology, a diameter of between 17-25 μm and an intercalated location within exocrine acincar rosettes. In some embodiments, the isolated population of pancreatic β-like cells is produced by increasing the protein expression in the a population of cells of endoderm origin of at least two transcription factors, which can be accomplished using a vector, such as a viral vector or a non-viral vector.

In some embodiments, the vector comprises a nucleic acid sequence encoding a Ngn3 polypeptide or a functional fragment thereof, and/or comprises a nucleic acid sequence encoding a Pdx1 polypeptide or a functional fragment thereof and/or comprises a nucleic acid sequence encoding a MafA polypeptide or a functional fragment thereof.

In some embodiments, the isolated population of pancreatic β-like cells comprise pancreatic β-like cells from a population of non-insulin producing cells of endoderm origin, such as a population of pancreatic cells. In some embodiments, such pancreatic cells are selected from the group consisting of: exocrine cells, pancreatic duct cells and an acinar pancreatic cells or a heterogeneous population thereof. In some embodiments, a population of non-insulin producing cells of endoderm origin are a population of liver cells and/or a population of gall bladder cells. In some embodiments, a population of non-insulin producing cells of endoderm origin is a heterogenous population of non-insulin producing cells of endoderm origin. In some embodiments, a population of non-insulin producing cells of endoderm origin is a heterogenous population of pancreas cells, which may include or exclude endogenous pancreatic β-cells. In some embodiments, a population of non-insulin producing cells of endoderm origin is a heterogenous cell population consisting of cells selected from the group consisting of: pancreas cells, liver cells and gall bladder cells.

In some embodiments, the population of non-insulin producing cells of endoderm origin is a population of mammalian cells, for example, human cells. In some embodiments, a population of non-insulin producing cells of endoderm origin is obtained from a subject that has diabetes, or has an increased risk of developing diabetes, such as a subject at increased risk of Type I diabetes, Type II diabetes and pre-diabetes. In some embodiments, a population of non-insulin producing cells of endoderm origin is obtained from a subject that has a metabolic disorder, or has an increased risk of developing a metabolic disorder.

Another aspect of the present invention relates to a method for the treatment of a subject with diabetes, the method comprising administering a composition comprising an isolated population of pancreatic β-like cells according to the methods as disclosed herein.

Another aspect of the present invention relates to the use of the isolated population of pancreatic β-like cells produced by the methods as disclosed herein for administering to a subject in need thereof.

In some embodiments, pancreatic β-like cells are produced from non-insulin producing endoderm cells obtained from the same subject as the composition is administered to. In some embodiments, the subject has has, or has an increased risk of developing, diabetes, for example, where the subject has, or has increased risk of getting diabetes from the group consisting of: Type I diabetes, Type II diabetes and pre-diabetes. In some embodiments, the subject has, or has an increased risk of developing, a metabolic disorder.

Another aspect of the present invention relates to kits for producing pancreatic β-like cells as disclose herein. In some embodiments, a kit comprises (i) a nucleic acid sequence encoding a Ngn3 polypeptide or a functional fragment thereof; and/or (ii) a nucleic acid sequence encoding a Pdx1 polypeptide or a functional fragment thereof; and/or (iii) a nucleic acid sequence encoding a MafA polypeptide or a functional fragment thereof. In some embodiments, the kit further comprises instructions for reprogramming a cell of endoderm origin to a cell with at least two characteristics of a pancreatic β-cell according to the methods as disclosed herein.

Another aspect of the present invention relates to a composition comprising at least one non-insulin producing endodermal cell and at least one agent which increases the protein expression of at least two transcription factors selected from Ngn3, Pdx1 or MafA.

Another aspect of the present invention relates to methods of identifying agents that alone or in combination with other agents reprogram a cell of endoderm origin to a pancreatic β-like cell. In some embodiments, the method includes contacting one or more cells of endoderm origin with one or more test agents (simultaneously or at separate times) and determining the level of expression of one or more reprogramming genes as defined herein. In some embodiments, the β-cell reprogramming genes include, Pdx1, Ngn3, mafA, NeuroD, Nkx2.2, Nkx6.1, Pax4, Pax6 of Isl1. Where one or more test agents increase the level of expression of one or more of the foregoing genes above the level of expression found in the cell of endoderm origin, in the absence of one or more test agents, are considered agents for reprogramming cells of endoderm origin to a pancreatic β-like cell. The test agents may include, but are not limited to, small molecules, nucleic acids, peptides, polypeptides, immunoglobulins, and oligosaccarides. In some embodiments, the just-mentioned method includes determining the level of expression of one or more of Pdx1, Ngn3 or MafA. In some embodiments, the method includes determining the level of expression of one or more of Pdx1, Ngn3 or MafA. Expression levels can be determined by any means known by one of ordinary skill in the art, for example, by RT-PCR or immunological methods.

BRIEF DESCRIPTION OF THE DRAWINGS

FIG. 1A shows a schematic diagram of experimental strategy. Adenoviruses encoding bicistronic transcription factor (T.F.) and nuclear GFP (nGFP) via an IRES element (I) were injected into the pancreas of an adult mouse (Rag$^{-/-}$). FIG. 1B is a microscope pictorial image showing wild type (WT) pancreas is predominantly exocrine tissue with insulin$^+$ β-cells in islet (outlined). Nuclei stained blue with DAPI. FIG. 1C is a microscope pictorial image showing one month after infection with a combination of Ngn3, Pdx1, and MafA viruses (pAd-M3), numerous insulin$^+$ cells appear outside islets.

FIG. 2A is a bar graph showing quantification of nGFP-infected cell types 10 days after nGFP viral infection. Data presented as mean±s.d. n=3 animals. ~1,000 $nGFP^+$ cells/animal. FIG. 2B is a schematic demonstrating that double heterozygous $Cpa1CreER^{T2}$; R26R adults mice are injected with Tamoxifen™, which labels mature exocrine cells with β-galactosidase (β-Gal). Reprogramming is subsequently induced by infection with pAd-M3.

FIG. 3A is a bar graph showing a size comparison of exocrine cells (white bar), islet β-cells (gray bar), and pancreatic β-like cells (black bar). Data presented as mean±s.d. n=3 animals. >100 cells/animal. Three asterisks: p<0.001. FIG. 3B is electron micrograph of a β-cell (outlined) in an islet. FIG. 3C shows an example of a pancreatic β-like cell situated between two exocrine cells. Endogenous and pancreatic β-like cells contain small insulin granules (In) and lack zymogen granules (Zy) of exocrine cells and extensive endoplasmic reticulum (ER). Nuc: nucleus. Scale bar: 2 um.

FIG. 4A is a graph showing improvement of fasting blood glucose level in diabetic mice after injection with pAd-M3 (diamond), compared with controls with nGFP virus (square). Triangle: non-diabetic controls. STZ: streptozotocin. Arrows indicate timing of injection. n=6-8 animals. FIG. 4B shows a histogram comparing non-fasting serum insulin levels 6 weeks after injection. n=6-8 animals. FIG. 4C is a histogram showing the average $insulin^+$ β-cell number per section 8 weeks after injection. n=3 animals. Both islet and pancreatic β-like cells were counted for the pAd-M3 samples. One asterisk, p<0.05; two asterisks, p<0.01; three asterisks, p<0.001. Data presented as mean±s.d.

FIG. 5A shows a pancreatic β-like cell (outlined) with a nucleus (N) and small granules on a section double immunostained for GFP (15 nm gold particles) and insulin (5 nm gold particles). FIG. 5B shows a region of the nucleus (green square in 5A) showing GFP staining. FIG. 5C shows a high magnified picture of the secretory granules (red square in FIG. 5A) showing insulin staining. Arrows in FIGS. 5B and 5C indicate gold particles. FIG. 5D shows an exocrine cell on the same section with large zymogen granules and dense endoplasmic reticulum. FIG. 5E and 5F show high magnification images of examples of nucleus and granules, no gold particles found. Samples harvested one month after M3 induction.

FIG. 6A shows a yen diagram of the number of differentially expressed genes in pancreatic β-like cells (550 genes) and islet cells (560 genes), and number of genes similarly expressed by both the pancreatic β-like cells and islet cells (1501 genes). The inventors prepared cRNA from three samples; (i) FACS sorted GFP+ cells from M3 infected samples (1 month) that contain ~22% reprogrammed insulin+ cells (e.g. pancreatic β-like cells); (ii) isolated whole islets (islet cells); and (iii) pancreatic non-islet cells (non-islet cells). As there are no FACS markers for mouse endocrine or β-cells, the GFP+ cells could not be further purified. Expression profile analysis was carried out with Illumina arrays and showed that in comparison to non-islet samples, 2051 genes are enriched in reprogrammed cells whereas 2061 genes are enriched in whole islets. Of these endocrine enriched genes, 1501 transcripts overlap. Due to contamination by exocrine cells, many exocrine transcripts were detected in the GFP+ sample. FIG. 6B shows a histogram of an example of the array analysis. Genes specific to endocrine cells are highly enriched in both the islet samples and the reprogrammed cell samples. N=3 independent repeats. Data presented as mean±s.d.

FIG. 8 shows an example of RT-PCR analysis with primer set specific for Ngn3 viral transgene showed that virus injected into the pancreas does not spread to other internal organs such as liver, intestine, spleen and kidney. Samples harvested 10 days after injection of pAd M3 into the pancreas. On immuofluresence analysis, GPF was detected in the pancreas only, and no GFP was detected in the liver, spleen or kidney (data not shown).

FIG. 9 shows RT-PCR analysis performed with primer sets specific for viral transgenes. Transgene expression was strongly reduced by 30 days and no longer detectable by 60 days in samples infected with pAd-M3. GADPH serves as control.

DETAILED DESCRIPTION OF THE INVENTION

Figure 1:
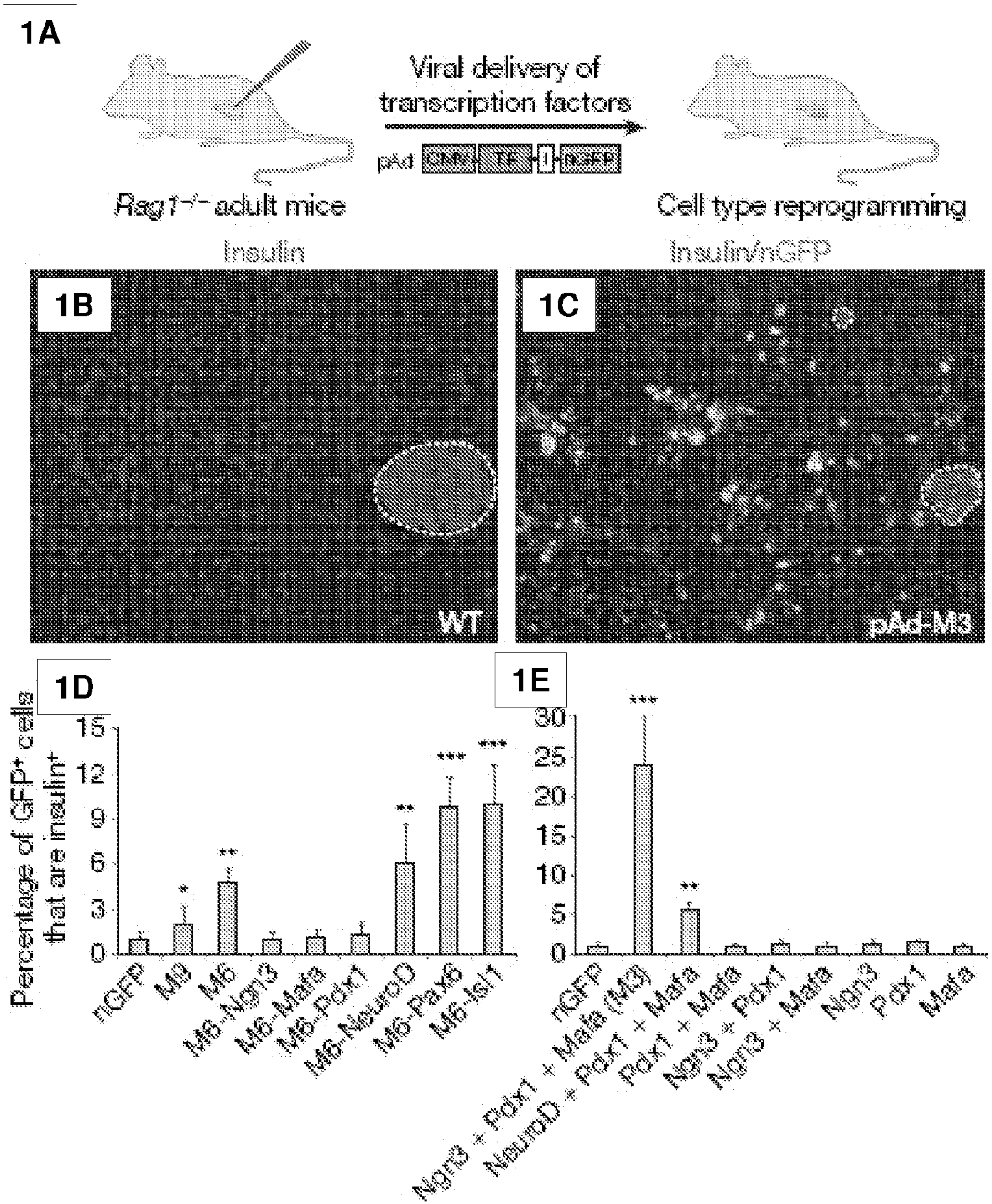
FIGS. 1A-1C shows a combination of three transcription factors induces insulin$^+$ cells in adult mouse pancreas in vivo.
FIG. 1D and FIG. 1E are graphs showing quantification of induction one month after infection. M9, M6: mixture of 9 and 6 different viruses, respectively. Data presented as mean±s.d. n=3 animals. ~1,000 $nGFP^+$ cells/animal. Asterisk, P<0.05; two asterisks, p<0.01; three asterisks, p<0.001.

The present invention provides compositions and methods for producing pancreatic β-like cells from a cell of endoderm origin. In some embodiments, the present invention provides compositions and methods for direct reprogramming of cells of endoderm origin to a pancreatic β-like cell, without the cell of endoderm origin becoming an induced pluripotent stem cell (iPS) intermediate prior to being reprogrammed to a pancreatic β-like cell.

The present invention relates to a population of pancreatic β-like cells from cells of endoderm origin, and methods and compositions for the direct reprogramming cells, such as cells of endoderm origin to a pancreatic β-like cell. In particular, the present invention relates to a method for reprogramming a cell of endoderm origin, such as a pancreatic cell (e.g. an exocrine pancreatic cell, a pancreatic duct cell, acinar pancreatic cell), or a liver cell by increasing the protein expression of at least two transcription factors selected from any of Ngn3, Pdx1 and MafA in the cell of endoderm origin. In some embodiments, the method comprises increasing the expression of at least three transcription factors selected from Ngn3, Pdx1 and MafA. In some embodiments, the method comprises increasing the protein expression of a functional fragment of at least two transcription factors selected from Ngn3, Pdx1 and MafA in a cell of endoderm origin. In some embodiments, the method further comprises increasing the protein expression of additional transcription factors in addition to at least two selected from Ngn3, Pdx1 and MafA.

Accordingly, the present invention relates to methods, compositions and kits for producing a reprogrammed pancreatic β-cell from a cell of endoderm origin. Other embodiments of the present invention relate to an isolated population of a reprogrammed pancreatic β-cell produced by increasing the protein expression of at least two transcription factors selected from any combination of Ngn3, Pdx1 and MafA in the cell of endoderm origin.

In some embodiments, the pancreatic β-like cell produced by the methods as disclosed herein expresses at least 15% of the amount of insulin expressed by an endogenous pancreatic β-cell, or at least about 20% or at least about 30%, or at least about 40%, or at least about 50%, or at least about 60%, or at least about 70%, or at least about 80%, or at least about 90%, or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic β-cell, or alternatively exhibits at least two characteristics of an endogenous pancreatic β-cell, for example, but not limited to, secretion of insulin in response to glucose, and expression of β-cell markers, such as for example, c-peptide, Pdx-1 and glut-2.

In some embodiments, an isolated population of pancreatic β-like cells produced by the methods and compositions as disclosed herein is a mammalian pancreatic β-like cell, for example, a human pancreatic β-like cell.

In some embodiments, an isolated population of pancreatic β-like cells and compositions are produced by a method comprising contacting a cell or a population of cells of endoderm origin with an agent, such as a nucleic acid agent, peptide, polypeptide aptamer, antibody, antibody fragment, ribosomes, small molecules, RNAi agents, ribosomes and the like, which increase the protein expression of at least two transcription factors selected from any combination of Ngn3, Pdx1 and MafA in the cell of endoderm origin. In some embodiments, the method to produce an isolated population of pancreatic β-like cells comprises introducing a nucleic acid sequence encoding at least two of the transcription factors Ngn3, Pdx1 and MafA, or functional fragments thereof into the cell of endoderm origin. In some embodiments, the nucleic acid sequence encoding at least two of the transcription factors Ngn3, Pdx1 and MafA, or functional fragments thereof is expressed transiently for a transient increase the protein expression of the polypeptides Ngn3, Pdx1 and MafA in the cell of endoderm origin.

In some embodiments, the method comprises increasing the protein expression of any of the transcription factors Pdx1, Ngn3, and MafA of SEQ ID NOs 1-3, or functional fragments of proteins of SEQ ID NO: 1-3 respectively for mouse polypeptide, or SEQ ID NO: 31-33 or functional fragments of proteins 31-33 respectively for human polypeptide sequences.

In some embodiments, the method to produce an isolated population of pancreatic β-like cells comprises introducing a nucleic acid sequence encoding at least two of the transcription factors Pdx1, Ngn3, and MafA, or functional fragments thereof into the cell of endoderm origin, where a nucleic acid sequences can be selected from any of SEQ ID NO: 34-39 or fragments thereof. In some embodiments, the nucleic acid sequence encoding at least two of the transcription factors Pdx1, Ngn3, and MafA, or functional fragments thereof (i.e. any sequence selected from SEQ ID NO: 34-39 or fragments thereof) is expressed transiently for a transient increase the protein expression of at least two of the polypeptides selected from Pdx1 (SEQ ID NOs: 1 or 31), Ngn3 (SEQ ID NOs: 2 or 32), and MafA (SEQ ID NOs: 3 or 33), or functional fragments thereof in the cell of endoderm origin.

Definitions:

For convenience, certain terms employed herein, in the specification, examples and appended claims are collected here. Unless otherwise defined, all technical and scientific terms used herein have the same meaning as commonly understood by one of ordinary skill in the art to which this invention belongs.

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. A partial reversal of differentiation produces a partially induced pluriotent (PiPS) cell. Reprogramming also encompasses partial reversion of the differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The term "differentiated cell" is meant any primary cell that is not, in its native form, pluripotent as that term is defined herein. It should be noted that placing many primary cells in culture can lead to some loss of fully differentiated characteristics. However, simply culturing such cells does not, on its own, render them pluripotent. The transition to pluripotency requires a reprogramming stimulus beyond the stimuli that lead to partial loss of differentiated character in culture. Reprogrammed pluripotent cells also have the characteristic of the capacity of extended passaging without loss of growth potential, relative to primary cell parents, which generally have capacity for only a limited number of divisions in culture. Stated another way, the term "differentiated cell" refers to a cell of a more specialized cell type derived from a cell of a less specialized cell type (e.g., a stem cell such as an induced pluripotent stem cell) in a cellular differentiation process.

As used herein, the term "somatic cell" refers to are any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro. Unless otherwise indicated the methods for reprogramming somatic cells of endoderm origin to a β-cell can be performed both in vivo and in vitro (where in vivo is practiced when somatic cells of endoderm origin are present within a subject, and where in vitro is practiced using isolated somatic cells of endoderm origin maintained in culture). In some embodiments, where somatic cells of endodermal origin are cultured in vitro, the somatic cells of endodermal cells are cultured in an organotypic pancreatic slice culture, as described in, e.g., meneghel-Rozzo et al., (2004), Cell Tissue Res, 316(3); 295-303, which is incorporated herein in its entirety by reference.

As used herein, the term "adult cell" refers to a cell found throughout the body after embryonic development.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of respiratory and digestive tracts and the liver and pancreas.

The term "a cell of endoderm origin" as used herein refers to a cell of endoderm origin includes any cell which has developed from an endoderm cell. Without wishing to be bound by theory, liver and pancreas progenitors develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "pancreatic β-like cell" as used herein refers to a cell produced by the methods as disclosed herein which expresses at least 15% of the amount of insulin expressed by an endogenous pancreatic β-cell, or at least about 20% or at least about 30%, or at least about 40%, or at least about 50%, or at least about 60%, or at least about 70%, or at least about 80%, or at least about 90%, or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic β-cell, or alternatively exhibits at least one, or at least two characteristics of an endogenous pancreatic β-cell, for example, but not limited to, secretion of insulin in response to glucose, and expression of β-cell markers, such as for example, c-peptide, Pdx-1 and glut-2. The pancreatic β-like cell is sometimes referred herein to as the "reprogrammed cell" or "reprogrammed β-cell", which are used interchangeably herein with the term "pancreatic β-like cell".

As used herein, the term "endogenous β-cell" refers to an insulin producing cell of the pancreas or a cell of a pancreatic β-cell (beta cell) phenotype. The phenotype of a pancreatic β-cell is well known by persons of ordinary skill in the art, and include, for example, secretion of insulin in response to an increase in glucose level, expression of markers such as c-peptide, PDX-1 polypeptide and Glut 2, as well as distinct morphological characteristics such as organized in islets in pancreas in vivo, and typically have small spindle like cells of about 9-15 μm diameter.

As used herein, the term "insulin producing cell" includes endogenous β-cells as that term is described herein, as well as pancreatic β-like cells as that term is described herein, that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. A population of pancreatic β-like cells or insulin producing cells made by the present invention may contain β-cells or β-like cells (e.g., cells that have at least two characteristics of an endogenous β-cell). The novelty of the present composition and methods is not negated by the presence of cells in the population that produce insulin naturally (e.g., beta cells). It is also contemplated that the population of pancreatic β-like cells may also contain non-insulin producing cells (i.e. cells of β-cell like phenotype with the exception they do not produce or secrete insulin).

The term "non-insulin producing endodermal cell" as used herein is meant any cell of endoderm origin that does not naturally synthesize, express, or secrete insulin constitutively or inducibly. Thus, the term "non-insulin producing endodermal cells" as used herein excludes pancreatic beta cells. Examples of non-insulin producing endodermal cells that can be used in the methods of the present invention include pancreatic non-beta cells, such as amylase producing cells, acinar cells, cells of ductal adenocarcinoma cell lines (e.g., CD18, CD11, and Capan-I cells (see Busik et al., 1997; Schaffert et al. 1997). Non-pancreatic cells of endoderm origin could also be used, for example, non-pancreatic stem cells and cells of other endocrine or exocrine organs, including, for example, liver cells, tymus cells, thyroid cells, intestine cells, lung cells and pituitary cells. In some embodiments, the non-insulin producing endodermal cells can be mammalian cells or, even more specifically, human cells. Examples of the present method using mammalian pancreatic non-islet, pancreatic amylase producing cells, pancreatic acinar cells are provided herein.

The term "progenitor cell" is used herein to refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

The term "exocrine cell" as used herein refers to a cell of an exocrine gland, i.e. a gland that discharges its secretion via a duct. In particular embodiments, an exocrine cells refers to a pancreatic exocrine cell, which is a pancreatic cell that produces enzymes that are secreted into the small intestine. These enzymes help digest food as it passes through the gastrointestinal tract. Pancratic exocrine cells are also known as islets of Langerhans, that secrete two hormones, insulin and glucagon. A pancreatic exocrine cell can be one of several cell types: alpha-2 cells (which produce the hormone glucagon); or β-cells (which manufacture the hormone insulin); and alpha-1 cells (which produce the regulatory agent somatostatin). Non-insulin producing exocrine cells as used herein refers to alpha-2 cells or alpha-1 cells. Note, the term pancreatic exocrine cells encompasses "pancreatic endocrine cells" which refer to a pancreatic cell that produces hormones (e.g., insulin (produced from β-cells) and glucagon (produced by alpha-2 cells) that are secreted into the bloodstream.

The term "pancreas" refers to a glandular organ that secretes digestive enzymes and hormones. In humans, the pancreas is a yellowish organ about 7 in. (17.8 cm) long and 1.5 in. (3.8 cm) wide. It lies beneath the stomach and is connected to the small intestine intestine, muscular hoselike portion of the gastrointestinal tract extending from the lower end of the stomach (pylorus) to the anal opening. Most of the pancreatic tissue consists of grapelike clusters of cells that produce a clear fluid (pancreatic juice) that flows into the duodenum through a common duct along with bile from the liver. Pancreatic juice contains three digestive enzymes: tryptase, amylase, and lipase, that, along with intestinal enzymes, complete the digestion of proteins, carbohydrates, and fats, respectively. Scattered among the enzyme-producing cells of the pancreas are small groups of endocrine cells, called the islets of Langerhans, that secrete two hormones, insulin and glucagon. The pancreatic islets contain several types of cells: alpha-2 cells, which produce the hormone glucagon; beta cells, which manufacture the hormone insulin; and alpha-1 cells, which produce the regulatory agent somatostatin. These hormones are secreted directly into the bloodstream, and together, they regulate the level of glucose in the blood. Insulin lowers the blood sugar level and increases the amount of glycogen (stored carbohydrate) in the liver; glucagon has the opposite action. Failure of the insulin-secreting cells to function properly results in diabetes diabetes or diabetes mellitus.

The term a "β-cell reprogramming gene", as used herein, refers to a gene whose expression, contributes to the direct reprogramming of cells of endoderm origin, i.e. somatic cells of endoderm origin to a cell with a pancreatic β-cell like phenotype, i.e. a cell which exhibits at least two characteristics of an endogenous pancreatic β-cell. A β-cell reprogramming gene can be, for example, genes encoding transcription factors Pdx1 (SEQ ID NO:1 or 31), Ngn3 (SEQ ID NO: 2 or 32), or MafA (SEQ ID NO: 3 or 33). Other β-cell reprogramming genes encode transcription factors including, but are not limited to, NeuroD (SEQ ID NO:4), Nkx2.2 (SEQ ID NO:5), Nkx6.1 (SEQ ID NO:6), Pax4 (SEQ ID NO:7), Pax6 (SEQ ID NO:8) or Isl (SEQ ID NO:9).

The term "β-cell reprogramming factor" or "β-cell reprogramming polypeptide" refers to an expression product of a β-cell reprogramming gene. Expression of an exogenously introduced β-cell reprogramming factor may be transient, i.e., it may be needed during at least a portion of the direct reprogramming process in order to induce the direct reprogramming of a cell of endoderm origin to a pancreatic β-like cell like phenotype and/or establish a stable pancreatic β-like cell but afterwards not required to maintain the survival or propagation of the pancreatic β-like cell. For example, the β-cell reprogramming factor may induce expression of endogenous genes whose function is associated with reprogramming cells of endoderm origin to a pancreatic β-cell phenotype. These genes may then maintain the reprogrammed cells as differentiated pancreatic β-like cells, as disclosed herein. A β-cell reprogramming factor can be, for example, transcription factors Pdx1 (SEQ ID NO:1 or 31), Ngn3 (SEQ ID NO: 2 or 32), or MafA (SEQ ID NO: 3 or 33). Other β-cell reprogramming factors are transcription factors including, but are not limited to, NeuroD (SEQ ID NO:4), Nkx2.2 (SEQ ID NO:5), Nkx6.1 (SEQ ID NO:6), Pax4 (SEQ ID NO:7), Pax6 (SEQ ID NO:8) or Isl (SEQ ID NO:9).

The term "β-cell reprogramming agent" refers to any agent which increases the protein expression of a β-cell reprogramming gene, as that term is described herein. Preferably, a β-cell reprogramming agent increases the expression of a β-cell reprogramming factor selected from transcription factors Pdx1 (SEQ ID NO:1 or 31), Ngn3 (SEQ ID NO: 2 or 32), or MafA (SEQ ID NO: 3 or 33). A β-cell reprogramming agent includes a β-cell reprogramming factor as that term is defined herein, or any other agent which increases the expression of a β-cell reprogramming gene, such as increases the protein expression of Pdx1, Ngn3 or MafA.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. ScL USA 87:22264-2268, 1990) modified as in Karlin and Altschul, Proc. Natl. Acad. ScL USA 90:5873-5877, 1993 is incorporated into the NBLAST and XBLAST programs of Altschul et al. (Altschul, et al., J. MoI. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL www.ncbi.nlm.nih.gov for these programs. In a specific embodiment, percent identity is calculated using BLAST2 with default parameters as provided by the NCBI.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of pancreatic β-like cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not pancreatic β-like cells or their progeny as defined by the terms herein. In some embodiments, the present invention encompasses methods to expand a population of pancreatic β-like cells, wherein the expanded population of pancreatic β-like cells is a substantially pure population of pancreatic β-like cells.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a nonpolypeptide moiety covalently or noncovalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The terms "polypeptide variant" refers to any polypeptide differing from a naturally occurring polypeptide by amino acid insertion(s), deletion(s), and/or substitution(s). Variants may be naturally occurring or created using, e g., recombinant DNA techniques or chemical synthesis. In some embodiments amino acid "substitutions" are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments not more than 1%, 5%, 10%, 15% or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

By "amino acid sequences substantially homologous" to a particular amino acid sequence (e.g. Pdx1, Ngn3 or MafA) is meant polypeptides that include one or more additional amino acids, deletions of amino acids, or substitutions in the amino acid sequence of Pdx1, Ngn3 or MafA without appreciable loss of functional activity as compared to wild-type Pdx1, Ngn3 or MafA polypeptides in terms of the ability to produce pancreatic β-like cells from cells of endoderm origin (i.e. directly reprogram cells of endoderm origin to pancreatic β-like cell like cells). For example, the deletion can consist of amino acids that are not essential to the presently defined differentiating activity and the substitution(s) can be conservative (i.e., basic, hydrophilic, or hydrophobic amino acids substituted for the same). Thus, it is understood that, where desired, modifications and changes may be made in the amino acid sequence of Pdx1, Ngn3 or MafA, and a protein having like characteristics still obtained. It is thus contemplated that various changes may be made in the amino acid sequence of the Pdx1, Ngn3 or MafA amino acid sequence (or underlying nucleic acid sequence) without appreciable loss of biological utility or activity and possibly with an increase in such utility or activity. In some embodiments, the amino acid sequences substantially homologous to a particular amino acid sequence are at least 70%, e.g., 75%, 80%85%, 90%, 95% or another percent from 70% to 100%, in intergers thereof, identical to the particular amino acid sequence.

As used herein, "Pdx1" is refers to the Pdx1 protein of Genebank accession No: NM_008814 (mouse) (SEQ ID NO:1) or NP_000200.1 (Human)(SEQ ID NO: 31), or Gene ID: 3651. The term Pdx1 also encompasses species variants, homologues, allelic forms, mutant forms, and equivalents thereof, including conservative substitutions, additions, deletions therein not adversely affecting the structure of function. Pdx1 is referred in the art as aliases; pancreatic and duodenal homeobox 1, IDX-1, STF-1, PDX-1, MODY4, Ipf1. Human Pdx1 is encoded by nucleic acid corresponding to GenBank Accession No: NM_000209 (human) (SEQ ID NO:34) or NM_008814 (mouse)(SEQ ID NO: 37). Pdx1 protein is a transcriptional activator of several genes, including insulin, somatostatin, glucokinase, islet amyloid polypeptide, and glucose transporter type 2 (GLUT2). Pdx1 is a nuclear protein is involved in the early development of the pancreas and plays a major role in glucose-dependent regulation of insulin gene expression. Defects in the gene encoding the Pdx1 protein are a cause of pancreatic agenesis, which can lead to early-onset insulin-dependent diabetes mellitus (NIDDM), as well as maturity onset diabetes of the young type 4 (MODY4). The term "Pdx1", or "Pdx1 protein" as used herein refers to a polypeptide having a naturally occurring amino acid sequence of a Pdx1 protein or a fragment, variant, or derivative thereof that at least in part retains the ability of the naturally occurring protein to bind to DNA and activate gene transcription of insulin, somatostatin, glucokinase, islet amyloid polypeptide, and glucose transporter type 2 (GLUT2). In addition to naturally-occurring allelic variants of the pdx1 sequences that may exist in the population, it will be appreciated that, as is the case for virtually all proteins, a variety of changes can be introduced into the sequences of SEQ ID NO: 1 or SEQ ID NO: 31 (referred to as "wild type" sequences) without substantially altering the functional (biological) activity of the polypeptides. Such variants are included within the scope of the terms "Pdx1", "Pdx1 protein", etc.

As used herein, "Ngn3" is refers to the Ngn3 protein of Genebank accession No: NM_009719 (mouse) (SEQ ID NO:2) or NP_066279.2 (Human)(SEQ ID NO: 32); GeneID No: 50674. The term Ngn3 also encompasses species variants, homologues, allelic forms, mutant forms, and equivalents thereof, including conservative substitutions, additions, deletions therein not adversely affecting the structure of function. Ngn3 is referred in the art as aliases; neurogenin 3; Atoh5; Math4B; bHLHa7; NEUROG3. Human Ngn3 is encoded by nucleic acid corresponding to GenBank Accession No: NM_020999 (human) (SEQ ID NO:35) or NM_009719 (mouse)(SEQ ID NO: 38). Neurogenin-3 (NEUROG3) is expressed in endocrine progenitor cells and is required for endocrine cell development in the pancreas and intestine (Wang et al., 2006). It belongs to a family of basic helix-loop-helix transcription factors involved in the determination of neural precursor cells in the neuroectoderm (Gradwohl et al., 2000). The term "Ngn3", or "Ngn3 protein" as used herein refers to a polypeptide having a naturally occurring amino acid sequence of a Ngn3 protein or a fragment, variant, or derivative thereof that at least in part retains the ability of the naturally occurring protein to bind to DNA and activate gene transcription of NeuroD, Delta-like 1 (Dll1), HeyL, insulinoma-assiciated-1 (IA1), Nk2.2, Notch, Hes5, Isl1, Somatastain receptor 2 (Sstr2) and other genes as disclosed in Serafimidis et al., Stem cells; 2008; 26; 3-16, which is incorporated herein in its entirety by reference. In addition to naturally-occurring allelic variants of the Ngn3 sequences that may exist in the population, it will be appreciated that, as is the case for virtually all proteins, a variety of changes can be introduced into the sequences of SEQ ID NO: 2 or SEQ ID NO: 32 (referred to as "wild type" sequences) without substantially altering the functional (biological) activity of the polypeptides. Such variants are included within the scope of the terms "Ngn3", "Ngn3 protein", etc.

As used herein, "MafA" is refers to the MafA protein of Genebank accession No: NM_194350 (mouse) (SEQ ID NO:3) or NP_963883.2 (Human)(SEQ ID NO: 33); GeneID No: 389692. The term MafA also encompasses species variants, homologues, allelic forms, mutant forms, and equivalents thereof, including conservative substitutions, additions, deletions therein not adversely affecting the structure of function. MafA is referred in the art as aliases; v-maf musculoaponeurotic fibrosarcoma oncogene homolog A (avian), hMafA; RIPE3b1; MAFA. Human MafA is encoded by nucleic acid corresponding to GenBank Accession No: NM_201589 (human) (SEQ ID NO:36) or NM_194350 (mouse) (SEQ ID NO: 39). MAFA is a transcription factor that binds RIPE3b, a conserved enhancer element that regulates pancreatic beta cell-specific expression of the insulin gene (INS; MIM 176730) (Olbrot et al., 2002). The term "MafA", or "MafA" protein" as used herein refers to a polypeptide having a naturally occurring amino acid sequence of a MafA" protein or a fragment, variant, or derivative thereof that at least in part retains the ability of the naturally occurring protein to bind to DNA and activate gene transcription of Glut2 and pyruvate carboxylase, and other genes such as Glut2, Pdx-1, Nkx6.1, GLP-1 receptor, prohormone convertase-1/3 as disclosed in Wang et al., Diabetologia. 2007 February; 50(2): 348-358, which is incorporated herein by reference. In addition to naturally-occurring allelic variants of the MafA sequences that may exist in the population, it will be appreciated that, as is the case for virtually all proteins, a variety of changes can be introduced into the sequences of SEQ ID NO: 3 or SEQ ID NO: 33 (referred to as "wild type" sequences) without substantially altering the functional (biological) activity of the polypeptides. Such variants are included within the scope of the terms "MafA", "MafA protein", etc.

As used herein, "glucose transporter 2" refers to the Glut2 protein of Genebank accession NP_000331.1 (human) (SEQ ID NO: 46); NP_112474 (mouse) (SEQ ID NO: 47). The term Glut2 also encompasses species variants, homologues, allelic forms, mutant forms, and equivalents thereof, including conservative substitutions, additions, deletions therein not adversely affecting the structure of function. Glut2 is referred in the art as aliases; Glut2, Slc2a2, solute carrier family 2 (facilitated glucose transporter). Human Glut2 is encoded by nucleic acid corresponding to GenBank Accession No: NM_000340.1 (human) (SEQ ID NO: 48); NM_031197 (mouse) (SEQ ID NO: 49). In addition to naturally-occurring allelic variants of the Glut2 sequences that may exist in the population, it will be appreciated that, as is the case for virtually all proteins, a variety of changes can be introduced into the sequences of SEQ ID NO: 46 or SEQ ID NO: 47 (referred to as "wild type" sequences) without substantially altering the functional (biological) activity of the polypeptides, and such variants are included within the scope of the terms "Glut2", etc. Glucose transporter 2 isoform is an integral plasma membrane glycoprotein of the liver, islet beta cells, intestine, and kidney epithelium. It mediates facilitated bidirectional glucose transport. Because of its low affinity for glucose, it has been suggested as a glucose sensor. (GeneID: 6514). The sequences of the accession Nos. that have been assigned Sequence Identifier numbers are incorporated herein in their entirety.

As used herein, "glucokinase" or "GCK" are used interchangeably herein and refer to the GCK protein of Genebank accession NP_000153.1 (human) (SEQ ID NO: 50); NP_034422.2 (mouse) (SEQ ID NO: 51). The term GCK also encompasses species variants, homologues, allelic forms, mutant forms, and equivalents thereof, including conservative substitutions, additions, deletions therein not adversely affecting the structure of function. GCK is referred in the art as aliases; glucokinase (hexokinase 4); GK; GLK; HK4; HHF3; HKIV; HXKP; MODY2; GCK. Human GCK is encoded by nucleic acid corresponding to GenBank Accession No: NM_000162.3 (human) (SEQ ID NO: 52); NM_010292.4 (mouse) (SEQ ID NO: 53). In addition to naturally-occurring allelic variants of the GCK sequences that may exist in the population, it will be appreciated that, as is the case for virtually all proteins, a variety of changes can be introduced into the sequences of SEQ ID NO: 50 or SEQ ID NO: 51 (referred to as "wild type" sequences) without substantially altering the functional (biological) activity of the polypeptides, and such variants are included within the scope of the terms "GCK", etc. The sequences of the accession Nos. that have been assigned Sequence Identifier numbers are incorporated herein in their entirety.

As used herein, "prohormone convertase" or "PC1/3" are used interchangeably herein and refer to the PC1/3 protein of Genebank accession NP_000430.3 (human) (SEQ ID NO: 54); NP_038656.1 (mouse) (SEQ ID NO: 55). The term PC1/3 also encompasses species variants, homologues, allelic forms, mutant forms, and equivalents thereof, including conservative substitutions, additions, deletions therein not adversely affecting the structure of function. PC1/2 is referred in the art as aliases; proprotein convertase subtilisin/kexin type 1; PC1, PC3, SPC3; PCSK1; Nec-1, Nec1, Phpp-1. Human PC1/3 is encoded by nucleic acid corresponding to GenBank Accession NM_000439 (human) (SEQ ID NO: 56); NM_013628.2 (mouse) (SEQ ID NO: 57). In addition to naturally-occurring allelic variants of the PC1/3 sequences that may exist in the population, it will be appreciated that, as is the case for virtually all proteins, a variety of changes can be introduced into the sequences of SEQ ID NO: 54 or SEQ ID NO: 55 (referred to as "wild type" sequences) without substantially altering the functional (biological) activity of the polypeptides, and such variants are included within the scope of the terms "PC1/3", etc. The protein encoded by this gene belongs to the subtilisin-like proprotein convertase family. The members of this family are proprotein convertases that process latent precursor proteins into their biologically active products. This encoded protein is a type I proinsulin-processing enzyme that plays a key role in regulating insulin biosynthesis. It is also known to cleave proopiomelanocortin, prorenin, proenkephalin, prodynorphin, prosomatostatin and progastrin. Mutations in this gene are thought to cause obesity. This encoded protein is associated with carcinoid tumors. The use of alternate polyadenylation sites has been found for this gene, as well as multiple alternatively spliced transcript variants. The sequences of the accession Nos. that have been assigned Sequence Identifier numbers are incorporated herein in their entirety.

As used herein, "NeuroD" refers to the NeuroD protein of Genebank accession NP_002491.2 (human) (SEQ ID NO:

58); NP_035024.1 (mouse) (SEQ ID NO: 59). The term NeuroD also encompasses species variants, homologues, allelic forms, mutant forms, and equivalents thereof, including conservative substitutions, additions, deletions therein not adversely affecting the structure of function. NeuroD is referred in the art as aliases; neurogenic differentiation 1; BETA2; BHF-1; NEUROD; bHLHa3; NEUROD1. NeuroD is encoded by nucleic acid corresponding to GenBank Accession No: NM_002500.2 (human) (SEQ ID NO: 60); NM_010894.2 (mouse) (SEQ ID NO: 61). In addition to naturally-occurring allelic variants of the NeuroD sequences that may exist in the population, it will be appreciated that, as is the case for virtually all proteins, a variety of changes can be introduced into the sequences of SEQ ID NO: 58 or SEQ ID NO: 59 (referred to as "wild type" sequences) without substantially altering the functional (biological) activity of the polypeptides, and such variants are included within the scope of the terms "NeuroD", etc. The NeuroD gene encodes a member of the NeuroD family of basic helix-loop-helix (bHLH) transcription factors, and the NeuroD protein forms heterodimers with other bHLH proteins and activates transcription of genes that contain a specific DNA sequence known as the E-box. It regulates expression of the insulin gene, and mutations in this gene result in type II diabetes mellitus. The sequences of the accession Nos. that have been assigned Sequence Identifier numbers are incorporated herein in their entirety.

As used herein, "NK2 homeobox 2" or "Nkx2.2" are used interchangeably herein and refer to the Nkx2.2 protein of Genebank accession Nos: NP_002500.1 (human) (SEQ ID NO: 62); NP_001071100.1 (mouse) (SEQ ID NO: 63). The term Nkx2.2 also encompasses species variants, homologues, allelic forms, mutant forms, and equivalents thereof, including conservative substitutions, additions, deletions therein not adversely affecting the structure of function. Nkx2.2 is referred in the art as aliases; NK2 homeobox 2; NKX2B; NKX2.2; NKX2-2; tinman. Nkx2.2 is encoded by nucleic acid corresponding to GenBank Accession No: NM_002509.2 (human) (SEQ ID NO: 64); NM_001077632.1 (mouse) (SEQ ID NO: 65). In addition to naturally-occurring allelic variants of the Nkx2.2 sequences that may exist in the population, it will be appreciated that, as is the case for virtually all proteins, a variety of changes can be introduced into the sequences of SEQ ID NO: 62 or SEQ ID NO: 63 (referred to as "wild type" sequences) without substantially altering the functional (biological) activity of the polypeptides, and such variants are included within the scope of the terms "Nkx2.2", etc. The sequences of the accession Nos. that have been assigned Sequence Identifier numbers are incorporated herein in their entirety.

As used herein, "NK6 homeobox 1" or "Nkx6.1" are used interchangeably herein and refer to the Nkx6.1 protein of Genebank accession Nos: NP_006159.2 (human) (SEQ ID NO: 66); NP_659204.1 (mouse) (SEQ ID NO: 67). The term Nxk6.1 also encompasses species variants, homologues, allelic forms, mutant forms, and equivalents thereof, including conservative substitutions, additions, deletions therein not adversely affecting the structure of function. Nkx6.1 is referred in the art as aliases; NK6 homeobox 1; NKX6A; NKX6.1 and NKX6-1. Nkx6.1 is encoded by nucleic acid corresponding to GenBank Accession No: NM_006168.2 (human) (SEQ ID NO: 68); NM_144955.2 (mouse) (SEQ ID NO: 69). In addition to naturally-occurring allelic variants of the Nkx6.1 sequences that may exist in the population, it will be appreciated that, as is the case for virtually all proteins, a variety of changes can be introduced into the sequences of SEQ ID NO: 66 or SEQ ID NO: 67 (referred to as "wild type" sequences) without substantially altering the functional (biological) activity of the polypeptides, and such variants are included within the scope of the terms "Nkx6.1", etc. In the pancreas, NKX6.1 is required for the development of beta cells and is a potent bifunctional transcription regulator that binds to AT-rich sequences within the promoter region of target genes Iype et al. (2004). The sequences of the accession Nos. that have been assigned Sequence Identifier numbers are incorporated herein in their entirety.

As used herein the term "c-peptide" refers to the connecting peptide which connects the A and B chains of the insulin protein hormone involved in the regulation of blood sugar levels. By way of background, insulin is produced in the liver as: its precursor proinsulin, consisting of the B and A chains of insulin linked together via a connecting C-peptide (hereinafter this C-peptide derived from the proinsulin molecule is referred to as "insulin C-peptide"). The term c-peptide also encompasses species variants, homologues, allelic forms, mutant forms, and equivalents thereof, including conservative substitutions, additions, deletions therein not adversely affecting the structure of function. The protein sequence for human C-peptide is disclosed as SEQ ID NO: 1 in U.S. Pat. No. 6,558,924 (which is incorporated herein in its entirity by reference and is herein referred to as SEQ ID NO: 102). The sequences of the accession Nos. that have been assigned Sequence Identifier numbers are incorporated herein in their entirety.

As used herein, the term "insulin" or "INS" refers to the protein of Genebank Nos: NM_000207.2 (human) (SEQ ID NO: 70); NM_008386.3 (mouse) (SEQ ID NO: 71). The term insulin also encompasses species variants, homologues, allelic forms, mutant forms, and equivalents thereof, including conservative substitutions, additions, deletions therein not adversely affecting the structure of function. Insulin is referred in the art as aliases; Ins-1; Ins2-rs1; Ins1. Insulin is encoded by nucleic acid corresponding to GenBank Accession No: NM_000207.2 (human) (SEQ ID NO: 72); NM_008386.3 (mouse) (SEQ ID NO: 73). In addition to naturally-occurring allelic variants of the insulin sequences that may exist in the population, it will be appreciated that, as is the case for virtually all proteins, a variety of changes can be introduced into the sequences of SEQ ID NO: 72 or SEQ ID NO: 73 (referred to as "wild type" sequences) without substantially altering the functional (biological) activity of the polypeptides, and such variants are included within the scope of the terms "insulin", etc. Insulin is a protein hormone involved in the regulation of blood sugar levels. Insulin is produced in the liver or pancreas as: its precursor proinsulin, consisting of the B and A chains of insulin linked together via a connecting C-peptide. Insulin itself is comprised of only the B and A chains. The sequences of the accession Nos. that have been assigned Sequence Identifier numbers are incorporated herein in their entirety.

As used herein, "Amylase" or "AMY" are used interchangeably herein and refer to the amylase protein of Genebank accession NP_000690.1 (human) (SEQ ID NO: 74); NP_001036177.1 (mouse) (SEQ ID NO: 75). The term amylase also encompasses species variants, homologues, allelic forms, mutant forms, and equivalents thereof, including conservative substitutions, additions, deletions therein not adversely affecting the structure of function. GCK is referred in the art as aliases; AMY2; AMY2B; amylase, alpha 2B (pancreatic). Amylase is encoded by nucleic acid corresponding to GenBank Accession No: NM_000699.2 (human) (SEQ ID NO: 76); NM_001042712.1 (mouse)

(SEQ ID NO: 77). In addition to naturally-occurring allelic variants of the amylase sequences that may exist in the population, it will be appreciated that, as is the case for virtually all proteins, a variety of changes can be introduced into the sequences of SEQ ID NO: 74 or SEQ ID NO: 75 (referred to as "wild type" sequences) without substantially altering the functional (biological) activity of the polypeptides, and such variants are included within the scope of the terms "amylase", etc. Amylases are secreted proteins that hydrolyze 1,4-alpha-glucoside bonds in oligosaccharides and polysaccharides, and thus catalyze the first step in digestion of dietary starch and glycogen. The human genome has a cluster of several amylase genes that are expressed at high levels in either salivary gland or pancreas. This gene encodes an amylase isoenzyme produced by the pancreas. The sequences of the accession Nos. that have been assigned Sequence Identifier numbers are incorporated herein in their entirety.

As used herein, "Glucagon" refers to the glucagon protein of Genebank accession Nos: NP_002045.1 (pro-protein) (human) (SEQ ID NO: 78); NP_032126.1 (mouse) (SEQ ID NO: 79). The term Glucagon also encompasses species variants, homologues, allelic forms, mutant forms, and equivalents thereof, including conservative substitutions, additions, deletions therein not adversely affecting the structure of function. glucagon is referred in the art as aliases; GLP1; GLP2; GRPP; GCG; glicentin-related polypeptide, glucagon-like peptide 1, glucagon-like peptide 2. Glucagon is encoded by nucleic acid corresponding to GenBank Accession No: NM_002054.2 (human) (SEQ ID NO: 80); NM_008100.3 (mouse) (SEQ ID NO: 81). In addition to naturally-occurring allelic variants of the glucagon sequences that may exist in the population, it will be appreciated that, as is the case for virtually all proteins, a variety of changes can be introduced into the sequences of SEQ ID NO: 78 or SEQ ID NO: 78 (referred to as "wild type" sequences) without substantially altering the functional (biological) activity of the polypeptides, and such variants are included within the scope of the terms "glucagon", etc. The glucagon protein encoded by this gene is actually a preproprotein that is cleaved into four distinct mature peptides. One of these, glucagon, is a pancreatic hormone that counteracts the glucose-lowering action of insulin by stimulating glycogenolysis and gluconeogenesis. Glucagon is a ligand for a specific G-protein linked receptor whose signalling pathway controls cell proliferation. The sequences of the accession Nos. that have been assigned Sequence Identifier numbers are incorporated herein in their entirety.

As used herein, "somatostatin/pancreatic polypeptide" or "SomPP" are used interchangeably herein and refer to the pancreatic polypeptide protein of Genebank accession Nos: NP_001039.1 (human) (SEQ ID NO: 82); NP_033241.1 (mouse) (SEQ ID NO: 83). The term pancreatic polypeptide also encompasses species variants, homologues, allelic forms, mutant forms, and equivalents thereof, including conservative substitutions, additions, deletions therein not adversely affecting the structure of function. Pancreatic polypeptide is referred in the art as aliases; somatostatin-14; somatostatin-28; SST. Pancreatic polypeptide is encoded by nucleic acid corresponding to GenBank Accession No: NM_001048.3 (human) (SEQ ID NO: 84); NM_009215.1 (mouse) (SEQ ID NO: 85). In addition to naturally-occurring allelic variants of the Pancreatic polypeptide sequences that may exist in the population, it will be appreciated that, as is the case for virtually all proteins, a variety of changes can be introduced into the sequences of SEQ ID NO: 82 or SEQ ID NO: 83 (referred to as "wild type" sequences) without substantially altering the functional (biological) activity of the polypeptides, and such variants are included within the scope of the terms "pancreatic polypeptide", etc. The hormone somatostatin/pancreatic polypeptide has active 14 aa and 28 aa forms that are produced by alternate cleavage of the single preproprotein encoded by this gene. Somatostatin is expressed throughout the body and inhibits the release of numerous secondary hormones by binding to high-affinity G-protein-coupled somatostatin receptors. This hormone is an important regulator of the endocrine system through its interactions with pituitary growth hormone, thyroid stimulating hormone, and most hormones of the gastrointestinal tract. Somatostatin also affects rates of neurotransmission in the central nervous system and proliferation of both normal and tumorigenic cells. The sequences of the accession Nos. that have been assigned Sequence Identifier numbers are incorporated herein in their entirety.

As used herein, "Ptf1a" or "pancreas specific transcription factor, 1a" are used interchangeably herein and refer to the Pf1a protein of Genebank accession NP_835455.1 (human) (SEQ ID NO: 86); NP_061279.1 (mouse) (SEQ ID NO: 87). The term Ptf1a also encompasses species variants, homologues, allelic forms, mutant forms, and equivalents thereof, including conservative substitutions, additions, deletions therein not adversely affecting the structure of function. Ptf1a is referred in the art as aliases; pancreas specific transcription factor, 1a; PTF1-p48, bHLHa29 PTF1p48. Ptf1a is encoded by nucleic acid corresponding to GenBank Accession No: NM_178161.2 (human) (SEQ ID NO: 88); NM_018809.1 (mouse) (SEQ ID NO: 89). In addition to naturally-occurring allelic variants of the Ptf1a sequences that may exist in the population, it will be appreciated that, as is the case for virtually all proteins, a variety of changes can be introduced into the sequences of SEQ ID NO: 50 or SEQ ID NO: 51 (referred to as "wild type" sequences) without substantially altering the functional (biological) activity of the polypeptides, and such variants are included within the scope of the terms "Ptf1a", etc. This gene encodes a protein that is a component of the pancreas transcription factor 1 complex (PTF1) and is known to have a role in mammalian pancreatic development. The protein plays a role in determining whether cells allocated to the pancreatic buds continue towards pancreatic organogenesis or revert back to duodenal fates. The protein is thought to be involved in the maintenance of exocrine pancreas-specific gene expression including elastase 1 and amylase. Mutations in this gene cause cerebellar agenesis and loss of expression is seen in ductal type pancreas cancers. The sequences of the accession Nos. that have been assigned Sequence Identifier numbers are incorporated herein in their entirety.

As used herein, "Ck19" refers to the Ck19 protein of Genebank accession NP_002267.2 (human) (SEQ ID NO: 90); NP_032497.1 (mouse) (SEQ ID NO: 91). The term Ck19 also encompasses species variants, homologues, allelic forms, mutant forms, and equivalents thereof, including conservative substitutions, additions, deletions therein not adversely affecting the structure of function. Ck19 is referred in the art as aliases; keratin 19, K19, CK19, K1CS, MGC15366; Krt19. Ck19 is encoded by nucleic acid corresponding to GenBank Accession NM_002276.4 (human) (SEQ ID NO: 92); NM_008471.2 (mouse) (SEQ ID NO: 93). In addition to naturally-occurring allelic variants of the Ck19 sequences that may exist in the population, it will be appreciated that, as is the case for virtually all proteins, a variety of changes can be introduced into the sequences of SEQ ID NO: 90 or SEQ ID NO: 91 (referred to as "wild type" sequences) without substantially altering the functional (biological) activity of the polypeptides, and such variants are included within the scope of the terms "Ck19", etc. The Ck19 protein encoded by this gene is a member of the keratin family. The keratins are intermediate filament proteins responsible for the structural integrity of epithelial cells and are subdivided into cytokeratins and hair keratins. The type I cytokeratins consist of acidic proteins which are arranged in pairs of heterotypic keratin chains Unlike its related family members, this smallest known acidic cytokeratin is not paired with a basic cytokeratin in epithelial cells. It is specifically expressed in the periderm, the transiently superficial layer that envelopes the developing epidermis. The sequences of the accession Nos. that have been assigned Sequence Identifier numbers are incorporated herein in their entirety.

As used herein, "nestin" refers to the nestin protein of Genebank accession NP_006608.1 (human) (SEQ ID NO: 94); NP_057910.3 (mouse) (SEQ ID NO: 95). The term nestin also encompasses species variants, homologues, allelic forms, mutant forms, and equivalents thereof, including conservative substitutions, additions, deletions therein not adversely affecting the structure of function. Nestin is referred in the art as aliases; FLJ21841; Nbla00170; NES. Nestin is encoded by nucleic acid corresponding to GenBank Accession No: NM_006617.1 (human) (SEQ ID NO: 96); NM_016701.3 (mouse) (SEQ ID NO: 97). In addition to naturally-occurring allelic variants of the Nestin sequences that may exist in the population, it will be appreciated that, as is the case for virtually all proteins, a variety of changes can be introduced into the sequences of SEQ ID NO: 94 or SEQ ID NO: 95 (referred to as "wild type" sequences) without substantially altering the functional (biological) activity of the polypeptides, and such variants are included within the scope of the terms "Nestin", etc. Nestin is an intermediate filament protein that was first identified with a monoclonal antibody by Hockfield and McKay (1985). It is expressed predominantly in stem cells of the central nervous system in the neural tube. The sequences of the accession Nos. that have been assigned Sequence Identifier numbers are incorporated herein in their entirety.

As used herein, "vimentin" refers to the vimentin of Genebank accession NP_003371.2 (human) (SEQ ID NO: 98); NP_035831.2 (mouse) (SEQ ID NO: 99). The term vimentin also encompasses species variants, homologues, allelic forms, mutant forms, and equivalents thereof, including conservative substitutions, additions, deletions therein not adversely affecting the structure of function. Vemintin is referred in the art as aliases; FLJ36605; VIM. Vimentin is encoded by nucleic acid corresponding to GenBank Accession No: NM_003380.2 (human) (SEQ ID NO: 100); NM_011701.3 (mouse) (SEQ ID NO: 101). In addition to naturally-occurring allelic variants of the vementin sequences that may exist in the population, it will be appreciated that, as is the case for virtually all proteins, a variety of changes can be introduced into the sequences of SEQ ID NO: 98 or SEQ ID NO: 99 (referred to as "wild type" sequences) without substantially altering the functional (biological) activity of the polypeptides, and such variants are included within the scope of the terms "vimentin", etc. The vimentin gene encodes a member of the intermediate filament family. Intermediate filamentents, along with microtubules and actin microfilaments, make up the cytoskeleton. The protein encoded by this gene is responsible for maintaining cell shape, integrity of the cytoplasm, and stabilizing cytoskeletal interactions. It is also involved in the immune response, and controls the transport of low-density lipoprotein (LDL)-derived cholesterol from a lysosome to the site of esterification. It functions as an organizer of a number of critical proteins involved in attachment, migration, and cell signaling. Mutations in this gene causes a dominant, pulverulent cataract. The sequences of the accession Nos. that have been assigned Sequence Identifier numbers are incorporated herein in their entirety.

The term a "variant" in referring to a polypeptide could be, e.g., a polypeptide at least 80%, 85%, 90%, 95%, 98%, or 99% identical to full length polypeptide. The variant could be a fragment of full length polypeptide The variant could be a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest such as the ability to directly reprogram endodermal cells (e.g. pancreatic exocrine cells) to pancreatic β-like cells. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had one or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

One of skill in the art will be aware of, or will readily be able to ascertain, whether a particular polypeptide variant, fragment, or derivative is functional using assays known in the art. For example, the ability of a variant of a Pdx1 (SEQ ID NO: 1 or SEQ ID NO:31) or Ngn3 (SEQ ID NO:2 or 32) or MafA (SEQ ID NO: 3 or 33) polypeptide to reprogram cells of endoderm origin to pancreatic β-like cells can be assessed using the assays as disclose herein in the Examples. Other convenient assays include measuring the ability to activate transcription of a reporter construct containing a Pdx1 or Ngn3 or MafA binding site operably linked to a nucleic acid sequence encoding a detectable marker such as luciferase. One assay involves determining whether the Pdx1 or Ngn3 or MafA variant induces a cell of endoderm origin (such as a pancreatic exocrine cell) to secrete insulin in the presence of a polypeptide at least two wild type polypeptides of Pdx1, Ngn3 or MafA (i.e. not selecting the polypeptide of which the variant is being assessed). Insulin secretion can be determined using any suitable method, e.g., immunoblotting. Such assays may readily be adapted to identify or confirm activity of agents that directly reprogram cells of endoderm origin to pancreatic β-like cells. In certain embodiments of the invention a functional variant or fragment has at least 50%, 60%, 70%, 80%, 90%, 95% or more of the activity of the full length wild type polypeptide.

The term "functional fragments" as used herein regarding Pdx1, Ngn3 or MafA polypeptides or other β-cell reprogramming factors having amino acid sequences substantially homologous thereto means a polypeptide sequence of at least 5 contiguous amino acids of Pdx1 (SEQ ID NO: 1 or 31), Ngn3 (SEQ ID NO: 2 or 32) or MafA (SEQ ID NO: 3 or 33), or other β-cell reprogramming factors having amino acid sequences substantially homologous thereto, wherein the functional fragment polypeptide sequence is about at least 50%, or 60% or 70% or at 80% or 90% or 100% or greater, for example 1.5-fold, 2-fold, 3-fold, 4-fold or greater than 4-fold as effective at direct reprogramming cells of endoderm origin as the corresponding wild type Pdx1 (SEQ ID NO: 1 or 31), Ngn3 (SEQ ID NO: 2 or 32) or MafA (SEQ ID NO: 3 or 33) polypeptides as described herein. The functional fragment polypeptide may have additional functions that can include decreased antigenicity, increased DNA binding (as in transcription factors), or altered RNA binding (as in regulating RNA stability or degradation).

The term "vector" refers to a carrier DNA molecule into which a DNA sequence can be inserted for introduction into a host cell. Preferred vectors are those capable of autonomous replication and/or expression of nucleic acids to which they are linked Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

As used herein, the term "adenovirus" refers to a virus of the family Adenovirida. Adenoviruses are medium-sized (90-100 nm), nonenveloped (naked) icosahedral viruses composed of a nucleocapsid and a double-stranded linear DNA genome.

As used herein, the term "non-integrating viral vector" refers to a viral vector that does not integrate into the host genome; the expression of the gene delivered by the viral vector is temporary. Since there is little to no integration into the host genome, non-integrating viral vectors have the advantage of not producing DNA mutations by inserting at a random point in the genome. For example, a non-integrating viral vector remains extra-chromosomal and does not insert its genes into the host genome, potentially disrupting the expression of endogenous genes. Non-integrating viral vectors can include, but are not limited to, the following: adenovirus, alphavirus, picornavirus, and vaccinia virus. These viral vectors are "non-integrating" viral vectors as the term is used herein, despite the possibility that any of them may, in some rare circumstances, integrate viral nucleic acid into a host cell's genome. What is critical is that the viral vectors used in the methods described herein do not, as a rule or as a primary part of their life cycle under the conditions employed, integrate their nucleic acid into a host cell's genome. It goes without saying that an iPS cell generated by a non-integrating viral vector will not be administered to a subject unless it and its progeny are free from viral remnants.

As used herein, the term "viral remnants" refers to any viral protein or nucleic acid sequence introduced using a viral vector. Generally, integrating viral vectors will incorporate their sequence into the genome; such sequences are referred to herein as a "viral integration remnant". However, the temporary nature of a non-integrating virus means that the expression, and presence of, the virus is temporary and is not passed to daughter cells. Thus, upon passaging of a re-programmed cell the viral remnants of the non-integrating virus are essentially removed.

As used herein, the term "free of viral integration remnants" and "substantially free of viral integration remnants" refers to iPS cells that do not have detectable levels of an integrated adenoviral genome or an adenoviral specific protein product (i.e., a product other than the gene of interest), as assayed by PCR or immunoassay. Thus, the iPS cells that are free (or substantially free) of viral remnants have been cultured for a sufficient period of time that transient expression of the adenoviral vector leaves the cells substantially free of viral remnants.

The terms "regulatory sequence" and "promoter" are used interchangeably herein, and refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue, such as cells of neural origin, e.g. neuronal cells. The term also covers so-called "leaky" promoters, which regulate expression of a selected nucleic acid primarily in one tissue, but cause lesser expression in other tissues as well.

The term "phenotype" refers to one or a number of total biological characteristics that define the cell or organism under a particular set of environmental conditions and factors, regardless of the actual genotype.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein, "the presence of lower amounts of a marker in the β-like cell as compared to the cell of endoderm origin from which is was derived" refers to an amount of a marker protein or gene product (e.g. mRNA) that is significantly decreased in the β-like cell as compared to the amount of the same marker present in the cell of endoderm origin from which is was derived. "significantly decreased" means that the differences between the compared levels is statistically significant. The levels of the marker level can be represented by arbitrary units, for example as units obtained from a densitometer, luminometer, or an Elisa plate reader.

As used herein, "the presence of higher amounts of a marker in the β-like cell as compared to the cell of endoderm origin from which is was derived" refers to an amount of a marker protein or gene product (e.g. mRNA) that is significantly increased in the β-like cell as compared to the amount of the same marker present in the cell of endoderm origin from which is was derived. "significantly increased" means that the differences between the compared levels is statistically significant. The levels of the marker level can be represented by arbitrary units, for example as units obtained from a densitometer, luminometer, or an Elisa plate reader.

As used herein, the term "transcription factor" refers to a protein that binds to specific parts of DNA using DNA binding domains and is part of the system that controls the transfer (or transcription) of genetic information from DNA to RNA.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. In the context of a cell that is of endoderm origin or is "endodermal linage" this means the cell was derived from an endodermal cell and can differentiate along the endodermal lineage restricted pathways, such as one or more developmental lineage pathways which give rise to definitive endoderm cells, which in turn can differentiate into liver cells, thymus, pancreas, lung and intestine.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "xenogeneic" refers to cells that are derived from different species.

The term "β-cell reprogramming factor" refers to a gene, RNA, or protein that promotes or contributes to cell reprogramming, e.g., in vitro. In aspects of the invention relating to reprogramming factor(s), the invention provides embodiments in which the reprogramming factor(s) are of interest for reprogramming somatic cells to pluripotency in vitro. Examples of reprogramming factors of interest for reprogramming somatic cells to pluripotency in vitro are Oct4, Nanog, Sox2, Lin28, Klf4, c-Myc, and any gene/protein that can substitute for one or more of these in a method of reprogramming somatic cells in vitro. "Reprogramming to a pluripotent state in vitro", or "reprogramming to pluripotency in vitro", is used herein to refer to in vitro reprogramming methods that do not require and typically do not include nuclear or cytoplasmic transfer or cell fusion, e.g., with oocytes, embryos, germ cells, or pluripotent cells. Any embodiment or claim of the invention may specifically exclude compositions or methods relating to or involving nuclear or cytoplasmic transfer or cell fusion, e.g., with oocytes, embryos, germ cells, or pluripotent cells.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla* luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

A "reporter gene" as used herein encompasses any gene that is genetically introduced into a cell that adds to the phenotype of the stem cell. Reporter genes as disclosed in this invention are intended to encompass fluorescent, luminescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny. A reporter gene is generally operatively linked to sequences that regulate its expression in a manner dependent upon one or more conditions which are monitored by measuring expression of the reporter gene. In some cases, expression of the reporter gene may be determined in live cells. Where live cell reporter gene assays are used, reporter gene expression may be monitored at multiple timepoints, e.g., 2, 3, 4, 5, 6, 8, or 10 or more timepoints. In some cases, where a live cell reporter assay is used, reporter gene expression is monitored with a frequency of at least about 10 minutes to about 24 hours, e.g., 20 minutes, 1 hour, 2 hrs, 3 hours, 4 hours, 5 hours, 6 hours, 7 hours, 8 hours, 9 hours, 10 hours, 12 hours, 18 hours, or another frequency from any interger between about 10 minutes to about 24 hours.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

As used herein, the terms "administering," "introducing" and "transplanting" are used interchangeably in the context of the placement of pancreatic β-like cells of the invention into a subject, by a method or route which results in at least partial localization of the pancreatic β-like cells at a desired site. The pancreatic β-like cells can be directly to the pancreas, or alternatively be administered by any appropriate route which results in delivery to a desired location in the subject where at least a portion of the cells or components of the cells remain viable. The period of viability of the cells after administration to a subject can be as short as a few hours, e. g. twenty-four hours, to a few days, to as long as several years.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The term "tissue" refers to a group or layer of specialized cells which together perform certain special functions. The term "tissue-specific" refers to a source of cells from a specific tissue.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Direct Reprogramming:

The process of altering the cell phenotype of a differentiated cell (i.e. a first cell), such as a somatic cell to a differentiated cell of a different phenotype (i.e. a second cell) without the first differentiated cell being completely reprogrammed to a less differentiated phenotype intermediate is referred to as "direct reprogramming". Stated another way, cells of one type can be converted to another type in a process by what is commonly referred to in the art as cellular reprogramming or lineage reprogramming.

Direct reprogramming (i.e. cellular reprogramming), which encompasses a process of switching the phenotype of a differentiated cell to the phenotype of a different differentiated cell, without the complete reversal of the differentiation state of the somatic cell, is distinct from "reprogramming to a pluripotent state" which typically refers to a process that completely reverses the differentiation state of a somatic cell to a cell with a stem cell-like phenotype.

As disclosed herein, the present invention relates to compositions and methods for the direct reprogramming of a cell of endoderm origin, such as a somatic cell which is of endoderm origin (e.g. pancreatic exocrine cells, pancreatic acinar cell, liver cells etc.) to a cell of an insulin producing phenotype, such as a cell with pancreatic β-cell characteristics. Such a direct reprogrammed cell as disclosed herein is referred to as a "pancreatic β-like cell". In certain embodiments of the invention, reprogramming a cell of endoderm origin causes the cell of endoderm origin to assume a pancreatic β-cell like state, without being completely reprogrammed to a pluripotent state prior to assuming the β-cell like phenotype.

In some embodiments, the methods and compositions of the present invention can be practiced on cells of endoderm origin that are fully differentiated and/or restricted to giving rise only to cells of that particular type. The cell of endoderm origin can be either partially or terminally differentiated prior to direct reprogramming.

The present invention relates to compositions and methods for reprogramming a cell of endoderm origin, such as a somatic cell, (e.g., a pancreatic cell such as a pancreatic exocrine cell, or a pancreatic duct cell or a pancreatic acrine cell, or a liver cell) to a β-cell. The invention provides methods for reprogramming endodermal cells to a different phenotype, such as a pancreatic β-cell phenotype. The resulting cells are referred to herein as "pancreatic β-like cells" herein, or in some embodiments as induced β-cells if reprogrammed to a pluripotent state.

Cells of Endoderm Origin

The present invention relates to a method of direct reprogramming cells of an endoderm origin to pancreatic β-like cells. In some embodiments, cells of endoderm origin are the preferred starting material. In some embodiments, a population of pancreatic β-like cells is produced by increasing the protein expression of at least two transcription factors selected from Pdx1, Ngn3 and MafA in a cell of endoderm origin. Accordingly in all aspects of the present invention, the population of cells of endoderm origin can comprise any cell type of endoderm origin, for example, but not limited to, a liver cell and pancreatic cell, such as a pancreatic endodermal cell, pancreatic anciar cell, pancreatic duct cell and the like. In alternative embodiments, the population of cells of endoderm origin can comprise a mixture or combination of different cells of endoderm origin, for example a mixture of cells such as a liver cell, a pancreatic cell, such as a pancreatic endodermal cell, pancreatic anciar cell, pancreatic duct cell.

In some embodiments, the population of cells of endoderm origin is a substantially pure population of pancreatic exocrine cells, or substantially pure population of pancreatic duct cells or in some embodiments a substantially pure population of liver cells (e.g hepatocytes). In some embodiments, a population of cells of endoderm origin is substantially free of insulin-producing cells, such as β-cells.

In some embodiments, a population of cells of endoderm origin is a population of somatic cells or differentiated cells. In some embodiments, the population of cells of endoderm origin are substantially free or devoid of embryonic stem cells or pluripotent cells or iPS cells.

In some embodiments, a cell of endoderm origin is genetically modified. In some embodiments, the cell of endoderm origin comprises one or more nucleic acid sequences encoding at the proteins of least two transcription factors selected from Pdx1 (SEQ ID NO:1 or 31), Ngn3 (SEQ ID NO: 2 or 32) or MafA (SEQ ID NO: 3 or 33) or functional variants or functional fragments thereof.

In some embodiments, cells of endoderm origin can be isolated from a subject, for example as a tissue biopsy, such as, for example, a liver biopsy or biopsy of the pancreas. In some embodiments, the cells of endoderm origin are maintained in culture by methods known by one of ordinary skill in the art, and in some embodiments, propagated prior to being directly reprogrammed into pancreatic β-like cells by the methods as disclosed herein.

Further, the cell of endoderm origin can be from any mammalian species, with non-limiting examples including a murine, bovine, simian, porcine, equine, ovine, or human cell. For clarity and simplicity, the description of the methods herein refers to pancreatic exocrine cells as cells of endoderm origin, but it should be understood that all of the methods described herein can be readily applied to other cell types of endoderm origin. In one embodiment, the cell of endoderm origin is derived from a human individual.

In some embodiments, a subject from which the cells of endoderm origin are obtained is a mammalian subject, such a human subject, and in some embodiments, the subject is suffering from diabetes and/or a metabolic disorder. In such embodiments, the cells of endoderm origin can be reprogrammed to pancreatic β-like cells ex vivo by the methods as described herein and then administered to the subject from which the cells were harvested in a method to treat the subject for diabetes or a metabolic disorder.

In some embodiments, cells of endoderm origin are located within a subject (in vivo) and are directly reprogrammed to become pancreatic β-like cells by the methods as disclosed herein in vivo, for example as disclosed in the Examples demonstrating direct reprogramming pancreatic exocrine cells to pancreatic β-like cells in vivo by transducing the pancreatic cells with a viral vector, such as adenovirus which has the ability to express three transcription factors Pdx1, Ngn3 and MafA in the pancreatic exocrine cell.

In some embodiments, such contacting may be performed by maintaining the cell of endoderm origin in culture medium comprising the agent(s). In some embodiments the cells of endoderm origin can be genetically engineered. In some embodiments, a cells of endoderm origin can be genetically engineered to express one or more β-cell reprogramming factors as disclosed herein, for example express at least one a polypeptide selected from Pdx1 (SEQ ID NO:1 or 31) or Ngn3 (SEQ ID NO: 2 or 32) or MafA (SEQ ID NO: 3 or 33), or an amino acid sequences substantially homologous thereof, or functional fragments or functional variants thereof.

Where the cell of endoderm origin is maintained under in vitro conditions, conventional tissue culture conditions and methods can be used, and are known to those of skill in the art. Isolation and culture methods for various cells are well within the abilities of one skilled in the art.

In the methods of the present invention cells of endoderm origin (e.g. exocrine cells, pancreatic exocrine cells, acinar pancreatic cells, liver cells and gall bladder cells) can, in general, be cultured under standard conditions of temperature, pH, and other environmental conditions, e.g., as adherent cells in tissue culture plates at 37° C. in an atmosphere containing 5-10% $CO_2$. The cells and/or the culture medium are appropriately modified to achieve direct reprogramming to pancreatic β-like cells as described herein. In certain embodiments, cells of endoderm origin (e.g. exocrine cells, pancreatic exocrine cells, acinar pancreatic cells, liver cells and gall bladder cells) can be cultured on or in the presence of a material that mimics one or more features of the extracellular matrix or comprises one or more extracellular matrix or basement membrane components. In some embodiments Matrigel™ is used. Other materials include proteins or mixtures thereof such as gelatin, collagen, fibronectin, etc. In certain embodiments of the invention, cells of endoderm origin (e.g. exocrine cells, pancreatic exocrine cells, acinar pancreatic cells, liver cells and gall bladder cells) can be cultured in the presence of a feeder layer of cells. Such cells may, for example, be of murine or human origin. They can also be irradiated, chemically inactivated by treatment with a chemical inactivator such as mitomycin c, or otherwise treated to inhibit their proliferation if desired. In other embodiments cells of endoderm origin (e.g. exocrine cells, pancreatic exocrine cells, acinar pancreatic cells, liver cells and gall bladder cells) are cultured without feeder cells.

Methods of Direct Reprogramming Cells of Endodermal Origin to a Pancreatic β-Like Cell Generating reprogrammed pancreatic β-cells by reprogramming cells of endoderm origin (e.g, pancreatic exocrine cells, pancreatic duct cells, liver cells etc.) using the methods of the present invention has a number of advantages. First, the methods of the present invention allow one to generate autologous pancreatic β-like cells, which are cells specific to and genetically matched with an individual. The cells are derived from cells of endoderm origin (e.g, pancreatic exocrine cells, pancreatic duct cells, liver cells etc.) obtained from the individual. In general, autologous cells are less likely than non-autologous cells to be subject to immunological rejection.

Second, the methods of the present invention allow the artisan to generate pancreatic β-like cells without using embryos, oocytes, and/or nuclear transfer technology. Herein, the applicants' results demonstrate that (i) cells of endoderm origin (e.g, pancreatic exocrine cells, pancreatic duct cells, liver cells etc.) can be directly reprogrammed to become pancreatic β-like cells, without the need to be fully reprogrammed to a pluripotent state, therefore minimizing the risk of differentiation into unwanted cell types or risk of teratomas formation.

Also encompassed in the methods of the present invention is a method of direct reprogramming cells of endoderm origin (e.g, pancreatic exocrine cells, pancreatic duct cells, liver cells etc.) by means other than engineering the cells to express β-cell reprogramming factors, i.e., by contacting the cells of endoderm origin with a β-cell reprogramming agent other than a nucleic acid or viral vector capable of being taken up and causing a stable genetic modification to the cells. In particular, the invention encompasses the recognition that extracellular signaling molecules, e.g., molecules that when present extracellularly bind to cell surface receptors and activate intracellular signal transduction cascades, are of use to reprogram somatic cells. The invention further encompasses the recognition that activation of such signaling pathways by means other than the application of extracellular signaling molecules is also of use to directly reprogram cells of endoderm origin. In addition, the methods of the present invention relate to methods of identification of the pancreatic β-like cells that are detectable based on morphological criteria, without the need to employ a selectable marker. The present disclosure thus reflects several fundamentally important advances in the area of somatic cell reprogramming technology, in particular direct reprogramming technology.

While certain aspects of the invention are exemplified herein using three main β-cell reprogramming factors, e.g., Pdx1 (SEQ ID NO:1 or 31), Ngn3 (SEQ ID NO: 2 or 32) and MafA (SEQ ID NO: 3 or 33) transcription factors, the methods of the invention encompass use of any other β-cell reprogramming factors in replace of any one of Pdx1, Ngn3 or MafA, where the other β-reprogramming factors includes, for example, but is not limited to, NeuroD (SEQ ID NO: 4); Nkx2.2 (SEQ ID NO: 5); Nkx6.1 (SEQ ID NO: 6); Pax4 (SEQ ID NO: 7); Pax6 (SEQ ID NO: 8); Isl1 (SEQ ID NO: 9) or functional variants, homologues or functional fragments thereof for the purposes of directly reprogramming cells of endoderm origin to pancreatic β-like cells.

One aspect of the present invention relates to direct reprogramming cells of endoderm origin (e.g. exocrine cells, pancreatic exocrine cells, acinar pancreatic cells, liver cells and gall bladder cells) to pancreatic β-like cells.

Another aspect of the present invention relates to methods to produce a population of isolated pancreatic β-like cells by increasing the protein expression of at least two β-cell reprogramming factors in a population of cells of endoderm origin (e.g. exocrine cells, pancreatic exocrine cells, acinar pancreatic cells, liver cells and gall bladder cells). In some embodiments, cells of endoderm origin (e.g. exocrine cells, pancreatic exocrine cells, acinar pancreatic cells, liver cells and gall bladder cells) can be treated in any of a variety of ways to cause direct reprogramming of the endodermal cell to a pancreatic β-like cells according to the methods of the present invention. For example, in some embodiments, the treatment can comprise contacting the cells with one or more agent(s), herein referred to as a "β-cell reprogramming agent" or a "β-cell reprogramming factor" which increases the protein expression of at least two of the transcription factors selected from Pdx1, Ngn3, or MafA, or increases the protein expression of a functional homologue or a functional fragment of at least two of Pdx1, Ngn3, or MafA polypeptides in the cell of endoderm origin.

Accordingly, one aspect of the present invention provides a method of direct reprogramming a cell, for example, a cell of endoderm origin by contacting a cell of endoderm origin with one or more agents, such as β-cell reprogramming agents or β-cell reprogramming factors to reprogram the cell of endoderm origin (e.g., a first cell) into a cell with pancreatic β-cell like phenotype (e.g. reprogrammed into a second cell type).

In some embodiments, the method comprises reprogramming a cell of endoderm origin by increasing the protein expression of at least two of the following transcription factors Pdx1, Ngn3 or MafA in the cell of endoderm origin, wherein the expression is for sufficient amount of time, typically transient increase in expression, to allow the reprogramming of the cell to become a cell which exhibits at least two characteristics of a endogenous pancreatic β-cell, for example at least two of the following characteristics; secretion of insulin in response to glucose, expression of c-peptide, or Pdx1 or MafA or Glut2 or lack of expression of Ngn3.

In some embodiments, the method comprises reprogramming a cell of endoderm origin by increasing the protein expression of all three of following transcription factors Pdx1 (SEQ ID NO:1 or 31), Ngn3 (SEQ ID NO: 2 or 32) and MafA (SEQ ID NO: 3 or 33) in the cell of endoderm origin. The increase in expression of the transcription factors can be done all at the same time (e.g. concurrently), or alternatively, subsequently in any order.

In some embodiments, the method comprises substituting the increase in the protein expression of Ngn3 with an increase in the protein expression of Neuro D (SEQ ID NO: 4) or a peptide substantially homologous to SEQ ID NO: 4 or a functional fragment or functional variant of SEQ ID NO:4 in the cell of endoderm origin. For example, the present invention also encompasses a method comprises reprogramming a cell of endoderm origin by increasing the protein expression of at least 2, or at least 3 of following transcription factors Pdx1 (SEQ ID NO:1 or 31), Neuro D (SEQ ID NO: 4) and MafA (SEQ ID NO: 3 or 33) in the cell of endoderm origin.

In some embodiments, the method comprises substituting the increase in the protein expression of any of Pdx1, Ngn3 or MafA with an increase in the protein expression of any other β-cell reprogramming factor selected from Neuro D (SEQ ID NO: 4); Nkx2.2 (SEQ ID NO: 5); Nkx6.1 (SEQ ID NO: 6); Pax4 (SEQ ID NO: 7); Pax6 (SEQ ID NO: 8); Isl1 (SEQ ID NO: 9) or functional variants, polypeptides with amino acids substantially homologues or functional fragments thereof in the cell of endoderm origin. In some embodiments, the method comprises reprogramming a cell of endoderm origin by expressing at least 2, or at least 3, or at least 4 or at least 5, or at least 6, or at least 7 or at least 8, or at least 9 or any combination of transcription factors selected from, for example, but is not limited to, Pdx1 (SEQ ID NO:1 or 31), Ngn3 (SEQ ID NO: 2 or 32) and MafA (SEQ ID NO: 3 or 33); NeuroD (SEQ ID NO: 4); Nkx2.2 (SEQ ID NO: 5); Nkx6.1 (SEQ ID NO: 6); Pax4 (SEQ ID NO: 7); Pax6 (SEQ ID NO: 8); Isl1 (SEQ ID NO: 9) or functional variants, polypeptides with amino acids substantially homologues or functional fragments thereof in a cell of endoderm origin to reprogram to a β-like cell.

In some embodiments, increasing the protein expression can be by any means known by one of ordinary art, for example can include introduction of nucleic acid encoding one or more of the transcription factors, or contacting the cell of endoderm origin with an agent (e.g. a β-cell reprogramming agent or factor) which reprograms the cell of endoderm origin to a cell with β-cell like phenotype.

In some embodiments, a β-cell reprogramming agent is a vector comprising a nucleotide sequence encoding the polypeptide Pdx1 (SEQ ID NO:1 or 31) or encoding a polypeptide substantially homologous to SEQ ID NO:1 or 31 or a functional variant or functional fragment of polypeptides of sequences SEQ ID NO:1 or 31. In such embodiments, the nucleotide sequence comprises SEQ ID NO: 34 or 35 or a fragment or variant thereof.

In some embodiments, a β-cell reprogramming agent is a vector comprising a nucleotide sequence encoding the polypeptide Ngn3 (SEQ ID NO:2 or 32) or encoding a polypeptide substantially homologous to SEQ ID NO:2 or 32 or a functional variant or functional fragment of polypeptides of sequences SEQ ID NO:2 or 32. In such embodiments, the nucleotide sequence comprises SEQ ID NO: 36 or 37 or a fragment or variant thereof.

In some embodiments, a β-cell reprogramming agent is a vector comprising a nucleotide sequence encoding the polypeptide MafA (SEQ ID NO:3 or 33) or encoding a polypeptide substantially homologous to SEQ ID NO:1 or 31 or a functional variant or functional fragment of polypeptides of sequences SEQ ID NO:3 or 33. In such embodiments, the nucleotide sequence comprises SEQ ID NO: 38 or 39 or a fragment or variant thereof.

In some embodiments, the vector is a viral vector. In some embodiments, the viral vector is a non-integrating viral vector. While retroviral vectors incorporate into the host cell genome and can potentially disrupt normal gene function, non-integrating vectors have the advantage of controlling expression of a gene product by extra-chromosomal transcription. It follows that since non-integrating vectors do not become part of the host genome, non-integrating vectors tend to express a nucleic acid transiently in a cell population. This is due in part to the fact that the non-integrating vectors as used herein are rendered replication deficient. Thus, non-integrating vectors have several advantages over retroviral vectors including but not limited to: (1) no disruption of the host genome, and (2) transient expression, and (3) no remaining viral integration products.

Some non-limiting examples of non-integrating vectors include adenovirus, baculovirus, alphavirus, picornavirus, and vaccinia virus. In one embodiment, the non-integrating viral vector is an adenovirus. The advantages of non-integrating viral vectors further include the ability to produce them in high titers, their stability in vivo, and their efficient infection of host cells.

While it is known that some non-integrating vectors integrate into the host genome at extremely low frequencies (i.e., $10^{-4}$ to $10^{-5}$), a non-integrating vector, as the term is used herein, refers to vectors having a frequency of integration of less than 0.1% of the total number of infected cells; preferably the frequency of integration is less than 0.01%, less than 0.001%, less than 0.0001%, or less than 0.000001% (or lower) of the total number of infected cells. In one embodiment, the vector does not integrate at all. In another embodiment, the viral integration remnants of the virus are below the detection threshold as assayed by PCR (for nucleic acid detection) or immunoassay (for protein detection). In general, pancreatic β-like cells produced by the methods described herein should be assayed for an integration event by the viral vector using, for example, PCR-mediated detection of the viral genome prior to administering a population of pancreatic β-like cells to a subject. Any pancreatic β-like cells with detectable integration products should not be administered to a subject.

The viral titer necessary to achieve a desired (i.e., effective) level of gene expression in a host cell is dependent on many factors, including, for example, the cell type, gene product, culture conditions, co-infection with other viral vectors, and co-treatment with other agents, among others. It is well within the abilities of one skilled in the art to test a range of titers for each virus or combination of viruses by detecting the expression levels of either (a) a marker expression product, or (b) a test gene product. Detection of protein expression in cells can be achieved by several techniques including Western blot analysis, immuno-cytochemistry, and fluorescence-mediated detection, among others. It is contemplated that experiments are first optimized by testing a variety of titer ranges for each cell type under the desired culture conditions. Once an optimal titer of a virus or a cocktail of viruses is determined, then that protocol will be used to induce the reprogramming of somatic cells.

In addition to viral titers, it is also important that the infection and induction times are appropriate with respect to different cells. For example, as discussed in the Examples section herein, initial attempts with an adenoviral vector were deemed unsuccessful due to an inadequate induction time. Upon recognition of this important consideration and considerable lengthening of induction time, induced pluripotent stem cells were produced using an adenoviral vector. With the knowledge provided herein that length of time is an important variable in induced pluripotent stem cell induction, one of skill in the art can test a variety of time points for infection or induction using a non-integrating vector and recover induced pluripotent stem cells from a given somatic cell type.

In some embodiments, the vector is a non-viral polycystronic vector as disclosed in Gonzalez et al., Proc. Natl. Acad. Sci. USA 2009 106:8918-8922; Carey et al., PNAS, 2009; 106; 157-162, WO/2009/065618 and WO/2000/071096 and Okita et al., Science 7, 2008: 322; 949-953, which are all incorporated herein in their entirety by reference.

In other embodiments, the methods or the present invention encompass non-viral means to increase the expression of the transcription factors (e.g. Pdx1, Ngn3 or MafA) in a cell of endoderm origin for the purposes for reprogramming to a pancreatic β-like cell as disclosed herein. For example, in one embodiment, naked DNA technology can be used, for example nucleic acid encoding the polypeptides of least two transcription factors of SEQ ID NOs 1-3 or 31-33 can be introduced into a cell of endoderm origin for the purposes of reprogramming the cell to a β-like cell. Methods of naked DNA technology are well known in the art, and are disclosed in U.S. Pat. No. 6,265,387 (which is incorporated herein in its entirety by reference) which describes a method of delivering naked DNA into a hepatocyte in vivo the via bile duct. U.S. Pat. No. 6,372,722 (which is incorporated herein in its entirety by reference) describes a method of naked DNA delivery to a secretory gland cell, for example, a pancreatic cell, a mammary gland cell, a thyroid cell, a thymus cell, a pituitary gland cell, and a liver cell.

In some embodiments, another non-viral means to increase the expression of the transcription factors (e.g. Pdx1, Ngn3 or MafA) in a cell of endoderm origin include use of piggyBac transposon vectors, as disclosed in U.S. Pat. Nos. 7,129,083, and 6,5518,25; U.S. Patent Application 2009/0042297 and International Patent Application WO/2007/100821 which are incorporated herein in their entirety by reference.

Other non-viral means to increase the expression of the transcription factors (e.g. Pdx1, Ngn3 or MafA) in a cell of endoderm origin for the purposes for reprogramming to a pancreatic β-like cell are also encompassed for use in the methods as disclosed herein.

In one embodiment, one can contact the cells of endoderm origin with polypeptides or peptides of Pdx1 (SEQ ID NO:1 or 31), Neuro D (SEQ ID NO: 4) and MafA (SEQ ID NO: 3 or 33) or functional variants, polypeptides with amino acids substantially homologues or functional fragments thereof in a cell of endoderm origin to reprogram to a β-like cell. Alternatively, one can use aptamers or antibodies or any other agent which activates and increases the expression of the transcription factors (e.g. Pdx1, Ngn3 or MafA) in a cell of endoderm origin.

In alternative embodiments, one can contact the cell of endoderm origin with a small molecule or combination of small molecules (e.g. chemical complementation) to increase the expression of at least two transcription factors in the cell of endoderm origin.

Thus, in some embodiments, the contacting step will typically be for at least twenty-four hours. By "at least twenty-four hours," is meant twenty-four hours or greater. Specifically, the cells of endoderm origin can be contacted with β-cell reprogramming agent (e.g. small molecule, polypeptide, nucleic acid, nucleic acid analogues, etc) for about 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 hours up to 3, 4, 5, 6, 7, or more days or any particular intervening time in hours or minutes within the above range. Preferably the cells of endoderm origin can be contacted with the β-cell reprogramming factor for seven days.

In another embodiment, the present invention provides a method of reprogramming cells of endoderm origin comprising contacting the cell of endoderm origin with at least 1 or at least 2 or at least 3 polypeptides selected from the group of Pdx1, Ngn3 or MafA, or having amino acid sequences substantially homologous thereto, and functional fragments or functional variants thereof. In some embodiments, the present invention provides a method of reprogramming cells of endoderm origin comprising contacting the cell of endoderm origin with at least 1 or at least 2 or at least 3 polypeptides selected from the group of polypeptides of SEQ ID NO: 4-29, or having amino acid sequences substantially homologous thereto, and functional fragments or functional variants thereof.

Where the β-cell reprogramming factor is a polypeptide, e.g. a polypeptide of Pdx1, Ngn3 or MafA, the dosages of Pdx1, Ngn3 or MafA polypeptides, their active fragments or related growth factors to be used in the in vivo or in vitro methods and processes of the invention preferably range from about 1 pmoles/kg/minute to about 100 nmoles/kg/minute for continuous administration and from about 1 nmoles/kg to about 40 mmoles/kg for bolus injection. Preferably, the dosage of Pdx1, Ngn3 or MafA polypeptides in in vitro methods will be 10 pmoles/kg/min to about 100 nmoles/kg/min, and in in vivo methods from about 0.003 nmoles/kg/min to about 48 nmoles/kg/min. More preferably, the dosage of Pdx1, Ngn3 or MafA polypeptides in in vitro methods ranges from about 100 picomoles/kg/minute to about 10 nanomoles/kg/minute, and in in vivo methods from about 0.03 nanomoles/kg/minute to about 4.8 nanomoles/kg/minute. In some embodiments, the preferred dosage of Pdx1, Ngn3 or MafA polypeptides, or other polypeptides of sequences SEQ ID NO: 4-29 in in vitro methods is 1 pmoles/kg/min to about 10 nmoles/kg/mine, and in in vivo from about 1 pmole/kg to about 400 pmoles/kg for a bolus injection. The more preferred dosage of the preferred dosage of Pdx1, Ngn3 or MafA polypeptides, or other polypeptides of sequences SEQ ID NO: 4-29 in in vitro methods ranges from about 10 pmole/kg/minute to about 1 nmole/kg/minute, and in in vivo from about 10 pmoles/kg to about 40 pmoles/kg for a bolus injection.

Confirming Presence of a Pancreatic β-Like Cell from a Cell of Endoderm Origin.

A pancreatic β-like cell as disclosed herein, produced by the methods as disclosed herein, e.g. by increasing the protein expression of at least 2 transcription factors of Pdx1, Ngn3, or MafA in the cell of endoderm origin, is a cell with the phenotypic characteristics of an endogenous β-cell such that is produces insulin. The pancreatic β-like cell can have all the phenotypic characteristics of an endogenous β-cell or may have less than all the phenotypic characteristics of an endogenous β-cell. In some embodiments, the pancreatic β-like cell can produce insulin but otherwise maintain at least one phenotypic characteristic of the endodermal cell from which it as reprogrammed from. For example, in some embodiments, a cell of endoderm origin (e.g. a non-insulin producing endoderm cell, such as a pancreatic amylase producing cell (i.e., pancreatic acinar cell), that is subjected to an increase in at least two transcription factors as disclosed herein can continue to express amylase, typical of an amylase producing cell, but, unlike the typical amylase producing cell, also produces insulin. Thus, a continuum between complete phenotypic change and a single phenotypic change is possible. An increase in proliferation of cells of endoderm origin may precede the reprogramming to β-like cells which produce insulin, and "reprogramming" is not meant to exclude any proliferation that accompanies the change of the cell to an insulin producing β-cell like phenotype.

To confirm the reprogramming of a cell of endoderm origin to a β-like cells, isolated clones can be tested for the expression of a marker of β-cells. Such expression identifies the cells as pancreatic β-like cells. Markers for pancreatic β-like cells can be selected from the non-limiting group including c-peptide, Glut2 and Pdx1. Additionally, pancreatic β-like cells secrete insulin in the response to glucose, for example an increase in glucose level. Other makers for the pancreatic β-like cells include, for example, but are not limited to an increase in expression of Insulin (INS), NeuroD, NKX6 transcription factor related, locus 1 (NKX6.1), Nkx2.2, NeuroD, Glut2, glucokinase (GCK), prohormone convertase (PC1/3) and/or connecting peptide (C-peptide) by a stastistially significant amount as compared to the cell of endoderm origin from which the β-like cell was reprogrammed from.

Figure 6:
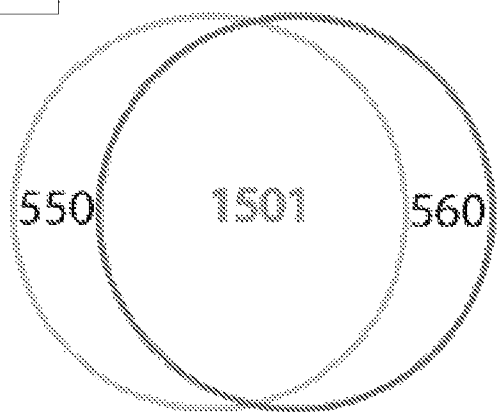
FIGS. 6A-6B show the expression profile comparison of pancreatic β-like cells and islet cells.
Figure 6:
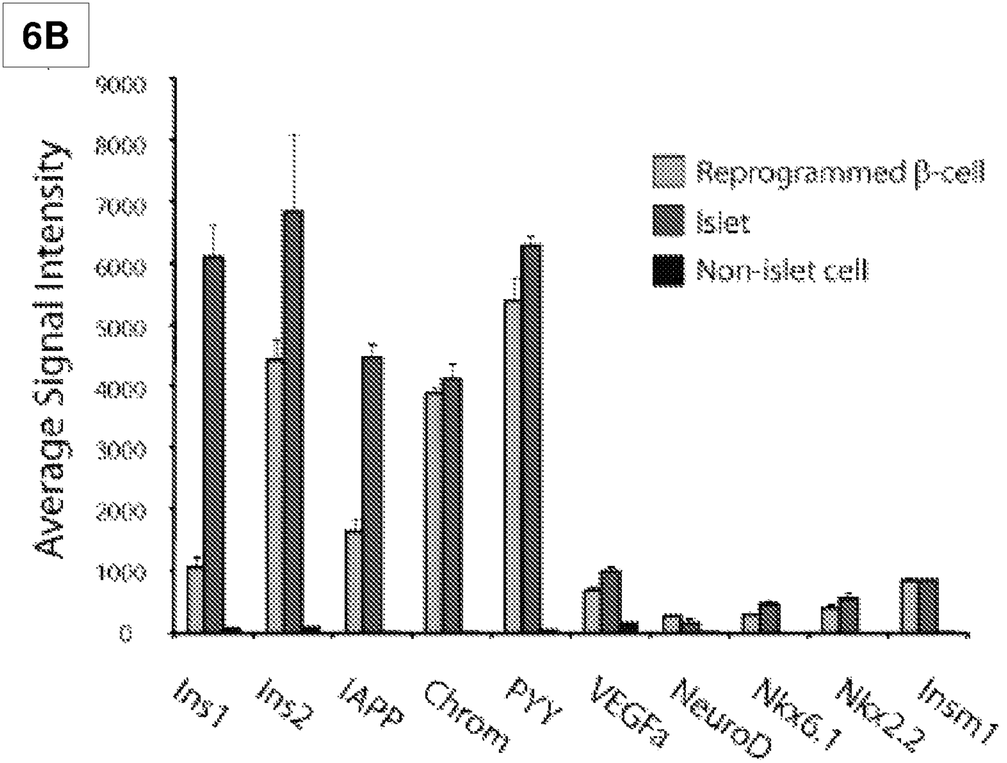

In some embodiments, pancreatic β-like cells can be identified by the expression of markers as disclosed herein in the Examples, and in FIG. 6B, which include decrease in the expression of Ins1, Ins2, IAPP as compared to endogenous pancreatic β-cells, but an increase as compared to non-insulin producing cells of endocrine origin. In some embodiments, the the pancreatic β-like cells as disclosed herein have an increased expression of a marker selected from, for example, Ins1, Ins2, IAPP, Chrom, PYY, i.e. the expression is increased by a statistically significant amount in the pancreatic β-like cell as compared to the cell of endoderm origin from which the cell was reprogrammed from.

In some embodiments, the pancreatic β-like cell produced by the methods as disclosed herein secretes at least 15%, or at least 25% or at least 30% of the insulin that endogenous β-cells secrete, or alternatively, in some embodiments, a pancreatic β-like cell exhibits at least two characteristics of an endogenous pancreatic β-cell, for example, but not limited to, secretion of insulin in response to glucose, and expression of β-cell markers, such as for example, c-peptide, Pdx-1, Glut-2. In some embodiments, the β-like cell express insulin. In some embodiments, the β-like cells express VEGF. In some embodiments, the β-like cell expresses other cell markers, such as GCK, PC1/3, and transcription factors NeuroD, Nkx2.2 and Nkx6.2. In some embodiments, the β-like cell express GCK, PC1/3, NeuroD, Nkx2.2 and Nkx6 at a statistically significant increased level as compared to the cell of endoderm origin from which the β-like cell arises. In some embodiments, the β-like cell expresses insulin at a statistically significant increased level as compared to the cell of endoderm origin from which the β-like cell arises. In some embodiments, the β-like cell expresses VEGF at a statistically significant increased level as compared to the cell of endoderm origin from which the β-like cell arises.

In some embodiments, the β-like cell does not express markers Amylase, Ptf1a, Ck19 (Krt19), somatastatin/pancreatic polypeptide (SomPP), glucagon, mesenchymal markers, Nestin, Vimentin or Tuji. In some embodiments, the β-like cell expresses Amylase, Ptf1a, Ck19 (Krt19), somatastatin/pancreatic polypeptide (SomPP), glucagon, mesenchymal markers, Nestin, Vimentin or Tuji at at a statistically significant decreased level as compared to the cell of endoderm origin from which the β-like cell arise.

In another embodiment, a pancreatic β-like cell expresses or secretes Insulin, i.e. the expression is increased by a statistically significant amount as compared to the cell of endoderm origin from which the cell was reprogrammed from. In some embodiments, the pancreatic β-like cells expresses at least about 15%, or at least about 20% or at least about 30% or at least about 40% or at least about 50% or at least about 60% or at least about 70% or at least about 80% or at least about 90% or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic β-cell.

In another embodiment, a pancreatic β-like cell does not express or secrete a hormone (e.g., glucagon, somatostatin, pancreatic polypeptide), i.e. the expression is decreased by a statistically significant amount as compared to the cell of endoderm origin from which the cell was reprogrammed from.

In one embodiment, the pancreatic β-like cell produced by the methods as disclosed herein has decreased or absent expression of a marker selected from, for example, amylase, ptf1a, Ck19, Nestin, Vimentin, Tuji) i.e. the expression is decreased by a statistically significant amount in the pancreatic β-like cell as compared to the cell of endoderm origin from which the cell was reprogrammed from.

Methods for detecting the expression of such markers are well known in the art, and include, for example, RT-PCR and immunological methods that detect the presence of the encoded polypeptides, such as ELISA.

In some embodiments, a pancreatic β-like cells produced by the methods as disclosed herein can be identified based on unique morphological characteristics. In some embodiments, the pancreatic β-like cells are located intercalated within anicar rosettes in the pancreas, as discussed in the Examples and FIG. 1B. Thus, in some embodiments, the pancreatic β-like cells have a unique localization in the pancrease as compared to endogenous pancreatic β-cells in vivo, where endogenous pancreatic β-cells are organized into islet.

In some embodiments, the pancreatic β-like cells are between about 17-25 μm in diameter, for example, at least about 14 μm, or at least about 15 μm, or about at least 16 μm, or at least about 17 μm, or at least about 18 μm, or at least about 19 μm, or at least about 20 μm, or at least about 21 μm, or at least about 22 μm, or at least about 23 μm, or at least about 24 μm, or at least about 25 μm, or at least about 26 μm, or at least about 27 μm, or greater than about 27 μm in diameter. Thus, in some embodiments, the pancreatic β-like cells have a larger diameter as compared to endogenous pancreatic β-cells in vivo. In some embodiments, the pancreatic β-like cells have a stastisically significant larger diameter as compared to endogenous pancreatic β-cells in vivo. Typically, Endogenous pancreatic β-cells are about 9-15 μm in diameter.

Figure 3:
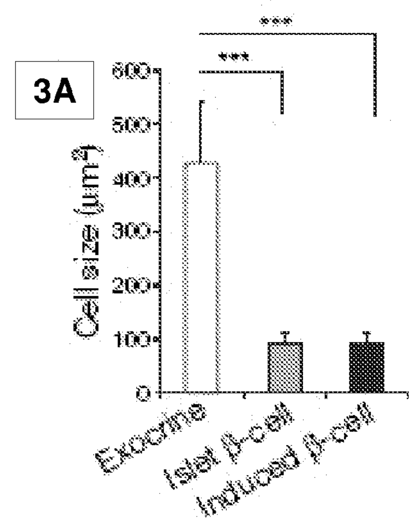
FIGS. 3A-3C show endogenous and pancreatic β-like cells are indistinguishable in morphology and ultrastructure.
Figure 3:
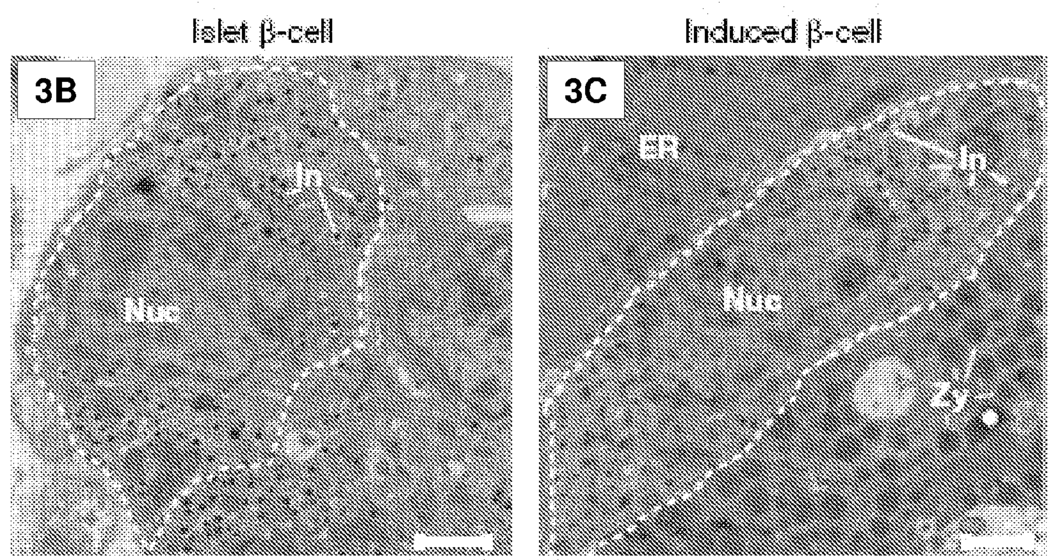

In some embodiments, the pancreatic β-like cells in vivo have a cobblestone like gross morphology cell appearance, as disclosed in the Examples and in FIG. 3B, which is distinct from endogenous β-cells in vivo, which have a smaller spindle like morphology (see FIG. 3A). Thus, in some embodiments, a population of pancreatic β-like cells can be distinguished from a population of endogenous β-like cells based on morphology, such as size, cell appearance and cell localization. In some embodiments, a population of pancreatic β-like cells in vivo can be distinguished from a population of endogenous β-like cells in vivo based on morphology, such as size, cell appearance and cell localization.

In some embodiments, the present invention relates to an isolated population of pancreatic β-like cells produced by the methods as disclosed herein. In some embodiments, pancreatic β-like cells can be isolated by methods known in the art, for example FACs sorting, as disclosed in Liu et al., Journal Sichuan University, medical science edition, 209; 40(1); 153-6 or Liu et al., J Biol Chem, 1998; 273, 22201-22208, which are incorporated herein by reference).

Monitoring the Production of Pancreatic β-Like Cells from Cells of Endoderm Origin The progression of a cell of endoderm origin to a pancreatic β-like cell can be monitored by determining the expression of markers characteristic of endogenous β-cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of pancreatic β-like cell as well as the lack of significant expression of markers characteristic of the cell of endoderm origin from which it was derived is determined.

As described in connection with monitoring the production of a pancreatic β-like cell, qualitative or semi-quantitative techniques, such as blot transfer methods and immunocytochemistry, can be used to measure marker expression. Alternatively, marker expression can be accurately quantitated through the use of technique such as Q-PCR. Additionally, it will be appreciated that at the polypeptide level, many of the markers of pancreatic islet hormone-expressing cells are secreted proteins. As such, techniques for measuring extracellular marker content, such as ELISA, may be utilized.

As set forth in the Examples below, markers of pancreatic β-like cell include the expression of markers, but are not limited to, insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide). As set forth in the Examples below, markers of pancreatic β-like cell include the lack of expression of, but are not limited to, Amylase (Amy), Glucagon, somatostatin/pancreatic polypeptide (SomPP), Ptf1a, the duct marker Ck19 (also known as Krt19), and mesenchymal markers Nestin and Vimentin.

The pancreatic β-like cell produced by the processes described herein express one or more of the above-listed markers, thereby producing the corresponding gene products. However, it will be appreciated that pancreatic β-like cella need not express all of the above-described markers. For example, pancreatic β-like cells reprogrammed from cells of endoderm origin do not always express INS.

Because endogenous β-cells do not substantially express the Ngn3, the transition of a cell of endoderm origin to a pancreatic β-like cell can be validated by monitoring the decrease in expression of NGN3 while monitoring the increase in expression of one or more of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide). In addition to monitoring the increase and/or decrease in expression of one or more the above-described markers, in some processes, the expression of genes indicative endogenous β-cells can also be monitored.

It will be appreciated that insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) marker expression is induced over a range of different levels in pancreatic β-cells depending on the differentiation conditions. As such, in some embodiments described herein, the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in pancreatic β-like cells is at least about 2-fold higher to at least about 10,000-fold higher than the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in a cell of endoderm origin from which the pancreatic β-like cell was derived.

In other embodiments, the expression of the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in pancreatic β-like cells is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in a cell of endoderm origin from which the pancreatic β-like cell was derived.

In other embodiments, the expression of the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in pancreatic β-like cells is infinitely higher than than the expression of insulin (INS), NKX6 transcription factor related, locus 1 (NKX6.1), Nkx2.2, NeuroD, Glut2, glucokinase (GCK), prohormone convertase (PC1/3) and/or connecting peptide (C-peptide) in a cell of endoderm origin from which the pancreatic β-like cell was derived.

It will also be appreciated that the MafA marker expression increases, for example, in the β-like cells over a range of different levels in β-like cells. As such, in some embodiments described herein, the expression of the MafA marker in pancreatic β-like cell is at least about 2-fold higher to at least about 10,000-fold higher than the expression of MafA marker expression in a cell of endoderm origin from which the pancreatic β-like cell was derived. In other embodiments, the expression of the MAFA marker in pancreatic β-like cell is at least about 4-fold higher, at least about 6-fold higher, at least about 8-fold higher, at least about 10-fold higher, at least about 15-fold higher, at least about 20-fold higher, at least about 40-fold higher, at least about 80-fold higher, at least about 100-fold higher, at least about 150-fold higher, at least about 200-fold higher, at least about 500-fold higher, at least about 750-fold higher, at least about 1000-fold higher, at least about 2500-fold higher, at least about 5000-fold higher, at least about 7500-fold higher or at least about 10,000-fold higher than the expression of the MAFA markers a cell of endoderm origin from which the pancreatic β-like cell was derived.

In some embodiments of the processes described herein, the amount of hormone release from a population of pancreatic β-like cell can be determined. For example, the amount of insulin release, can be monitored. In a preferred embodiment, the amount of insulin secreted in response to glucose (GSIS) is measured. In still other embodiments, secreted breakdown or by-products produced by the pancreatic β-like cell, such as c-peptide and islet amyloid protein, can be monitored.

It will be appreciated that methods of measuring the expression of secreted proteins are well known in the art. For example, an antibody against one or more hormones produced by islet cells can be used in ELISA assays.

In some embodiments of the present invention, insulin release by a pancreatic β-like cell is measured by measuring C-peptide release. C-peptide is a cleavage product that is produced in equal molar amounts to insulin during the maturation of pro-insulin. Measuring C-peptide is advantageous because its half life is longer than that of insulin. Methods of measuring C-peptide release are well known in the art, for example, ELISA using anti-C-peptide monoclonal antibody (Linco Research, St. Louis, Mo.). In some embodiments of the present invention, pancreatic β-like cells produced from cells of endoderm origin secrete at least about 50 pmol of C-peptide (insulin)/μg of cellular DNA, at least about 100 pmol of C-peptide (insulin)/μg of cellular DNA, at least about 150 pmol of C-peptide (insulin)/μg of cellular DNA, at least about 200 pmol of C-peptide (insulin)/μg of cellular DNA, at least about 250 pmol of C-peptide (insulin)/μg of cellular DNA, at least about 300 pmol of C-peptide (insulin)/μg of cellular DNA, at least about 350 pmol of C-peptide (insulin)/μg of cellular DNA, at least about 400 pmol of C-peptide (insulin)/μg of cellular DNA, at least about 450 pmol of C-peptide (insulin)/μg of cellular DNA, at least about 500 pmol of C-peptide (insulin)/μg of cellular DNA, at least about 550 pmol of C-peptide (insulin)/μg of cellular DNA, at least about 600 pmol of C-peptide (insulin)/μg of cellular DNA, at least about 650 pmol of C-peptide (insulin)/μg of cellular DNA, at least about 700 pmol of C-peptide (insulin)/μg of cellular DNA, at least about 750 pmol of C-peptide (insulin)/μg of cellular DNA, at least about 800 pmol of C-peptide (insulin)/μg of cellular DNA, at least about 850 pmol of C-peptide (insulin)/μg of cellular DNA, at least about 900 pmol of C-peptide (insulin)/μg of cellular DNA, at least about 950 pmol of C-peptide (insulin)/μg of cellular DNA or at least about 1000 pmol of C-peptide (insulin)/.mu.g of cellular DNA. In preferred embodiments, the pancreatic β-like cells are cells that secrete a single type of islet cell hormone (for example, the cells secrete only insulin). In certain preferred embodiments, the insulin is secreted in response to glucose. In other embodiments, the pancreatic β-like cells are cells are cells that secrete insulin in addition to other factors, for example, VEGF.

In some embodiments, the pancreatic β-like cells are cells process greater than about 80% of the insulin produced by a non-insulin producing cell of endoderm origin from which it was derived. In some embodiments, a pancreatic β-like cell is a cell that process greater than about 85%, greater than about 90%, greater than about 91%, greater than about 92%, greater than about 93%, greater than about 94%, greater than about 95%, greater than about 96%, greater than about 97%, greater than about 98% or greater than about 99% of the insulin produced a non-insulin producing cell of endoderm origin from which it was derived.

Methods of Identifying Agents for Reprogramming Cells of Endodermal Origin to a Pancreatic β-Like Cell.

Another aspect of the present invention relates to methods of identifying agents that alone or in combination with other agents reprogram a cell of endoderm origin to a pancreatic β-like cell. In some embodiments, the method includes contacting one or more cells of endoderm origin with one or more test agents (simultaneously or at separate times) and determining the level of expression of one or more reprogramming genes as defined herein. In some embodiments, the β-cell reprogramming genes include, Pdx1, Ngn3, mafA, NeuroD, Nkx2.2, Nkx6.1, Pax4, Pax6 of Isl1. Where one or more test agents increase the level of expression of one or more of the foregoing genes above the level of expression found in the cell of endoderm origin, in the absence of one or more test agents, are considered agents for reprogramming cells of endoderm origin to a pancreatic β-like cell. The test agents may include, but are not limited to, small molecules, nucleic acids, peptides, polypeptides, immunoglobulins, and oligosaccarides. In some embodiments, the just-mentioned method includes determining the level of expression of one or more of Pdx1, Ngn3 or MafA. In some embodiments, the method includes determining the level of expression of one or more of Pdx1, Ngn3 or MafA. Expression levels can be determined by any means known by one of ordinary skill in the art, for example, by RT-PCR or immunological methods.

Of particular interest are screening assays for agents that are active reprogramming human cells of endoderm origin to pancreatic β-like cells. A wide variety of assays may be used for this purpose, including immunoassays for protein binding; determination of cell growth, differentiation and functional activity; production of factors; and the like.

In the screening method of the invention for agents, the cells of endoderm origin are contacted with the agent of interest, and the effect of the agent assessed by monitoring output parameters, such as expression of reprogramming genes such as, but not limited to Pdx1, Ngn3 or MafA, cell viability, β-like cell characteristics, and the like. The cells may be freshly isolated, cultured, genetically engineered as described above, or the like. The s cells of endoderm origin may be environmentally induced variants of clonal cultures: e.g. split into independent cultures and grown under distinct conditions, for example with or without virus; in the presence or absence of other cytokines or combinations thereof. Alternatively, the cells of endoderm origin may be variants with a desired pathological characteristic. For example, the desired pathological characteristic includes a mutation and/or polymorphism which contribute to disease pathology.

In alternative embodiments, the methods of the invention can be used to screen for agents in which some cells of endoderm origin comprising a particular mutation and/or polymorphism respond differently compared with cells of endoderm origin without the mutation and/or polymorphism, therefore the methods can be used for example, to assess an effect of a particular drug and/or agent on stem cells from a defined subpopulation of people and/or cells, therefore acting as a high-throughput screen for personalized medicine and/or pharmogenetics. The manner in which cells respond to an agent, particularly a pharmacologic agent, including the timing of responses, is an important reflection of the physiologic state of the cell.

The agent used in the screening method can be selected from a group of a chemical, small molecule, chemical entity, nucleic acid sequences, an action; nucleic acid analogues or protein or polypeptide or analogue of fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof. The agent may be applied to the media, where it contacts the cell (such as cells of endoderm origin) and induces its effects. Alternatively, the agent may be intracellular within the cell (e.g. cells of endoderm origin) as a result of introduction of the nucleic acid sequence into the cell and its transcription resulting in the production of the nucleic acid and/or protein agent within the cell. An agent also encompasses any action and/or event the cells (e.g. cells of endoderm origin) are subjected to. As a non-limiting examples, an action can comprise any action that triggers a physiological change in the cell, for example but not limited to; heat-shock, ionizing irradiation, cold-shock, electrical impulse, light and/or wavelength exposure, UV exposure, pressure, stretching action, increased and/or decreased oxygen exposure, exposure to reactive oxygen species (ROS), ischemic conditions, fluorescence exposure etc. Environmental stimuli also include intrinsic environmental stimuli defined below. The exposure to agent may be continuous or non-continuous.

In some embodiments, the agent is an agent of interest including known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

Parameters are quantifiable components of cells of endoderm origin, particularly the expression of genes (e.g., protein expression or mRNA expression) such as, one or more in any combination of Pdx1, Ngn3 or MafA. In some embodiments, expression of one or more, in any combination of Pdx1, Ngn3, mafA, NeuroD, Nkx2.2, Nkx6.1, Pax4, Pax6 of Isl1 that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values. In some embodiments, the assay is a computerized assay or a robotic high-throughput system operated through a computer interface.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for effect on the cells of endoderm origin by adding the agent to at least one and usually a plurality of cells of endoderm origin, usually in conjunction with cells of endoderm origin lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method. In some embodiments, agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Optionally, the cells of endoderm origin used in the screen can be manipulated to express desired gene products. Gene therapy can be used to either modify a cell to replace a gene product or add or knockdown a gene product. In some embodiments the genetic engineering is done to facilitate regeneration of tissue, to treat disease, or to improve survival of the β-like cells following implantation into a subject (i.e. prevent rejection). Techniques for transfecting cells are known in the art.

A skilled artisan could envision a multitude of genes which would convey beneficial properties to the transfected β-like cell or, more indirectly, to the cells of endoderm origin used for reprogramming. The added gene may ultimately remain in the recipient cell and all its progeny, or may only remain transiently, depending on the embodiment. For example, genes encoding angiogenic factors could be transfected into cells of endoderm origin. Such genes would be useful for inducing collateral blood vessel formation as the cell was reprogrammed to a β-like cell. It some situations, it may be desirable to transfect the cell with more than one gene.

In some instances, it is desirable to have the gene product secreted. In such cases, the gene product preferably contains a secretory signal sequence that facilitates secretion of the protein. For example, if the desired gene product is an angiogenic protein, a skilled artisan could either select an angiogenic protein with a native signal sequence, e.g. VEGF, or can modify the gene product to contain such a sequence using routine genetic manipulation (See Nabel et al., 1993).

The desired gene can be transfected into the cell using a variety of techniques. Preferably, the gene is transfected into the cell using an expression vector. Suitable expression vectors include plasmid vectors (such as those available from Stratagene, Madison Wis.), viral vectors (such as replication defective retroviral vectors, herpes virus, adenovirus, adeno-virus associated virus, and lentivirus), and non-viral vectors (such as liposomes or receptor ligands).

The desired gene is usually operably linked to its own promoter or to a foreign promoter which, in either case, mediates transcription of the gene product. Promoters are chosen based on their ability to drive expression in restricted or in general tissue types, for example in cells of endoderm origin, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are well known to those of skill in the art (U.S. Pat. Nos. 5,830,698; 5,789,215; 5,721,367 and 5,612,205). By "targeting genes" it is meant that the entire or a portion of a gene residing in the chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Enrichment, Isolation and/or Purification of a Population of Pancreatic β-Like Cells.

Another aspect of the present invention relates to the isolation of a population of pancreatic β-like cells from a heterogeneous population of cells, such a comprising a mixed population of pancreatic β-like cells and cells on endoderm origin from which the pancreatic β-cells were derived. A population of pancreatic β-like cells produced by any of the above-described processes can be enriched, isolated and/or purified by using an affinity tag that is specific for such cells. Examples of affinity tags specific for pancreatic β-like cells are antibodies, ligands or other binding agents that are specific to a marker molecule, such as a polypeptide, that is present on the cell surface of pancreatic β-like cells but which is not substantially present on other cell types (i.e. on the cells of endoderm origin) that would be found in the heterogeneous population of cells produced by the methods described herein. In some processes, an antibody which binds to a cell surface antigen on human pancreatic islet cells is used as an affinity tag for the enrichment, isolation or purification of pancreatic β-like cells produced by in vitro methods, such as the methods described herein. Such antibodies are known and commercially available. For example, a monoclonal antibody that is highly specific for a cell surface marker on human islet cells is available from USBiological, Swampscott, Mass. (Catalog Number P2999-40). Other examples include the highly specific monoclonal antibodies to glycoproteins located on the pancreatic islet cell surface, which have been described by Srikanta, et al., (1987) Endocrinology, 120:2240-2244, the disclosure of which is incorporated herein by reference in its entirety. A preferred example of an affinity tag for mature pancreatic β-like cells, such as those derived from cells of endoderm origin, is NCAM. Antibodies against NCAM are commercially available, for example from Abcam (Cambridge, Mass.).

The skilled artisan will readily appreciate that the processes for making and using antibodies for the enrichment, isolation and/or purification of pancreatic β-like cells are also readily adaptable for the enrichment, isolation and/or purification of pancreatic β-like cells. For example, in some embodiments, the reagent, such as an NCAM antibody, is incubated with a cell population containing pancreatic β-like cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FITC-conjugated antibody that is capable of binding to the primary antibody. The cells are then washed, centrifuged and resuspended in buffer. The cell suspension is then analyzed and sorted using a fluorescence activated cell sorter (FACS). Antibody-bound, fluorescent cells are collected separately from non-bound, non-fluorescent, thereby resulting in the isolation of such cell types.

In preferred embodiments of the processes described herein, the isolated cell composition comprising pancreatic β-like cells can be further purified by using an alternate affinity-based method or by additional rounds of sorting using the same or different markers that are specific for pancreatic β-like cells. For example, in some embodiments, FACS sorting is used to first isolate Pdx1-positive pancreatic β-like cells from Pdx1 negative cells from cell populations comprising pancreatic β-like cells. Sorting the Pdx1 positive cells again using FACS to isolate cells that are Pdx1 positive enriches the cell population for pancreatic β-like cells that express markers characteristic of this cell type, including NKX6.1, MAFA, ISL1 or PAX6 and other markers as disclosed herein. In other embodiments, FACS sorting is used to separate cells by negatively sorting for a marker that is present on most cells in the cell population other than the pancreatic β-like cells. An example of such a negative sort is the use of Tuji, which is a marker that is not substantially expressed on the surface of pancreatic β-like cells after the first round of enrichment.

In some embodiments of the processes described herein, pancreatic β-like cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label pancreatic β-like cells using the methods described above. For example, in some embodiments, at least one copy of a nucleic acid encoding GFP or a biologically active fragment thereof is introduced into a cell of endoderm origin, preferably a human cell of endoderm origin, downstream of the NKX6.1 promoter such that the expression of the GFP gene product or biologically active fragment thereof is under control of the NKX6.1 promoter. In some embodiments, the entire coding region of the nucleic acid, which encodes NKX6.1, is replaced by a nucleic acid encoding GFP or a biologically active fragment thereof. In other embodiments, the nucleic acid encoding GFP or a biologically active fragment thereof is fused in frame with at least a portion of the nucleic acid encoding NKX6.1, thereby generating a fusion protein. In such embodiments, the fusion protein retains a fluorescent activity similar to GFP.

It will be appreciated that promoters other than the NKX6.1 promoter can be used provided that the promoter corresponds to a marker that is expressed in pancreatic β-like cells. One exemplary marker is NKX2.2 or NeuroD, or Pdx1 or MafA.

Fluorescently marked cells, such as the above-described cells of endoderm origin, are differentiated to pancreatic β-like cells as described previously above. Because pancreatic β-like cells express the fluorescent marker gene, whereas other cell types do not, pancreatic β-like cells can be separated from the other cell types. In some embodiments, cell suspensions comprising a population of a mixture of fluorescently-labeled pancreatic β-like cells and unlabeled non-pancreatic β-like cells (i.e. cells of endoderm origin from which the pancreatic β-like cells were derived) are sorted using a FACS. Pancreatic β-like cells can be collected separately from non-fluorescing cells (i.e. the cells of endoderm origin which have not been reprogrammed to become pancreatic β-like cells), thereby resulting in the isolation of pancreatic β-like cells. If desired, the isolated cell compositions comprising pancreatic β-like cells can be further purified by additional rounds of sorting using the same or different markers that are specific for pancreatic β-like cells.

In preferred processes, pancreatic β-like cells are enriched, isolated and/or purified from other non-pancreatic β-like cells (i.e. from the cells of endoderm origin which have not been reprogrammed to become pancreatic β-like cells) after the cell population is induced to reprogram towards pancreatic β-like cell using the methods and compositions as disclosed herein.

In addition to the procedures just described, pancreatic β-like cells may also be isolated by other techniques for cell isolation. Additionally, pancreatic β-like cells may also be enriched or isolated by methods of serial subculture in growth conditions which promote the selective survival or selective expansion of the pancreatic β-like cells.

Using the methods described herein, enriched, isolated and/or purified populations of pancreatic β-like cells can be produced in vitro from cells of endoderm origin, which have undergone sufficient reprogramming to produce at least some pancreatic β-like cells. In a preferred method, the cells of endoderm origin are reprogrammed primarily into pancreatic β-like cells. Some preferred enrichment, isolation and/or purification methods relate to the in vitro production of pancreatic β-like cells from human cells of endoderm origin.

Using the methods described herein, isolated cell populations of pancreatic β-like cells are enriched in pancreatic β-like cells content by at least about 2- to about 1000-fold as compared to a population before reprogramming of the cells of endoderm origin. In some embodiments, pancreatic β-like cells can be enriched by at least about 5- to about 500-fold as compared to a population before reprogramming of the cells of endoderm origin. In other embodiments, pancreatic β-like cells can be enriched from at least about 10- to about 200-fold as compared to a population before reprogramming of the cells of endoderm origin. In still other embodiments, pancreatic β-like cells can be enriched from at least about 20- to about 100-fold as compared to a population before reprogramming of the cells of endoderm origin. In yet other embodiments, pancreatic β-like cells can be enriched from at least about 40- to about 80-fold as compared to a population before reprogramming of the cells of endoderm origin. In certain embodiments, pancreatic β-like cells can be enriched from at least about 2- to about 20-fold as compared to a population before reprogramming of the cells of endoderm origin.

Compositions Comprising Pancreatic β-Like Cells

Some embodiments of the present invention relate to cell compositions, such as cell cultures or cell populations, comprising pancreatic β-like cells, wherein the pancreatic β-like cells are cells, which have been derived from cells e.g. human cells of endoderm origin, which express or exhibit one or more characteristics of an endogenous pancreatic β-cell or alternatively, express at least 15% of the insulin secreted by an endogenous pancreatic β-cell. In accordance with certain embodiments, the pancreatic β-like cells are mammalian cells, and in a preferred embodiment, such cells are human pancreatic β-like cells.

Other embodiments of the present invention relate to compositions, such as cell cultures or cell populations, comprising pancreatic β-like cells. In such embodiments, cells that are of endoderm origin comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the cell population.

Certain other embodiments of the present invention relate to compositions, such as cell cultures or cell populations, comprising pancreatic β-like cells. In some embodiments, cells of endoderm origin from which the pancreatic β-cells are derived comprise less than about 25%, less than about 20%, less than about 15%, less than about 10%, less than about 5%, less than about 4%, less than about 3%, less than about 2% or less than about 1% of the total cells in the culture. In certain embodiments, pre-primitive streak cells comprise less than about 25%, less than about 20%, less than about 15%, less than about 10%, less than about 5%, less than about 4%, less than about 3%, less than about 2% or less than about 1% of the total cells in the culture.

Additional embodiments of the present invention relate to compositions, such as cell cultures or cell populations, produced by the processes described herein and which comprise pancreatic β-like cells as the majority cell type. In some embodiments, the processes described herein produce cell cultures and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% pancreatic β-like cells. In preferred embodiments, the cells of the cell cultures or cell populations comprise human cells. In other embodiments, the processes described herein produce cell cultures or cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about IT %, at least about 10%, at least about 9%, at least about 8%, at least about 7%, at least about 6%, at least about 5%, at least about 4%, at least about 3%, at least about 2% or at least about 1% pancreatic β-like cells. In preferred embodiments, the cells of the cell cultures or cell populations comprise human cells. In some embodiments, the percentage of pancreatic β-like cells in the cell cultures or populations is calculated without regard to the feeder cells remaining in the culture.

Still other embodiments of the present invention relate to compositions, such as cell cultures or cell populations, comprising mixtures of pancreatic β-like cells and cells of endoderm origin. For example, cell cultures or cell populations comprising at least about 5 pancreatic β-like cells for about every 95 cell of endoderm origin can be produced. In other embodiments, cell cultures or cell populations comprising at least about 95 pancreatic β-like cells for about every 5 cell of endoderm origin can be produced. Additionally, cell cultures or cell populations comprising other ratios of pancreatic β-like cells to cell of endoderm origin are contemplated. For example, compositions comprising at least about 1 pancreatic β-like cells for about every 1,000,000, or at least 100,000 cells, or a least 10,000 cells, or at least 1000 cells or 500, or at least 250 or at least 100 or at least 10 cells of endocrine origin can be produced.

Further embodiments of the present invention relate to compositions, such as cell cultures or cell populations, comprising human cells, including human pancreatic β-like cells which express at least 15% of the level of insulin as compared to endogenous pancreatic β-cells.

In preferred embodiments of the present invention, cell cultures and/or cell populations of pancreatic β-like cells comprise human pancreatic β-like cells, that are non-recombinant cells. In such embodiments, the cell cultures and/or cell populations are devoid of or substantially free of recombinant human pancreatic β-like cells.

In some embodiments of the cell cultures and/or cell populations described herein, the pancreatic β-like cells secrete more than one pancreatic hormone. In other embodiments of the cell cultures and/or cell populations described herein, the pancreatic β-like cells s secrete a single pancreatic hormone. In preferred embodiments, the hormone is insulin. In even more preferred embodiments, the pancreatic β-like cells are responsive to glucose. In other embodiments, human pancreatic β-like cells from cells of endoderm origin secrete insulin in an amount similar to or greater than the amount of insulin secreted by pancreatic beta cells of the human pancreas in vivo.

Using the processes described herein, compositions comprising pancreatic β-like cells are substantially free of other cell types can be produced. In some embodiments of the present invention, the pancreatic β-like cell populations or cell cultures produced by the methods described herein are substantially free of cells that significantly express the Amylase, Ck19, glucogon, somatastatin, pancreatic polypeptide, Ptf1a or other markers.

Use of the Pancreatic β-Like Cells

Another aspect of the present invention further provides a method of treating diabetes in a subject diagnosed with Type 1 diabetes, comprising administering to the subject a population of pancreatic β-like cells.

In an alternative embodiment, the present invention provides a method of treating diabetes in a subject with, or at increased risk of developing diabetes a composition comprising at least one agent which increases the protein expression of at least two transcription factors selected from the group selected from Pdx1, Ngn3 or MafA, or administering a nucleic acid sequence encoding the polypeptides of least two transcription factors selected from Pdx1 (SEQ ID NO:1 or 31), Ngn3 (SEQ ID NO: 2 or 32) or MafA (SEQ ID NO: 3 or 33), or polypeptides with amino acid sequences substantially homologous thereto, and functional fragments or functional variants thereof by continuous infusion for at least twenty-four hours.

If the transcription factor has a fairly long half-life, the β-cell reprogramming agent which increases the protein expression of the transcription factor can be administered by bolus at least once. The treatment methods are effective to treat diabetes in a subject with Type 1 diabetes, because the β-cell reprogramming agent promotes the reprogramming of cells of endoderm origin (e.g. non-insulin producing pancreatic cells) in the subject into insulin producing cells (e.g. pancreatic β-like cells), as described in detail herein.

The present invention also provides a method of treating diabetes in a subject, comprising obtaining a population of cells of endoderm origin, for example non-insulin producing cells of endoderm origin from a subject, e.g. from the subject being treated, or from a donor subject; increasing the protein expression of at least two, or all three transcription factors selected Pdx1, Ngn3, MafA in the population of cells of endoderm origin in vitro, for example by the methods as described herein, thereby promoting reprogramming of the population of cells of endoderm origin into pancreatic β-like cells (i.e. insulin-producing cells); and administering a substantially pure population of pancreatic β-like cells to the diabetic subject.

In the method of treating diabetes, wherein the cells of endoderm origin are from a donor, the donor can be a cadaver. As a further embodiment of the present invention, the cells of endoderm origin can be allowed to proliferate in vitro prior to increasing the protein expression of at least two, or in some embodiments 3 of the transcription factors selected Pdx1, Ngn3, MafA. Preferably, promoting reprogramming of cells of endoderm origin into pancreatic β-like cells as disclosed herein will result in greater than about 20% reprogramming of cells of endoderm origin into pancreatic β-like cells. Even more preferably, greater than about 25%, 30%, 35%, 40%, 45%, 50%, 55%, 60%, 65%, 70%, 75%, 80%, 85%, or 90% of the cells of endoderm origin will be reprogrammed into β-like cells.

In some embodiments, altering the surface antigens of the pancreatic β-like cells produced by the methods as disclosed herein can reduce the likelihood that pancreatic β-like cells will cause an immune response. The pancreatic β-like cells with altered surface antigens can then be administered to the diabetic subject. The cell surface antigens can be altered prior to, during, or after the non-insulin producing cells are differentiated into insulin-producing cells.

The subject of the invention can include individual humans, domesticated animals, livestock (e.g., cattle, horses, pigs, etc.), pets (like cats and dogs).

By "diabetes" is meant diabetes mellitus, a metabolic disease characterized by a deficiency or absence of insulin secretion by the pancreas. As used throughout, "diabetes" includes Type 1, Type 2, Type 3, and Type 4 diabetes mellitus unless otherwise specified herein.

As used herein, the term diabetes refers to is a syndrome of disordered metabolism, usually due to a combination of hereditary and environmental causes, resulting in abnormally high blood sugar levels (hyperglycemia). The two most common forms of diabetes are due to either a diminished production of insulin (in type 1), or diminished response by the body to insulin (in type 2 and gestational). Both lead to hyperglycemia, which largely causes the acute signs of diabetes: excessive urine production, resulting compensatory thirst and increased fluid intake, blurred vision, unexplained weight loss, lethargy, and changes in energy metabolism. Diabetes can cause many complications. Acute complications (hypoglycemia, ketoacidosis, or nonketotic hyperosmolar coma) may occur if the disease is not adequately controlled. Serious long-term complications (i.e. chronic side effects) include cardiovascular disease (doubled risk), chronic renal failure, retinal damage (which can lead to blindness), nerve damage (of several kinds), and microvascular damage, which may cause impotence and poor wound healing. Poor healing of wounds, particularly of the feet, can lead to gangrene, and possibly to amputation.

Type 1 diabetes (Type 1 diabetes, Type I diabetes, T1D, T1DM, IDDM, juvenile diabetes) is an autoimmune disease that results in the permanent destruction of insulin-producing beta cells of the pancreas.

Type 2 diabetes (non-insulin-dependent diabetes mellitus (NIDDM), or adult-onset diabetes) is a metabolic disorder that is primarily characterized by insulin resistance (diminished response by the body to insulin), relative insulin deficiency, and hyperglycemia.

In some embodiments, a subject is pre-diabetic, which can be characterized, for example, as having elevated fasting blood sugar or elevated post-prandial blood sugar.

In other embodiments, a subject who has diabetes or pre-diabetes is being treated with one or more agents, including, for example, a biguanide, preferably metformin, a thiazolidinedione (e.g., a TZD such as rosiglitazone or pioglitazone), an alpha glucosidase inhibitor, such as acarbose or voglibose, a glucagon-like peptide agonist (e.g., a GLP-1 agonist), a dipeptidylpeptidase 4 (e.g., DPP4) inhibitor or insulin.

Accordingly, the methods described herein can be combined with other methods of treating pre-diabetes, lowering blood glucose in a subject, decreasing hemoglobinA1c in a subject, inhibiting gluconeogenesis in a subject, decreasing post-prandial glucose in a subject (e.g., treating post-prandial hyperglycemia), treating type I diabetes, treating type II diabetes, or treating a metabolic disorder, comprising administering a treatment, for example, administering, an agent described herein, for example an anti-diabetic agent. Examples of anti-diabetic agents include a glucosidase inhibitor, a thiazolidinedione (e.g., TZD), an insulin sensitizer, a glucagon-like peptide-1 (GLP-1), insulin, a PPAR α/γ dual agonist, an aP2 inhibitor and/or a DPP4 inhibitor. Examples of a glucosidase inhibitor include acarbose (disclosed in U.S. Pat. No. 4,904,769), voglibose, miglitol (disclosed in U.S. Pat. No. 4,639,436), which may be administered in a separate dosage form or the same dosage form. Examples of a PPARγ agonist includes a thiazolidinedione (e.g., TZD) such as rosiglitazone (AVANDIA®), pioglitazone (ACTOS®), englitazone, and darglitazone, which may be administered in a separate dosage form or the same dosage form. An example of a DPP4 inhibitor includes PHX1149, which is being developed by Phenomix®.

Methods of Identifying Reprogramming Factors

Described herein is a strategy to identify adult cell reprogramming factors by re-expressing multiple embryonic genes in living adult animals. A focus on embryonic genes is based in part on regeneration studies in newts, frogs and fish, where it has been shown that dedifferentiation of adult cells to progenitors, a form of cellular reprogramming, is accompanied by reactivation of embryonic regulators[3,17,18].

To search for factors that could reprogram adult cells into β-cells, transcription factors (TF) were evaluated, a class of genes enriched for factors that regulate cell fates during embryogenesis. An in situ hybridization screen of more than 1,100 TFs identified groups of TFs with cell type specific expressions in the embryonic pancreas[19]. There are at least twenty TFs expressed in mature β-cells and their immediate precursors, the endocrine progenitors (Table. 1). Of these, nine genes (herein referred to "β-cell reprogramming genes") exhibit β-cell developmental phenotypes when mutated[20,21], and these were selected for initial reprogramming experiments.

Mature exocrine and duct cells of the adult pancreas were chosen as target cells for reprogramming, rather than cells from other organs. It was reasoned that these targets come from the endoderm, as do β-cells[22], and that any pancreatic β-like cells would reside in their native environment which might promote their survival and/or maturation. In addition, this approach allows for a direct comparison of endogenous and pancreatic β-like cells. The transcription factors were delivered into the pancreas in adenoviral vectors. It has been shown that adenovirus preferentially infects pancreatic exocrine cells, but not islet cells[23], and since most endogenous β-cells reside within islets (FIG. 1*b*), any newly formed (reprogrammed) β-cells could be easily detected as extra-islet insulin+ cells.

Kits

The cells and components such as one or more transcription factors can be provided in a kit. The kit includes (a) the cells and components described herein, e.g., a composition(s) that includes a cell and component(s) described herein, and, optionally (b) informational material. The informational material can be descriptive, instructional, marketing or other material that relates to the methods described herein and/or the use of a compound(s) described herein for the methods described herein.

The informational material of the kits is not limited in its form. In one embodiment, the informational material can include information about production of a cell, the nature of the components such as the transcription factor, concentration of components, date of expiration, batch or production site information, and so forth. In one embodiment, the informational material relates to methods for administering the cells or other components.

In one embodiment, the informational material can include instructions to administer a compound(s) component such as a transcription factor described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a component(s) described herein to a suitable subject, e.g., a human, e.g., a human having or at risk for a disorder described herein or to a cell in vitro.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In addition to a compound(s) described herein, the composition of the kit can include other ingredients, such as a solvent or buffer, a stabilizer, a preservative, and/or an additional agent, e.g., for reprogramming a cell of endoderm origin, such as a somatic cell (e.g., in vitro or in vivo) or for treating a condition or disorder described herein. Alternatively, the other ingredients can be included in the kit, but in different compositions or containers than a component described herein. In such embodiments, the kit can include instructions for admixing a component(s) described herein and the other ingredients, or for using a component(s) described herein together with the other ingredients, e.g., instructions on combining the two agents prior to administration.

The kit can include one or more containers for the composition containing a component(s) described herein. In some embodiments, the kit contains separate containers (e.g., two separate containers for the two agents), dividers or compartments for the component(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a component described herein. The containers of the kits can be air tight, waterproof (e.g., impermeable to changes in moisture or evaporation), and/or light-tight.

The kit optionally includes a device suitable for administration of the component, e.g., a syringe, inhalant, pipette, forceps, measured spoon, dropper (e.g., eye dropper), swab (e.g., a cotton swab or wooden swab), or any such delivery device.

Pharmaceutical Compositions Comprising a Population of Pancreatic β-Like Cells:

In another aspect of the invention, the methods provide use of an isolated population of the pancreatic β-like cells as disclosed herein. In one embodiment of the invention, an isolated population of the pancreatic β-like cells as disclosed herein may be used for the production of a pharmaceutical composition, for the use in transplantation into subjects in need of treatment, e.g. a subject that has, or is at risk of developing diabetes, for example but not limited to subjects with congenital and acquired diabetes. In one embodiment, an isolated population of the β-like cells may be genetically modified. In another aspect, the subject may have or be at risk of diabetes and/or metabolic disorder. In some embodiments, an isolated population of the pancreatic β-like cells as disclosed herein may be autologous and/or allogenic. In some embodiments, the subject is a mammal, and in other embodiments the mammal is a human.

The use of an isolated population of the pancreatic β-like cells as disclosed herein provides advantages over existing methods because the vβ-like cells can be reprogrammed from cells of endoderm origin obtained or harvested from the subject administered an isolated population of the pancreatic β-like cells. This is highly advantageous as it provides a renewable source of cells with pancreatic β-cell characteristics for transplantation into a subject, in particular a substantially pure population of pancreatic β-like cells that do not have the risks and limitations of β-like cells derived from other systems, such as from ES cell based systems, or iPS cells which have risks of formation of teratomas (Lafamme and Murry, 2005, Murry et al, 2005; Rubart and Field, 2006).

In another embodiment, an isolated population of pancreatic β-like cells can be used as models for studying properties of islet β-cells or pancreatic β-cells, or pathways of development of cells of endoderm origin into pancreatic β-cells. In some embodiments, the pancreatic β-like cells may be genetically engineered to comprise markers operatively linked to promoters that are expressed when a marker is expressed or secreted, for example, a marker can be operatively linked to an insulin promoter, so that the marker is expressed when the pancreatic β-like cells express and secrete insulin. In some embodiments, a population of pancreatic β-like cells can be used as a model for studying the differentiation pathway of cells which differentiate into islet β-cells or pancreatic β-like cells. In other embodiments, the pancreatic β-like cells may be used as models for studying the role of islet β-cells in the pancreas and in the development of diabetes and metabolic disorders. In some embodiments, the pancreatic β-like cells can be from a normal subject, or from a subject which carries a mutation and/or polymorphism (e.g. in the gene Pdx1 which leads to early-onset insulin-dependent diabetes mellitus (NIDDM), as well as maturity onset diabetes of the young type 4 (MODY4), which can be use to identify small molecules and other therapeutic agents that can be used to treat subjects with diabetes with a mutation or polymorphism in Pdx1. In some embodiments, the pancreatic β-like cells may be genetically engineered to correct the polymorphism in the Pdx1 gene prior to being administered to a subject in the therapeutic treatment of a subject with diabetes. In some embodiments, the pancreatic β-like cells may be genetically engineered to carry a mutation and/or polymorphism.

In one embodiment of the invention relates to a method of treating diabetes or a metabolic disorder in a subject comprising administering an effective amount of a composition comprising a population of pancreatic β-like cells as disclosed herein to a subject with diabetes and/or a metabolic disorder. In a further embodiment, the invention provides a method for treating diabetes, comprising administering a composition comprising a population of pancreatic β-like cells as disclosed herein to a subject that has, or has increased risk of developing diabetes in an effective amount sufficient to produce insulin in response to increased blood glucose levels.

In one embodiment of the above methods, the subject is a human and a population of pancreatic β-like cells as disclosed herein are human cells. In some embodiments, the invention contemplates that a population of pancreatic β-like cells as disclosed herein are administered directly to the pancreas of a subject, or is administered systemically. In some embodiments, a population of pancreatic β-like cells as disclosed herein can be administered to any suitable location in the subject, for example in a capsule in the blood vessel or the liver or any suitable site where administered population of pancreatic β-like cells can secrete insulin in response to increased glucose levels in the subject.

The present invention is also directed to a method of treating a subject with diabetes or a metabolic disorder which occurs as a consequence of genetic defect, physical injury, environmental insult or conditioning, bad health, obesity and other diabetes risk factors commonly known by a person of ordinary skill in the art. Efficacy of treatment can be monitored by clinically accepted criteria and tests, which include for example, (i) Glycated hemoglobin (A1C) test, which indicates a subjects average blood sugar level for the past two to three months, by measuring the percentage of blood sugar attached to hemoglobin, the oxygen-carrying protein in red blood cells. The higher your blood sugar levels, the more hemoglobin has sugar attached. An A1C level of 6.5 percent or higher on two separate tests indicates the subject has diabetes. A test value of 6-6.5% suggest the subject has prediabetes. (ii) Random blood sugar test. A blood sample will be taken from the subject at a random time, and a random blood sugar level of 200 milligrams per deciliter (mg/dL)-11.1 millimoles per liter (mmol/L), or higher indicated the subject has diabetes. (iii) Fasting blood sugar test. A blood sample is taken from the subject after an overnight fast. A fasting blood sugar level between 70 and 99 mg/dL (3.9 and 5.5 mmol/L) is normal. If the subjects fasting blood sugar levels is 126 mg/dL (7 mmol/L) or higher on two separate tests, the subject has diabetes. A blood sugar level from 100 to 125 mg/dL (5.6 to 6.9 mmol/L) indicates the subject has prediabetes. (iv) Oral glucose tolerance test. A blood sample will be taken after the subject has fasted for at least eight hours or overnight and then ingested a sugary solution, and the blood sugar level will be measured two hours later. A blood sugar level less than 140 mg/dL (7.8 mmol/L) is normal. A blood sugar level from 140 to 199 mg/dL (7.8 to 11 mmol/L) is considered prediabetes. This is sometimes referred to as impaired glucose tolerance (IGT). A blood sugar level of 200 mg/dL (11.1 mmol/L) or higher may indicate diabetes.

In some embodiments, the effects of administration of a population of β-like cells as disclosed herein to a subject in need thereof is associated with improved exercise tolerance or other quality of life measures, and decreased mortality. The effects of cellular therapy can be evident over the course of days to weeks after the procedure. However, beneficial effects may be observed as early as several hours after the procedure, and may persist for several years.

In some embodiments, a population of β-like cells as disclosed herein may be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting a population of β-like cells as disclosed herein into the pancreas or at an alternative desired location. The cells may be administered to a recipient pancreas by injection, or administered by intramuscular injection.

The compositions comprising a population of β-like cells as disclosed herein have a variety of uses in clinical therapy, research, development, and commercial purposes. For therapeutic purposes, for example, a population of β-like cells as disclosed herein may be administered to enhance insulin production in response to increase in blood glucose level for any perceived need, such as an inborn error in metabolic function, the effect of a disease condition (e.g. diabetes), or the result of significant trauma (i.e. damage to the pancreas or loss or damage to islet β-cells). In some embodiments, a population of β-like cells as disclosed herein are administered to the subject not only help restore function to damaged or otherwise unhealthy tissues, but also facilitate remodeling of the damaged tissues.

To determine the suitability of cell compositions for therapeutic administration, the cells can first be tested in a suitable animal model. At one level, cells are assessed for their ability to survive and maintain their phenotype in vivo. Cell compositions can be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or beta-galactosidase); that have been prelabeled (for example, with BrdU or [3H] thymidine), or by subsequent detection of a constitutive cell marker (for example, using human-specific antibody). The presence and phenotype of the administered population of β-like cells can be assessed by immunohistochemistry or ELISA using human-specific antibody, or by RT-PCR analysis using primers and hybridization conditions that cause amplification to be specific for human polynucleotides, according to published sequence data.

A number of animal models for testing diabetes are available for such testing, and are commonly known in the art, for example as disclosed in U.S. Pat. No. 6,187,991 which is incorporated herein by reference, as well as rodent models; NOD (non-obese mouse), BB_DB mice, KDP rat and TCR mice, and other animal models of diabetes as described in Rees et al, Diabet Med. 2005 April; 22(4):359-70; Srinivasan K, et al., Indian J Med Res. 2007 March; 125(3):451-7; Chatzigeorgiou A, et al., In Vivo. 2009 March-April; 23(2):245-58, which are incorporated herein by reference.

In some embodiments, a population of pancreatic β-like cells as disclosed herein may be administered in any physiologically acceptable excipient, where the cells may find an appropriate site for regeneration and differentiation. In some embodiments, a population of pancreatic β-like cells as disclosed herein can be introduced by injection, catheter, or the like. In some embodiments, a population of β-like cells as disclosed herein can be frozen at liquid nitrogen temperatures and stored for long periods of time, being capable of use on thawing. If frozen, a population of pancreatic β-like cells will usually be stored in a 10% DMSO, 50% FCS, 40% RPMI 1640 medium. Once thawed, the cells may be expanded by use of growth factors and/or feeder cells associated with culturing β-cells and pancreatic β-like cells as disclosed herein.

In some embodiments, a population of pancreatic β-like cells as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of pancreatic β-like cells as disclosed herein will be adapted in accordance with the route and device used for administration. In some embodiments, a composition comprising a population of pancreatic β-like cells can also comprise or be accompanied with one or more other ingredients that facilitate the engraftment or functional mobilization of the pancreatic β-like cells. Suitable ingredients include matrix proteins that support or promote adhesion of the pancreatic β-like cells, or complementary cell types, especially endothelial cells. In another embodiment, the composition may comprise resorbable or biodegradable matrix scaffolds.

In some embodiments, a population of pancreatic β-like cells as disclosed herein may be genetically altered in order to introduce genes useful in the β-like cells, e.g. repair of a genetic defect in an individual, selectable marker, etc., or genes useful in selection against non-insulin producing β-like cells or for the selective suicide of implanted pancreatic β-like cells. In some embodiments, a population of pancreatic β-like cells can also be genetically modified to enhance survival, control proliferation, and the like. In some embodiments, a population of pancreatic β-like cells as disclosed herein can be genetically altering by transfection or transduction with a suitable vector, homologous recombination, or other appropriate technique, so that they express a gene of interest. In one embodiment, a pancreatic β-like cell is transfected with genes encoding a telomerase catalytic component (TERT), typically under a heterologous promoter that increases telomerase expression beyond what occurs under the endogenous promoter, (see International Patent Application WO 98/14592, which is incorporated herein by reference). In other embodiments, a selectable marker is introduced, to provide for greater purity of the population of pancreatic β-like cells. In some embodiments, a population of pancreatic β-like cells may be genetically altered using vector containing supernatants over a 8-16 h period, and then exchanged into growth medium for 1-2 days. Genetically altered pancreatic β-like cells can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, a population of pancreatic β-like cells as disclosed herein can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, such as somatostatin, glucagon, and other factors.

Many vectors useful for transferring exogenous genes into target pancreatic β-like cells as disclosed herein are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. In some embodiments, combinations of retroviruses and an appropriate packaging cell line may also find use, where the capsid proteins will be functional for infecting the pancreatic β-like cells as disclosed herein. Usually, pancreatic β-like cells and virus will be incubated for at least about 24 hours in the culture medium. In some embodiments, the pancreatic β-like cells are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, a population of pancreatic β-like cells as disclosed herein are suitable for administering systemically or to a target anatomical site. A population of pancreatic β-like cells can be grafted into or nearby a subject's pancreas, for example, or may be administered systemically, such as, but not limited to, intra-arterial or intravenous administration. In alternative embodiments, a population of pancreatic β-like cells of the present invention can be administered in various ways as would be appropriate to implant in the pancreatic or secretory system, including but not limited to parenteral, including intravenous and intraarterial administration, intrathecal administration, intraventricular administration, intraparenchymal, intracranial, intracisternal, intrastriatal, and intranigral administration. Optionally, a population of pancreatic β-like cells are administered in conjunction with an immunosuppressive agent.

In some embodiments, a population of pancreatic β-like cells can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of pancreatic β-like cells can be administered to a subject the following locations: clinic, clinical office, emergency department, hospital ward, intensive care unit, operating room, catheterization suites, and radiologic suites.

In other embodiments, a population of pancreatic β-like cells is stored for later implantation/infusion. A population of pancreatic β-like cells may be divided into more than one aliquot or unit such that part of a population of pancreatic β-like cells is retained for later application while part is applied immediately to the subject. Moderate to long-term storage of all or part of the cells in a cell bank is also within the scope of this invention, as disclosed in U.S. Patent Application Serial No. 20030054331 and Patent Application No. WO03024215, and is incorporated by reference in their entireties. At the end of processing, the concentrated cells may be loaded into a delivery device, such as a syringe, for placement into the recipient by any means known to one of ordinary skill in the art.

In some embodiments, a population of pancreatic β-like cells can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of pancreatic β-like cells may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of pancreatic β-like cells could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid' adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 2002/0182211, which is incorporated herein by reference. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

Pharmaceutical compositions comprising effective amounts of a population of pancreatic β-like cells are also contemplated by the present invention. These compositions comprise an effective number of pancreatic β-like cells, optionally, in combination with a pharmaceutically acceptable carrier, additive or excipient. In certain aspects of the present invention, a population of pancreatic β-like cells are administered to the subject in need of a transplant in sterile saline. In other aspects of the present invention, a population of pancreatic β-like cells are administered in Hanks Balanced Salt Solution (HBSS) or Isolyte S, pH 7.4. Other approaches may also be used, including the use of serum free cellular media. In one embodiment, a population of pancreatic β-like cells are administered in plasma or fetal bovine serum, and DMSO. Systemic administration of a population of pancreatic β-like cells to the subject may be preferred in certain indications, whereas direct administration at the site of or in proximity to the diseased and/or damaged tissue may be preferred in other indications.

In some embodiments, a population of pancreatic β-like cells can optionally be packaged in a suitable container with written instructions for a desired purpose, such as the reconstitution or thawing (if frozen) of a population of pancreatic β-like cells prior to administration to a subject.

In one embodiment, an isolated population of the β-like cells as disclosed herein are administered with a differentiation agent. In one embodiment, the β-like cells are combined with the differentiation agent to administration into the subject. In another embodiment, the cells are administered separately to the subject from the differentiation agent. Optionally, if the cells are administered separately from the differentiation agent, there is a temporal separation in the administration of the cells and the differentiation agent. The temporal separation may range from about less than a minute in time, to about hours or days in time. The determination of the optimal timing and order of administration is readily and routinely determined by one of ordinary skill in the art.

The methods described herein can be used, for example, to directly reprogram a first cell (e.g., a differentiated cell, an adult cell or a somatic cell) of a first cell type (e.g. pancreatic exocrine cell) into a cell of a second cell type (e.g., pancreatic β-like cell) without reversion to a pluripotent stem cell state. The reprogrammed cells can be used for regenerative medicine (e.g., tissue repair and regeneration) and to study differentiation and disease mechanisms/pathology.

Accordingly, in one aspect, the disclosure features a method of reprogramming a cell, the method comprising: providing a first cell of a first cell type (i.e. a cell of endoderm origin) wherein the first cell is a differentiated cell; and treating the first cell with one or more components to thereby reprogram the first cell into a cell of a second cell type (e.g. a β-like cell).

In one embodiment, the second cell type is a differentiated cell, an adult cell or a somatic cell.

In one embodiment, the second cell type is a human cell or a mouse cell.

In one embodiment, the second cell type is not an iPS cell.

In one embodiment, the second cell type is reprogrammed directly from the first cell type.

In one embodiment, the reprogramming does not produce an iPS cell.

In one embodiment, the reprogramming is performed in a subject (e.g., an animal such as a human or mouse).

In one embodiment, the subject is a human.

In one embodiment, the reprogramming is performed ex-vivo.

In one embodiment, the subject is suffering from a metabolic disorder (e.g., diabetes (e.g., Type I diabetes or Type II diabetes)).

In one embodiment, the subject is being treated for a metabolic disorder (e.g., pre-diabetes, Type I diabetes or Type II diabetes).

In one embodiment, the first cell type is different from the second cell type.

In one embodiment, both the first cell type and the second cell type are derived from the endoderm.

In one embodiment, the expression of a hormone (e.g., glucagon, somatostatin, pancreatic polypeptide) is down-regulated by a statistically significant amount in the second cell type relative to the first cell type.

In one embodiment, the expression of a marker (e.g., Glut2, GCK, PC1/3, NeuroD, Nkx2.2, Nkx6.1 or C-peptide) is up-regulated by a statistically significant amount in the second cell type relative to the first cell type.

In one embodiment, the expression of a marker (e.g., amylase, ptf1a, Ck19, Nestin, Vimentin, Tuji) is down-regulated by a statistically significant amount in the second cell type relative to the first cell type.

In one embodiment, both the first cell type and the second cell type are pancreatic cells.

In one embodiment, the first cell type is a pancreatic exocrine cell.

In one embodiment, the second cell has one or more properties of a pancreatic β-cell (e.g., size, shape or secretion of insulin).

In one embodiment, the second cell type (e.g. pancreatic β-like cell) is a cell type that secretes insulin.

In one embodiment, the expression of a hormone (e.g., insulin) is up-regulated by a statistically significant amount in the second cell type relative to the first cell-type.

In one embodiment, the level of glucose tolerance in the subject is increased by a statistically significant amount after the first cell type (e.g. cell of endoderm origin) is reprogrammed to the second cell type (e.g. a pancreatic β-like cell).

In one embodiment, the insulin level in the serum of the subject is increased by a statistically significant amount after the first cell type (e.g. cell of endoderm origin) is reprogrammed to the second cell type (e.g. a pancreatic β-like cell).

In one embodiment, the cells of the second cell type (e.g. pancreatic β-like cell) in a subject remain present in a statistically significant amount up to 10, 20, 30, 40, 50, 60, 70, 80, 90 or greater days.

In one embodiment, the component is a transcription factor.

In one embodiment, the transcription factor is an embryonic transcription factor.

In one embodiment, the transcription factor is selected from the group consisting of Pdx1, Ngn3, NeuroD, Nkx2.2, Nkx6.1, Pax4, Pax6, Isl1 and MafA.

In one embodiment, the transcription factor is selected from the group consisting of Ngn3, Pdx1 and MafA.

In one embodiment, the first cell of the first cell type (e.g. cell of endoderm origin) is reprogrammed to the cell of the second cell type (e.g. pancreatic β-like cell) by treating the first cell with at least one transcription factor selected from the group consisting of Ngn3, Pdx1 and MafA.

In one embodiment, the first cell of the first cell (e.g. cell of endoderm origin) type is reprogrammed to the cell of the second cell type (e.g. pancreatic β-like cell) by treating the first cell with at least two transcription factors selected from the group consisting of Ngn3, Pdx1 and MafA.

In one embodiment, the first cell of the first cell type (e.g. cell of endoderm origin) is reprogrammed to the cell of the second cell type (e.g. pancreatic β-like cell) by treating the first cell with at least three transcription factors (e.g., Ngn3, Pdx1 and MafA).

In one embodiment, the transcription factor is delivered into the first cell in a viral vector.

In one embodiment, the viral vector is an adenoviral vector.

In one embodiment, a plurality of the first cells of the first cell type are reprogrammed to a plurality of the cells of the second cell type.

In one embodiment, the method further comprises isolating a population of the cells of the second cell type (e.g., wherein at least 5%, 10%, 15%, 20%, 25%, 30%, 35%, 50%, 75% or greater are of the subject cell type).

In one embodiment, at least 20%, 30%, 40%, 50%, 60%, 70%, 80%, 90% or greater of the cells of the first cell type that have been treated with one or more components are reprogrammed to the cells of the second cell type.

In one embodiment, (e.g., where the method is performed ex-vivo) the method further comprises implanting the cells of the second cell type into a subject (e.g., a subject suffering from a metabolic disorder (e.g., pre-diabetes, Type I diabetes or Type II diabetes)).

In one embodiment, the cells of the first and second time are from the subject into whom the cells are implanted. In one embodiment, the cells of the second cell type are from a donor different than the subject (e.g., a relative of the subject).

In one embodiment, the cells of the second cell type (e.g. pancreatic β-like cell) are surgically implanted.

In one embodiment, the first differentiated human cell of a first cell type (e.g. cell of endoderm origin) is reprogrammed to a differentiated human cell of a second cell type (e.g. a pancreatic β-like cell) in vivo. In one embodiment, the first differentiated human cell of a first cell type (e.g. cell of endoderm origin) is reprogrammed to a differentiated human cell of a second cell type (e.g. a pancreatic β-like cell) ex vivo.

In one embodiment, the first differentiated mouse cell of a first cell type is reprogrammed to a differentiated mouse cell of a second cell type in vivo. In one embodiment, the first differentiated human cell of a first cell type is reprogrammed to a differentiated human cell of a second cell type ex vivo.

In another aspect, this invention features a method of evaluating a transcription factor (TF) for the ability to reprogram a differentiated cell of a first type (e.g. cell of endoderm origin) into a differentiated cell of a second type (e.g. pancreatic β-like cell). The method includes: selecting a TF having the following properties, it is expressed in one or both of the second cell type or a precursor of the second cell type, when mutated it results in a non-wildtype phenotype in the second cell type (or in a tissue which includes the second cell type); contacting the TF with a cell of the first type; and evaluating whether the cell has become a cell of the second type, thereby evaluating a TF for the ability to reprogram differentiated cell of a first type into a differentiated cell of a second type.

In one embodiment, the reprogramming of a cell of endoderm origin does not produce an iPS cell.

In one embodiment, the second cell type (e.g. pancreatic β-like cell) is reprogrammed directly from the first cell type (e.g. cell of endoderm origin).

In one embodiment, the first cell type is different from the second cell type.

In one embodiment, both the first cell type and the second cell type come from the endoderm.

In one embodiment, the second cell type is a differentiated cell, an adult cell or a somatic cell.

In one embodiment, the second cell type is a human cell or a mouse cell.

In one embodiment, both the first cell type and the second cell type are pancreatic cells.

In one embodiment, the first cell type is a pancreatic exocrine cell.

In one embodiment, the second cell has one or more properties of a β-cell (e.g., size, shape or secretion of insulin).

In one embodiment, the second cell type is a cell type that secretes insulin.

In one embodiment, the expression of a hormone (e.g., insulin) is up-regulated by a statistically significant amount in the second cell type relative to the first cell-type.

In one embodiment, the expression of a hormone (e.g., glucagon, somatostatin, pancreatic polypeptide) is down-regulated by a statistically significant amount in the second cell type relative to the first cell type.

In one embodiment, the expression of a marker (e.g., Glut2, GCK, PC1/3, NeuroD, Nkx2.2, Nkx6.1 or C-peptide) is up-regulated by a statistically significant amount in the second cell type relative to the first cell type.

In one embodiment, the expression of a marker (e.g., amylase, ptf1a, Ck19, Nestin, Vimentin, Tuji) is down-regulated by a statistically significant amount in the second cell type relative to the first cell type.

In one embodiment, the transcription factor is an embryonic transcription factor.

In one embodiment, the transcription factor is delivered into the first cell in a viral vector.

In one embodiment, the viral vector is an adenoviral vector.

In one embodiment, a plurality of the first cells of the first cell type are reprogrammed to a plurality of the cells of the second cell type.

In one embodiment, at least 20%, 30%, 40%, 50%, 60%, 70%, 80%, 90% or greater of the cells of the first cell type (e.g. cell of endoderm origin) that have been treated with one or more components (i.e. β-cell reprogramming agents or factors) are reprogrammed to the cells of the second cell type (e.g. a pancreatic β-cell".

In another aspect, the invention features a kit comprising: a first differentiated cell of a first cell type; reagents for treating the first cell with one or more components to thereby reprogram the first cell into a cell of a second cell type; and instructions for reprogramming a cell.

In one embodiment, the second cell type is a differentiated cell.

In one embodiment, the second cell type is a differentiated cell, an adult cell or a somatic cell.

In one embodiment, the second cell type is a human cell or a mouse cell.

In one embodiment, the second cell type is not an iPS cell.

In one embodiment, the second cell type is reprogrammed directly from the first cell type.

In one embodiment, the reprogramming does not produce iPS cells.

In one embodiment, the reprogramming is performed in a subject.

In one embodiment, the subject is a human.

In one embodiment, the subject is suffering from a metabolic disorder (e.g., diabetes (e.g., Type I diabetes or Type II diabetes)).

In one embodiment, the subject is being treated for a metabolic disorder (e.g., pre-diabetes, Type I diabetes or Type II diabetes).

In one embodiment, the first cell type is different from the second cell type.

In one embodiment, both the first cell type and the second cell type are derived from the endoderm.

In one embodiment, the expression of a hormone (e.g., glucagon, somatostatin, pancreatic polypeptide) is down-regulated by a statistically significant amount in the second cell type relative to the first cell type.

In one embodiment, the expression of a marker (e.g., Glut2, GCK, PC1/3, NeuroD, Nkx2.2, Nkx6.1 or C-peptide) is up-regulated by a statistically significant amount in the second cell type relative to the first cell type.

In one embodiment, the expression of a marker (e.g., amylase, ptf1a, Ck19, Nestin, Vimentin, Tuji) is down-regulated by a statistically significant amount in the second cell type relative to the first cell type.

In one embodiment, both the first cell type and the second cell type are pancreatic cells.

In one embodiment, the first cell type is a pancreatic exocrine cell.

In one embodiment, the second cell has one or more properties of a β-cell (e.g., size, shape or secretion of insulin)

In one embodiment, the second cell type is a cell type that secretes insulin.

In one embodiment, the expression of a hormone (e.g., insulin) is up-regulated by a statistically significant amount in the second cell type relative to the first cell-type.

In one embodiment, the level of glucose tolerance in the subject is increased by a statistically significant amount after the first cell type is reprogrammed to the second cell type.

In one embodiment, the insulin level in the serum of the subject is increased by a statistically significant amount after the first cell type is reprogrammed to the second cell type.

In one embodiment, the cells of the second cell type in a subject remain present in a statistically significant amount up to 10, 20, 30, 40, 50, 60, 70, 80, 90 or greater days.

In one embodiment, the component is a transcription factor.

In one embodiment, the transcription factor is an embryonic transcription factor.

In one embodiment, the transcription factor is selected from the group consisting of Pdx1, Ngn3, NeuroD, Nkx2.2, Nkx6.1, Pax4, Pax6, Isl1 and MafA.

In one embodiment, the transcription factor is selected from the group consisting of Ngn3, Pdx1 and MafA.

In one embodiment, the first cell of the first cell type is reprogrammed to the cell of the second cell type by treating the first cell with at least one transcription factor selected from the group consisting of Ngn3, Pdx1 and MafA.

In one embodiment, the first cell of the first cell type is reprogrammed to the cell of the second cell type by treating the first cell with at least two transcription factors selected from the group consisting of Ngn3, Pdx1 and MafA.

In one embodiment, the first cell of the first cell type is reprogrammed to the cell of the second cell type by treating the first cell with at least three transcription factors (e.g., Ngn3, Pdx1 and MafA).

In one embodiment, the transcription factor is delivered into the first cell in a viral vector.

In one embodiment, the viral vector is an adenoviral vector.

In one embodiment, a plurality of the first cells of the first cell type are reprogrammed to a plurality of the cells of the second cell type.

In one embodiment, the method further comprises isolating a population of the cells of the second cell type (e.g., wherein at least 5%, 10%, 15%, 20%, 25%, 30%, 35%, 50%, 75% or greater are of the subject cell type).

In one embodiment, at least 20%, 30%, 40%, 50%, 60%, 70%, 80%, 90% or greater of the cells of the first cell type that have been treated with one or more components are reprogrammed to the cells of the second cell type.

In one embodiment, the method further comprises implanting the cells of the second cell type into a subject (e.g., a subject suffering from a metabolic disorder (e.g., pre-diabetes, Type I diabetes or Type II diabetes)).

In one embodiment, the cells of the second cell type are from a donor different than the subject (e.g., a relative of the subject).

In one embodiment, the cells of the second cell type are surgically implanted.

In one embodiment, the first differentiated human cell of a first cell type is reprogrammed to a differentiated human cell of a second cell type in vivo.

In one embodiment, the first differentiated mouse cell of a first cell type is reprogrammed to a differentiated mouse cell of a second cell type in vivo.

In another aspect, the invention features a method of culturing a first differentiated cell of a first cell type in culture medium, wherein the medium contains one or more components to thereby reprogram the first cell to a cell of a second cell type.

In one embodiment, the second cell type is a differentiated cell, an adult cell or a somatic cell.

In one embodiment, the second cell type is a human cell or a mouse cell.

In one embodiment, the second cell type is not an iPS cell.

In one embodiment, the second cell type is reprogrammed directly from the first cell type.

In one embodiment, the reprogramming does not produce iPS cells.

In one embodiment, the first cell type is different from the second cell type.

In one embodiment, both the first cell type and the second cell type are derived from the endoderm.

In one embodiment, the expression of a hormone (e.g., glucagon, somatostatin, pancreatic polypeptide) is down-regulated by a statistically significant amount in the second cell type relative to the first cell type.

In one embodiment, the expression of a marker (e.g., Glut2, GCK, PC1/3, NeuroD, Nkx2.2, Nkx6.1 or C-peptide) is up-regulated by a statistically significant amount in the second cell type relative to the first cell type.

In one embodiment, the expression of a marker (e.g., amylase, ptf1a, Ck19, Nestin, Vimentin, Tuji) is down-regulated by a statistically significant amount in the second cell type relative to the first cell type.

In one embodiment, both the first cell type and the second cell type are pancreatic cells.

In one embodiment, the first cell type is a pancreatic exocrine cell.

In one embodiment, the second cell has one or more properties of a β-cell (e.g., size, shape or secretion of insulin)

In one embodiment, the second cell type is a cell type that secretes insulin.

In one embodiment, the expression of a hormone (e.g., insulin) is up-regulated by a statistically significant amount in the second cell type relative to the first cell-type.

In one embodiment, the component is a transcription factor.

In one embodiment, the transcription factor is an embryonic transcription factor.

In one embodiment, the transcription factor is selected from the group consisting of Pdx1, Ngn3, NeuroD, Nkx2.2, Nkx6.1, Pax4, Pax6, Isl1 and MafA.

In one embodiment, the transcription factor is selected from the group consisting of Ngn3, Pdx1 and MafA.

In one embodiment, the first cell of the first cell type is reprogrammed to the cell of the second cell type by treating the first cell with at least one transcription factor selected from the group consisting of Ngn3, Pdx1 and MafA.

In one embodiment, the first cell of the first cell type is reprogrammed to the cell of the second cell type by treating the first cell with at least two transcription factors selected from the group consisting of Ngn3, Pdx1 and MafA.

In one embodiment, the first cell of the first cell type is reprogrammed to the cell of the second cell type by treating the first cell with at least three transcription factors (e.g., Ngn3, Pdx1 and MafA).

In one embodiment, the transcription factor is delivered into the first cell in a viral vector.

In one embodiment, the viral vector is an adenoviral vector.

In one embodiment, a plurality of the first cells of the first cell type are reprogrammed to a plurality of the cells of the second cell type.

In one embodiment, the method further comprises isolating a population of the cells of the second cell type (e.g., wherein at least 5%, 10%, 15%, 20%, 25%, 30%, 35%, 50%, 75% or greater are of the subject cell type).

In one embodiment, at least 20%, 30%, 40%, 50%, 60%, 70%, 80%, 90% or greater of the cells of the first cell type that have been treated with one or more components are reprogrammed to the cells of the second cell type.

An isolated cell population, isolated from a method described herein.

A non-human subject comprising a cell derived from a method described herein.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The present invention may be as defined in any one of the following numbered paragraphs.

1. A method for reprogramming a cell of endoderm origin, the method comprising increasing the protein expression of at least two transcription factors selected from Pdx1, Ngn3, or MafA in the cell of enodermal origin, wherein the cell of enodermal origin is reprogrammed to exhibit at least two characteristics of a pancreatic β-cell.
2. The method of claim 1, wherein the protein expression of Pdx1, Ngn3, and MafA are increased in the cell of enodermal origin.
3. The method of claim 1 or 2, wherein the cell of endoderm origin is a pancreatic cell. (includes amylase-producing pancreatic cells)
4. The method of any of claims 1 to 3, wherein the pancreatic cell is a exocrine cell.
5. The method of any of paragraphs 1 to 3, wherein the pancreatic cell is a pancreatic duct cell.
6. The method of any of paragraphs 1 to 3, wherein the pancreatic cell is an acinar pancreatic cell.
7. The method of any of paragraphs 1 to 3, wherein the cell of endoderm origin is a liver cell.
8. The method of any of paragraphs 1 to 3, wherein the cell of endoderm origin is a gall bladder cell.
9. The method of any of paragraphs 1 to 3, wherein a characteristic of a pancreatic β-cell phenotype is secreting insulin in response to glucose.
10. The method of any of paragraphs 1 to 9, wherein a characteristic of a pancreatic β-cell phenotype is expression of at least one marker selected from the group consisting of: Ngn3−, Pdx1+ and MafA+.
11. The method of any of paragraphs 1 to 9, wherein the protein expression of a transcription factor selected from Pdx1, Ngn3, or MafA is increased by contacting the cell of endoderm origin with an agent which increases the expression of the transcription factor.
12. The method of paragraph 11, wherein the agent is selected from the group consisting of: a nucleotide sequence, a protein, an aptamer and small molecule, ribosome, RNAi agent and peptide-nucleic acid (PNA) and anologues or variants thereof.
13. The method of any of paragraphs 1 to 12, wherein protein expression is increased by introducing at least one nucleic acid sequence encoding a transcription factor protein selected from Pdx1, Ngn3, or MafA, or encoding a functional fragment thereof, in the cell of endoderm origin.
14. The method of paragraph 13, wherein the protein expression of Pdx1 is increased by introducing a nucleic acid sequence encoding a Pdx1 polypeptide comprising SEQ ID NO: 2 or 32 or a functional fragment of SEQ ID NO: 2 or 32 into the cell of endoderm origin.
15. The method of paragraphs 13 or 14, wherein the protein expression of Ngn3 is increased by introducing a nucleic acid sequence encoding a Ngn3 polypeptide comprising SEQ ID NO: 2 or 32 or a functional fragment of SEQ ID NO: 2 or 32 into the cell of endoderm origin.
16. The method of any of paragraphs 13 to 15, wherein the protein expression of MafA is increased by introducing a nucleic acid sequence encoding a MafA polypeptide comprising SEQ ID NO: 3 or 33 or a functional fragment of SEQ ID NO: 3 or 33 into the cell of endoderm origin.
17. The method of any of paragraphs 13 to 16, wherein the nucleic acid sequence is in a vector.
18. The method of paragraph 17, wherein the vector is a viral vector or a non-viral vector.
19. The method of paragraph 18, wherein the vector is a viral vector comprising a genome that does not integrate into the host cell genome.
20. The method of any of paragraphs 1 to 19, wherein the cell of endoderm origin is in vitro.
21. The method of any of paragraphs 1 to 19, wherein the cell of endoderm origin is ex vivo.
22. The method of any of paragraphs 1 to 19, wherein the cell of endoderm origin is in vivo or present in a subject.
23. The method of paragraph 22, wherein the subject is a human subject.
24. The method of paragraphs 22 and 23, wherein the subject has, or is at risk of developing, diabetes.
25. The method of paragraph 24, wherein the diabetes is selected from the group consisting of: Type I diabetes, Type II diabetes and pre-diabetes.
26. The method of paragraphs 22 and 23, wherein the subject has or is at risk of developing a metabolic disorder.
27. The method of any of paragraphs 1 to 26, wherein the cell of endoderm origin is a mammalian cell.
28. The method of paragraph 27, wherein the mammalian cell is a human cell.
29. The method of any of paragraphs 1 to 28, wherein the method further comprises contacting the cell of endoderm origin with at least one agent which increases the protein expression of at least one of the transcription factors selected from the group consisting of: NeuroD, Nkx2.2, Nkx6.1, Pax4, Pax6 or Isl1.

30. The method of any of paragraphs 1 to 29, wherein the pancreatic β-cell expresses a marker selected from the group consisting of: he markers method further comprises contacting the cell of endoderm origin with at least one agent which increases the protein expression of at least one of the transcription factors selected from the group consisting of: NeuroD, Nkx2.2, Nkx6.1, Pax4, Pax6 or Isl1.
31. The method of any of paragraphs 1 to 30, wherein the pancreatic β-cell is a pancreatic β-like cell.
32. The method of paragraph 31, wherein the pancreatic β-like cell has an increased expression of a marker selected from the group consisting of: c-peptide, glucose transporter 2 (Glut2), glucokinase (GCK), prohormone convertase 1/3 (PC1/3), β-cell transcription factors NeuroD, Nkx2.2 and Nkx6.1 by a statistically significant amount relative to the cell of endoderm origin from which the pancreatic β-like cell was derived.
33. The method of paragraph 31, wherein the pancreatic β-like cell has a decreased expression of a marker selected from the group consisting of: Amylase (Amy), glucagon, somatostatin/pancreatic polypeptide (SomPP), Ck19, Nestin, Vimentin and Tuji by a statistically significant amount relative to the cell of endoderm origin from which the pancreatic β-like cell was derived.
34. An isolated population of pancreatic β-like cells obtained from a population of non-insulin producing cells of endoderm origin by a process comprising increasing the protein expression of at least two transcription factors selected from Ngn3, Pdx1 or MafA, or a functional fragment thereof, in the non-insulin producing cells of endoderm origin.
35. The isolated population of pancreatic β-like cells of paragraph 34, wherein the expression is transient expression.
36. The isolated population of pancreatic β-like cells of paragraphs 34 or 35, wherein the pancreatic β-like cells secrete insulin in response to an increase in glucose.
37. The isolated population of pancreatic β-like cells of paragraphs 34 and 36, wherein the pancreatic β-like cell have a distinct morphology and localization as compared to endogenous pancreatic β-cells.
38. The isolated population of pancreatic β-like cells of paragraph 37, wherein the pancreatic β-like cells have at least one characteristic selected from the group consisting of: cobblestone cell morphology, a diameter of between 17-25 μm and an intercalated location within exocrine acincar rosettes.
39. The isolated population of pancreatic β-like cells of paragraph 34, wherein the increase in the protein expression of at least two transcription factors is accomplished using a vector.
40. The isolated population of pancreatic β-like cells of paragraph 39, wherein the vector is a viral vector or a non-viral vector.
41. The isolated population of pancreatic β-like cells of paragraphs 39 or 40, wherein the vector comprises a nucleic acid sequence encoding a Ngn3 polypeptide or a functional fragment thereof.
42. The isolated population of pancreatic β-like cells of paragraphs 39 or 40, wherein the vector comprises a nucleic acid sequence encoding a Pdx1 polypeptide or a functional fragment thereof.
43. The isolated population of pancreatic β-like cells of paragraphs 39 or 40, wherein the vector comprises a nucleic acid sequence encoding a MafA polypeptide or a functional fragment thereof.
44. The isolated population of pancreatic β-like cells of paragraphs 39, wherein the population of non-insulin producing cells of endoderm origin is a population of pancreatic cells.
45. The isolated population of pancreatic β-like cells of paragraphs 44, wherein the pancreatic cells are selected from the group consisting of: exocrine cells, pancreatic duct cells and an acinar pancreatic cells or a heterogeneous population thereof.
46. The isolated population of pancreatic β-like cells of any of paragraphs 34 to 45, wherein the population of non-insulin producing cells of endoderm origin is a population of liver cells.
47. The isolated population of pancreatic β-like cells of any of paragraphs 34 to 46, wherein the population of non-insulin producing cells of endoderm origin is a population of gall bladder cells.
48. The isolated population of pancreatic β-like cells of any of paragraphs 34 to 45, wherein the population of non-insulin producing cells of endoderm origin is a population of mammalian cells.
49. The isolated population of pancreatic β-like cells of paragraphs 48, wherein the mammalian cells are human cells.
50. The isolated population of pancreatic β-like cells of any of paragraphs 34 to 49, wherein the population of non-insulin producing cells of endoderm origin is obtained from a subject that has diabetes, or has an increased risk of developing diabetes.
51. The isolated population of pancreatic β-like cells of paragraph 50, wherein the diabetes is selected from the group consisting of: Type I diabetes, Type II diabetes and pre-diabetes.
52. The isolated population of pancreatic β-like cells of any of paragraphs 34 to 49, wherein the population of non-insulin producing cells of endoderm origin is obtained from a subject that has a metabolic disorder, or has an increased risk of developing a metabolic disorder.
53. A method for the treatment of a subject with diabetes, the method comprising administering a composition comprising an isolated population of pancreatic β-like cells according to paragraphs 34 to 52.
54. The method of paragraph 53, wherein the pancreatic β-like cells are produced from non-insulin producing endoderm cells obtained from the same subject as the composition is administered to.
55. The method of paragraph 53, wherein the subject has, or has an increased risk of developing, diabetes.
56. The method of any of paragraphs 53 to 55, wherein the diabetes is selected from the group consisting of: Type I diabetes, Type II diabetes and pre-diabetes.
57. The method of any of paragraphs 53 to 55, wherein the subject has, or has an increased risk of developing, a metabolic disorder.
58. Use of the isolated population of pancreatic β-like cells according to paragraphs 27 to 45 for administering to a subject in need thereof.
59. The use of paragraph 58, wherein the subject has, or has an increased risk of developing, diabetes.
60. The use of paragraph 59, wherein the diabetes is selected from the group consisting of: Type I diabetes, Type II diabetes and pre-diabetes.
61. The use of paragraph 58, wherein the subject has, or has an increased risk of developing, a metabolic disorder.
62. The use of any of paragraphs 58 to 61, wherein the pancreatic β-like cells are produced from non-insulin producing endoderm cell obtained from the same subject as the pancreatic β-like cells are administered to.

63. A kit comprising:
  a. a nucleic acid sequence encoding a Ngn3 polypeptide or a functional fragment thereof; and/or
  b. a nucleic acid sequence encoding a Pdx1 polypeptide or a functional fragment thereof; and/or
  c. a nucleic acid sequence encoding a MafA polypeptide or a functional fragment thereof
64. The kit of paragraph 63, further comprising instructions for reprogramming a cell of endoderm origin to a cell with at least two characteristics of a pancreatic β-cell using the methods according to paragraphs 1 to 33.
65. A composition comprising at least one non-insulin producing endodermal cell and at least one agent which increases the protein expression of at least two transcription factors selected from Ngn3, Pdx1 or MafA.
66. A method for identifying an agent for reprogramming a cell of endoderm origin to a pancreatic β-like cell, comprising contacting the cell of endoderm origin with one or more test agents, determining the level of one or more β-cell reprogramming genes, and identifying the one or more test agents as an agent for reprogramming a cell of endoderm origin to a pancreatic β-like cell if the expression level of the β-cell reprogramming gene is higher in the cell of endoderm origin following the contacting step than the cell of endoderm origin in the absence of the contacting step.
67. The method of paragraph 66, wherein the one or more reprogramming genes comprise one or more of Pdx1, Ngn3, MafA, NeuroD, Nkx2.2, Nkx6.1, Pax4, Pax6 or Isl1.
68. The method of paragraphs 66 or 67, wherein the one or more reprogramming genes comprise at least two of one or more of Pdx1, Ngn3 and MafA.
69. The method of any of paragraph 66 to 68, wherein the one or more reprogramming genes comprise Pdx1, Ngn3 and MafA.

The following Examples are provided to illustrate the present invention, and should not be construed as limiting thereof.

EXAMPLES

The examples presented herein relate to the methods and compositions for producing reprogrammed pancreatic β-cells, for example from cells of endoderm origin such as pancreatic exocrine cells and other endodermal cells, such as liver cells, by increasing the expression of at least two transcription factors selected from Ngn3, Pdx1 or MafA, for example by using nucleic acid sequences to encoding the transcription factors Ngn3, Pdx1 or MafA or functional fragments thereof. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods

Adenovirus Construction and Purification.

Genes of interest were first cloned into a shuttle vector containing an IRES-nGFP, then into the pAd/CMV/V5-DEST adenoviral vector (invitrogen). High titer virus (>1×$10^{10}$ pfu/ml) was obtained by purification with the AdEasy Kit (Stratagene).

Animals, Surgery, Physiological Studies.

$Rag1^{-/-}$ and $Rag1^{-/-}$; NOD animals were obtained from Jackson Labs. Adult animals (>2 month) were injected with 100 ul (>1×$10^9$ pfu) of purified adenovirus directly into the splenic lobe of the dorsal pancreas. Blood glucose was measured with Ascensia Elite Blood Glucose Meter. Insulin levels were determined with an Ultrasensitive Insulin ELISA kit (Alpco).

Immunohistochemistry, BrdU Labeling, TUNEL Analysis.

This was performed as previously described[37]. 1 mg/ml BrdU was provided in drinking water for BrdU labeling following surgery. Apoptotic cells were recognized by TUNEL labeling with a TMR red Cell Death kit (Roche).

Electron Microscopy.

Dissected pancreas was fixed in 4% paraformaldehyde and 0.1% glutaraldehyde for 2 hours at room temperature. For conventional transmission electron microscopy, samples were further fixed by osmium tetroxide, embedded in Epon resin and sectioned at 60-80 nm. For immuno-gold labeling, ultrathin sections were cut at −120° C. and stained with gold conjugated antibodies. Images were obtained with a Tecnai™ $G^2$ Spirit BioTWIN transmission electron microscope.

Viral Injection, Tissue Harvest.

For adult pancreas, ~100 ul of purified virus was injected directly into 2-3 foci of the dorsal splenic lobe with a 3/10 cc Insulin Syringe (Becton Dickinson). For skeletal muscle, ~20 ul virus was injected into the upper thigh. At the time of tissue harvest, the infected portion of the tissue was visualized by GFP fluorescence and dissected out. For adult pancreas, typically ~50% of the dorsal pancreas was taken.

Immunohistochemistry.

Adult mouse pancreata were fixed by immersion in 4% paraformaldehyde for 2 hours at 4 C. Samples were subsequently incubated in 30% sucrose solution overnight and embedded with OCT compound.

The following primary antibodies were used: rat anti-E-cadherin (Zymed), rat anti-PECAM1 (Pharmingen), goat anti-Ngn3 (Santa Cruz), guinea pig anti-Insulin (Dako), guinea pig anti-Glucagon (Linco), guinea pig anti-Pancreatic polypeptide (Linco), rabbit anti-somatostatin (Dako), rabbit anti-pancreatic polypeptide (Dako), goat anti-Somatostatin (Santa Cruz), goat anti-Pdx1 (Santa Cruz), guinea pig anti-Pdx1 (gift of Dr. Chris Wright), goat anti-βgalactosidase (Biogenesis), goat anti-Amylase (Santa Cruz), mouse anti-BrdU (Amersham), rabbit anti-mafA (Bethyl), chick anti-Nestin (Ames), chick anti-Vimentin (Chemicon), goat anti-Glut2 (Santa Cruz), Goat anti-VEGF (R&D), rabbit anti-PC1/3 (Chemicon), goat anti-glucokinase (Santa Cruz), rabbit anti-Ck19 (Melton lab stock), rabbit anti-chromogranin A/B (RDI), rabbit anti-Ptf1a (gift of Dr. Helena Edlund), goat anti-NeuroD (Santa Cruz), rabbit anti-Nkx6.1 (BCBC), rabbit anti-Sox9 (Santa Cruz), goat anti-Nkx2.2 (Santa Cruz), and rabbit anti-c-peptide (Linco).

Rodamin-Red-X, FITC, Cy5 and Alexa dye conjugated donkey secondary antibodies were obtained from the Jackson Immunoresearch laboratories and the Molecular Probes Inc. Tyramide amplification system (PerkinElmer) was used for PC1/3 and glucokinase staining. Immunofluorescence pictures were taken with a Zeiss LSM 510 META confocal microscope.

Cpa1CreER$^{T2}$ Labeling of Mature Exocrine Cells.

Cpa1CreER$^{T2}$;R26R double heterozygous animals were generated by mating homozygous Cpa1CreER$^{T2}$ males with R26R homozygous females (Jackson lab). Two month old Cpa1CreER$^{T2}$;R26R adults were injected with Tamoxifen at 6 mg per animal every third day for 4 times to label mature exocrine cells.

Physiological Studies.

Diabetic animals were produced with Intraperineal injection of streptozotocin (120 ug/g body weight) after overnight fasting with 2 month old adult animals of the Rag1 strain (Jackson lab). Hyperglycemic animals that display >250 mg/dl fasting blood glucose levels for at least 2 consecutive days were used for experiments.

Fasting blood glucose was measured on tail vein blood with an Ascensia Elite Glucometer (Bayer, Elkhart, Ind.) after 6-8 hr fasting. Non-fasting insulin level was determined from tail vein blood collected around 9 to 10 AM with an Ultrasensitive Insulin ELISA kit (Alpco, Windham, N.H.).

Average β-cell number per section was determined by sectioning through the entire pancreas at 15 um and collecting every third sections. Twenty randomly selected sections were immunostained for Insulin and DAPI to visualize individual β-cells. Total number of β-cells were counted and averaged from 3 animals.

Glucose tolerance test was performed by fasting animals over night (12 hr), followed by intraperineal injection of glucose (3 g/kg body weight).

Electron Microscopy.

Small pieces of pancreatic samples (1-2 mm) were fixed with 4% paraformaldehyde and 0.1% glutaraldehyde for 2 hours at room temperature. For conventional electron microscopy, samples were further refixed with a mixture of 1% Osmiumtetroxide (OsO4)+1.5% Potassiumferrocyanide (KFeCN6) for 2 hours, washed in water and stained in 1% aqueous uranyl acetate for 1 hour followed by dehydration in grades of alcohol (50%, 70%, 95%, 2×100%) and propyleneoxide (1 hr), then infiltrated in propyleneoxide:Epon 1:1 ON and embedded in TAAB Epon. (Marivac Canada Inc. St. Laurent, Canada). Ultrathin sections (about 60-80 nm) were cut on a Reichert Ultracut-S microtome, picked up on to coppergrids, stained with 0.2% lead citrate and examined in a "Tecnai G$^2$ Spirit BioTWIN" Transmission electron microscope. Images were taken with a 2 k AMT CCD camera.

For immuno-electron microscopy, fixed samples were infiltrated with 2.3M sucrose in PBS for 30 minutes then frozen in liquid nitrogen. Frozen samples were sectioned at −120° C., the sections transferred to formvar-carbon coated copper grids and floated on PBS until the immunogold labeling is carried out. The gold labeling was carried out at room temperature on a piece of parafilm. All antibodies and protein A gold were diluted 1% BSA. The diluted antibody solution was centrifuged 1 minute at 14 000 rpm prior to labeling to avoid possible aggregates. Grids were floated on drops of 1% BSA for 10 minutes to block for unspecific labeling, transferred to 5 μl drops of primary antibody and incubated for 30 minutes. The grids were then washed in 4 drops of PBS for a total of 15 minutes, transferred to 5 μl drops of Protein-A gold (G. Posthuma, University of Utrecht, the Netherlands) for 20 minutes, washed in 4 drops of PBS for 15 minutes and 6 drops of double distilled water.

For double labeling, after the first Protein A gold incubation, grids were washed in 4 drops of PBS for a total of 15 minutes then transferred to a drop of 0.2% Glutaraldehyde in PBS for 5 minutes, washed in 4 drops of PBS/0.15M glycine (to quench free aldehyde groups) then the send primary antibody is applied, followed by PBS wash and different size Protein-A gold as above. Antibodies used were rabbit anti-GFP (invitrogen) and guinea pig anti-Insulin (Dako).

Contrasting/embedding of the labeled grids was carried out on ice in 0.3% uranyl acetete (Electron Microcopy Sciences) in 2% methyl cellulose (SIGMA) for 10 minutes. Grids were picked up with metal loops (diameter slightly larger than the grid) and the excess liquid was removed by streaking on a filterpaper (Whatman #1), leaving a thin coat of methyl cellulose (bluish interference color when dry).

The grids were examined in a Tecnai G$^2$ Spirit BioTWIN transmission electron microscope and images were recorded with an AMT 2 k CCD camera.

FACS Analysis, Islet Isolation, Gene Profiling.

For FACS sorting of GFP+ cells, Pancreata infected by the M3 inducing factors for one month were perfused through the common bile duct, digested with liberase and Elastase (Roche), and further dissociated into single cells with EDTA incubation. GFP+ cells were isolated by fluorescent activated cell sorting (FACS) with FACSaria (BD Bioscience). Staining of sorted cells indicate that ~70% are GFP$^+$ and ~22% of total sorted cell are insulin$^+$.

Islets were isolated by Liberase digestion of pancreas of Pdx1-GFP animals. Islets picked manually under a fluorescent dissecting scope. Pancreatic cells devoid of GFP+ islets were collected as non-islet sample. RNA was extracted with TRIZOL™ reagent (Invitrogen). Biotin labeled cRNA probes synthesized with the ILLUMINA TOTAL PREP RNA AMPLIFICATION KIT® (Ambion). Gene profiling performed with Sentrix BeadChip Array MouseRef-8 v1.1 (illumina) that contains probes for ~19,000 genes. Data analyzed with the BeadStudio software. For identifying differentially enriched genes, the following parameters suggested by illumina were used: P value<0.05, Diff score>30, Average signal>100.

RT-PCR.

Pancreatic tissues were harvested and immediately frozen in liquid nitrogen (LN2). Total RNA was extracted with the RNeasy kit (Qiagen). First strand cDNA was synthesizes with Superscript III kit (invitrogen). 30 cycles of semi-quantitative RT-PCR was performed with standard protocol. The following primer pairs were used:

```
Ngn3 viral transgene: ~350 bp;
Ngn3.F:
CAG ACG CTG CGC ATA GCG GAC CAC;   (SEQ ID NO: 40)

IRES2.R:
GCG GCT TCG GCC AGT AAC GTT AG     (SEQ ID NO: 41)

Pdx1 viral transgene: ~1.2 kb;
Pdx1.F:
GGA GCA AGA TTG TGC GGT GAC CTC;   (SEQ ID NO: 42)

IRES2.R:
GCG GCT TCG GCC AGT AAC GTT AG     (SEQ ID NO: 41)

MafA viral transgene: ~300 bp;
MafA.F:
ACA TTC TGG AGA GCG AGA AGT GCC;   (SEQ ID NO: 43)

IRES2.R:
GCG GCT TCG GCC AGT AAC GTT AG     (SEQ ID NO: 41)

GADPH: ~400 bp;
F:
ACC ACA GTC CAT GCC ATC AC;        (SEQ ID NO: 44)

R:
TCC ACC ACC CTG TTG CTG TA         (SEQ ID NO: 45)
```

Example 1

Induction of $Insulin^+$ Cells in Adult Mice.

Adenovirus that co-expresses each transcription factor (TF) together with nuclear GFP (nGFP) was purified. All nine viruses were pooled and injected as a mixture (referred to herein as "M9", for mixture of 9 different transcription factors) into the pancreata of 2 month old adult mice (FIG. 1*a*). The immune-deficient $Rag1^{-/-}$ strain was used to avoid complications associated with viral elicited immune response[24]. One month after viral delivery, immunohistochemistry revealed a modest increase of extra-islet $insulin^+$ cells among viral infected cells ($nGFP^+$) in 2 out of 3 animals (FIG. 1D). To determine which of the nine factors are required, individual factors were removed from the pool one at a time. Pools lacking Nkx2.2, Nkx6.1, or Pax4 continued to produce increased extra-islet insulin cells (data not shown), suggesting that these genes are dispensable. Results for the other six genes were inconclusive. The inventors conducted another round of factor withdrawal with mixtures of the remaining six genes (M6) and three of them, Ngn3, Pdx1, and MafA, proved to be absolutely required (FIG. 1D). The combination of these three factors (referred to as M3) converts >20% of infected cells to insulin cells (red cells with green nuclei, FIG. 1C, 1E). Notably, single factors or combinations of any two factors do not elicit this effect (FIG. 1E). NeuroD (also known as Neurod1) can functionally replace Ngn3 in M3, but the resulting cocktail has reduced induction efficiency (FIG. 1E).

The inventors performed antibody labeling to confirm that these three inducing factors are co-expressed in the induced insulin cells (data not shown). In particular, the inventors performed co-expression analysis of the reprogramming effect of M3 factors in different cell types. To differentiate viral transgenes from endogenous genes, a Flag tagged Pdx1 (at C-terminus) and a Myc tagged MafA (at N-terminus) were used together with untagged Ngn3 to infect pancreas, mouse embryonic fibroblasts (at a MOI: 50), or skeletal muscle. Expression of M3 induced insulin expression in pancreas in vivo, but not in embryonic mouse fibroblasts in vitro or skeletal muscle in vivo (data not shown). Samples were analyzed after 10 days, and quantification showed that 97.5%, >99%, and 97.7% of $Insulin^+$ cells co-express Ngn3, Pdx1.flag, and myc.MafA, respectively, in the pancreas sample, demonstrating that the majority of pancreatic β-like cells induced are $insulin^+$ cells which also co-express all three factors (data not shown). Immunohistological analysis of cultured fibroblasts demonstrated >98% of $nGFP^+$ cells co-express all three factors (data not shown), whereas in skeletal muscle, 92%, 86.6% and 89% of $nGFP^+$ cells express Ngn3, Pdx1-flag and myc.MafA, respectively, demonstrating that most of them co-express M3 factors (data not shown). >500 $insulin^+$ or $nGFP^+$ cells were counted per condition in the analysis.

The inventors identified that the percentage of insulin cells among infected cells increases with progressive removal of factors from the pool such that M3 induces more $insulin^+$ cells than M6, whereas M6 is better than M9 (FIG. 1D, 1E). This is likely due to the fact that a constant volume of virus was injected into each animal, regardless of the viral combinations. The effective concentration of Ngn3, Pdx1 and MafA viruses in a cocktail, therefore, increases when fewer factors are included. New $insulin^+$ cells are detected 3 days after injection, but the expression level is low.

The intensity of insulin staining increases gradually so that by day 10, the level is comparable to that of endogenous β-cells (data not shown). In particular, the inventors demonstrated by immunostaining a progressive increase of insulin expression levels during M3 induction, where immunostaining was performed on samples harvested at different time points after M3 induction. 2 μm confocal images were taken with identical settings at non-saturating levels, and insulin staining analysed. Insulin staining was first detected at 3 days post induction (data not shown), and increases at day 7 and appears to reach that of islet β-cell level at day 10 (data not shown). No further increases were seen at day 30 (data not shown).

These new insulin cells are still present after 3 months, the longest time point the inventors analyzed, and remain as scattered individual cells or small clusters and do not form islets (FIG. 1C). The reprogramming effect of the three factors appears to be rather specific for pancreatic exocrine cells: infection of skeletal muscle in vivo or fibroblasts in vitro with M3 did not induce insulin expression, despite extensive co-expression of the three factors in the target cells (data not shown).

Example 2

The New $Insulin^+$ Cells Originate from Differentiated Exocrine Cells.

Lineage analysis was performed to determine the origin of the new $insulin^+$ cells. The five major cell types in the adult pancreas can be detected with lineage-specific molecular markers: exocrine (Amylase), duct (Ck19), endocrine (insulin, glucagon, somatostatin, pancreatic polypeptide), vascular (PECAM), and mesenchymal cells (Nestin, Vimentin). Upon injection with a control nGFP virus, the vast majority of infected cells (>95%) were found to be mature $amylase^+$ exocrine cells (FIG. 2A), consistent with prior reports[23]. Non-exocrine cells together account for approximately 5% of infected population. Since more than 20% of M3 infected cells become $insulin^+$ 10 days after viral delivery, this suggests that non-exocrine cells can contribute, at most, to a minor fraction of these new $insulin^+$ cells. As there is little cell death and no enhanced proliferation during this reprogramming (data not shown), the majority of insulin cells would thus appear to originate from mature exocrine cells.

The inventors analyzed proliferation and apoptosis of pancreatic β-like cells by immunostaining (data not shown). In particular, continuous BrdU labeling was performed for 10 days immediately after pAd-M3 viral injection and the BrdU cells identified. 3.2% of pancreatic β-like cells and 12.9% of islet β-cells in the same animals incorporated BrdU over this period (n=3 animals. >1,000 $insulin^+$ cells/animal, data not shown). The inventors also performed TUNEL labeling for analysis of apoptosis. TUNEL labeling revealed a general lack of apoptosis among pancreatic cells during reprogramming (data not shown) or among reprogrammed new β-cells (data not shown). The inventors discovered that 2 days after infection, insulin expression is not yet detectable (data not shown). Apoptotic cells at this stage do not correlate with viral infection ($nGFP^+$).

Figure 2:
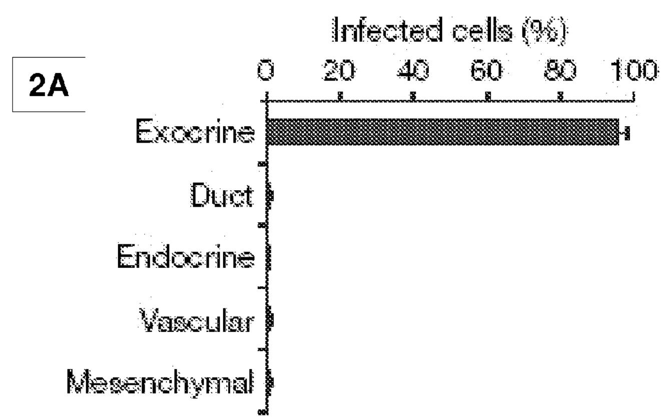
FIGS. 2A-2B show induced new β-cells originate from differentiated exocrine cells.

To confirm the exocrine origin of the new $insulin^+$ cells, the inventors genetically labeled mature exocrine cells with a mouse line ($Cpa1CreER^{T2}$) that expresses an inducible form of Cre recombinase ($CreER^{T2}$) specifically in adult exocrine cells[19] (FIG. 2B). When crossed with the R26R reporter line, tamoxifen induction in double heterozygous $Cpa1CreER^{T2}$;R26R adults indelibly labels 5-10% of mature exocrine cells with β-galactosidase (βgal) (data not shown); no label is found in other cell types. In particular, 10 days after nGFP viral infection, the most of the β-gal positive cells are are $Amylase^+$ (Amy) mature exocrine cells, not duct cells (Ck19$^+$) (data not shown). Following pAd-M3 injection, many βgal$^+$ cells become insulin$^+$ (data not shown), demonstrating direct evidence that mature exocrine cells give rise to new insulin$^+$ cells. The inventors demonstrated 10 days after infection, many βgal$^+$ insulin$^+$ cells are present, as detected by triple immunostaining with insulin/GFP/βgal (data not shown).

Example 3

Pancreatic β-Like Cells Closely Resemble Endogenous Pancreatic Islet β-Cells.

The inventors next examined the new insulin cells to determine the extent to which they have been reprogrammed. Morphologically, exocrine cells are large with a cobble stone appearance (data not shown) whereas islet β-cells are much smaller and spindle shaped (data not shown). In particular, a comparison of immunostaining with Insulin/E-cadherin and nGFP of islet β-cells and pancreatic β-like cells show they are similar in size and shape but distinctly different from exocrine cells (data not shown). E-cadherin staining was used to visualize cell boundaries.

When dissociated into single cells, the diameter of Amylase$^+$ exocrine cells range from 25-17 um whereas insulin$^+$ β-cells range from 9-15 um. The induced cells are indistinguishable from islet β-cells in size and shape (FIG. 3A).

At the ultrastructural level, the reprogrammed cells have all the hallmarks of islet β-cells (FIGS. 3B and 3C). They possess the small dense secretory granules characteristic of insulin granules, and lack the large zymogen granules and dense assemblies of endoplasmic reticulum (ER) that are characteristic of exocrine cells (FIGS. 3B and 3C). Immunoelectron microscopy further showed that the pancreatic β-like cells express both GFP in the nucleus and abundant insulin in the granules (FIGS. 5A-5F). Interestingly, the induced β-cells often appear on the electron micrograph as intercalated within exocrine acinar rosettes (FIG. 3D). In wild type pancreatic samples, rare single or small clusters of β-cells reside outside islets, but they often associate with duct but not exocrine cells. The unique position of induced cells likely reflects their exocrine origin.

Molecular marker analysis reveals that most of the insulin$^+$ cells coexpress genes essential for β-cell endocrine function including glucose transporter 2 (Glut2, also known as Slc2a2, expressed in 92.8% of the new insulin$^+$ cells), glucokinase (GCK, 96.7%), prohormone convertase (PC1/3, 86.7%) (data not shown), and key β-cell transcription factors NeuroD (88.9%), Nkx2.2 (85.3%), and Nkx6.1 (85.9%) (data not shown). The induced insulin cells express C-peptide (data not shown). In particular, the inventors discovered by immunostaining one month after infection with pAd-M3, that most Insulin$^+$ pancreatic β-like cells coexpress molecular markers specific for endocrine genes: glucose transporter 2 (Glut2), glucokinase (GCK), prohormone convertase 1/3 (PC1/3), and β-cell transcription factors NeuroD, Nkx2.2, and Nkx6.1 (data not shown). Some reprogrammed cells express marker genes but not insulin. The pancreatic β-like cells do not express Amylase, glucagon, or somatostatin/pancreatic polypeptide (SomPP), but do express c-peptide (c-peptide) (data not shown).

Expression profile analysis of the reprogrammed cells further indicates a strong overlap of endocrine-enriched genes between reprogrammed cells and islet cells, demonstrating a high degree of similarity between their endocrine programs (FIGS. 6A and 6B).

The new β-cells do not express exocrine genes such as Amylase or Ptf1a, the duct marker Ck19 (also known as Krt19), mesenchymal markers Nestin and Vimentin, nor the neuronal marker Tuji (data not shown). Nor do the new β-cells express any other pancreatic hormones such as glucagon, somatostatin or pancreatic polypeptide (data not shown). Thus, the new β-cells do not exhibit a hybrid or mixed phenotype, indicating silencing of non-β-cell programs.

The primary function of β-cells is to synthesize and release insulin. To facilitate the release of insulin into the circulation, β-cells, unique among pancreatic cell types, synthesize vascular endothelial growth factor (VEGF) which promotes local angiogenic remodeling[25]. Notably, pancreatic β-like cells similarly synthesize VEGF and induce angiogenesis so that blood vessels form next to these new cells (data not shown). In particular, immunostaining analysis demonstrated new pancreatic β-like cells synthesize vascular endothelial growth factor (VEGF), and induce local angiogenic remodeling. Note the close proximity of blood vessels (PECAM+) with the pancreatic β-like cells versus control infected cells (data not shown). Quantification indicates that in nGFP controls, 32% of infected cells lie adjacent to blood vessels whereas 61% and 83% of pancreatic β-like cells are directly juxtaposed to blood vessels 10 days and 30 days after induction, respectively.

Figure 4:
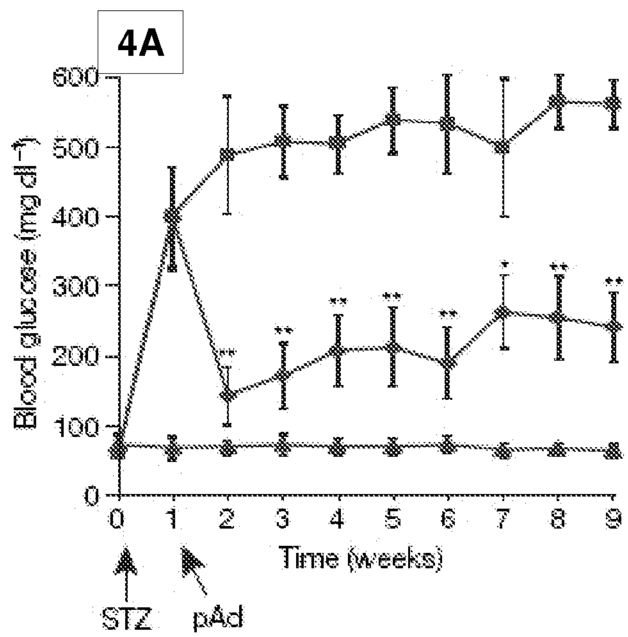
FIGS. 4A-4C show induced new pancreatic β-like cells remodel vasculature and ameliorate hyperglycemia.
Figure 4:
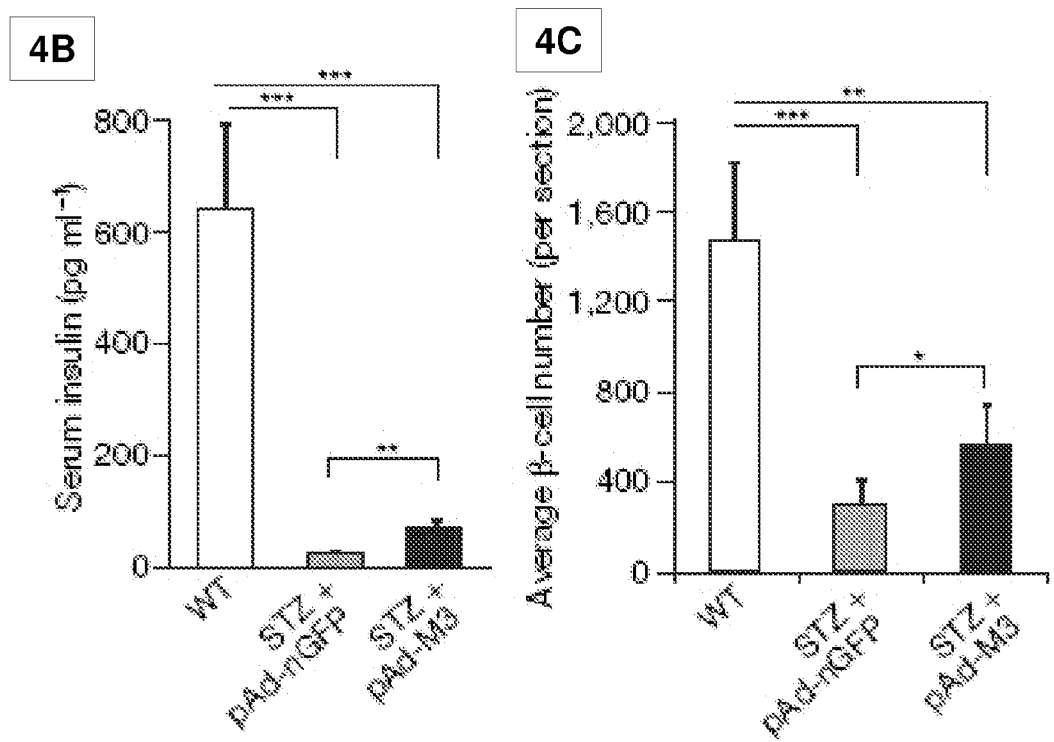
Figure 5:
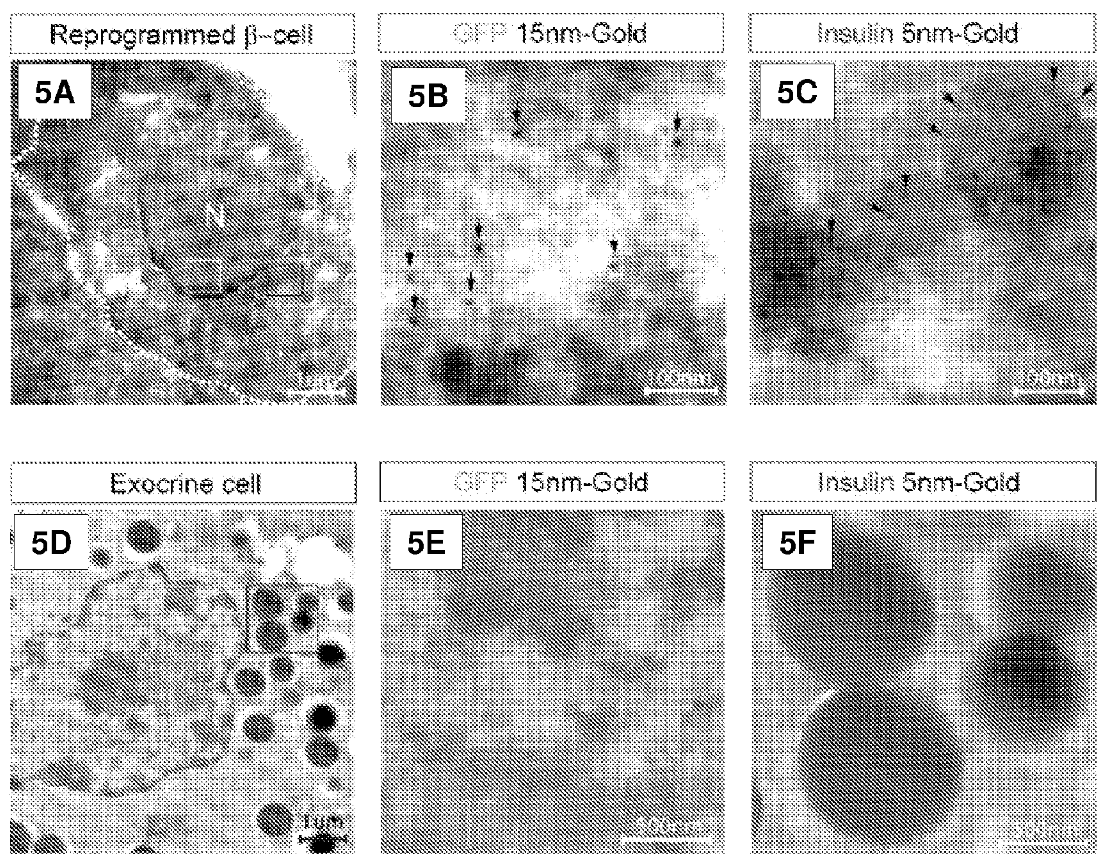
FIGS. 5A-5F show immuno-electron microscopy of pancreatic β-like cells.
Figure 7:
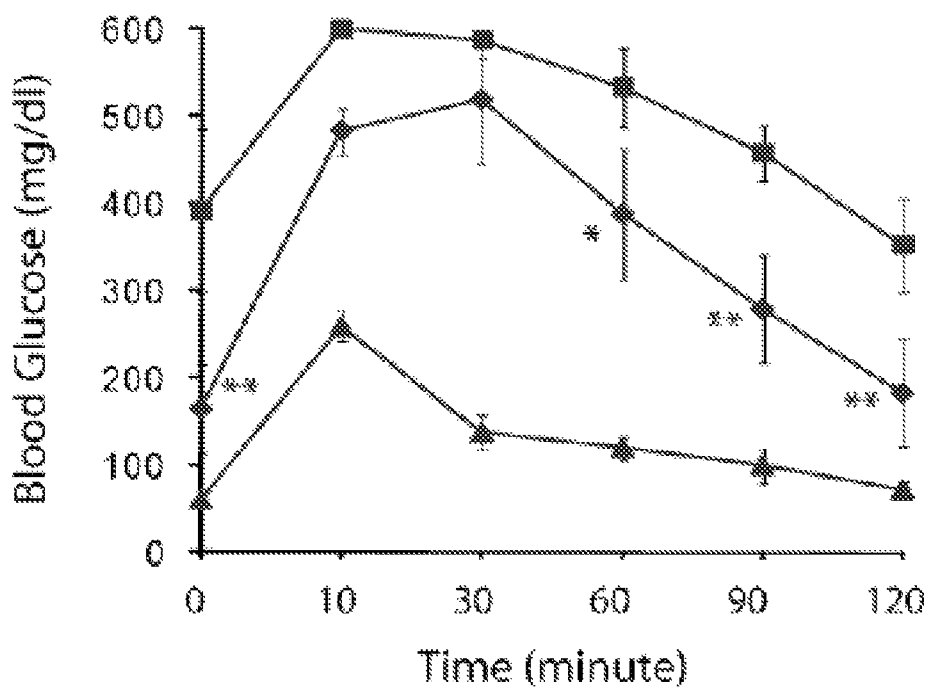
FIG. 7 is a graph showing results of a glucose tolerance test. Improved glucose tolerance in diabetic mice after injection with pAd-M3 (diamond), compared with controls with nGFP virus (square). Triangle: non-diabetic controls. Diabetic mice were generated by streptozotocin administration. n=6-8 animals. One asterisk, p<0.05; two asterisks, p<0.01. Data presented as mean±s.d.
Figure 8:
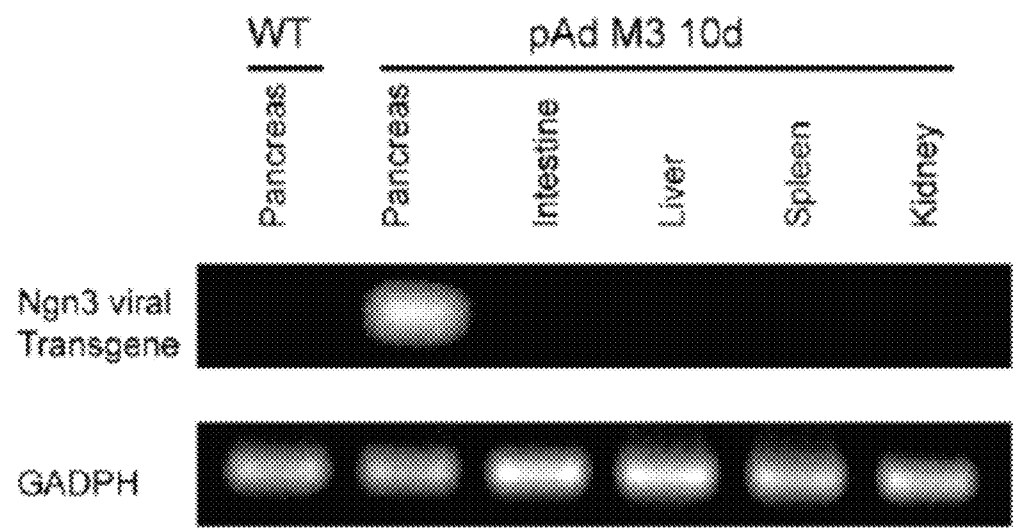
FIG. 8 shows lack of spread of virus from pancreas to other organs and lack of spontaneous conversion of other cell types to β-cells in streptozotocin treated animals.
Figure 9:
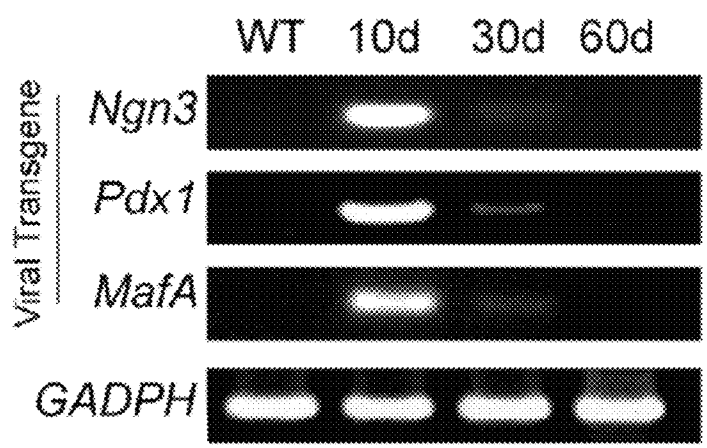
FIG. 9 shows down regulation of viral genes from pancreatic β-like cells.

To test whether pancreatic β-like cells release insulin, mice were rendered diabetic by streptozotocin (STZ) injection which specifically ablates islet β-cells. When subsequently injected with pAd-M3, fasting blood glucose levels of hyperglycemic animals show a significant and long lasting improvement compared to animals injected with control (nGFP) virus (FIG. 4A). In addition, the pAd-M3 animals show increased glucose tolerance (FIG. 7), have increased insulin levels in the serum (non-fasting, P<0.01, FIG. 4B), and possess large numbers of pancreatic β-like cells (FIG. 5C). RT-PCR analysis and direct observation revealed that virus injected into the pancreas does not spread to other internal organs such as liver and intestine that, theoretically, could modulate insulin secretion and/or response (FIG. 8). In addition, the inventors found no evidence that STZ treated animals show spontaneous conversion of exocrine cells to β-cells (FIG. 9). As the data in FIG. 4 shows, the total number of pancreatic β-like cells is rather small compared to the number of β-cells in normal animals and this may account for the limitation to the effectiveness in restoring glucose homeostasis. Alternatively, as the new β-cells are not reorganized into islet structures, this may limit their effectiveness. All together, these data show that pancreatic β-like cells can produce and secrete insulin in vivo.

Transient expression of inducing factors results in a long-lasting β-cell phenotype. The inventors' results thus far support the contention that a combination of three transcription factors fully reprograms exocrine cells to β-cells in vivo. To determine whether continued presence of these factors is required to maintain the phenotype of reprogrammed cells, the inventors used RT-PCR and primers specific to viral transgenes to detect their presence. Transgene expression from all three viruses was substantially diminished after one month and was undetectable after 2 months (FIG. 9). Ngn3 protein was undetectable by antibody staining one month after infection (data not shown). In particular, immunostaining for Ngn3 at different time points after pAd-M3 infection demonstrated a strong Ngn3 expression at day 10, which largely disappears by day 30 (data not shown). Time course immunostaining for Pdx1 and MafA was also performed (data not shown), where expression of both Pdx1 and MafA remains strong over the 60 day period examined. Pdx1 and MafA protein expression in the pancreatic β-like cells, however, remains consistently strong even after 2 months, indicating the activation of endogenous genes (data not shown). These results are consistent with the fact that endogenous islet β-cells do not express Ngn3, but do express Pdx1 and MafA[20,21]. Thus, a transient expression of the inducing factors is sufficient to convert exocrine cells to a stable new β-cell state.

Example 4

B-Cell Reprogramming does not Involve Dedifferentiation.

In principle, the conversion of exocrine cells to β-cells could be direct or involve dedifferentiation to common progenitors which then redifferentiate into β-cells. Indeed, exocrine and β-cells share a common progenitor during embryogenesis that is characterized by rapid division and expression of genes including Sox9 and Hnf6 (also known as Onecut1[19]). Continuous BrdU labeling over the first 10 days of reprogramming, however, shows that few pancreatic β-like cells (3.2%) have divided (data not shown). In comparison, 12.9% of endogenous islet β-cells in the same animals incorporated BrdU (supplemental FIG. 3). In addition, the inventors detected no induction of Sox9 or Hnf6 (data not shown). These results suggest that in vivo reprogramming of exocrine to β-cells is a direct conversion of cell types and does not involve dedifferentiation. The inventors can not formally exclude the possibility that a very transient or partial dedifferentiation may occur, but the inventors' results indicate that extensive replication and reversion to a dedifferentiated cell for an appreciable time does not occur.

The inventors' results provide evidence that fully differentiated exocrine cells can be reprogrammed into cells that closely resemble β-cells in adult animals by a combination of just three transcription factors.

Table 1.

Three classes of pancreatic transcription factors. The list of genes was compiled from reference 16 and other publications. Note that the endocrine progenitor genes and adult beta cell genes overlap extensively, but have little overlap with pancreatic progenitor genes. Nine genes that exhibit β-cells phenotypes when mutated were selected for further analysis (shown in bold italic).

| Gene Name | Mouse GeneBank | SEQ ID NO: |
|---|---|---|
| | Pancreatic Progenitor | |
| Pdx1 | NM_008814 | SEQ ID NO: 1 |
| Ptf1a | NM_018809 | SEQ ID NO: 10 |
| Sox9 | NM_011448 | SEQ ID NO: 11 |
| Hnf6 | NM_008262 | SEQ ID NO: 12 |
| Hnf1b | NM_009330 | SEQ ID NO: 13 |
| Hnf3b | NM_010446 | SEQ ID NO: 14 |
| Hnf4a | NM_008261 | SEQ ID NO: 15 |
| Hex | NM_008245 | SEQ ID NO: 16 |
| Prox1 | NM_008937 | SEQ ID NO: 17 |
| Hb9 | NM_019944 | SEQ ID NO: 18 |
| Nr5a2 | NM_030676 | SEQ ID NO: 19 |
| | Endocrine Progenitor | |
| Ngn3 | NM_009719 | SEQ ID NO: 2 |
| MafA | NM_194350 | SEQ ID NO: 3 |
| NeuroD | NM_010894 | SEQ ID NO: 4 |
| Nkx2.2 | NM_010919 | SEQ ID NO: 5 |
| Nkx6.1 | NM_144955 | SEQ ID NO: 6 |
| Pax4 | NM_011038 | SEQ ID NO: 7 |
| Pax6 | NM_013627 | SEQ ID NO: 8 |
| Isl1 | NM_021459 | SEQ ID NO: 9 |
| MafB | NM_010658 | SEQ ID NO: 20 |
| Brn4 | NM_008901 | SEQ ID NO: 21 |
| Arx | NM_007492 | SEQ ID NO: 22 |
| Myt1 | NM_008665 | SEQ ID NO: 23 |
| Wbscr14 | NM_021455 | SEQ ID NO: 24 |
| VDR | NM_009504 | SEQ ID NO: 25 |
| IA1 | | SEQ ID NO: 26 |
| | Adult Beta cell | |
| Pdx1 | NM_008814 | SEQ ID NO: 1 |
| NeuroD | NM_010894 | SEQ ID NO: 4 |
| MafA | NM_194350 | SEQ ID NO: 3 |
| Nkx2.2 | NM_010919 | SEQ ID NO: 5 |
| Nkx6.1 | NM_144955 | SEQ ID NO: 6 |
| Pax6 | NM_013627 | SEQ ID NO: 8 |
| Isl1 | NM_021459 | SEQ ID NO: 9 |
| Foxo1 | NM_019739 | SEQ ID NO: 27 |
| Hnf1a | NM_009327 | SEQ ID NO: 28 |
| Hnf3a | NM_008259 | SEQ ID NO: 29 |
| Hnf4a | NM_008261 | SEQ ID NO: 30 |

The practice of the present invention will employ, unless otherwise indicated, conventional techniques of mouse genetics, developmental biology, cell biology, cell culture, molecular biology, transgenic biology, microbiology, recombinant DNA, and immunology, which are within the skill of the art. Such techniques are described in the literature. See, for example, Current Protocols in Cell Biology, ed. by Bonifacino, Dasso, Lippincott-Schwartz, Harford, and Yamada, John Wiley and Sons, Inc., New York, 1999; Manipulating the Mouse Embryos, A Laboratory Manual, 3rd Ed., by Hogan et al., Cold Spring Contain Laboratory Press, Cold Spring Contain, New York, 2003; Gene Targeting: A Practical Approach, IRL Press at Oxford University Press, Oxford, 1993; and Gene Targeting Protocols, Human Press, Totowa, N.J., 2000. All patents, patent applications and references cited herein are incorporated in their entirety by reference.

The present invention is well adapted to carry out the objects and obtain the ends and advantages mentioned, as well as those inherent therein. The methods, systems and kits are representative of certain embodiments, are exemplary, and are not intended as limitations on the scope of the invention. Modifications therein and other uses are also contemplated herein. These modifications are encompassed within the spirit of the invention and are defined by the scope of the claims. Varying substitutions and modifications may be made to the invention disclosed herein without departing from the scope and spirit of the invention.

The articles "a" and an as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, e.g., in Markush group or similar format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth herein. It should also be understood that any embodiment of the invention can be explicitly excluded from the claims, regardless of whether the specific exclusion is recited in the specification. For example, any cell of endoderm origin, any agent, any somatic cell type, any β-cell reprogramming agent, etc., may be excluded.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" is intended to encompass numbers that fall within a range of ±10% of a number, in some embodiments within ±5% of a number, in some embodiments within ±1%, in some embodiments within ±0.5% of a number, in some embodiments within ±0.1% of a number unless otherwise stated or otherwise evident from the context (except where such number would impermissibly exceed 100% of a possible value).

Certain claims are presented in dependent form for the sake of convenience, but Applicant reserves the right to rewrite any dependent claim in independent form to include the limitations of the independent claim and any other claim(s) on which such claim depends, and such rewritten claim is to be considered equivalent in all respects to the dependent claim in whatever form it is in (either amended or unamended) prior to being rewritten in independent format. It should also be understood that, unless clearly indicated to the contrary, in any methods claimed herein that include more than one act, the order of the acts of the method is not necessarily limited to the order in which the acts of the method are recited, but the invention includes embodiments in which the order is so limited.

REFERENCES

All references cited herein are incorporated herein by reference in their entirety as if each individual publication or patent or patent application was specifically and individually indicated to be incorporated by reference in its entirety.

Many modifications and variations of this invention can be made without departing from its spirit and scope, as will be apparent to those skilled in the art. The specific embodiments described herein are offered by way of example only, and the invention is to be limited only in terms of the appended claims, along with the full scope of equivalents to which such claims are entitled.

1. Weissman, I. L. Stem cells: units of development, units of regeneration, and units in evolution. *Cell* 100, 157-68 (2000).

2. Slack, J. M. Metaplasia and transdifferentiation: from pure biology to the clinic. *Nat Rev Mol Cell Biol* 8, 369-78 (2007).

3. Brockes, J. P. & Kumar, A. Plasticity and reprogramming of differentiated cells in amphibian regeneration. *Nat Rev Mol Cell Biol* 3, 566-74 (2002).

4. Hadorn, E. Transdetermination in cells. *Sci Am* 219, 110-4 passim (1968).

5. Gurdon, J. B. From nuclear transfer to nuclear reprogramming: the reversal of cell differentiation. *Annu Rev Cell Dev Biol* 22, 1-22 (2006).

6. Hochedlinger, K. & Jaenisch, R. Nuclear reprogramming and pluripotency. *Nature* 441, 1061-7 (2006).

7. Takahashi, K. & Yamanaka, S. Induction of pluripotent stem cells from mouse embryonic and adult fibroblast cultures by defined factors. *Cell* 126, 663-76 (2006).

8. Takahashi, K. et al. Induction of pluripotent stem cells from adult human fibroblasts by defined factors. *Cell* 131, 861-72 (2007).

9. Yu, J. et al. Induced Pluripotent Stem Cell Lines Derived from Human Somatic Cells. *Science* (2007).

10. Meissner, A., Wernig, M. & Jaenisch, R. Direct reprogramming of genetically unmodified fibroblasts into pluripotent stem cells. *Nat Biotechnol* 25, 1177-81 (2007).

11. Wernig, M. et al. In vitro reprogramming of fibroblasts into a pluripotent ES-cell-like state. *Nature* 448, 318-24 (2007).

12. Park, I. H. et al. Reprogramming of human somatic cells to pluripotency with defined factors. *Nature* 451, 141-6 (2008).

13. Choi, J. et al. MyoD converts primary dermal fibroblasts, chondroblasts, smooth muscle, and retinal pigmented epithelial cells into striated mononucleated myoblasts and multinucleated myotubes. *Proc Natl Acad Sci USA* 87, 7988-92 (1990).

14. Xie, H., Ye, M., Feng, R. & Graf, T. Stepwise reprogramming of B cells into macrophages. *Cell* 117, 663-76 (2004).

15. Cobaleda, C., Jochum, W. & Busslinger, M. Conversion of mature B cells into T cells by dedifferentiation to uncommitted progenitors. *Nature* 449, 473-7 (2007).

16. Shen, C. N., Slack, J. M. & Tosh, D. Molecular basis of transdifferentiation of pancreas to liver. *Nat Cell Biol* 2, 879-87 (2000).

17. Whitehead, G. G., Makino, S., Lien, C. L. & Keating, M. T. fgf20 is essential for initiating zebrafish fin regeneration. *Science* 310, 1957-60 (2005).

18. Tanaka, E. M. Cell differentiation and cell fate during urodele tail and limb regeneration. *Curr Opin Genet Dev* 13, 497-501 (2003).

19. Zhou, Q. et al. A multipotent progenitor domain guides pancreatic organogenesis. *Dev Cell* 13, 103-14 (2007).

20. Murtaugh, L. C. & Melton, D. A. Genes, signals, and lineages in pancreas development. *Annu Rev Cell Dev Biol* 19, 71-89 (2003).

21. Jensen, J. Gene regulatory factors in pancreatic development. *Dev Dyn* 229, 176-200 (2004).

22. Gu, G., Dubauskaite, J. & Melton, D. A. Direct evidence for the pancreatic lineage: NGN3+ cells are islet progenitors and are distinct from duct progenitors. *Development* 129, 2447-57 (2002).

23. Wang, A. Y., Peng, P. D., Ehrhardt, A., Storm, T. A. & Kay, M. A. Comparison of adenoviral and adeno-associated viral vectors for pancreatic gene delivery in vivo. *Hum Gene Ther* 15, 405-13 (2004).

24. Wang, A. Y., Ehrhardt, A., Xu, H. & Kay, M. A. Adenovirus transduction is required for the correction of diabetes using Pdx-1 or Neurogenin-3 in the liver. *Mol Ther* 15, 255-63 (2007).

25. Lammert, E. et al. Role of VEGF-A in vascularization of pancreatic islets. *Curr Biol* 13, 1070-4 (2003).

26. Konstantinova, I. et al. EphA-Ephrin-A-mediated beta cell communication regulates insulin secretion from pancreatic islets. *Cell* 129, 359-70 (2007).

27. Ferber, S. et al. Pancreatic and duodenal homeobox gene 1 induces expression of insulin genes in liver and ameliorates streptozotocin-induced hyperglycemia. *Nat Med* 6, 568-72 (2000).

28. Kaneto, H. et al. PDX-1/VP16 fusion protein, together with NeuroD or Ngn3, markedly induces insulin gene transcription and ameliorates glucose tolerance. *Diabetes* 54, 1009-22 (2005).

29. Miyatsuka, T. et al. Ectopically expressed PDX-1 in liver initiates endocrine and exocrine pancreas differentiation but causes dysmorphogenesis. *Biochem Biophys Res Commun* 310, 1017-25 (2003).

30. Baeyens, L. et al. In vitro generation of insulin-producing beta cells from adult exocrine pancreatic cells. *Diabetologia* 48, 49-57 (2005).

31. Sapir, T. et al. Cell-replacement therapy for diabetes: Generating functional insulin-producing tissue from adult human liver cells. *Proc Natl Acad Sci USA* 102, 7964-9 (2005).

32. Heremans, Y. et al. Recapitulation of embryonic neuroendocrine differentiation in adult human pancreatic duct cells expressing neurogenin 3. *J Cell Biol* 159, 303-12 (2002).

33. Gasa, R. et al. Proendocrine genes coordinate the pancreatic islet differentiation program in vitro. *Proc Natl Acad Sci USA* 101, 13245-50 (2004).

34. Morton, R. A., Geras-Raaka, E., Wilson, L. M., Raaka, B. M. & Gershengorn, M. C. Endocrine precursor cells from mouse islets are not generated by epithelial-to-mesenchymal transition of mature beta cells. *Mol Cell Endocrinol* 270, 87-93 (2007).

35. Gershengorn, M. C. et al. Epithelial-to-mesenchymal transition generates proliferative human islet precursor cells. *Science* 306, 2261-4 (2004).

36. De Robertis, E. M. & Gurdon, J. B. Gene activation in somatic nuclei after injection into amphibian oocytes. *Proc Natl Acad Sci USA* 74, 2470-4 (1977).

37. Dor, Y., Brown, J., Martinez, O. I. & Melton, D. A. Adult pancreatic beta-cells are formed by self-duplication rather than stem-cell differentiation. *Nature* 429, 41-6 (2004).

SEQUENCE LISTING:

SEQ ID NO: 1-polypeptide sequence of mouse pdx1
(accession no NM_008814)
MNSEEQYYAATQLYKDPCAFQRGPVPEFSANPPACLYMGRQPPP

PPPPQFTSSLGSLEQGSPPDISPYEVPPLASDDPAGAHLHHHLPAQLGLAHPPPGPFP

NGTEPGGLEEPNRVQLPFPWMKSTKAHAWKGQWAGGAYTAEPEENKRTRTAYTRAQLL

ELEKEFLFNKYISRPRRVELAVMLNLTERHIKIWFQNRRMKWKKEEDKKRSSGTPSGG

GGGEEPEQDCAVTSGEELLAVPPLPPPGGAVPPGVPAAVREGLLPSGLSVSPQPSSIA

PLRPQEPR

SEQ ID NO: 2-polypeptide sequence of mouse Ngn3
(accession No NP_033849.3)
MAPHPLDALTIQVSPETQQPFPGASDHEVLSSNSTPPSPTLIPR

DCSEAEVGDCRGTSRKLRARRGGRNRPKSELALSKQRRSRRKKANDRERNRMHNLNSA

LDALRGVLPTFPDDAKLTKIETLRFAHNYIWALTQTLRIADHSFYGPEPPVPCGELGS

PGGGSNGDWGSIYSPVSQAGNLSPTASLEEFPGLQVPSSPSYLLPGALVFSDFL

SEQ ID NO: 3-polypeptide sequence of mouse MafA
MAAELAMGAELPSSPLAIEYVNDFDLMKFEVKKEPPEAERFCHR

LPPGSLSSTPLSTPCSSVPSSPSFCAPSPGTGGGAGGGGSAAQAGGAPGPPSGGPGTV

GGASGKAVLEDLYWMSGYQHHLNPEALNLTPEDAVEALIGSGHHGAHHGAHHPAAAAA

YEAFRGQSFAGGGGADDMGAGHHHGAHHTAHHHHSAHHHHHHHHHHGGSGHHGGGAGH

GGGGAGHHVRLEERFSDDQLVSMSVRELNRQLRGFSKEEVIRLKQKRRTLKNRGYAQS

-continued

SEQUENCE LISTING:

CRFKRVQQRHILESEKCQLQSQVEQLKLEVGRLAKERDLYKEKYEKLAGRGGPGGAGG

AGFPREPSPAQAGPGAAKGAPDFFL

SEQ ID NO: 31-amino acid sequence of HUMAN pdx1 (accession no NP_000200.1)
MNGEEQYYAATQLYKDPCAFQRGPAPEFSASPPACLYMGRQPPP

PPPHPFPGALGALEQGSPPDISPYEVPPLADDPAVAHLHHHLPAQLALPHPPAGPFPE

GAEPGVLEEPNRVQLPFPWMKSTKAHAWKGQWAGGAYAAEPEENKRTRTAYTRAQLLE

LEKEFLFNKYISRPRRVELAVMLNLTERHIKIWFQNRRMKWKKEEDKKRGGGTAVGGG

GVAEPEQDCAVTSGEELLALPPPPPPGGAVPPAAPVAAREGRLPPGLSASPQPSSVAP

RRPQEPR

SEQ ID NO: 32-amino acid sequence of HUMAN (*Homo sapiens*) neurogenin 3 (NEUROG3), Ngn3 (GeneBank No: NP_066279.2)
MTPQPSGAPTVQVTRETERSFPRASEDEVTCPTSAPPSPTRTRG

NCAEAEEGGCRGAPRKLRARRGGRSRPKSELALSKQRRSRRKKANDRERNRMHNLNSA

LDALRGVLPTFPDDAKLTKIETLRFAHNYIWALTQTLRIADHSLYALEPPAPHCGELG

SPGGSPGDWGSLYSPVSQAGSLSPAASLEERPGLLGATFSACLSPGSLAFSDFL

SEQ ID NO: 33-amino acid sequence of HUMAN MafA (accession no: NP_963883.2)
MAAELAMGAELPSSPLAIEYVNDFDLMKFEVKKEPPEAERFCHR

LPPGSLSSTPLSTPCSSVPSSPSFCAPSPGTGGGGGAGGGGGSSQAGGAPGPPSGGPG

AVGGTSGKPALEDLYWMSGYQHHLNPEALNLTPEDAVEALIGSGHHGAHHGAHHPAAA

AAYEAFRGPGFAGGGGADDMGAGHHHGAHHAAHHHHAAHHHHHHHHHHGGAGHGGGAG

HHVRLEERFSDDQLVSMSVRELNRQLRGFSKEEVIRLKQKRRTLKNRGYAQSCRFKRV

QQRHILESEKCQLQSQVEQLKLEVGRLAKERDLYKEKYEKLAGRGGPGSAGGAGFPRE

PSPPQAGPGGAKGTADFFL

SEQ ID NO: 34-mRNA sequence of HUMAN pdx1 (accession no NM_000209)

```
  1 gggtggcgcc gggagtggga acgccacaca gtgccaaatc cccggctcca gctcccgact

 61 cccggctccc ggctcccggc tcccggtgcc caatcccggg ccgcagccat gaacggcgag

121 gagcagtact acgcggccac gcagctttac aaggacccat gcgcgttcca gcgaggcccg

181 gcgccggagt tcagcgccag ccccccctgcg tgcctgtaca tgggccgcca gcccccgccg

241 ccgccgccgc acccgttccc tggcgccctg ggcgcgctgg agcagggcag cccccggac

301 atctccccgt acgaggtgcc cccctcgcc gacgaccccg cggtggcgca ccttcaccac

361 cacctcccgg ctcagctcgc gctcccccac ccgcccgccg ggcccttccc ggagggagcc

421 gagccgggcg tcctggagga gcccaaccgc gtccagctgc ctttcccatg gatgaagtct

481 accaaagctc acgcgtggaa aggccagtgg gcaggcggcg cctacgctgc ggagccggag

541 gagaacaagc ggacgcgcac ggcctacacg cgcgcacagc tgctagagct ggagaaggag

601 ttcctattca acaagtacat ctcacggccg cgccgggtgg agctggctgt catgttgaac

661 ttgaccgaga gacacatcaa gatctggttc caaaaccgcc gcatgaagtg gaaaaaggag

721 gaggacaaga agcgcggcgg cgggacagct gtcgggggtg gcggggtcgc ggagcctgag

781 caggactgcg ccgtgacctc cggcgaggag cttctggcgc tgccgccgcc gccgcccccc

841 ggaggtgctg tgccgcccgc tgccccgtt gccgcccgag agggccgcct gccgcctggc

901 cttagcgcgt cgccacagcc ctccagcgtc gcgcctcggc ggccgcagga accacgatga
```

-continued

SEQUENCE LISTING:

```
 961 gaggcaggag ctgctcctgg ctgaggggct tcaaccactc gccgaggagg agcagagggc
1021 ctaggaggac cccgggcgtg gaccacccgc cctggcagtt gaatggggcg gcaattgcgg
1081 ggcccacctt agaccgaagg ggaaaacccg ctctctcagg cgcatgtgcc agttggggcc
1141 ccgcgggtag atgccggcag gccttccgga agaaaaagag ccattggttt ttgtagtatt
1201 ggggccctct tttagtgata ctggattggc gttgtttgtg gctgttgcgc acatccctgc
1261 cctcctacag cactccacct tgggacctgt ttagagaagc cggctcttca aagacaatgg
1321 aaactgtacc atacacattg gaaggctccc taacacacac agcggggaag ctgggccgag
1381 taccttaatc tgccataaag ccattcttac tcgggcgacc cctttaagtt tagaaataat
1441 tgaaaggaaa tgtttgagtt ttcaaagatc ccgtgaaatt gatgccagtg gaatacagtg
1501 agtcctcctc ttcctcctcc tcctcttccc cctccccttc ctcctcctcc tcttcttttc
1561 cctcctcttc ctcttcctcc tgctctcctt tcctcccct cctcttttcc ctcctcttcc
1621 tcttcctcct gctctccttt cctccccctc ctctttctcc tcctcctcct cttcttcccc
1681 ctcctctccc tcctcctctt cttccccctc ctctccctcc tcctcttctt ctccctcctc
1741 ttcctcttcc tcctcttcca cgtgctctcc tttcctcccc ctcctcttgc tccccttctt
1801 ccccgtcctc ttcctcctcc tcctcttctt ctccctcctc ttcctcctcc tctttcttcc
1861 tgacctcttt ctttctcctc ctcctccttc tacctcccct tctcatccct cctcttcctc
1921 ttctctagct gcacacttca ctactgcaca tcttataact tgcacccctt tcttctgagg
1981 aagagaacat cttgcaaggc agggcgagca gcggcagggc tggcttagga gcagtgcaag
2041 agtccctgtg ctccagttcc acactgctgg cagggaaggc aagggggac gggcctggat
2101 ctgggggtga gggagaaaga tggacccctg ggtgaccact aaaccaaaga tattcggaac
2161 tttctattta ggatgtggac gtaattcctg ttccgaggta gaggctgtgc tgaagacaag
2221 cacagtggcc tggtgcgcct tggaaaccaa caactattca cgagccagta tgaccttcac
2281 atctttagaa attatgaaaa cgtatgtgat tggagggttt ggaaaaccag ttatcttatt
2341 taacatttta aaaattacct aacagttatt tacaaacagg tctgtgcatc ccaggtctgt
2401 cttcttttca aggtctgggc cttgtgctcg ggttatgttt gtgggaaatg cttaataaat
2461 actgataata tgggaagaga tgaaaactga ttctcctcac tttgtttcaa acctttctgg
2521 cagtgggatg attcgaattc acttttaaaa ttaaattagc gtgttttgtt ttg
```

SEQ ID NO: 35 nucleotide mRNA sequence for human Ngn 3
(accession no NM_020999) 1167 bp mRNA

```
  1 cctcggaccc cattctctct tcttttctcc tttggggctg gggcaactcc caggcggggg
 61 cgcctgcagc tcagctgaac ttggcgacca gaagcccgct gagctcccca cggccctcgc
121 tgctcatcgc tctctattct tttgcgccgg tagaaaggat gacgcctcaa ccctcgggtg
181 cgcccactgt ccaagtgacc cgtgagacgg agcggtcctt ccccagagcc tcggaagacg
241 aagtgacctg ccccacgtcc gccccgccca gccccactcg cacacggggg aactgcgcag
301 aggcggaaga gggaggctgc cgaggggccc cgaggaagct ccgggcacgg cgcgggggac
361 gcagccggcc taagagcgag ttggcactga gcaagcagcg acggagtcgg cgaaagaagg
421 ccaacgaccg cgagcgcaat cgaatgcaca acctcaactc ggcactggac gccctgcgcg
481 gtgtcctgcc caccttccca gacgacgcga agctcaccaa gatcgagacg ctgcgcttcg
541 cccacaacta catctgggcg ctgactcaaa cgctgcgcat agcggaccac agcttgtacg
601 cgctggagcc gccggcgccg cactgcgggg agctgggcag cccaggcggt tcccccgggg
```

-continued

SEQUENCE LISTING:

```
 661 actgggggtc cctctactcc ccagtctccc aggctggcag cctgagtccc gccgcgtcgc
 721 tggaggagcg acccgggctg ctgggggcca ccttttccgc ctgcttgagc ccaggcagtc
 781 tggctttctc agattttctg tgaaaggacc tgtctgtcgc tgggctgtgg gtgctaaggg
 841 taagggagag ggagggagcc gggagccgta gagggtggcc gacggcggcg gccctcaaaa
 901 gcacttgttc cttctgcttc tccctggctg accccctggcc ggcccaggcc tccacggggg
 961 cggcaggctg ggttcattcc ccggccctcc gagccgcgcc aacgcacgca acccttgctg
1021 ctgcccgcgc gaagtgggca ttgcaaagtg cgctcatttt aggcctcctc tctgccacca
1081 ccccataatc tcattcaaag aatactagaa tggtagcact acccggccgg agccgcccac
1141 cgtcttgggt cgccctaccc tcactca
```

SEQ ID NO: 36 nucleotide mRNA sequence for HUMAN MafA (accession no: NM_201589) 1062 bp mRNA

```
   1 atggccgcgg agctggcgat gggcgccgag ctgcccagca gcccgctggc catcgagtac
  61 gtcaacgact tcgacctgat gaagttcgag gtgaagaagg agcctcccga ggccgagcgc
 121 ttctgccacc gcctgccgcc aggctcgctg tcctcgacgc cgctcagcac gccctgctcc
 181 tccgtgccct cctcgcccag cttctgcgcg cccagcccgg gcaccggcgg cggcggcggc
 241 gcgggggggcg gcggcggctc gtctcaggcc gggggcgccc ccgggccgcc gagcgggggc
 301 cccggcgccg tcgggggcac ctcggggaag ccggcgctgg aggatctgta ctggatgagc
 361 ggctaccagc atcacctcaa ccccgaggcg ctcaacctga cgcccgagga cgcggtggag
 421 gcgctcatcg gcagcggcca ccacggcgcg caccacggcg cgcaccaccc ggcggccgcc
 481 gcagcctacg aggctttccg cggcccgggc ttcgcgggcg gcggcggagc ggacgacatg
 541 ggcgccggcc accaccacgg cgcgcaccac gccgcccacc atcaccacgc cgcccaccac
 601 caccaccacc accaccacca ccatggcggc gcgggacacg gcggtggcgc gggccaccac
 661 gtgcgcctgg aggagcgctt ctccgacgac cagctggtgt ccatgtcggt gcgcgagctg
 721 aaccggcagc tccgcggctt cagcaaggag gaggtcatcc ggctcaagca gaagcggcgc
 781 acgctcaaga accgcggcta cgcgcagtcc tgccgcttca agcgggtgca gcagcggcac
 841 attctggaga gcgagaagtg ccaactccag agccaggtgg agcagctgaa gctggaggtg
 901 gggcgcctgg ccaaagagcg ggacctgtac aaggagaaat acgagaagct ggcgggccgg
 961 ggcggccccg ggagcgcggg cggggccggt ttcccgcggg agccttcgcc gccgcaggcc
1021 ggtcccggcg gggccaaggg cacggccgac ttcttcctgt ag
```

SEQ ID NO: 37-mRNA sequence of mouse pdx1 (accession no NM_008814)

```
   1 gtcaaagcga tctggggtgg cgtagagagt ccgcgagcca cccagcgcct aaggcctggc
  61 ttgtagctcc gacccggggc tgctggcccc caagtgccgg ctgccaccat gaacagtgag
 121 gagcagtact acgcggccac acagctctac aaggacccgt gcgcattcca gaggggcccg
 181 gtgccagagt tcagcgctaa ccccccctgcg tgcctgtaca tgggccgcca gcccccacct
 241 ccgccgccac cccagtttac aagctcgctg ggatcactgg agcagggaag tcctccggac
 301 atctccccat acgaagtgcc cccgctcgcc tccgacgacc cggctggcgc tcacctccac
 361 caccaccttc cagctcagct cgggctcgcc catccacctc ccggaccttt cccgaatgga
 421 accgagcctg gggggcctgga agagcccaac cgcgtccagc tccctttccc gtggatgaaa
 481 tccaccaaag ctcacgcgtg gaaaggccag tgggcaggag gtgcttacac agcggaaccc
 541 gaggaaaaca agaggacccg tactgcctac acccgggcgc agctgctgga gctggagaag
```

SEQUENCE LISTING:

```
 601 gaattcttat ttaacaaata catctcccgg ccccgccggg tggagctggc agtgatgttg
 661 aacttgaccg agagacacat caaaatctgg ttccaaaacc gtcgcatgaa gtggaaaaaa
 721 gaggaagata agaaacgtag tagcgggacc ccgagtgggg gcggtggggg cgaagagccg
 781 gagcaagatt gtgcggtgac ctcgggcgag gagctgctgg cagtgccacc gctgccacct
 841 cccggaggtg ccgtgccccc aggcgtccca gctgcagtcc gggagggcct actgccttcg
 901 ggccttagcg tgtcgccaca gccctccagc atcgcgccac tgcgaccgca ggaaccccgg
 961 tgaggacagc agtctgaggg tgagcgggtc tgggacccag agtgtggacg tgggagcggg
1021 cagctggata agggaactta acctaggcgt cgcacaagaa gaaaattctt gagggcacga
1081 gagccagttg ggtatagccg gagagatgct ggcagacttc tggaaaaaca gccctgagct
1141 tctgaaaact ttgaggctgc ttctgatgcc aagcgaatgg ccagatctgc ctctaggact
1201 ctttcctggg accaatttag acaacctggg ctccaaactg aggacaataa aaagggtaca
1261 aacttgagcg ttccaatacg gaccagc
```

SEQ ID NO: 38 nucleotide mRNA sequence for mouse Ngn 3
(accession No: NM_009719) 1540 bp mRNA linear

```
   1 atgcagctca gaaatccctc tgggtctcat cactgcagca gtggtcgagt acctcctcgg
  61 agcttttcta cgacttccag acgcaattta ctccaggcga gggcgcctgc agtttagcag
 121 aacttcagag ggagcagaga ggctcagcta tccactgctg cttgacactg accctatcca
 181 ctgctgcttg tcactgactg acctgctgct ctctattctt ttgagtcggg agaactagga
 241 tggcgcctca tcccttggat gcgctcacca tccaagtgtc cccagagaca caacaacctt
 301 ttcccggagc ctcggaccac gaagtgctca gttccaattc caccccacct agccccactc
 361 tcatacctag ggactgctcc gaagcagaag tgggtgactg ccgagggacc tcgaggaagc
 421 tccgcgcccg acgcggaggg cgcaacaggc ccaagagcga gttggcactc agcaaacagc
 481 gaagaagccg gcgcaagaag gccaatgatc gggagcgcaa tcgcatgcac aacctcaact
 541 cggcgctgga tgcgctgcgc ggtgtcctgc ccaccttccc ggatgacgcc aaacttacaa
 601 agatcgagac cctgcgcttc gcccacaact acatctgggc actgactcag acgctgcgca
 661 tagcggacca cagcttctat ggcccggagc cccctgtgcc ctgtggagag ctggggagcc
 721 ccggaggtgg ctccaacggg gactggggct ctatctactc cccagtctcc caagcgggta
 781 acctgagccc cacggcctca ttggaggaat tccctggcct gcaggtgccc agctccccat
 841 cctatctgct cccgggagca ctggtgttct cagacttctt gtgaagagac ctgtctggct
 901 ctgggtggtg ggtgctagtg gaaagggagg ggaccagagc cgtctggagt gggaggtagt
 961 ggaggctctc aagcatctcg cctcttctgg ctttcactac ttggatccct agccctctca
1021 cagggcttaa ctaggcttct catcggtacc cttgctgctg cgcacagcag acattggggg
1081 ctgctcttct cttaactctc ctcggtgcag ccacatcaaa ctctcgctcc aagcatttga
1141 gaatggtagc actacctagt tggagactcc catacttcct ggtgagtctg ccctcattca
1201 aatctgccgg cctccgacca tccatcactt tttccagggt gacctaatcc agtgttgcgt
1261 cttacctcac tggctcctcc atccagctct tggcccatag atgatgttcg tcgtctttac
1321 tgcccgctac atgcagggtt tctgagcttc tccattctgc cttagtccac gaaggtgatc
1381 tgccttcttc tgcacttttc aagtcgttac ccttccccca agggagacca ggctgtgaac
1441 cggaaagccc tagcctatgg ctagagcatc tctccaactt gtctcccgtg tctaaagtgt
1501 gagttgcagg gacggttcct gaagcactgt ttgtctccct
```

-continued

```
SEQUENCE LISTING:

SEQ ID NO: 39 nucleotide mRNA sequence for mouse MafA
(GeneBank No: NM_194350) 1080 bp mRNA linear
   1 atggccgcgg agctggcgat gggcgcagag ctgcccagca gcccactggc catcgagtac

  61 gtcaacgact tcgacctgat gaagttcgag gtgaagaagg agccgcccga ggccgagcgc

 121 ttctgccacc gcctgccgcc cggctcgctg tcctcgacgc ccctcagcac gccctgctcc

 181 tcggtgccct cttcgcccag cttctgcgca cccagcccgg gcacaggcgg cggcgcgggc

 241 ggcgggggca gcgcggctca ggccgggggc gccccggggc cgccgagtgg aggccccggc

 301 actgtcgggg gcgcctcagg aaaagcggtg ctggaggatc tgtactggat gagcgggtac

 361 cagcaccacc tgaaccccga ggcgctcaac ctgacgccgg aggacgcggt ggaggcgctc

 421 atcggcagc ggccaccacgg cgcgcaccac ggcgcgcatc acccggcggc tgctgcggcc

 481 tatgaggcc ttccggggtca gagcttcgcg ggcggcggcg gcgcggacga catgggtgcc

 541 ggccaccac cacggcgcaca ccacactgcc caccatcatc actctgccca ccatcaccat

 601 caccaccat caccaccacgg aggctctggc caccacggcg gaggcgcggg tcacggcgga

 661 ggcggcgca ggccaccacgt gcgcttggag gagcgcttct ccgacgacca gctggtatcc

 721 atgtccgtg cgggagctgaa ccggcagctc cgcggcttca gcaaggagga ggtcatccga

 781 ctgaaacag aagcggcgcac gctcaagaac cgcggctacg cgcagtcgtg ccgcttcaag

 841 cgggtgcag cagcggcacat tctggagagc gagaagtgcc agctccagag ccaggtggag

 901 cagctgaag ctggaggtggg gcgtctggcc aaggagcggg acctgtacaa ggagaaatac

 961 gagaagttg gcgggccgggg cggccccggg ggcgcgggcg gggccggctt ccctcgggag

1021 ccctcgcca gcgcaggctgg ccccggggcg gccaaaggcg cacccgactt ctttctgtga
```

What is claimed:

1. A method for reprogramming a first differentiated cell of exocrine origin to a second differentiated cell that exhibits at least two characteristics of a pancreatic β-cell, does not express pancreatic hormones other than insulin and does not express amylase, the method comprising increasing protein expression of transcription factors Pdx-1, Ngn3 and MaFA in the first differentiated cell of exocrine origin, thereby reprogramming the first differentiated cell of exocrine origin to a second differentiated cell that exhibits at least two characteristics of a pancreatic β-cell, does not express pancreatic hormones other than insulin and does not express amylase, wherein the first differentiated cell of exocrine origin is isolated from a subject or located in vivo within the subject.

2. The method of claim 1, wherein a characteristic of a pancreatic β-cell is secreting insulin in response to glucose.

3. The method of claim 1, wherein a characteristic of a pancreatic β-cell is expression of at least one marker selected from the group consisting of: Ngn3−, Pdx1+ and MafA+.

4. The method of claim 1, wherein the protein expression of the transcription factors is increased by contacting the first differentiated cell of exocrine origin with agents which increase the expression of the transcription factors.

5. The method of claim 1, wherein the first differentiated cell of exocrine origin is in vitro.

6. The method of claim 1, wherein the first differentiated cell of exocrine origin is ex vivo.

7. The method of claim 1, wherein the first differentiated cell of exocrine origin is in vivo or present in a subject.

8. The method of claim 7, wherein the subject has, or is at risk of developing, diabetes or a metabolic disorder.

9. The method of claim 1, wherein the first differentiated cell of exocrine origin is a mammalian cell.

10. The method of claim 1, wherein the method further comprises contacting the first differentiated cell of exocrine origin with at least one agent which increases the protein expression of at least one of the transcription factors selected from the group consisting of: NeuroD, Nkx2.2, Nkx6.1, Pax4, Pax6 or Isl1.

11. The method of claim 1, wherein the second cell exhibiting at least two characteristics of a pancreatic β cell has an increased expression of a marker selected from the group consisting of: c-peptide, glucose transporter 2 (Glut2), glucokinase (GCK), prohormone convertase 1/3 (PC1/3), β-cell transcription factors NeuroD, Nkx2.2 and Nkx6.1 by a statistically significant amount relative to the first differentiated cell of ended exocrine origin from which the second cell that exhibits at least two characteristics of a pancreatic β cell was derived.

12. The method of claim 1, wherein the second cell that exhibits at least two characteristics of a pancreatic βcell has a decreased expression of a marker selected from the group consisting of: Ck19, Nestin, Vimentin and Tuji by a statistically significant amount relative to the first differentiated cell of exocrine origin from which the β cell was derived.

* * * * *